(12) United States Patent
Fuji et al.

(10) Patent No.: US 12,012,410 B2
(45) Date of Patent: Jun. 18, 2024

(54) SUBSTITUTED PYRAZOLO[1,5-a]PYRAZINES FOR SPINAL MUSCULAR ATROPHY

(71) Applicant: REBORNA BIOSCIENCES, INC., Kanagawa (JP)

(72) Inventors: Koji Fuji, Kanagawa (JP); Takeshi Yamasaki, Kanagawa (JP); Shunya Suzuki, Kanagawa (JP); Koji Ono, Kanagawa (JP); Hiroki Takahagi, Kanagawa (JP)

(73) Assignee: REBORNA BIOSCIENCES, INC., Kanagawa (JP)

( * ) Notice: Subject to any disclaimer, the term of this patent is extended or adjusted under 35 U.S.C. 154(b) by 260 days.

(21) Appl. No.: 17/255,843

(22) PCT Filed: Jun. 27, 2019

(86) PCT No.: PCT/JP2019/025732
§ 371 (c)(1),
(2) Date: Dec. 23, 2020

(87) PCT Pub. No.: WO2020/004594
PCT Pub. Date: Jan. 2, 2020

(65) Prior Publication Data
US 2022/0287748 A1   Sep. 15, 2022

(30) Foreign Application Priority Data
Jun. 27, 2018 (JP) ................. 2018-122551

(51) Int. Cl.
| A61K 31/4985 | (2006.01) |
| A61P 21/00 | (2006.01) |
| C07D 487/04 | (2006.01) |
| G01N 33/50 | (2006.01) |
| A61C 8/00 | (2006.01) |

(52) U.S. Cl.
CPC ............ C07D 487/04 (2013.01); A61P 21/00 (2018.01); G01N 33/5023 (2013.01); *A61C 8/0096* (2013.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS

| 4,251,531 | A | 2/1981 | Doria et al. |
| 2003/0036652 | A1 | 2/2003 | Bakthavatchalam et al. |
| 2012/0208796 | A1 | 8/2012 | Ratcliffe et al. |
| 2012/0294930 | A1 | 11/2012 | Ren et al. |
| 2013/0102602 | A1 | 4/2013 | Hour et al. |
| 2015/0005289 | A1 | 1/2015 | Qi et al. |
| 2015/0030588 | A1 | 1/2015 | Jessen et al. |
| 2015/0126515 | A1 | 5/2015 | Chen et al. |
| 2015/0320727 | A1 | 11/2015 | Ren et al. |
| 2015/0329499 | A1 | 11/2015 | Golden et al. |
| 2016/0089371 | A1 | 3/2016 | Liu et al. |

FOREIGN PATENT DOCUMENTS

| CN | 102573846 A | 7/2012 |
| CN | 102666540 A | 9/2012 |
| CN | 103491962 A | 1/2014 |
| CN | 104204804 A | 12/2014 |
| CN | 108026046 A | 5/2018 |
| JP | 2004-520299 A | 7/2004 |
| JP | 2013-502423 A | 1/2013 |
| JP | 2013-507417 A | 3/2013 |
| JP | 2014-506600 A | 3/2014 |
| JP | 2014-533284 A | 12/2014 |
| JP | 2015-508075 A | 3/2015 |
| JP | 2015-511224 A | 4/2015 |
| JP | 2016-512835 A | 5/2016 |
| WO | 2002/48152 A2 | 6/2002 |
| WO | 2010/019236 A1 | 2/2010 |
| WO | 2011/022439 A1 | 2/2011 |
| WO | 2011/045258 A1 | 4/2011 |
| WO | 2012/148540 A1 | 11/2012 |
| WO | 2013/071264 A1 | 5/2013 |
| WO | 2013/101974 A1 | 7/2013 |
| WO | 2013/112788 A1 | 8/2013 |
| WO | 2013/119916 A2 | 8/2013 |
| WO | 2013/130689 A1 | 9/2013 |
| WO | 2013/142236 A1 | 9/2013 |

(Continued)

OTHER PUBLICATIONS

Chowdhury et al., Amino acid derived quinazolines as Rock/PKA inhibitors. Bioorg Med Chem Lett. Mar. 15, 2013;23(6):1592-9.
Fang et al., Synthesis and biological evaluation of 4-quinazolinones as Rho kinase inhibitors. Bioorg Med Chem Lett. Mar. 15, 2011;21(6):1844-8.
Hour et al., 6-Alkylamino- and 2,3-Dihydro-3'-methoxy-2-phenyl-4-quinazolinones and Related Compounds: Their Synthesis, Cytotoxicity, and Inhibition of Tubulin Polymerization. Journal of Medicinal Chemistry. 2000;43(23):4479-4487.
Lopez et al., Synthesis and Preliminary Cytotoxic and Antifungal Evaluation of Some 6-N, N-Dialkyl 2-Aryl-4(3h)-Quinazolinone Derivatives. Heterocyclic Communications. 2001;7(5):473-480.

(Continued)

*Primary Examiner* — Douglas M Willis
(74) *Attorney, Agent, or Firm* — McCarter & English, LLP; Xin Zhang

(57) ABSTRACT

A prophylactic or therapeutic agent for spinal muscular atrophy according to the present invention includes a compound represented by the formula (I) or a salt thereof:

[Chemical formula 1]

(I)

the variables are described herein.

19 Claims, 8 Drawing Sheets

(56) References Cited

FOREIGN PATENT DOCUMENTS

| WO | 2014/151147 A1 | 9/2014 |
|---|---|---|
| WO | 2014/209841 A2 | 12/2014 |
| WO | 2015/024876 A2 | 2/2015 |
| WO | 2015/095446 A1 | 6/2015 |
| WO | 2015/095449 A1 | 6/2015 |
| WO | 2015/105657 A1 | 7/2015 |
| WO | 2015/173181 A1 | 11/2015 |
| WO | 2015/197503 A1 | 12/2015 |
| WO | 2016/184832 A1 | 11/2016 |
| WO | 2017/015562 A1 | 1/2017 |
| WO | 2017/080967 A1 | 5/2017 |
| WO | 2018/140514 A1 | 8/2018 |

OTHER PUBLICATIONS

Wang et al., Mechanistic studies of a small-molecule modulator of SMN2 splicing. Proc Natl Acad Sci U S A. May 15, 2018;115(20):E4604-E4612.

Hour et al., Molecular modelling, synthesis, cytotoxicity and antitumour mechanisms of 2-aryl-6-substituted quinazolinones as dual-targeted anti-cancer agents. Br J Pharmacol. Aug. 2013;169(7):1574-86.

Khadka et al., Substituted 2-arylquinazolinones: Design, synthesis, and evaluation of cytotoxicity and inhibition of topoisomerases. Eur J Med Chem. Oct. 20, 2015;103:69-79.

Liu et al., MJ-66 induces malignant glioma cells G2/M phase arrest and mitotic catastrophe through regulation of cyclin B1/Cdk1 complex. Neuropharmacology. Nov. 2014;86:219-27.

Naryshkin et al., Motor neuron disease. SMN2 splicing modifiers improve motor function and longevity in mice with spinal muscular atrophy. Science. Aug. 8, 2014;345(6197):688-93.

Palacino et al., SMN2 splice modulators enhance U1-pre-mRNA association and rescue SMA mice. Nat Chem Biol. Jul. 2015; 11(7):511-7.

Pinard et al., Discovery of a Novel Class of Survival Motor Neuron 2 Splicing Modifiers for the Treatment of Spinal Muscular Atrophy. J Med Chem. May 25, 2017;60(10):4444-4457.

Ratni et al., Specific Correction of Alternative Survival Motor Neuron 2 Splicing by Small Molecules: Discovery of a Potential Novel Medicine to Treat Spinal Muscular Atrophy. J Med Chem. Jul. 14, 2016;59(13):6086-100.

Woll et al., Discovery and Optimization of Small Molecule Splicing Modifiers of Survival Motor Neuron 2 as a Treatment for Spinal Muscular Atrophy. J Med Chem. Jul. 14, 2016;59(13):6070-85.

Wu et al., 2-(Naphthalene-1-yl)-6-pyrrolidinyl-4-quinazolinone inhibits skin cancer M21 cell proliferation through aberrant expression of microtubules and the cell cycle. J Pharmacol Exp Ther. Sep. 2011;338(3):942-51.

International Search Report and Written Opinion for Application No. PCT/JP2019/025732, dated Oct. 15, 2019, 29 pages.

StandardFL-SMN:
5'-TCAGATAACATCAAGCCCAAATCTGCTCCATGGAACTCTTTTCTCC
CTCCACCACCCCCATGCCAGGGCCAAGACTGGGACCAGGAAAGATAAT
TCCCCCACCACCTCCCATATGTCCAGATTCTCTTGATGATGCTGATGCT
TTGGGAAGTATGTTAATTTCATGGTACATGAGTGGCTATCATACTGGCT
ATTATATGGGTTTCAGACAAAATCAAAAGAAGGAAGGTGCTCACATTC
CTTAAATTAAGGAGAAATGCTGGCATAGAGCAGCACTAAATGACACCAC
TAAAGAACGATCAGACAGATCTGGAATGTGAAGCGTTATAGAAGATAA
CTGGCCTCATTTCTTCAAATATCAAGTGTTGGGAAGAAAAAGGAAG
TGGAATGGGTAACTCTTCTTGATTAAAGTTATGTAATAACCAAATGCA
ATGTGAAATATTTACTGGACTCTATTTGAAAACCATCTGTAAAAGA
CTGGGGTGGGGT-3' (SEQ ID NO. 1)

Standard delta7:
5'-ACCACCCCCATGCCAGGGCCAAGACTGGGACCAGGAAAGCCAGGT
CTAAAATTCAATGGCCCACCACCGCCACCGCCACCACCACCCCACT
TACTATCATGCTGGCTGCCTCCATTTCCTTCTGGACCACCAATAATTCC
CCCACCACCTCCCATATGTCCAGATTCTCTTGATGATGCTGATGCTTTG
GGAAGTATGTTAATTTCATGGTACATGAGTGGCTATCATACTGGCTATT
ATATGGAAATGCTGGCATAGAGCAGCACTAAATGACACCACTAAAGAAA
CGATCAGACAGATCTGGAATGTGAAGCGTTATAGAAGATAACTGGCCTC
ATTTCTTCAAATATCAAGTGTTGGGAAGAAAAAGGAAGTGGAATGG
GTAACTCTTCTTGATTAAAGTTATGTAATAACCAAATGCAATGTGAAA
TATTTACTGGACTCTATTTGAAAACCATCTGTAAAAGACTGGGGTG
GGGGTGGGAGGCC-3' (SEQ ID NO. 2)

Standard GAPDH:
5'-AAATTGAGCCCGCAGCCTCCCGCTTCGCTCTCTGCTCCTCCTGTTC
GACAGTCAGCCGCATCTTCTTTTGCGTCGCCAGCCGAGCCACATCGCTC
AGACACCATGGGGAAGGTGAAGGTCGGAGTCAACGGATTTGGTCGTATT
GGGCGCCTGGTCACCAGGGCTGCTTTAACTCTGGTAAAGTGGATATTG
TTGCCATCAATGACCCCTTCATTGACCTCAACTACATGGTTTACATGTT
CCAATATGATTCCACCCATGGCAAATTCCATGGCACCGTCAAGGCTGAG
AACGGGAAGCTTGTCATCAATGGAAATCCCATCACCATCTTCCAGGAGC
GAGATCCTCCAAAATCAAGTGGGGCGATGCTGGCGCTGAGTACGTCGT
GGAGTCCACTGGCGTCTTCACCACCATGGAGAAGGCTGGGGCTCATTTG
CAGGGGGGAGCCAAAAGGGTCATCATCTCTGCCCCTCTGCTGATGCCC
CCATGTTCGTCAT-3' (SEQ ID NO. 7)

FIG. 1

(A) FOR FL-SMN DETECTION

003-Fw-FL-SMN:
5'-GCTCACATTCCTTAAATTAAGGAGAAA-3' (SEQ ID NO. 3)

005-Rv-SMN:
5'-TCCAGATCTGTCTGATCGTTTCTT-3' (SEQ ID NO. 5)

004-Probe-SMN:
5'-/56-FAM/CTGGCATAG/ZEN/AGCAGCACTAAATGACACCAC/31ABkFQ/-3' (SEQ ID NO. 4)

(B) FOR Delta7 DETECTION

006-Fw-delta7:
5'-TGGCTATCATACTGGCTATTATATGGAA-3' (SEQ ID NO. 6)

005-Rv-SMN:
5'-TCCAGATCTGTCTGATCGTTTCTT-3' (SEQ ID NO. 5)

004-Probe-SMN:
5'-/56-FAM/CTGGCATAG/ZEN/AGCAGCACTAAATGACACCAC/31ABkFQ/-3' (SEQ ID NO. 4)

FIG. 2

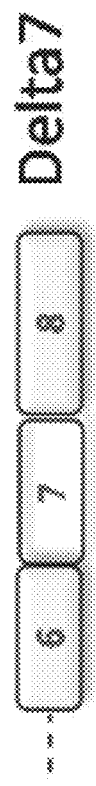
FIG. 3A
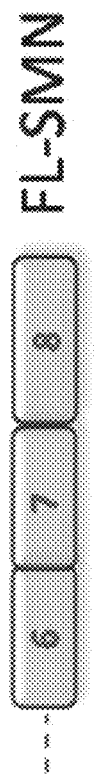
FIG. 3B
FIG. 3C
FIG. 3D
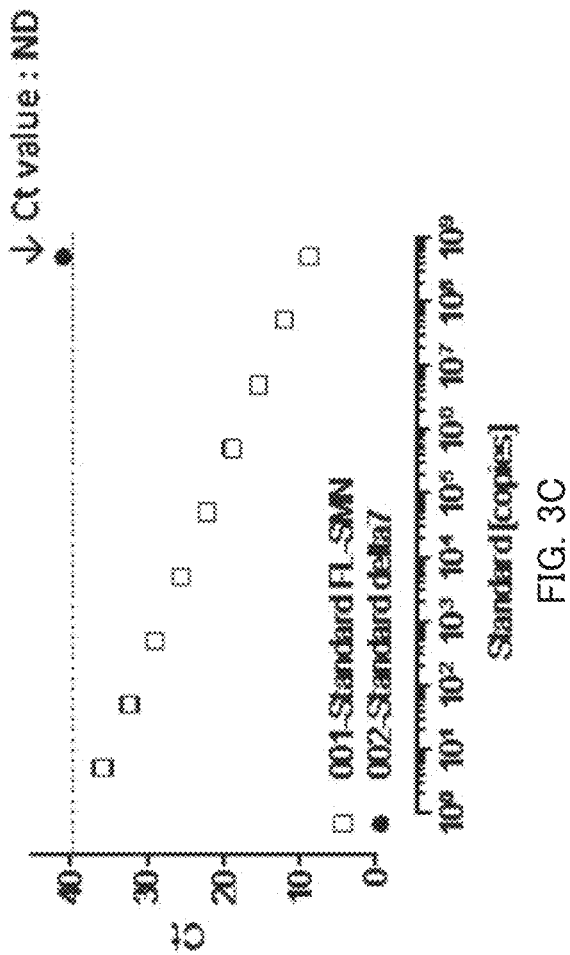
FIG. 3E

SUBSTITUTED PYRAZOLO[1,5-a]PYRAZINES FOR SPINAL MUSCULAR ATROPHY

CROSS-REFERENCE TO RELATED APPLICATIONS

This application is a U.S. national stage filing, under 35 U.S.C. § 371(c), of International Application No. PCT/JP2019/025732, filed on Jun. 27, 2019, which claims priority to Japanese Patent Application No. 2018-122551, filed on Jun. 27, 2018. The entire contents of each of the aforementioned applications are incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to prophylactic or therapeutic agents for spinal muscular atrophy.

Description of Related Art

Spinal muscular atrophy (SMA) is a neuromuscular atrophy caused by degeneration of the anterior horn cells of the spinal cord. It is an autosomal recessive genetic disorder whose causative gene lies on chromosome 5.

The causative gene of SMA has been known to be the survival motor neuron 1 (SMNJ) gene, which is located on chromosome 5q13d. SMA is developed in individuals who are homozygous for mutations inactivating this gene, such as null mutations or deletion mutations.

Chromosome 5q13d also contains the SMN2 gene, which is an inverted duplication of the SMN1 gene, with a C-to-T mutation at nucleotide position 6 in exon 7. Although this mutation is a nucleotide change that does not involve any amino acid substitution, it makes it easier to causes an alternative splicing event excluding exon 7. As a result, approximately 90% of the protein produced by the SMN2 gene is less functional, whereas approximately 10% is the same protein with its normal function as the one produced from the SMN1 gene. Thus, loss of function of the SMN1 gene causes a significant decrease in the amount of the protein with its normal function, even in the presence of the SMN2 gene, resulting in the onset of SMA.

The copy number of the SMN2 gene varies among patients with SMA; it has been known that those with higher copy numbers present milder symptoms. Thus, it is considered that increase of the amount of protein with its normal function would lead to a therapy for SMA.

Antisense compounds that regulate the splicing of the SMN2 mRNA have recently been developed (see, for example, WO2010/148249). The antisense compounds regulate SMN2 splicing such that it proceeds normally, thereby increasing the amount of the protein with its normal function, to ameliorate SMA symptoms.

Patent Literature 1: Unexamined Patent Application Publication No. WO2010/148249

BRIEF SUMMARY OF THE INVENTION

An object of the present invention is to provide prophylactic or therapeutic agents for spinal muscular atrophy.

An aspect of the present invention is a compound or a salt thereof, the compound being represented by the formula (I):

[Chemical formula 1]

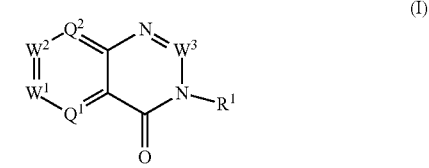

wherein:
W$^1$, W$^2$, and W$^3$ are each independently selected from the group consisting of C—R$^2$, C—R$^3$, C—R$^c$, and C—R$^d$, and are defined by one of the followings (i) to (iv):
(i) when W$^3$ is C—R$^2$, then W$^1$ is C—R$^3$, W$^2$ is C—R$^c$ or N, and R$^1$ is a hydrogen atom;
(ii) when W$^3$ is C—R$^3$, then W$^1$ is C—R$^2$, W$^2$ is C—R$^c$ or N, and R$^1$ is a hydrogen atom, C$_{1-8}$ alkyl, or C$_{1-8}$ alkoxy;
(iii) when W$^1$ is C—R$^2$, then W$^2$ is C—R$^c$ or N, W$^3$ is C—R$^d$, and R$^1$ is an aliphatic heterocycle containing one or more nitrogen atoms, the aliphatic heterocycle being optionally substituted with a non-aromatic substituent; and
(iv) when W$^2$ is C—R$^2$, W$^1$ is C—R$^c$, W$^3$ is C—R$^d$, and R$^1$ is an aliphatic heterocycle containing one or more nitrogen atoms, the aliphatic heterocycle being optionally substituted with a non-aromatic substituent;
R$^2$ is a 6- or more membered aromatic ring optionally substituted with a non-aromatic substituent;
R$^3$ is an aliphatic heterocycle containing one or more nitrogen atoms, the aliphatic heterocycle being optionally substituted with a non-aromatic substituent;
Q$^1$ is selected from C—R$^a$ and N;
Q$^2$ is selected from C—R b and N; and
R$^a$, R$^b$, R$^c$, and R$^d$ are each independently selected from the group consisting of a hydrogen atom, halogen, C$_{1-8}$ alkyl, C$_{1-8}$ alkoxy, and a cyano group.

In the formula (I), R$^2$ may be an 8- to 10-membered nitrogen-containing aromatic heterocyclic group containing two or more heteroatoms, the 8- to 10-membered nitrogen-containing aromatic heterocyclic group being optionally substituted with a non-aromatic substituent; and R$^3$ may be a 3- to 14-membered non-aromatic heterocyclic group containing one or more nitrogen atoms, the 3- to 14-membered non-aromatic heterocyclic group being optionally substituted with a non-aromatic substituent. In addition, R$^2$ may be an aromatic heterocycle selected from the group consisting of indazolyl, benzimidazolyl, pyrrolo[1,2-α]pyrazinyl, pyrrolo[1,2-b]pyridazinyl, pyrrolo[1,2-c]pyrimidinyl, pyrrolo[1,2-b]pyrimidinyl, imidazo[1,2-α]pyridinyl, pyrazolo[1,5-a]pyridinyl, imidazo[1,5-a]pyridinyl, pyrrolo[3,2-b]pyridinyl, pyrrolo[3,2-c]pyridinyl, pyrrolo[2,3-c]pyridinyl, pyrrolo[2,3 pyridinyl, 1,3-benzoxazolyl, 1,2-benzisoxazolyl, 2,1-benzisoxazolyl, furo[3,2-b]pyridinyl, furo[3,2-c]pyridinyl, furo[2,3-c]pyridinyl, furo[2,3 pyridinyl, pyrazolo[3,4-b]pyridinyl, 1H-pyrazolo[3,4-b]pyridinyl, pyrazolo[3,4-c]pyridinyl, 1H-pyrazolo[3,4-c]pyridinyl, pyrazolo[4,3-c]pyridinyl, pyrazolo[4,3 pyridinyl, pyrazolo[1,5 pyrazinyl, pyrazolo[1,5-c]pyrimidinyl, pyrazolo[1,5-c]pyrimidinyl, pyrazolo[1,5-b]pyridazinyl, imidazo[4,5-b]pyridinyl, imidazo[4,5-c]pyridinyl, imidazo[1,2-c]pyrimidinyl, imidazo[1,2-c]pyrazinyl, imidazo[1,2-c]pyrimidinyl, imidazo[1,2-b]pyridazinyl, imidazo[1,5-c]pyrimidinyl, imidazo[1,5-c]pyrazinyl, imidazo[1,5-c]pyrimidinyl, imidazo[1,5-b]pyridazinyl, pyrrolo[3,2-c]pyridazinyl, pyrrolo[3,2-d]pyrimidinyl, pyrrolo[2,3 pyrazinyl, pyrrolo[2,3-d]pyridazinyl, pyrrolo[2,3-d]pyrimidinyl, pyrrolo[2,3-c]pyridazinyl, oxazolo[5,4-b]pyridinyl, oxazolo[5,4-c]pyridinyl, oxazolo[4,5-c]pyridinyl, oxazolo[4,5-b]pyridinyl, [1,2,4]triazolo[1,5-a]pyridinyl, [1,2,4]triazolo[4,3-a]pyridinyl, purinyl, pyrazolo[3,4-d]pyrimidyl, pyrazolo[4,3-d]pyrimidyl, isoxazolo[5,4-d]pyrimidinyl, isoxazolo[4,5-d]pyrimidinyl, oxazolo[4,5-d]pyrimidinyl, and oxazolo[5,4-d]pyrimidinyl, the aromatic heterocycle being optionally substituted with one to three $R^4$ groups; $R^3$ may be an aliphatic heterocycle selected from the group consisting of azetidinyl, pyrrolidinyl, piperidinyl, piperazinyl, morpholinyl, azepanyl, 1,4-diazepanyl, 1,4-oxazepanyl, octahydropyrrolo[3,4-b]pyrrolyl, octahydropyrrolo[3,4-c]pyrrolyl, octahydropyrrolo[3,2-b]pyrrolyl, octahydro-1H-pyrrolo[3,2-b]pyridinyl, octahydro-5H-pyrrolo[3,2-c]pyridinyl, octahydro-1H-pyrrolo[2,3-c]pyridinyl, octahydro-6H-pyrrolo[3,4-b]pyridinyl, octahydro-1H-pyrrolo[3,4-c]pyridinyl, octahydro-1H-cyclopentapyrazine, octahydro-1H-pyrrolo[1,2-c]pyrazinyl, decahydro-2,6-naphthyridinyl, decahydro-2,7-naphthyridinyl, decahydro-1,6-naphthyridinyl, decahydro-1,7-naphthyridinyl, decahydro-quinoxalinyl, octahydro-2H-pyrido[1,2-c]pyrazinyl, 3-azabicyclo[3.1.0]hexyl, 1-azabicyclo[2.2.1]heptyl, 2-azabicyclo[2.2.1]heptyl, 7-azabicyclo[2.2.1]heptyl, 1-azabicyclo[2.2.2]octyl, 2-azabicyclo[2.2.2]octyl, 1-azabicyclo[3.2.1]octyl, 2-azabicyclo[3.2.1]octyl, 3-azabicyclo[3.2.1]octyl, 6-azabicyclo[3.2.1]octyl, 8-azabicyclo[3.2.1]octyl, 1-azabicyclo[3.2.2]nonyl, 2-azabicyclo[3.2.2]nonyl, 3-azabicyclo[3.2.2]nonyl, 6-azabicyclo[3.2.2]nonyl, 1-azabicyclo[3.3.1]nonyl, 2-azabicyclo[3.3.1]nonyl, 3-azabicyclo[3.3.1]nonyl, 9-azabicyclo[3.3.1]nonyl, 2,5-diazabicyclo[2.2.1]heptyl, 1,4-diazabicyclo[2.2.2]octyl, 2,5-diazabicyclo[2.2.2]octyl, 1,4-diazabicyclo[3.2.1]octyl, 2,6-diazabicyclo[3.2.1]octyl, 3,6-diazabicyclo[3.2.1]octyl, 3,8-diazabicyclo[3.2.1]octyl, 1,4-diazabicyclo[3.2.2]nonyl, 1,5-diazabicyclo[3.2.2]nonyl, 2,6-diazabicyclo[3.2.2]nonyl, 3,6-diazabicyclo[3.2.2]nonyl, 6,8-diazabicyclo[3.2.2]nonyl, 1-azaspiro[3.3]heptyl, 2-azaspiro[3.3]heptyl, 1-azaspiro[3.4]octyl, 2-azaspiro[3.4]octyl, 5-azaspiro[3.4]octyl, 6-azaspiro[3.4]octyl, 1-azaspiro[4.4]nonyl, 2-azaspiro[4.4]nonyl, 1-azaspiro[4.5]decanyl, 2-azaspiro[4.5]decanyl, 6-azaspiro[4.5]decanyl, 7-azaspiro[4.5]decanyl, 8-azaspiro[4.5]decanyl, 1,6-diazaspiro[3.3]heptyl, 2,6-diazaspiro[3.3]heptyl, 1,7-diazaspiro[4.4]nonyl, 2,7-diazaspiro[4.4]nonyl, 1,6-diazaspiro[3.5]nonyl, 1,7-diazaspiro[3.5]nonyl, 2,5-diazaspiro[3.5]nonyl, 2,6-diazaspiro[3.5]nonyl, 2,7-diazaspiro[3.5]nonyl, 5,8-diazaspiro[3.5]nonyl, 1,7-diazaspiro[4.5]decyl, 1,8-diazaspiro[4.5]decyl, 2,6-diazaspiro[4.5]decyl, 2,7-diazaspiro[4.5]decyl, 2,8-diazaspiro[4.5]decyl, and 6,9-diazaspiro[4.5]decyl, the aliphatic heterocycle being optionally substituted with one to three $R^5$ groups and optionally containing one to three double bonds, the aliphatic heterocycle optionally containing one to three carbonyl groups, each of the carbonyl groups having a carbon atom in a ring of the aliphatic heterocycle; $R^4$ and $R^5$ may be selected from the group consisting of:

(I) halogen;
(II) a cyano group;
(III) a nitro group;
(IV) a hydroxy group optionally substituted with a $C_{1-6}$ alkyl or $C_{1-10}$ cycloalkyl group optionally substituted with one to five substituents selected from the group consisting of:
  (a) halogen;
  (b) a cyano group;
  (c) a nitro group;
  (d) a $C_{1-6}$ alkoxy group;
  (e) a $C_{1-6}$ alkylamino group; and
  (f) a $C_{1-6}$ alkyl($C_{1-6}$ alkyl)amino group;
(V) an amino group optionally substituted with a $C_{1-6}$ alkyl or $C_{1-10}$ cycloalkyl group optionally substituted with one to five substituents selected from the group consisting of:
  (a) halogen;
  (b) a cyano group;
  (c) a nitro group;
  (d) a $C_{1-6}$ alkoxy group;
  (e) a $C_{1-6}$ alkylamino group; and
  (f) a $C_{1-6}$ alkyl($C_{1-6}$ alkyl)amino group; and
(VI) a $C_{1-6}$ alkyl or $C_{1-10}$ cycloalkyl group optionally substituted with one to five substituents selected from the group consisting of:
  (a) halogen;
  (b) a cyano group;
  (c) a nitro group;
  (d) a $C_{1-6}$ alkoxy group;
  (e) a $C_{1-6}$ alkylamino group; and
  (f) a $C_{1-6}$ alkyl($C_{1-6}$ alkyl)amino group.

The compound represented by the formula (I) may be 2-(4,6-dimethylpyrazolo[1,5-a]pyrazin-2-yl)-6-(4-methylpiperazin-1-yl)quinazolin-4(3H)-one.

Another aspect of the present invention is a medicament including, as an active ingredient, any one of the compounds described above or a salt thereof. This medicament may be a splicing regulator, may be an expression enhancer that enhances expression of normal SMN mRNA and/or normal SMN protein, or may be a prophylactic or therapeutic agent for spinal muscular atrophy.

Yet another aspect of the present invention is a splicing regulator, an expression enhancer that enhances expression of normal SMN mRNA and/or normal SMN protein, or a prophylactic or therapeutic agent for spinal muscular atrophy, which includes, as an active ingredient, any one of the compounds described above or a salt thereof.

Yet another aspect of the present invention is a method for prophylactic or therapeutic treatment of spinal muscular atrophy, the method including: administering an effective amount of any one of the compounds described above or a salt thereof to a mammal (except for human beings) having spinal muscular atrophy.

Still another aspect of the present invention is any one of the compounds described above or a salt thereof for use in prophylactic or therapeutic treatment of spinal muscular atrophy.

Still another aspect of the present invention is use of any one of the compounds described above or a salt thereof for manufacturing a prophylactic or therapeutic agent for spinal muscular atrophy.

Still another aspect of the present invention is a method of examining whether a compound or a salt thereof, the compound being represented by the formula (I):

[Chemical formula 1]

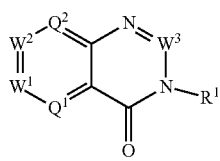

(I)

wherein:
W¹, W², and W³ are each independently selected from the group consisting of C—R², C—R³, C—R$^c$, and C—R$^d$, and are defined by one of the following (i) through (iv):
(i) when W³ is C—R², then W¹ is C—R³, W² is C—R$^c$ or N, and R¹ is a hydrogen atom;
(ii) when W³ is C—R³, then W¹ is C—R², W² is C—R$^c$ or N, and R¹ is a hydrogen atom, $C_{1-8}$ alkyl, or $C_{1-8}$ alkoxy;
(iii) when W¹ is C—R², then W² is C—R$^c$ or N, W³ is C—R$^d$, and R¹ is an aliphatic heterocycle containing one or more nitrogen atoms, the aliphatic heterocycle being optionally substituted with a non-aromatic substituent; and
(iv) when W² is C—R², W¹ is C—R$^c$, W³ is C—R$^d$, and R¹ is an aliphatic heterocycle containing one or more nitrogen atoms, the aliphatic heterocycle being optionally substituted with a non-aromatic substituent; R² is a 6- or more membered aromatic ring optionally substituted with a non-aromatic substituent;
R³ is an aliphatic heterocycle containing one or more nitrogen atoms, the aliphatic heterocycle being optionally substituted with a non-aromatic substituent;
Q¹ is selected from C—R$^a$ and N;
Q² is selected from C—R b and N; and
R$^a$, R$^b$, R$^c$, and R$^d$ are each independently selected from the group consisting of a hydrogen atom, halogen, $C_{1-8}$ alkyl, $C_{1-8}$ alkoxy, and a cyano group, enhances expression of normal SMN mRNA and/or normal SMN protein. This method may include the steps of: bringing a cell into contact with the compound or a salt thereof, the cell including an SMN gene with thymine at nucleotide position 6 in exon 7; and examining whether an expression level, in the cell, of SMN mRNA including exon 7 or SMN protein including an amino acid sequence encoded by exon 7 is elevated by the compound or a salt thereof. The expression may be examined using PCR or Western blotting.

BRIEF DESCRIPTION OF THE SEVERAL VIEWS OF THE DRAWINGS

FIG. 1 is a representation of nucleotide sequences of oligo DNA standards used in a Working Example of the present invention.

FIG. 2 is a representation of nucleotide sequences of primers and probes for PCR used in a Working Example of the present invention. (A) primers and a probe for PCR used for detecting FL-SMN containing exons 7 and 8 of SMN in succession; and (B) primers and a probe for PCR used for detecting Delta7 of SMN with exon 7 skipped.

FIG. 3 is a diagrammatic representation showing the principle of a qPCR system that specifically detects cDNA for FL-SMN with exon 7 and Delta7 without exon 7 in a Working Example of the present invention. (A) the structure of the SMN2 gene on the genome; (B) a mechanism of detecting FL-SMN cDNA; (C) a calibration curve generated using the FL-SMN oligo DNA standard; (D) a mechanism of detecting Delta7 cDNA, and (E) a calibration curve generated using the Delta7 oligo DNA standard.

FIG. 5-1 is a representation showing dose-dependent change in amounts of FL-SMN mRNA and Delta7 mRNA and increase of SMN protein for representative compounds in a Working Example of the present invention. The y-axis represents the percentages of the expression levels of the FL-SMN mRNA and Delta7 mRNA standardized against GAPDH or the expression levels of the SMN protein standardized against GAPDH relative to their respective controls (with the addition of DMSO) which are set as 100%, and the x-axis represents the concentrations of compounds;

FIG. 5-2 is a continuation of FIG. 5-1.
FIG. 5-3 is a continuation of FIG. 5-2.
FIG. 5-4 is a continuation of FIG. 5-3.

DETAILED DESCRIPTION OF THE INVENTION

Figure 4:
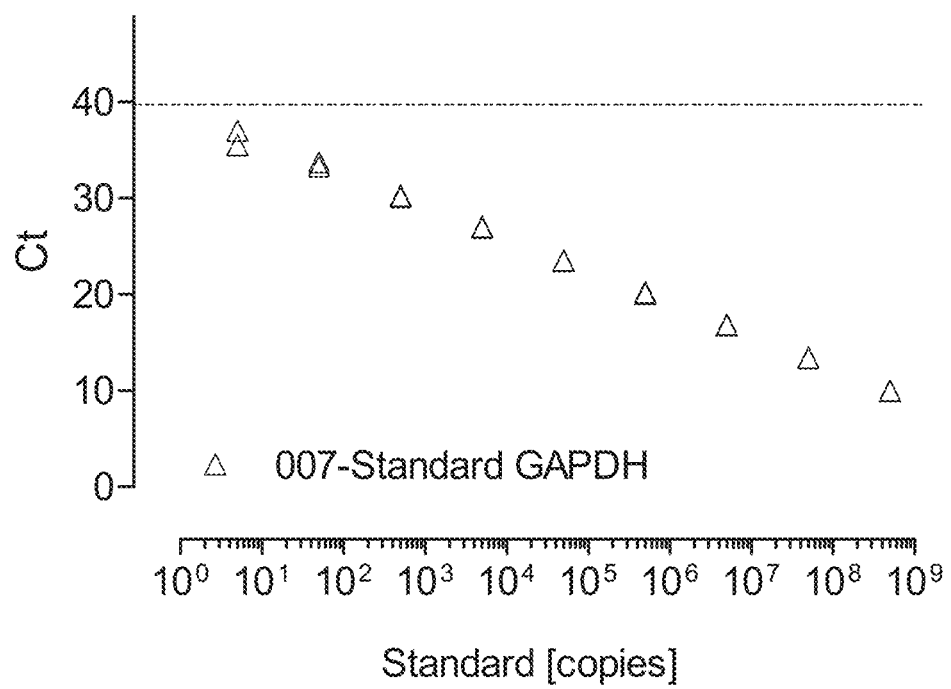
FIG. 4 shows a calibration curve generated using the GAPDH oligo DNA standard in a Working Example of the present invention.

Objects, characteristics, advantages, and ideas of the present invention are apparent to a person skilled in the art from the description of the present specification and a person skilled in the art can easily reproduce the present invention from the description of the present specification. Embodiments of the present invention, specific examples thereof and so forth, which are described in the following, indicate preferable embodiments of the present invention and are described for exemplification or explanation. The present invention is not limited thereto. It is apparent to a person skilled in the art that various alterations and modifications can be made on the basis of the description of the present specification within the intention and the scope of the present spirit disclosed in the present specification.
[Compound]
A compound according to an embodiment of the present invention is the one being represented by the formula (I) or a salt thereof:

[Chemical formula 1]

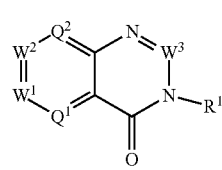

(I)

wherein:
W¹, W², and W³ are each independently selected from the group consisting of C—R², C—R³, C—R$^c$, and C—R$^d$, an are defined by one of the followings (i) to (iv):

(i) when $W^3$ is C—$R^2$, then $W^1$ is C—$R^3$, $W^2$ is C—$R^c$ or N, and $R^1$ is a hydrogen atom;
(ii) when $W^3$ is C—$R^3$, then $W^1$ is C—$R^2$, $W^2$ is C—$R^c$ or N, and $R^1$ is a hydrogen atom, $C_{1-8}$ alkyl, or $C_{1-8}$ alkoxy;
(iii) when $W^1$ is C—$R^2$, then $W^2$ is C—$R^c$ or N, $W^3$ is C—$R^d$, and $R^1$ is an aliphatic heterocycle containing one or more nitrogen atoms, the aliphatic heterocycle being optionally substituted with a non-aromatic substituent; and
(iv) when $W^2$ is C—$R^2$, $W^1$ is C—$R^c$, $W^3$ is C—$R^d$, and $R^1$ is an aliphatic heterocycle containing one or more nitrogen atoms, the aliphatic heterocycle being optionally substituted with a non-aromatic substituent;

$R^2$ is a 6- or more membered aromatic ring optionally substituted with a non-aromatic substituent;
$R^3$ is an aliphatic heterocycle containing one or more nitrogen atoms, the aliphatic heterocycle being optionally substituted with a non-aromatic substituent;
$Q^1$ is selected from C—$R^a$ and N;
$Q^2$ is selected from C—R b and N; and
$R^a$, $R^b$, $R^c$, and $R^d$ are each independently selected from the group consisting of a hydrogen atom, halogen, $C_{1-8}$ alkyl, $C_{1-8}$ alkoxy, and a cyano group.

In the formula (I), $R^2$ may be an 8- to 10-membered nitrogen-containing aromatic heterocyclic group containing two or more heteroatoms, the 8- to 10-membered nitrogen-containing aromatic heterocyclic group being optionally substituted with a non-aromatic substituent; and $R^3$ may be a 3- to 14-membered non-aromatic heterocyclic group containing one or more nitrogen atoms, the 3- to 14-membered non-aromatic heterocyclic group being optionally substituted with a non-aromatic substituent. In addition, $R^2$ may be an aromatic heterocycle selected from the group consisting of indazolyl, benzimidazolyl, pyrrolo[1,2-c]pyrazinyl, pyrrolo[1,2-b]pyridazinyl, pyrrolo[1,2-c]pyrimidinyl, pyrrolo[1,2-b]pyrimidinyl, imidazo[1,2-c]pyridinyl, pyrazolo[1,5-c]pyridinyl, imidazo[1,5-c]pyridinyl, pyrrolo[3,2-b]pyridinyl, pyrrolo[3,2-c]pyridinyl, pyrrolo[2,3-c]pyridinyl, pyrrolo[2,3 pyridinyl, 1,3-benzoxazolyl, 1,2-benzisoxazolyl, 2,1-benzisoxazolyl, furo[3,2-b]pyridinyl, furo[3,2-c]pyridinyl, furo[2,3-c]pyridinyl, furo[2,3 pyridinyl, pyrazolo[3,4-b]pyridinyl, 1H-pyrazolo[3,4-b]pyridinyl, pyrazolo[3,4-c]pyridinyl, 1H-pyrazolo[3,4-c]pyridinyl, pyrazolo[4,3-c] pyridinyl, pyrazolo[4,3 pyridinyl, pyrazolo[1,5 pyrazinyl, pyrazolo[1,5-c]pyrimidinyl, pyrazolo[1,5-c]pyrimidinyl, pyrazolo[1,5-b]pyridazinyl, imidazo[4,5-b]pyridinyl, imidazo[4,5-c]pyridinyl, imidazo[1,2-c]pyridinyl, imidazo[1,2-c]pyrazinyl, imidazo[1,2-c]pyrimidinyl, imidazo[1,2-b] pyridazinyl, imidazo[1,5-c]pyridinyl, imidazo[1,5-c] pyrazinyl, imidazo[1,5-c]pyrimidinyl, imidazo[1,5-b] pyridazinyl, pyrrolo[3,2-c]pyridazinyl, pyrrolo[3,2-d] pyrimidinyl, pyrrolo[2,3 pyrazinyl, pyrrolo[2,3-d] pyridazinyl, pyrrolo[2,3-d]pyrimidinyl, pyrrolo[2,3-c] pyridazinyl, oxazolo[5,4-b]pyridinyl, oxazolo[5,4-c] pyridinyl, oxazolo[4,5-c]pyridinyl, oxazolo[4,5-b]pyridinyl, [1,2,4]triazolo[1,5-c]pyridinyl, [1,2,4]triazolo[4,3-a]pyridinyl, purinyl, pyrazolo[3,4-d]pyrimidyl, pyrazolo[4,3-d]pyrimidyl, isoxazolo[5,4-d]pyrimidinyl, isoxazolo[4,5-d]pyrimidinyl, oxazolo[4,5-d]pyrimidinyl, and oxazolo[5,4-d] pyrimidinyl, the aromatic heterocycle being optionally substituted with one to three $R^4$ groups; $R^3$ may be an aliphatic heterocycle selected from the group consisting of azetidinyl, pyrrolidinyl, piperidinyl, piperazinyl, morpholinyl, azepanyl, 1,4-diazepanyl, 1,4-oxazepanyl, octahydropyrrolo[3,4-b]pyrrolyl, octahydropyrrolo[3,4-c]pyrrolyl, octahydropyrrolo[3,2-b]pyrrolyl, octahydro-1H-pyrrolo[3,2-b]pyridinyl, octahydro-5H-pyrrolo[3,2-c]pyridinyl, octahydro-1H-pyrrolo[2,3-c]pyridinyl, octahydro-6H-pyrrolo[3,4-b]pyridinyl, octahydro-1H-pyrrolo[3,4-c]pyridinyl, octahydro-1H-cyclopentapyrazine, octahydro-1H-pyrrolo[1,2-c]pyrazinyl, decahydro-2,6-naphthyridinyl, decahydro-2,7-naphthyridinyl, decahydro-1,6-naphthyridinyl, decahydro-1,7-naphthyridinyl, decahydro-quinoxalinyl, octahydro-2H-pyrido[1,2-c]pyrazinyl, 3-azabicyclo[3.1.0] hexyl, 1-azabicyclo[2.2.1]heptyl, 2-azabicyclo[2.2.1]heptyl, 7-azabicyclo[2.2.1]heptyl, 1-azabicyclo[2.2.2]octyl, 2-azabicyclo[2.2.2]octyl, 1-azabicyclo[3.2.1]octyl, 2-azabicyclo[3.2.1]octyl, 3-azabicyclo[3.2.1]octyl, 6-azabicyclo[3.2.1]octyl, 8-azabicyclo[3.2.1]octyl, 1-azabicyclo[3.2.2] nonyl, 2-azabicyclo[3.2.2]nonyl, 3-azabicyclo[3.2.2]nonyl, 6-azabicyclo[3.2.2]nonyl, 1-azabicyclo[3.3.1]nonyl, 2-azabicyclo[3.3.1]nonyl, 3-azabicyclo[3.3.1]nonyl, 9-azabicyclo[3.3.1]nonyl, 2,5-diazabicyclo[2.2.1]heptyl, 1,4-diazabicyclo[2.2.2]octyl, 2,5-diazabicyclo[2.2.2]octyl, 1,4-diazabicyclo[3.2.1]octyl, 2,6-diazabicyclo[3.2.1]octyl, 3,6-diazabicyclo[3.2.1]octyl, 3,8-diazabicyclo[3.2.1]octyl, 1,4-diazabicyclo[3.2.2]nonyl, 1,5-diazabicyclo[3.2.2]nonyl, 2,6-diazabicyclo[3.2.2]nonyl, 3,6-diazabicyclo[3.2.2]nonyl, 6,8-diazabicyclo[3.2.2]nonyl, 1-azaspiro[3.3]heptyl, 2-azaspiro[3.3]heptyl, 1-azaspiro[3.4]octyl, 2-azaspiro[3.4] octyl, 5-azaspiro[3.4]octyl, 6-azaspiro[3.4]octyl, 1-azaspiro[4.4]nonyl, 2-azaspiro[4.4]nonyl, 1-azaspiro[4.5]decanyl, 2-azaspiro[4.5]decanyl, 6-azaspiro[4.5]decanyl, 7-azaspiro[4.5]decanyl, 8-azaspiro[4.5]decanyl, 1,6-diazaspiro[3.3] heptyl, 2,6-diazaspiro[3.3]heptyl, 1,7-diazaspiro[4.4]nonyl, 2,7-diazaspiro[4.4]nonyl, 1,6-diazaspiro[3.5]nonyl, 1,7-diazaspiro[3.5]nonyl, 2,5-diazaspiro[3.5]nonyl, 2,6-diazaspiro[3.5]nonyl, 2,7-diazaspiro[3.5]nonyl, 5,8-diazaspiro[3.5] nonyl, 1,7-diazaspiro[4.5]decyl, 1,8-diazaspiro[4.5]decyl, 2,6-diazaspiro[4.5]decyl, 2,7-diazaspiro[4.5]decyl, 2,8-diazaspiro[4.5]decyl, and 6,9-diazaspiro[4.5]decyl, the aliphatic heterocycle being optionally substituted with one to three $R^5$ groups and optionally containing one to three double bonds, the aliphatic heterocycle optionally containing one to three carbonyl groups, each of the carbonyl groups having a carbon atom in a ring of the aliphatic heterocycle; $R^4$ and $R^5$ may be selected from the group consisting of:

(I) halogen;
(II) a cyano group;
(III) a nitro group;
(IV) a hydroxy group optionally substituted with a $C_{1-6}$ alkyl or $C_{1-10}$ cycloalkyl group optionally substituted with one to five substituents selected from the group consisting of:
  (a) halogen;
  (b) a cyano group;
  (c) a nitro group;
  (d) a $C_{1-6}$ alkoxy group;
  (e) a $C_{1-6}$ alkylamino group; and
  (f) a $C_{1-6}$ alkyl($C_{1-6}$ alkyl)amino group;
(V) an amino group optionally substituted with a $C_{1-6}$ alkyl or $C_{1-10}$ cycloalkyl group optionally substituted with one to five substituents selected from the group consisting of:
  (a) halogen;
  (b) a cyano group;
  (c) a nitro group;
  (d) a $C_{1-6}$ alkoxy group;
  (e) a $C_{1-6}$ alkylamino group; and
  (f) a $C_{1-6}$ alkyl($C_{1-6}$ alkyl)amino group; and (VI) a $C_{1-6}$ alkyl or $C_{1-10}$ cycloalkyl group optionally substituted with one to five substituents selected from the group consisting of:
(a) halogen;
(b) a cyano group;
(c) a nitro group;
(d) a $C_{1-6}$ alkoxy group;
(e) a $C_{1-6}$ alkylamino group; and
(f) a $C_{1-6}$ alkyl($C_{1-6}$ alkyl)amino group.

Salts of the respective compounds represented by the general formula (I) may be of any kind, and examples include acid salts, metal salts, and ammonium salts. The acid salts may be any of a wide variety, and examples include salts of inorganic acids such as hydrochloride, sulfate, and phosphate, and salts of organic acids such as acetate, maleate, fumarate, tartrate, and citrate. The metal salts may be any of a wide variety, and examples include salts of alkali metals such as sodium salts and potassium salts, salts of alkali earth metals such as calcium salts and magnesium salts, aluminum salts, and zinc salts. When molecules with the general formula (I) are isomers such as optical isomers, stereoisomers, constitutional isomers, or rotation isomers, each and mixtures thereof are also encompassed in the compounds represented by the general formula (I).

For example, when a compound represented by the general formula (I) exists as enantiomers, each of them separated from a racemic mixture/racemic compound is also encompassed in compounds represented by the general formula (I). Each of these isomers may be produced as a single compound using a known synthetic method or separation method (e.g., concentration, solvent extraction, column chromatography, or recrystallization).

A compound represented by the general formula (I) may be in the form of crystals; both compounds in the form of a single crystal or mixed crystals are also encompassed in the compounds represented by the general formula (I). Crystals can be prepared by crystallization of a compound using a known crystallization technique.

A compound represented by the general formula (I) may be in the form of pharmaceutically acceptable cocrystals or salt cocrystals. Cocrystals and salt cocrystals can be prepared using a known cocrystallization technique. Coformers of the compounds represented by the general formula (I) for the cocrystals or salt cocrystals may be, for example, acids (e.g., carboxylic acids, phosphoric acids, sugar acids, and sulfonic acids), amides, urea, bases, maltol, and amino acids. Suitable examples of the carboxylic acid include fumaric, citric, glutaric, malonic, succinic, maleic, malic, tartalic, mandelic, lactic, gluconic, acetic, benzoic, gentisic, salicylic, and hippuric acids. Suitable examples of the sugar acid include ascorbic acid. Suitable examples of the sulfonic acid include 2-naphthalenesulfonic acid, 10-camphorsulfonic acid, and methanesulfonic acid. Suitable examples of the amide include nicotinamide, benzamide, lactamide, glycolamide, and saccharin. Suitable examples of the base include tromethamine and meglumine. Suitable examples of the maltol include ethyl maltol. Suitable examples of the amino acid include tyrosine, alanine, serine, threonine, isoleucine, leucine, arginine, lysine, proline, tryptophan, valine, glutamic acid, aspartic acid, glycine, asparagine, methionine, cysteine, phenylalanine, glutamine, and histidine.

A compound represented by the general formula (I) may be in the form of a hydrate, an anhydrate, a solvate, or a non-solvate.

A compound represented by the general formula (I) may be labeled with an isotope (e.g., $^{2}H$, $^{3}H$, $^{11}C$, $^{14}C$, $^{35}S$, or $^{125}I$). Compounds represented by the general formula (I) which are labeled or substituted with an isotope can be used as PET tracers in positron emission tomography (PET) and are thus useful in some fields such as diagnosis.

A compound represented by the general formula (I) may be a prodrug. As used herein, the term "prodrug" refers to a compound that is converted into the corresponding compound represented by the general formula (I) through a reaction such as oxidation, reduction, or hydrolysis in vivo due to, for example, an enzyme or gastric acid under physiological conditions in the body. Examples of the prodrug of compounds represented by the general formula (I) include compounds that are counterparts of compounds represented by the general formula (I) with their amino groups modified by acylation, alkylation, or phosphorylation (e.g., compounds that are counterparts of compounds represented by the general formula (I) with their amino groups modified by eicosanoylation, alanylation, pentylaminocarbonylation, (5-methyl-2-oxo-1,3-dioxolen-4-yl)methoxycarbonylation, tetrahydrofuranylation, pyrrolidinylmethylation, pivaloyloxymethylation, or tert-butylation); compounds that are counterparts of compounds represented by the general formula (I) with their hydroxy groups modified by acylation, alkylation, phosphorylation, or borylation (e.g., compounds that are counterparts of compounds (I) with their hydroxy groups modified by acetylation, palmitoylation, propanoylation, pivaloylation, succinylation, fumarylation, alanylation, or dimethylaminomethylcarbonylation); compounds that are counterparts of compounds represented by the general formula (I) with their carboxy groups modified by esterification or amidation (e.g., compounds that are counterparts of compounds (I) with their carboxy groups modified by ethyl esterification, phenyl esterification, carboxymethyl esterification, dimethyl aminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyl oxycarbonyl ethyl esterification, or methyl amidation). Each of these compounds can be prepared from a compound represented by the general formula (I) using a known method.

A prodrug of a compound represented by the general formula (I) may be of the type that is transformed into the corresponding compound represented by the formula (I) under physiological conditions as described in "Pharmaceutical research and development," vol. 7, Molecular Design, pp. 163-198, Hirokawa Publishing Co. (1990).

[Methods Used for Producing Compounds]

Methods used for producing the above-mentioned compounds are described below.

Starting materials, reagents, and the resulting compounds in each stage of the following production methods may be in the form of their salts. Examples of such salt include those exemplified above for the compounds according to the present invention.

When a compound obtained in a certain stage exists in its free state, it can be converted into a desired salt using a known method. Conversely, when a compound obtained in a certain stage is a salt, it can be converted into its corresponding free form or into another kind of desired salt using a known method.

The compound(s) obtained in each stage can be used in a subsequent reaction or reactions as a reaction solution per se or after being partially or completely purified. Any purification technique may be used, and examples include concentration, crystallization, recrystallization, distillation, solvent extraction, fractional distillation, chromatography, and combinations thereof.

Symbols used in the following reaction schemes represent the same groups as those in the compounds mentioned above, unless otherwise specified. Starting compounds are easily available among commercial products or can be produced using a known method when no specific production method is mentioned.

The reaction time for each stage may depend on the reagent(s) and/or the solvent(s) used; however, it is typically from 1 minute to 48 hours, and preferably from 10 minutes to 8 hours, unless otherwise specified.

The reaction temperature for each stage may depend on the reagent(s) and/or the solvent(s) used; however, it is typically from −78° C. to 300° C., and preferably from −78° C. to 150° C., unless otherwise specified.

The pressure for each stage may depend on the reagent(s) and/or the solvent(s) used; however, it is typically from 1 atm to 20 atm, and preferably from 1 atm to 3 atm, unless otherwise specified.

A microwave synthesizer such as an Initiator synthesizer manufactured by Biotage may be used in one or more stages. The reaction temperature may depend on the reagent(s) and/or the solvent(s) used; however, it is typically from room temperature to 300° C., and preferably from 50° C. to 250° C., unless otherwise specified. The reaction time may depend on the reagent(s) and/or the solvent(s) used; however, it is typically from 1 minute to 48 hours, and preferably from 1 minute to 8 hours, unless otherwise specified.

In the reactions in all stages, the amount of the reagent used is from 0.5-20 equivalents, and preferably from 0.8-5 equivalents relative to the substrate, unless otherwise specified. When the reagent is a catalyst, the amount of the reagent used is from 0.001-1 equivalent(s), and preferably from 0.01-0.2 equivalents relative to the substrate. When the reagent also serves as a reaction solvent, the amount of the reagent is identical to the amount of the solvent.

In each stage, unless otherwise specified, compounds are reacted either in the absence of a solvent or in a suitable solvent in which one or more compounds are dissolved or suspended. Specific examples of the solvent include the following compounds in addition to those described in the Examples.

Alcohols: e.g., methanol, ethanol, 1-propanol, 2-propanol, 1-butanol, 1-butanol, 2-methyl-1-propanol, 2-methyl-2-propanol, 1-pentanol, 3-methyl-1-butanol, 2-methyl-2-butanol, and 2-methoxyethanol.

Ethers: e.g., diethyl ether, diphenyl ether, tetrahydrofuran, 1,2-dimethoxyethane, and cyclopentyl methyl ether.

Aromatic hydrocarbons: e.g., benzene, chlorobenzene, toluene, and xylene.

Saturated hydrocarbons: e.g., cyclohexane and hexane.

Amides: e.g., N,N-dimethylformamide, N,N-dimethylacetamide, and N-methylpyrrolidone.

Halogenated hydrocarbons: e.g., dichloromethane and carbon tetrachloride.

Nitriles: e.g., acetonitrile.

Sulfoxides: e.g., dimethyl sulfoxide.

Aromatic organic bases: e.g., pyridine.

Acid anhydrides: e.g., acetic anhydride.

Organic acids: e.g., formic acid, acetic acid, and trifluoroacetic acid.

Inorganic acids: e.g., hydrochloric acid and sulfuric acid.

Esters: e.g., ethyl acetate.

Ketones: e.g., acetone and methyl ethyl ketone.

Water.

Two or more of the above-mentioned solvents may be combined in an appropriate proportion.

In situations where a base is used in a chemical reaction in a certain stage, examples of the base used include the following compounds in addition to those described in the Examples.

Inorganic bases: e.g., lithium hydroxide, sodium hydroxide, potassium hydroxide, calcium hydroxide, magnesium hydroxide, and cesium hydroxide.

Basic bases: e.g., lithium carbonate, sodium carbonate, potassium carbonate, calcium carbonate, cesium carbonate, sodium hydrogen carbonate, and potassium hydrogen carbonate.

Organic bases: e.g., triethylamine, diethylamine, pyridine, 4-dimethylaminopyridine, N,N-dimethyl aniline, 1,4-diazabicyclo[2.2.2]octane, 1,8-diazabicyclo[5.4.0]-7-undecene, imidazole, and piperidine.

Metal alkoxides: e.g., sodium methoxide, sodium ethoxide, sodium tert-butoxide, and potassium tert-butoxide.

Alkali metal hydrides: e.g., sodium hydride and potassium hydride.

Metal amides: e.g., lithium amide, lithium diisopropylamide, lithium hexamethyldisilazide, sodium amide, lithium diisopropylamide, sodium hexamethyldisilazide, potassium amide, potassium diisopropylamide, and potassium hexamethyldisilazide.

Organic lithium compounds: e.g., n-butyl lithium, sec-buthyl lithium, and tert-buthyl lithium.

In situations where an acid or an acidic catalyst is used in a chemical reaction in a certain stage, examples of the acid and the acidic catalyst that can be used include the following compounds in addition to those described in the Working Examples.

Inorganic acids: e.g., hydrochloric acid, sulfuric acid, nitric acid, hydrobromic acid, and phosphoric acid.

Organic acids: e.g., acetic acid, trifluoroacetic acid, citric acid, p-toluenesulfonic acid, and 10-camphorsulfonic acid.

Lewis acids: e.g., boron trifluoride diethyl ether complex, zinc iodide, anhydrous aluminum chloride, anhydrous zinc chloride, and anhydrous iron chloride.

Unless otherwise specified, the chemical reaction(s) in each stage is/are carried out according to a known method such as the one described in, for example, "The Fifth Series of Experimental Chemistry," vol. 13-19 (The Chemical Society of Japan ed.); "Shin Jikken Kagaku Koza," vol. 14-15 (The Chemical Society of Japan ed.); "Seimitsu Yuki Kagaku (Reactions and Syntheses: In the Organic Chemistry Laboratory)," 2nd, rev. (L. F. Tietze & Th. Eicher, Nankodo Co., Ltd.); "Organic Name Reactions; The Reaction Mechanism and Essence" (Hideo Togo, KODANSHA LTD.); ORGANIC SYNTHESES. Collective Volume I-VII (John Wiley & Sons Inc.); Modern Organic Synthesis in the Laboratory: A Collection of Standard Experimental Procedures (Li, Jie Jack, OXFORD UNIVERSITY PRESS); Comprehensive Heterocyclic Chemistry III, vol. 1-14 (Elsevier Japan); Strategic Applications of Named Reactions in Organic Synthesis (translated by Kiyoshi Tomioka et al., Kagaku-Dojin Publishing Company, INC.); or Comprehensive Organic Transformations (VCH Publishers Inc.), 1989, or a method described in a Working Example in the present specification.

In respective stages, protection with a functional group and/or deprotection is/are carried out according to a known method such as the one described in, for example, "Protective Groups in Organic Synthesis, 4th ed.", Wiley-Interscience, 2007 (Theodora W. Greene, Peter G. M. Wuts); and "Protecting Groups 3rd ed." Thieme, 2004 (P. J. Kocienski), or a method described in a Working Example in the present specification.

Examples of protecting groups for hydroxy groups in alcohol or other compounds and phenolic hydroxy groups include ether protecting groups such as methoxymethyl ether, benzyl ether, t-butyldimethylsilyl ether, and tetrahydropyranyl ether; carboxylate ester protecting groups such as acetate ester; sulfonate ester protecting groups such as methanesulfonate ester; and carbonate ester protecting groups such as t-butyl carbonate. Examples of protecting groups for carbonyl groups in aldehyde include acetal protecting groups such as dimethyl acetal; and cyclic acetal protecting groups such as cyclic 1,3-dioxane. Examples of protecting groups for carbonyl groups in ketone include ketal protecting groups such as dimethyl ketal; cyclic ketal protecting groups such as cyclic 1,3-dioxane; oxime protecting groups such as O-methyloxime; and hydrazone protecting groups such as N,N-dimethylhydrazone. Examples of protecting groups for carboxyl groups include ester protecting groups such as methyl ester; and amide protecting groups such as N,N-dimethylamide. Examples of protecting groups for thiol include ether protecting groups such as benzyl thioether; and ester protecting groups such as thioacetate ester, thiocarboxylic acid, and thiocarbamate. Examples of protecting groups for amino groups, and aromatic heterocycles such as imidazole, pyrrole, and indole include carbamate protecting groups such as benzyl carbamate; amide protecting groups such as acetamide; alkyl amine protecting groups such as N-triphenylmethylamine; and sulfonamide protecting groups such as methanesulfonamide.

Protecting groups can be removed according to a known method such as the one involving the use of an acid, a base, ultraviolet radiation, hydrazine, phenylhydrazine, sodium N-methyldithiocarbamate, tetrabutylammonium fluoride, palladium acetate, trialkylsilyl halide (e.g., trimethylsilyl iodide and trimethylsilyl bromide) or a reduction method.

In situations where a compound is subjected to reduction in a certain stage, examples of the reducing agent used include metal hydrides such as lithium aluminum hydride, sodium triacetoxyborohydride, sodium cyanotrihydridoborate, diisobutylaluminum hydride (DIBAL-H), sodium borohydride, and tetramethylammonium triacetoxyborohydride; boranes such as borane tetrahydrofuran complex; Raney nickel; Raney cobalt; hydrogen; and formic acid. When a carbon-carbon double bond or triple bond is reduced, a method involving the use of a catalyst such as palladium on carbon or Lindlar's catalyst may be used.

In situations where a compound is subjected to oxidation in a certain stage, examples of the oxidant used include peroxides such as m-chloroperbenzoic acid (mCPBA), hydrogen peroxide, and t-butylhydroperoxide; perchlorates such as tetrabutylammonium perchlorate; chlorates such as sodium chlorate; chlorites such as sodium chlorite; periodic acids such as sodium periodate; hypervalent iodine reagents such as iodosylbenzene; reagents containing manganese such as manganese dioxide and potassium permanganate; lead compounds such as lead tetraacetate; reagents containing chromium such as pyridinium chlorochromate (PCC), pyridinium dichromate (PDC), and Jones reagent; halogen compounds such as N-bromosuccinimide (NBS); oxygen; ozone; sulfur trioxide-pyridine complex; osmium tetroxide; selenium dioxide; and 2,3-dichloro-5,6-dicyano-1,4-benzoquinone (DDQ).

In situations where a compound is subjected to nucleophilic aromatic substitution (SNAr reaction) in a certain stage, a nucleophile (e.g., amine or imidazole) and a base (e.g., a basic salt or an organic base) are used as reagents.

In situations where a compound is subjected to nucleophilic addition using carbanions, nucleophilic 1,4-addition (Michael addition) using carbanions, or nucleophilic substitution using carbanions in a certain stage, examples of the base used to generate carbanions include organic lithium compounds, metal alkoxides, inorganic bases, and organic bases.

In situations where a compound is subjected to reductive amination in a certain stage, examples of the reducing agent used include sodium triacetoxyborohydride, sodium cyanotrihydridoborate, borane-2-methylpyridine complex, hydrogen, and formic acid. When the substrate is an amine compound, examples of the carbonyl compound or its equivalent used include paraformaldehyde and formaldehyde solutions as well as aldehyde equivalents such as (1-ethoxycyclopropoxy)trimethylsilane, aldehydes such as acetaldehyde, and ketones such as cyclohexanone. When the substrate is a carbonyl compound, examples of the amine used include ammonia, primary amines such as methylamine, and secondary amines such as dimethylamine.

In situations where a compound is subjected to esterification, amidation or ureation in a certain stage, examples of the reagent used include acyl halides such as acid chlorides and acid bromides; and activated carboxylic acids such as acid anhydrides, activated esters, and sulfate esters. Examples of activating agents for carboxylic acids include carbodiimide condensing agents such as 1-ethyl-3-(3-dimethylaminopropyl)carbodiimide hydrochloride (WSCD); triazine condensing agents such as 4-(4,6-dimethoxy-1,3,5-triazin-2-yl)-4-methylmorpholinium chloride n-hydrate (DMT-MM); carbonate condensing agents such as 1,1-carbonyldiimidazole (CDI); diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate; O-(7-azabenzotriazol-1-yl)-N,N,N',N'-tetramethyluronium hexafluorophosphorate (HATU); propylphosphonic acid anhydride (T3P); sulfuric acid; and combinations thereof. When a carbodiimide condensing agent is used, an additive such as 1-hydroxybenzotriazole (HOBt), N-hydroxysuccinimide (HOSu) or dimethylaminopyridine (DMAP) may further be added to the reaction.

In situations where a compound is subjected to coupling (e.g., the Suzuki-Miyaura coupling, the Still coupling, the Buchwald-Hartwing cross-coupling, the Negishi coupling or the Heck reaction) in a certain stage, examples of the metal catalyst used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), and [1,1'-bis(diphenylphosphino)ferrocene]palladium(II) chloride; nickel compounds such as tetrakis(triphenylphosphine)nickel(0); rhodium compounds such as tris(triphenylphosphine)rhodium(III) chloride; cobalt compounds; copper compounds such as copper oxide and copper(I) iodide; and platinum compounds. A base may further be added to the reaction, and examples of such base include inorganic bases and basic salts.

In situations where an aromatic ring is halogenated in a certain stage, examples of the halogenating agent used include N-iodosuccinimide, N-bromosuccinimide (NBS), N-chlorosuccinimide (NCS), bromine, and sulfuryl chloride. In addition, reactions can be accelerated by applying heat or light or adding a radical initiator such as benzoyl peroxide or azobisisobutyronitrile to the reactions.

In situations where a compound is subjected to hydrolysis in a certain stage, an acid or a base is used as a reagent. For an acid hydrolysis of t-butyl ester, formic acid or triethylsilane may be added for the reductive trapping of t-butyl cations produced as by-products.

In situations where a compound is subjected to dehydration in a certain stage, examples of the dehydrating agent used include sulfuric acid, diphosphorus pentaoxide, phosphorus oxychloride, N,N'-dicyclohexylcarbodiimide, alumina, and polyphosphoric acid.

Examples of leaving groups used in respective stages include a hydroxy group, halogen atoms (e.g., a fluorine atom, a chlorine atom, a bromine atom, and an iodine atom), $C_{1-6}$ alkoxy groups (e.g., methoxy), $C_{6-14}$ aryl-oxy groups (e.g., phenoxy), acyloxy groups which may be substituted (e.g., acetyloxy and benzoyloxy), $C_{1-6}$ alkoxysulfonyloxy groups which may be substituted (e.g., methoxysulfonyloxy), $C_{1-6}$ alkyl sulfonyloxy groups which may be halogenated (e.g., methanesulfonyloxy, ethanesulfonyloxy, trichloromethanesulfonyloxy, trifluoromethanesulfonyloxy (triflate)), and $C_{6-14}$ arylsulfonyl-oxy groups which may be substituted [e.g., $C_{6-4}$ arylsulfonyloxy which may have one to three substituents selected from the group consisting of $C_{1-6}$ alkyl (e.g., methyl, ethyl, propyl, isopropyl, butyl, isobutyl, sec-butyl, tert-butyl, pentyl, and hexyl), $C_{1-6}$ alkoxy (e.g., methoxy, ethoxy, propoxy, isopropoxy, butoxy, isobutoxy, sec-butoxy, pentyloxy, and hexyloxy), and nitro; specific examples include benzenesulfonyloxy, m-nitrobenzenesulfonyloxy, p-toluenesulfonyloxy, and naphthylsulfonyloxy].

Methods used for producing compounds represented by the general formula (I) are described below. The final products of the compounds represented by the general formula (I) may be prepared as a single compound or mixed compounds.

Symbols used in the following reaction schemes represent the same groups as those in the compounds mentioned above, unless otherwise specified. Starting compounds are easily available among commercial products or can be produced using a known method or a modified version thereof when no specific production method is mentioned.

Depending on the kinds of substituents of a starting compound, a compound produced according to one of the following production methods can be used as a starting material to produce a starting compound with different substituents by applying known means.

[Production method 1]

Compounds represented by the general formula (Ia), corresponding to the general formula (I) in which $W^3$ is $C-R^2$, $W^1$ is $C-R^3$, $W^2$ is $C-R^c$, and $R^1$ is a hydrogen atom, can be produced from a compound represented by the general formula (IIa) or a compound represented by the general formula (VIa) according to the following production scheme or a modification thereof.

[Chemical formula 2]

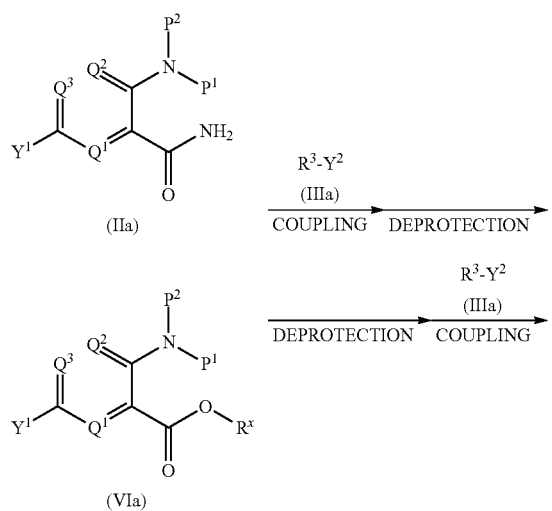

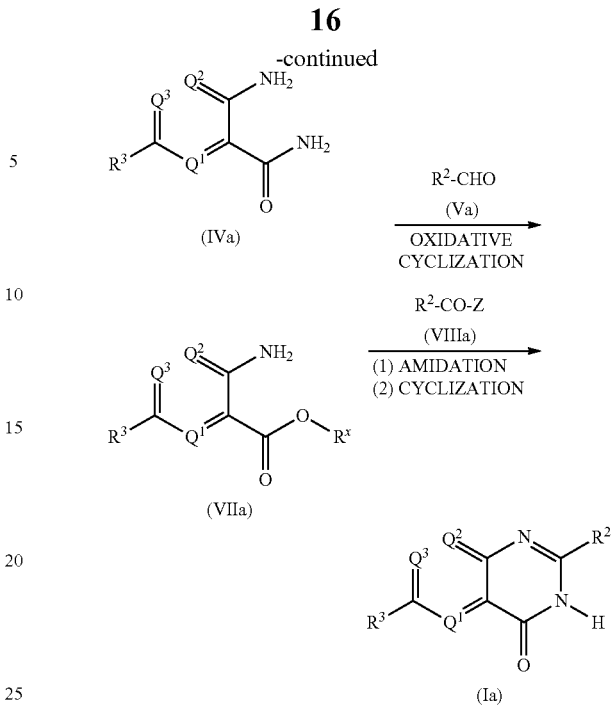

In the formulae, $Y^1$, $Y^2$, and Z each represents a leaving group. $Y^1$ and $Y^2$ each represents, as a leaving group, a boric acid group, a borate ester group, a nitrile group, a carbamate group which may be substituted, a carbonate group which may be substituted, an aminosulfonyloxy group which may be substituted, a $C_{1-6}$ alkyl-carbonyloxy group which may be substituted, a $C_{6-14}$ aryl-carbonyloxy group which may be substituted, or a $C_{6-14}$ aryl-phosphorate ester group which may be substituted;

$P^1$ and $P^2$ each represents a protecting group;

$R^x$ represents hydrogen or a $C_1$-$C_6$ alkyl group which may be substituted;

$Q^3$ is selected from $C-R^c$ and N; and other symbols represent the same groups as those in the compounds mentioned above.

The compounds represented by the general formula (Ia) can be produced by oxidative cyclization using a compound represented by the general formula (IVa) and a compound represented by the general formula (Va) or another compound represented by the general formula (Va) containing an aldehyde equivalent (e.g., dimethoxyacetal or diethoxyacetal) as a functional group in place of aldehyde, in the presence of an oxidant (e.g., iodine, oxygen, manganese dioxide, potassium permanganate, hydrogen peroxide, hydroperoxide, N-bromosuccinimide, N-iodosuccinimide, 2,3-dichloro-5,6-dicyano-p-benzoquinone, sodium bisulfate, copper(II) chloride, iron(III) chloride, palladium). The oxidative cyclization may be carried out in the presence of an acid (e.g., p-toluenesulfonic acid).

Compounds represented by the general formula (Va) can be produced using a known method.

The compounds represented by the general formula (Ia) can also be produced by the amidation of a compound represented by the general formula (IVa) with a compound represented by the general formula (VIIIa) and subsequent cyclization using a base (e.g., lithium hydroxide, sodium hydroxide, potassium hydroxide, sodium carbonate, potassium carbonate, cesium carbonate, sodium methoxide, or sodium ethoxide).

Compounds represented by the general formula (VIIIa) can be produced using a known method.

Compounds represented by the general formula (IVa) can be synthesized by a known coupling reaction of a compound represented by the general formula (Ha) and a compound represented by the general formula (Ma) and subsequent deprotection. The coupling reaction may be, for example, the Suzuki coupling, the Stille coupling, the Buchwald-Hartwig coupling, the Negishi coupling or the Heck reaction. The reagents such as a metal catalyst, a phosphine ligand, and a base can be used according to a known method (e.g., a method described in Copper-Mediated Cross-Coupling Reactions, G. Evano, N, Blanchard, Eds., John Wiley & Sons, Inc. (2014); in Metal-Catalyzed Cross-Coupling Reactions and More, A. de Meijere, S. Brase, M. Oestreich, Eds., Wiley-VCH Verlag GmbH & Co. KGaA (2014); in Palladium-Catalyzed Coupling Reactions: Practical Aspects and Future Developments, A. Molnar, Ed., Wiley-VCH Verlag GmbH & Co. KGaA (2013); in The Chemistry of Anilines, Z. Rappoport, Ed., John Wiley & Sons, Ltd (2007); in Metal-Catalyzed Cross-Coupling Reactions, 2nd Ed., A. de Meijere, F. Diederich, Eds., Wiley-VCH Verlag GmbH & Co. KGaA (2004); in Handbook of Organopalladium Chemistry for Organic Synthesis, E. Negishi, A. de Meijere, Eds., John Wiley & Sons, Inc. (2002); in Modern Amination Methods, A. Ricci, Ed., Wiley-VCH Verlag GmbH (2000); in Metal-Catalyzed Cross-Coupling Reactions, F. Diederich, P. J. Stang, Eds., Wiley-VCH Verlag GmbH (1998) with or without an appropriate modification).

The compounds represented by the general formula (IVa) can also be synthesized by the removal of the protecting group from a compound represented by the general formula (Ha) and subsequent coupling with a compound represented by the general formula (Ma).

Compounds represented by the general formula (Ha) and those represented by the general formula (Ma) can be produced using a known method.

The compounds represented by the general formula (Ia) can also be produced by oxidative cyclization using a compound represented by the general formula (VIIa) and a compound represented by the general formula (Va) or another compound represented by the general formula (Va) containing an aldehyde equivalent (e.g., dimethoxyacetal or diethoxyacetal) as a functional group in place of aldehyde, in the presence of an oxidant as well as ammonia or an ammonia equivalent (e.g., ammonium acetate or ammonium chloride).

The compounds represented by the general formula (Ia) can also be produced by the amidation of a compound represented by the general formula (VIIa) with a compound represented by the general formula (VIIIa) and subsequent cyclization using a base in the presence of ammonia or an ammonia equivalent (e.g., ammonium acetate or ammonium chloride).

Compounds represented by the general formula (VIIa) can be synthesized by the coupling of a compound represented by the general formula (VIa) and a compound represented by the general formula (Ma) and subsequent deprotection.

The compounds represented by the general formula (VIIa) can also be synthesized by the removal of the protecting group from a compound represented by the general formula (VIa) and subsequent coupling with a compound represented by the general formula (Ma).

A compound represented by the general formula (Ia) can also be produced from another compound represented by the general formula (Ia).

A compound represented by the general formula (IVa) can also be produced from another compound represented by the general formula (IVa) by a known conversion reaction.

A compound represented by the general formula (VIIa) can also be produced from another compound represented by the general formula (VIIa) by a known conversion reaction.

The compounds represented by the general formula (IVa) and those represented by the general formula (VIIa) can also be produced from a compound represented by the general formula (IX) or (XI) according to the following production scheme or a modification thereof.

[Chemical formula 3]

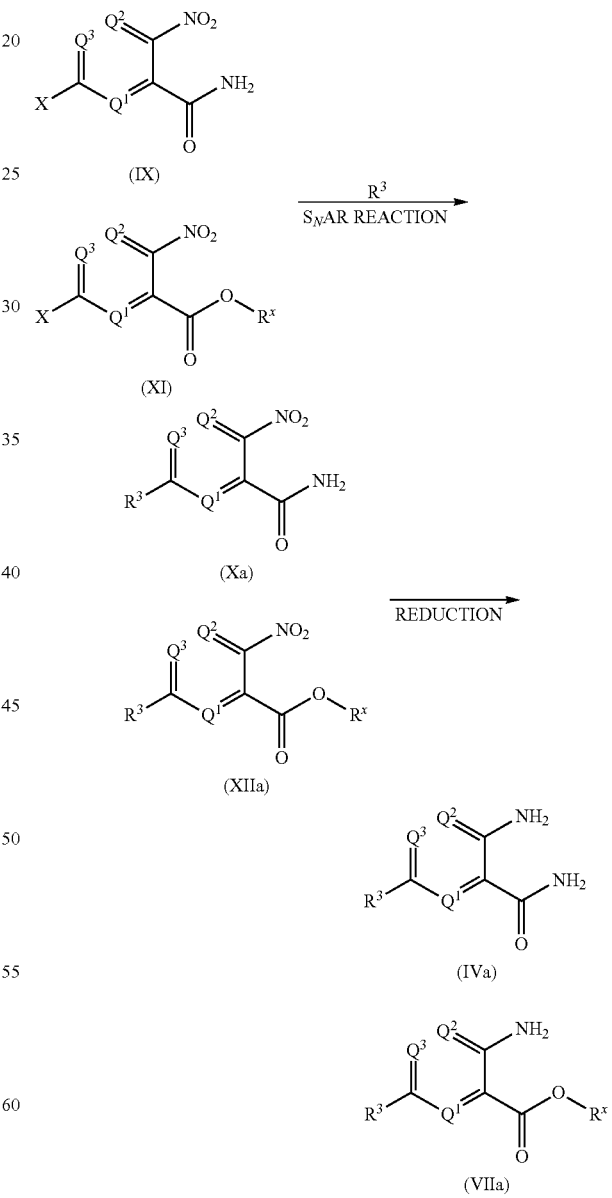

(In the formulae, X is a leaving group, and all symbols represent the same groups as those mentioned above.)

The compounds represented by the general formula (IVa) can also be produced by the reduction (e.g., hydrogenation using a metal catalyst) of a compound represented by the general formula (Xa).

Compounds represented by the general formula (Xa) can be produced by an SNAr reaction between a compound represented by the general formula (IX) and $R^3$ with a nucleophilic functional group.

Compounds represented by the general formula (IX) can be produced using a known method.

The compounds represented by the general formula (VIIa) can also be produced by the reduction (e.g., hydrogenation using a metal catalyst) of a compound represented by the general formula (XIIa).

Compounds represented by the general formula (XIIa) can be produced by an SNAr reaction between a compound represented by the general formula (XI) and $R^3$ with a nucleophilic functional group.

Compounds represented by the general formula (XI) can be produced using a known method.

A compound represented by the general formula (Xa) can also be produced from another compound represented by the general formula (Xa) by a known conversion reaction.

A compound represented by the general formula (XIIa) can also be produced from another compound represented by the general formula (XIIa) by a known conversion reaction.

A compound represented by the general formula (Xa) can also be produced from a compound represented by the general formula (XIIa) by a known conversion reaction.

[Production Method 2]

The compounds represented by the general formula (Ia), corresponding to the general formula (I) in which $W^3$ is C—$R^2$, $W^1$ is C—$R^3$, $W^2$ is C—$R^c$, and $R^1$ is a hydrogen atom, can also be produced from a compound represented by the general formula (XIIIa) or a compound represented by the general formula (XVa) according to the following production scheme or a modification thereof.

[Chemical formula 4]

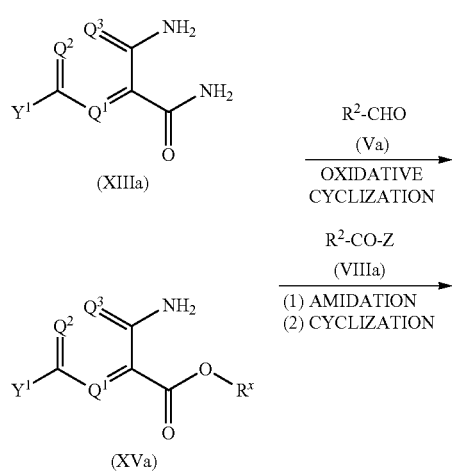

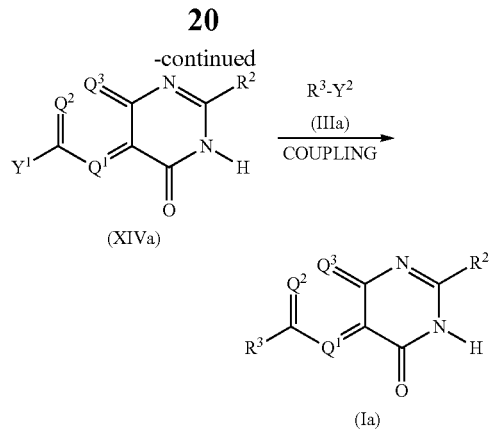

(The symbols in the formulae represent the same groups as those mentioned above.)

The compounds represented by the general formula (Ia) can also be produced by the coupling of a compound represented by the general formula (XIVa) and a compound represented by the general formula (Ma).

The compounds represented by the general formula (Ma) can be produced using a known method.

Compounds represented by the general formula (XIVa) can be produced by oxidative cyclization using a compound represented by the general formula (XIIIa) and a compound represented by the general formula (Va) in the presence of an oxidant. The oxidative cyclization may be carried out in the presence of an acid (e.g., p-toluenesulfonic acid).

Compounds represented by the general formula (XIIIa) and the compounds represented by the general formula (Va) can be produced using a known method.

The compounds represented by the general formula (XIVa) can also be produced by the amidation of a compound represented by the general formula (XIIIa) with a compound represented by the general formula (VIIIa) and subsequent cyclization using a base.

The compounds represented by the general formula (VIIIa) can be produced using a known method.

The compounds represented by the general formula (XIVa) can also be produced by oxidative cyclization using a compound represented by the general formula (XVa) and a compound represented by the general formula (Va) or another compound represented by the general formula (Va) containing an aldehyde equivalent (e.g., dimethoxyacetal or diethoxyacetal) as a functional group in place of aldehyde, in the presence of an oxidant as well as ammonia or an ammonia equivalent (e.g., ammonium acetate or ammonium chloride).

The compounds represented by the general formula (XIVa) can also be produced by the amidation of a compound represented by the general formula (XVa) with a compound represented by the general formula (Villa) and subsequent cyclization using a base in the presence of an ammonia equivalent (e.g., ammonium acetate or ammonium chloride).

Compounds represented by the general formula (XVa) can be produced using a known method.

A compound represented by the general formula (XIVa) can also be produced from another compound represented by the general formula (XIVa) by a known conversion reaction.

A compound represented by the general formula (Ia) can also be produced from another compound represented by the general formula (Ia) by a known conversion reaction.

[Production Method 3]

Compounds represented by the general formula (Ib), corresponding to the general formula (I) in which $W^3$ is $C-R^3$, $w^1$ is $C-R^2$, $W^2$ is $C-R^a$, and $R^1$ is a hydrogen atom, a $C_{1-8}$ alkyl group or a $C_{1-8}$ alkoxy group, can be produced from a compound represented by the general formula (IIb) or a compound represented by the general formula (VIb) according to the following production scheme or a modification thereof.

[Chemical formula 5]

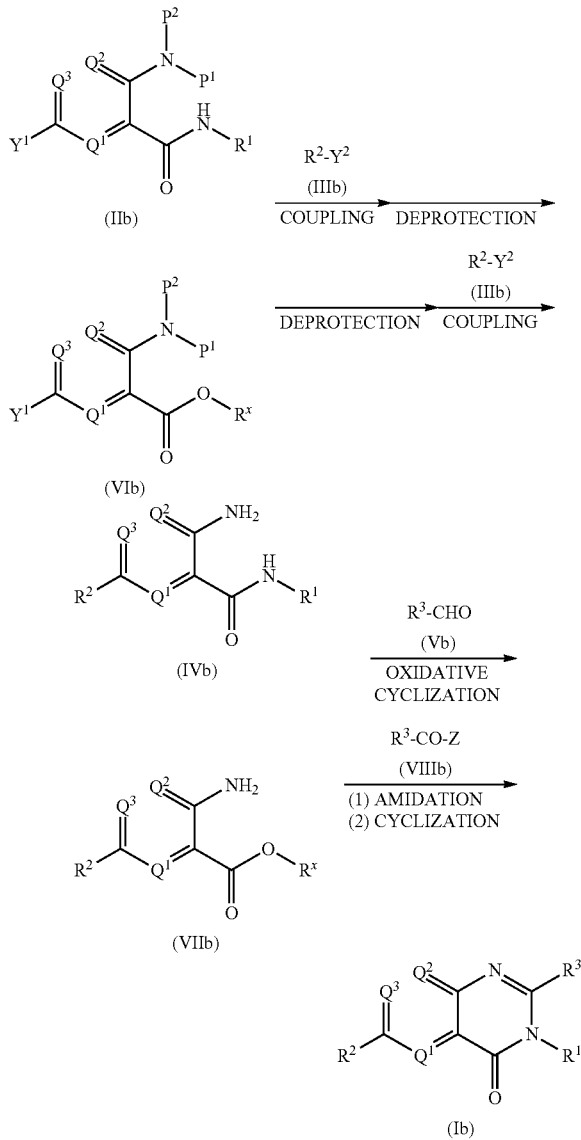

(The symbols in the formulae represent the same groups as those mentioned above.)

The compounds represented by the general formula (Ib) can be produced by oxidative cyclization using a compound represented by the general formula (IVb) and a compound represented by the general formula (Vb) or another compound represented by the general formula (Vb) containing an aldehyde equivalent (e.g., dimethoxyacetal or diethoxyacetal) as a functional group in place of aldehyde, in the presence of an oxidant. The oxidative cyclization may be carried out in the presence of an acid (e.g., p-toluenesulfonic acid).

Compounds represented by the general formula (Vb) can be produced using a known method.

The compounds represented by the general formula (Ib) can also be produced by the amidation of a compound represented by the general formula (IVb) with a compound represented by the general formula (VIIIb) and subsequent cyclization using a base.

Compounds represented by the general formula (VIIIb) can be produced using a known method.

Compounds represented by the general formula (IVb) can be synthesized by the coupling of a compound represented by the general formula (IIb) and a compound represented by the general formula (Mb) and subsequent deprotection.

The compounds represented by the general formula (IVb) can also be synthesized by the removal of the protecting group from a compound represented by the general formula (IIb) and subsequent coupling with a compound represented by the general formula (IxIIb).

Compounds represented by the general formula (IIb) and those represented by the general formula (IIIb) can be produced using a known method.

The compounds represented by the general formula (Ib) can also be produced by oxidative cyclization using a compound represented by the general formula (VIIb) and a compound represented by the general formula (Vb) or another compound represented by the general formula (Vb) containing an aldehyde equivalent (e.g., dimethoxyacetal or diethoxyacetal) as a functional group in place of aldehyde, in the presence of an oxidant and $R^1-NH_2$.

The compounds represented by the general formula (Ib) can also be produced by the amidation of a compound represented by the general formula (VIIb) with a compound represented by the general formula (VIIIb) and subsequent cyclization using a base in the presence of $R^1-NH_2$.

Compounds represented by the general formula (VIIb) can be synthesized by the coupling of a compound represented by the general formula (VIb) and a compound represented by the general formula (Mb) and subsequent deprotection.

The compounds represented by the general formula (VIIb) can also be synthesized by the removal of the protecting group from a compound represented by the general formula (VIb) and subsequent coupling with a compound represented by the general formula (Mb).

Compounds represented by the general formula (VIb) can be produced using a known method.

A compound represented by the general formula (Ib) can also be produced from another compound represented by the general formula (Ib) by a known conversion reaction.

A compound represented by the general formula (IVb) can also be produced from another compound represented by the general formula (IVb) by a known conversion reaction.

A compound represented by the general formula (VIIb) can also be produced from another compound represented by the general formula (VIIb) by a known conversion reaction.

[Production Method 4]

The compounds represented by the general formula (Ib), corresponding to the general formula (I) in which $W^3$ is $C-R^3$, $W^1$ is $C-R^2$, $W^2$ is $C-R^c$, and $R^1$ is a hydrogen atom, a $C_{1-8}$ alkyl group or a $C_{1-8}$ alkoxy group, can also be produced from a compound represented by the general formula (XIIIb) or a compound represented by the general formula (XVb) according to the following production scheme or a modification thereof.

[Chemical formula 6]

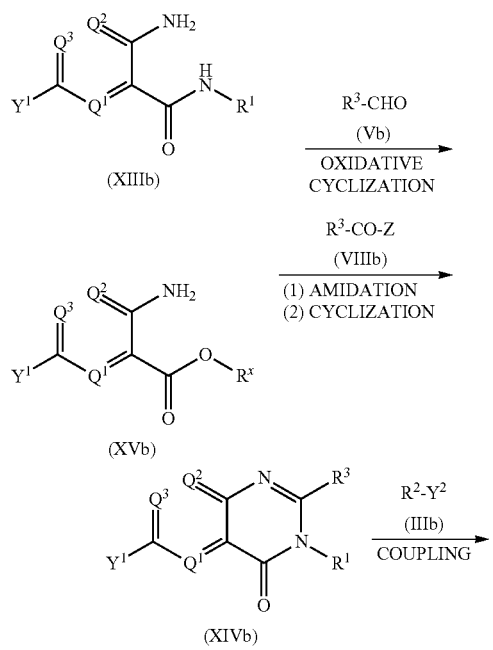

(The symbols in the formulae represent the same groups as those mentioned above.)

The compounds represented by the general formula (Ib) can also be produced by the coupling of a compound represented by the general formula (XIVb) and a compound represented by the general formula (Mb).

The compounds represented by the general formula (Mb) can be produced using a known method.

Compounds represented by the general formula (XIVb) can be produced by oxidative cyclization using a compound represented by the general formula (XIIIb) and a compound represented by the general formula (Vb) in the presence of an oxidant. The oxidative cyclization may be carried out in the presence of an acid (e.g., p-toluenesulfonic acid).

Compounds represented by the general formula (XIIIb) and the compounds represented by the general formula (Vb) can be produced using a known method.

The compounds represented by the general formula (XIVb) can also be produced by the amidation of a compound represented by the general formula (XIIIb) with a compound represented by the general formula (VIIIb) and subsequent cyclization using a base.

The compounds represented by the general formula (VIIIb) can be produced using a known method.

The compounds represented by the general formula (XIVb) can also be produced by oxidative cyclization using a compound represented by the general formula (XVb) and a compound represented by the general formula (Vb) or another compound represented by the general formula (Vb) containing an aldehyde equivalent (e.g., dimethoxyacetal or diethoxyacetal) as a functional group in place of aldehyde, in the presence of an oxidant and $R^1$—$NH_2$.

The compounds represented by the general formula (XIVb) can also be produced by the amidation of a compound represented by the general formula (XVb) with a compound represented by the general formula (VIIIb) and subsequent cyclization using a base in the presence of $R^1$—$NH_2$.

Compounds represented by the general formula (XVb) can be produced using a known method.

A compound represented by the general formula (XIVb) can also be produced from another compound represented by the general formula (XIVb) by a known conversion reaction.

A compound represented by the general formula (Ib) can also be produced from another compound represented by the general formula (Ib) by a known conversion reaction.

[Production Method 5]

Compounds represented by the general formula (Ic), corresponding to the general formula (I) in which $W^1$ is C—$R^2$ and $W^2$ and $W^3$ are C—$R^c$, and $R^1$ is $R^3$, can be produced from a compound represented by the general formula (IIc) or a compound represented by the general formula (VIc) according to the following production scheme or a modification thereof.

[Chemical formula 7]

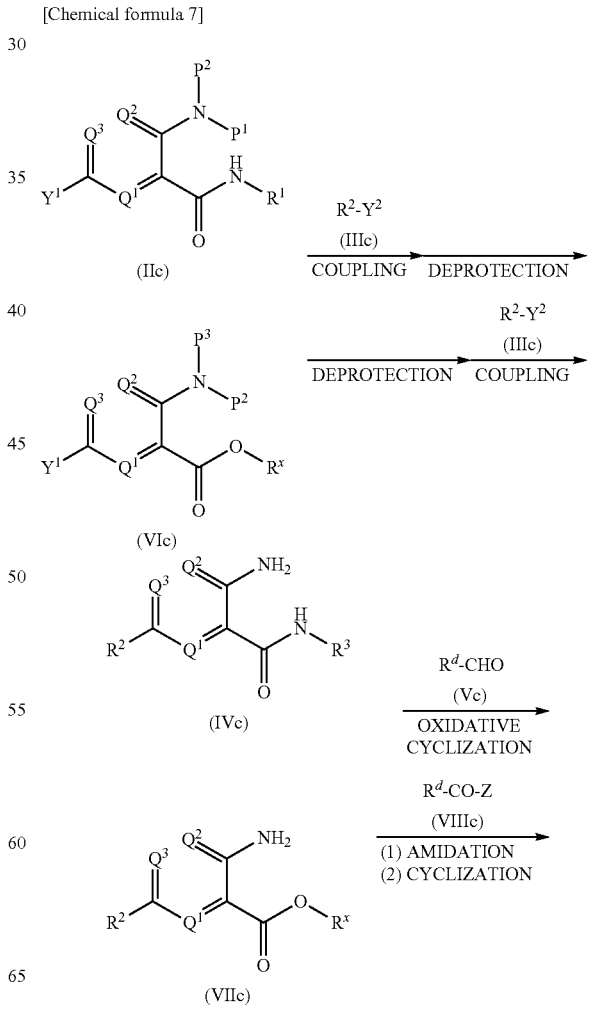

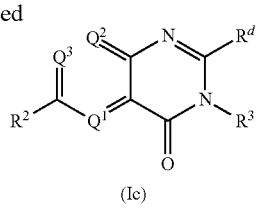

(Ic)

(The symbols in the formulae represent the same groups as those mentioned above.)

The compounds represented by the general formula (Ic) can be produced by oxidative cyclization using a compound represented by the general formula (IVc) and a compound represented by the general formula (Vc) or another compound represented by the general formula (Vc) containing an aldehyde equivalent (e.g., dimethoxyacetal or diethoxyacetal) as a functional group in place of aldehyde, in the presence of an oxidant. The oxidative cyclization may be carried out in the presence of an acid (e.g., p-toluenesulfonic acid).

Compounds represented by the general formula (Vc) can be produced using a known method.

The compounds represented by the general formula (Ic) can also be produced by the amidation of a compound represented by the general formula (IVc) with a compound represented by the general formula (VIIIc) and subsequent cyclization using a base.

Compound represented by the general formula (VIIIc) can easily be produced using a known method.

Compounds represented by the general formula (IVc) can be synthesized by the coupling of a compound represented by the general formula (IIc) and a compound represented by the general formula (Mc) and subsequent deprotection.

The compounds represented by the general formula (IVc) can also be synthesized by the removal of the protecting group from a compound represented by the general formula (IIc) and subsequent coupling with a compound represented by the general formula (Mc).

Compounds represented by the general formula (IIc) and those represented by the general formula (Mc) can be produced using a known method.

The compounds represented by the general formula (Ic) can also be produced by oxidative cyclization using a compound represented by the general formula (VIIc) and a compound represented by the general formula (Vc) or another compound represented by the general formula (Vc) containing an aldehyde equivalent (e.g., dimethoxyacetal or diethoxyacetal) as a functional group in place of aldehyde, in the presence of an oxidant and $R^3$—$NH_2$.

The compounds represented by the general formula (Ic) can also be produced by the amidation of a compound represented by the general formula (VIIc) with a compound represented by the general formula (VIIIe) and subsequent cyclization using a base in the presence of $R^3$—$NH_2$.

Compounds represented by the general formula (VIIc) can be synthesized by the coupling of a compound represented by the general formula (VIc) and a compound represented by the general formula (Mc) and subsequent deprotection.

The compounds represented by the general formula (VIIc) can also be synthesized by the removal of the protecting group from a compound represented by the general formula (VIc) and subsequent coupling with a compound represented by the general formula (Mc).

Compounds represented by the general formula (VIc) can be produced using a known method.

A compound represented by the general formula (Ic) can also be produced from another compound represented by the general formula (Ic) by a known conversion reaction.

A compound represented by the general formula (IVc) can also be produced from another compound represented by the general formula (IVc) by a known conversion reaction.

A compound represented by the general formula (VIIc) can also be produced from another compound represented by the general formula (VIIc) by a known conversion reaction.

Compounds represented by the general formula (Ic') in which W' is C—$R^2$, $W^2$ is C—$R^c$, $W^3$ is a hydrogen atom, and $R^1$ is $R^3$, can also be produced from a compound represented by the general formula (VIIc) according to the following scheme or a modification thereof.

[Chemical formula 8]

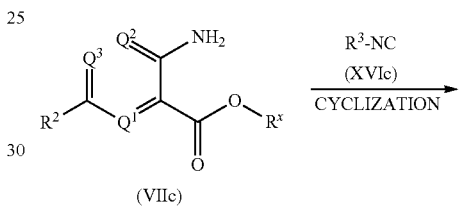

(VIIc)

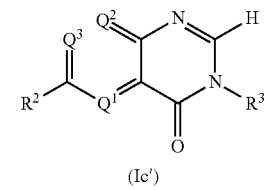

(Ic')

(The symbols in the formulae represent the same groups as those mentioned above.)

The compounds represented by the general formula (Ic') can also be produced by cyclization using a compound represented by the general formula (VIIc) and a compound represented by the general formula (XVIc). The cyclization may be carried out in the presence of an acid or a base.

Compounds represented by the general formula (XVIc) can be produced using a known method.

A compound represented by the general formula (Ic') can also be produced from another compound represented by the general formula (Ic') by a known conversion reaction.

[Production Method 6]

The compounds represented by the general formula (Ic), corresponding to the general formula (I) in which $W^1$ is C—$R^2$, $W^2$ and $W^3$ are C—$R^c$, and $R^1$ is $R^3$, can also be produced from a compound represented by the general formula (XIIIc) or a compound represented by the general formula (XV) according to the following production scheme or a modification thereof.

[Chemical formula 9]

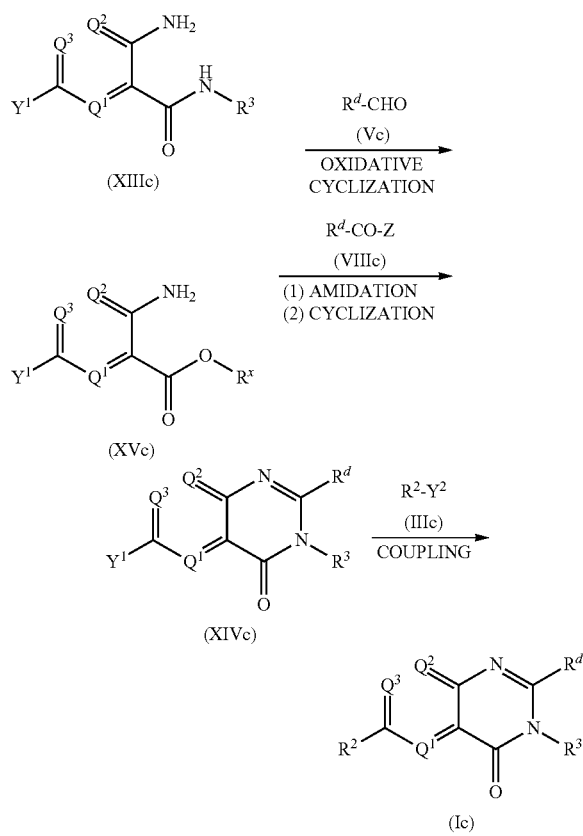

compound represented by the general formula (XVc) and a compound represented by the general formula (Vc) or another compound represented by the general formula (Vc) containing an aldehyde equivalent (e.g., dimethoxyacetal or diethoxyacetal) as a functional group in place of aldehyde, in the presence of an oxidant and $R^3$—$NH_2$.

The compounds represented by the general formula (XIVc) can also be produced by the amidation of a compound represented by the general formula (XVc) with a compound represented by the general formula (VIIIc) and subsequent cyclization using a base in the presence of $R^3$—$NH_2$.

Compounds represented by the general formula (XVc) can be produced using a known method.

A compound represented by the general formula (XIVc) can also be produced from another compound represented by the general formula (XIVc) by a known conversion reaction.

A compound represented by the general formula (Ic) can also be produced from another compound represented by the general formula (Ic) by a known conversion reaction.

The compounds represented by the general formula (Ic') in which $W^1$ is C—$R^2$, $W^2$ is C—$R^c$, $W^3$ is a hydrogen atom, and $R^1$ is $R^3$, can also be produced from a compound represented by the general formula (VIIc) according to the following production scheme or a modification thereof.

[Chemical formula 10]

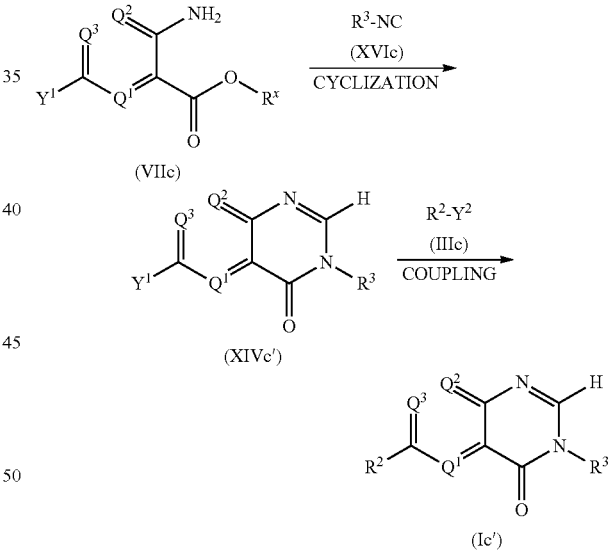

(The symbols in the formulae represent the same groups as those mentioned above.)

The compounds represented by the general formula (Ic) can also be produced by the coupling of a compound represented by the general formula (XIVc) and a compound represented by the general formula (Mc).

The compounds represented by the general formula (Mc) can be produced using a known method.

Compounds represented by the general formula (XIVc) can be produced by oxidative cyclization using a compound represented by the general formula (XIIIc) and a compound represented by the general formula (Vc) or another compound represented by the general formula (Vc) containing an aldehyde equivalent (e.g., dimethoxyacetal or diethoxyacetal) as a functional group in place of aldehyde, in the presence of an oxidant. The oxidative cyclization may be carried out in the presence of an acid (e.g., p-toluenesulfonic acid).

Compounds represented by the general formula (XIIIc) and the compounds represented by the general formula (Vc) can be produced using a known method.

The compounds represented by the general formula (XIVc) can also be produced by the amidation of a compound represented by the general formula (XIIIc) with a compound represented by the general formula (VIIIc) and subsequent cyclization using a base.

The compounds represented by the general formula (VIIIc) can be produced using a known method.

The compounds represented by the general formula (XIVc) can be produced by oxidative cyclization using a (The symbols in the formulae represent the same groups as those mentioned above.)

The compounds represented by the general formula (Ic') can also be produced by the coupling of a compound represented by the general formula (XIVc') and a compound represented by the general formula (Mc).

Compounds represented by the general formula (XIVc') can also be produced by cyclization using a compound represented by the general formula (VIIc) and a compound represented by the general formula (XVIc). The cyclization may be carried out in the presence of an acid or a base.

The compounds represented by the general formula (XVIc) can be produced using a known method.

A compound represented by the general formula (Ic') can also be produced from another compound represented by the general formula (Ic') by a known conversion reaction.

A compound represented by the general formula (XIVc') can also be produced from another compound represented by the general formula (XIVc') by a known conversion reaction.

[Production Method 7]

Compounds represented by the general formula (Id), corresponding to the general formula (I) in which $W^2$ is $C-R^2$, $W^1$ and $W^3$ are $C-R^c$, and $R^1$ is $R^3$, can also be produced from a compound represented by the general formula (IId) or a compound represented by the general formula (VId) according to the following production scheme or a modification thereof.

[Chemical formula 11]

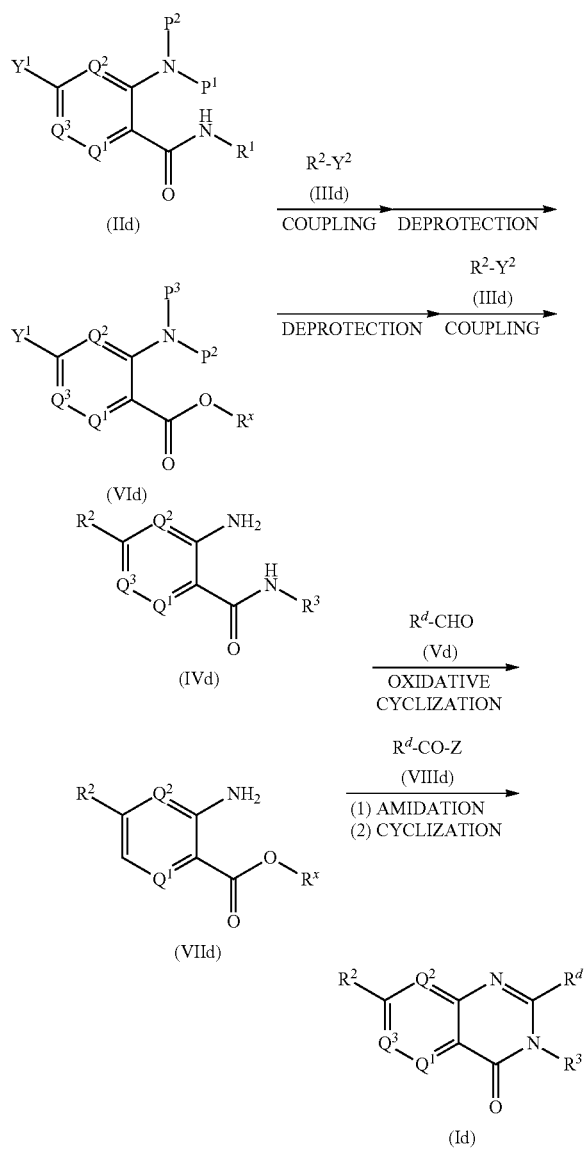

(The symbols in the formulae represent the same groups as those mentioned above.)

The compounds represented by the general formula (Id) can be produced by oxidative cyclization using a compound represented by the general formula (IVd) and a compound represented by the general formula (Vd) or another compound represented by the general formula (Vd) containing an aldehyde equivalent (e.g., dimethoxyacetal or diethoxyacetal) as a functional group in place of aldehyde, in the presence of an oxidant. The oxidative cyclization may be carried out in the presence of an acid (e.g., p-toluenesulfonic acid).

Compounds represented by the general formula (Vd) can be produced using a known method.

The compounds represented by the general formula (Id) can also be produced by the amidation of a compound represented by the general formula (IVd) with a compound represented by the general formula (VIIId) and subsequent cyclization using a base.

Compounds represented by the general formula (VIIId) can be produced using a known method.

Compounds represented by the general formula (IVd) can be synthesized by the coupling of a compound represented by the general formula (IId) and a compound represented by the general formula (IIId) and subsequent deprotection.

The compounds represented by the general formula (IVd) can also be synthesized by the removal of the protecting group from a compound represented by the general formula (IId) and subsequent coupling with a compound represented by the general formula (IIId).

Compounds represented by the general formula (IId) and those represented by the general formula (IIId) can be produced using a known method.

The compounds represented by the general formula (Id) can also be produced by oxidative cyclization using a compound represented by the general formula (VIId) and a compound represented by the general formula (Vd) or another compound represented by the general formula (Vd) containing an aldehyde equivalent (e.g., dimethoxyacetal or diethoxyacetal) as a functional group in place of aldehyde, in the presence of an oxidant and $R^3$—$NH_2$.

The compounds represented by the general formula (Id) can also be produced by the amidation of a compound represented by the general formula (VIId) with a compound represented by the general formula (VIIId) and subsequent cyclization using one of the bases mentioned above in the presence of $R^3$—$NH_2$.

Compounds represented by the general formula (VIId) can be synthesized by the coupling of a compound represented by the general formula (VId) and a compound represented by the general formula (IIId) and subsequent deprotection.

The compounds represented by the general formula (VIId) can also be synthesized by the removal of the protecting group from a compound represented by the general formula (VId) and subsequent coupling with a compound represented by the general formula (IIId).

Compounds represented by the general formula (VId) can be produced using a known method.

A compound represented by the general formula (Id) can also be produced from another compound represented by the general formula (Id) by a known conversion reaction.

A compound represented by the general formula (IVd) can also be produced from another compound represented by the general formula (IVd) by a known conversion reaction.

A compound represented by the general formula (VIId) can also be produced from another compound represented by the general formula (VIId) by a known conversion reaction.

Compounds represented by the general formula (Id') in which $W^2$ is C—$R^2$, $W^1$ is C—$R^c$, $W^3$ is a hydrogen atom, and $R^1$ is $R^3$, can also be produced from a compound represented by the general formula (VIId) according to the following production scheme or a modification thereof.

[Chemical formula 13]

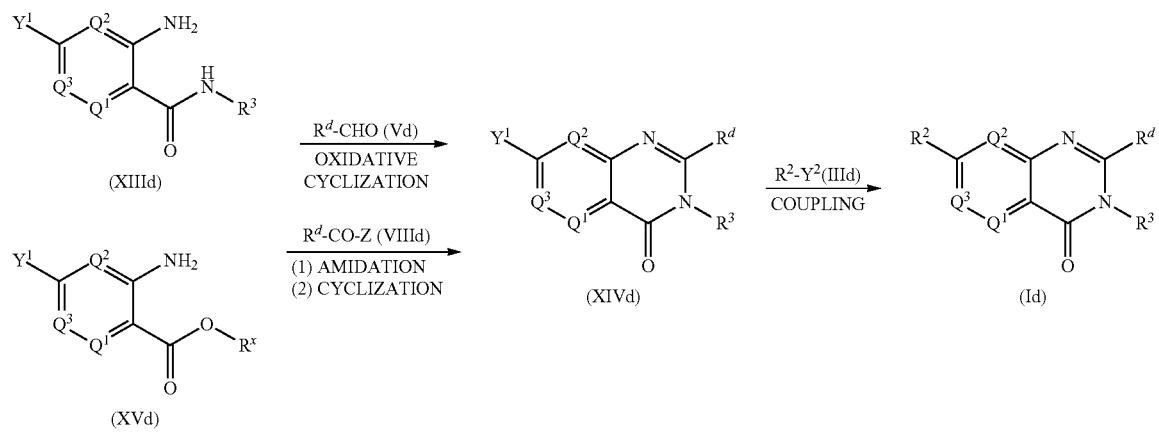

[Chemical formula 12]

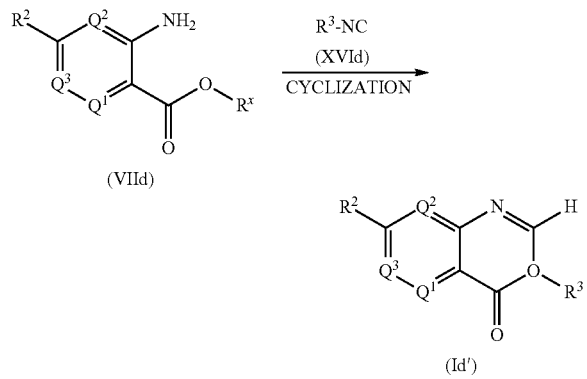

(The symbols in the formulae represent the same groups as those mentioned above.)

The compounds represented by the general formula (Id') can also be produced by cyclization using a compound represented by the general formula (VIId) and a compound represented by the general formula (XVId). The cyclization may be carried out in the presence of an acid or a base.

Compounds represented by the general formula (XVId) can be produced using a known method.

A compound represented by the general formula (Id') can also be produced from another compound represented by the general formula (Id') by a known conversion reaction.

[Production Method 8]

The compounds represented by the general formula (Id), corresponding to the general formula (I) in which $W^2$ is C—$R^2$, $W^1$ and $W^3$ are C—$R^c$, and $R^1$ is $R^3$, can be produced from a compound represented by the general formula (XIIId) or a compound represented by the general formula (XVd) according to the following production scheme or a modification thereof.

(The symbols in the formulae represent the same groups as those mentioned above.)

The compounds represented by the general formula (Id) can also be produced by the coupling of a compound represented by the general formula (XIVd) and a compound represented by the general formula (IIId).

The compounds represented by the general formula (IIId) can be produced using a known method.

Compounds represented by the general formula (XIVd) can be produced by oxidative cyclization using a compound represented by the general formula (XIIId) and a compound represented by the general formula (Vd) in the presence of an oxidant. The oxidative cyclization may be carried out in the presence of an acid (e.g., p-toluenesulfonic acid).

Compounds represented by the general formula (XIIId) the compounds represented by the general formula (Vd) can be produced using a known method.

The compounds represented by the general formula (XIVd) can also be produced by the amidation of a compound represented by the general formula (XIIId) with a compound represented by the general formula (VIIId) and subsequent cyclization using a base.

The compounds represented by the general formula (VIIId) can be produced using a known method.

The compounds represented by the general formula (XIVd) can be produced by oxidative cyclization using a compound represented by the general formula (XVd) and a compound represented by the general formula (Vd) or another compound represented by the general formula (Vd) containing an aldehyde equivalent (e.g., dimethoxyacetal or diethoxyacetal) as a functional group in place of aldehyde, in the presence of an oxidant and $R^1$—$NH_2$.

The compounds represented by the general formula (XIVd) can also be produced by the amidation of a compound represented by the general formula (XVd) with a compound represented by the general formula (VIIId) and subsequent cyclization using a base in the presence of $R^3$—$NH_2$.

Compounds represented by the general formula (XVd) can be produced using a known method.

A compound represented by the general formula (XIVd) can also be produced from another compound represented by the general formula (XIVd) by a known conversion reaction.

A compound represented by the general formula (Id) can also be produced from another compound represented by the general formula (Id) by a known conversion reaction.

The compounds represented by the general formula (Id') in which $W^2$ is C—$R^2$, W' is C—$R^c$, $W^3$ is a hydrogen atom, and $R^1$ is $R^3$, can also be produced from a compound represented by the general formula (VIId) according to the following production scheme or a modification thereof.

[Chemical formula 14]

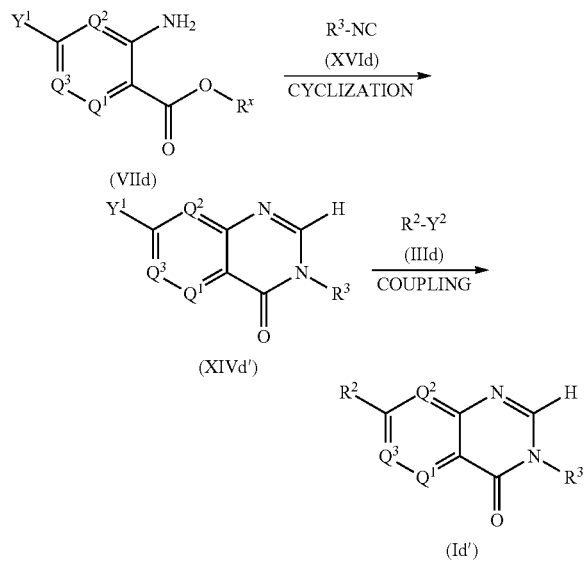

(The symbols in the formulae represent the same groups as those mentioned above.)

The compounds represented by the general formula (Id') can also be produced by the coupling of a compound represented by the general formula (XIVd') and a compound represented by the general formula (IIId).

Compounds represented by the general formula (XIVd') can also be produced by cyclization using a compound represented by the general formula (VIId) and a compound represented by the general formula (XVId). The cyclization may be carried out in the presence of an acid or a base.

The compounds represented by the general formula (XVId) can be produced using a known method.

A compound represented by the general formula (Id') can also be produced from another compound represented by the general formula (Id') by a known conversion reaction.

A compound represented by the general formula (XIVd') can also be produced from another compound represented by the general formula (XIVd') by a known conversion reaction. [Use of medicaments]

The above-mentioned compounds or their salts can enhance the expression of the normal SMN mRNA containing the nucleotide sequence corresponding to exon 7, or the normal SMN protein containing the amino acid sequence corresponding to exon 7, from a mutated SMN gene with thymine at nucleotide position 6 in exon 7. Therefore, the compounds or their salts are useful as expression enhancers that enhance the expression of the SMN mRNA containing the nucleotide sequence corresponding to exon 7 or of the SMN protein containing the amino acid sequence corresponding to exon 7.

By enhancing the expression of the SMN mRNA containing the nucleotide sequence corresponding to exon 7 or of the SMN protein containing the amino acid sequence corresponding to exon 7, it is possible to provide prophylactic or therapeutic treatment of SMA to patients with SMA who have a mutated SMN gene with thymine at nucleotide position 6 in exon 7 and thus have less or no function of the normal SMN protein. Therefore, the compounds or their salts are useful as medicaments, particularly, prophylactic or therapeutic agents for SMA.

As used herein, the term "normal SMN mRNA" refers to the transcript from the normal SMN gene which contains the nucleotide sequence corresponding to exon 7 and has a function to suppress the symptoms of SMA by increasing the amount of its translation product. As used herein, the term "normal SMN protein" refers to the expression product of the normal SMN gene which contains an amino acid sequence corresponding to exon 7 and has a function to suppress the symptoms of SMA by increasing the amount thereof.

"Prevention of SMA" refers to inhibition of the development of SMA, amelioration of the symptoms of SMA, or delay of the development of SMA by administration of an agent to an individual who has a mutated SMN gene with thymine at nucleotide position 6 in exon 7 and has a likelihood of developing SMA as a result of the reduction or loss of function of the normal SMN protein.

As used herein, the term "normal SMN gene" refers to a gene with cytosine at nucleotide position 6 in exon 7, which mostly (e.g., 80% or more, preferably 95% or more) expresses an SMN mRNA containing the nucleotide sequence corresponding to exon 7. The term "mutated SMN gene" refers to a gene with thymine at nucleotide position 6 in exon 7, which expresses mostly (e.g., 80% or more, preferably 95% or more) an SMN mRNA containing no nucleotide sequence corresponding to exon 7. Typically, the normal SMN gene is the SMN1 gene (Gene ID: 6606), with cytosine at nucleotide position 6 in exon 7, while the mutated SMN gene is the SMN2 gene (Gene ID: 6607), with thymine at nucleotide position 6 in exon 7. Accordingly, in the present specification, the SMN gene may be either the SMN1 gene or the SMN2 gene. In nature, however, the nucleotides at position 6 in exon 7 in most human individuals are cytosine and thymine in the SMN1 and SMN2 genes, respectively, and thus the SMN1 genes that occur naturally in many cases are normal SMN genes, whereas the SMN2 genes that occur naturally in many cases are mutated SMN genes; however, an SMN1 gene having a mutation of the nucleotide at position 6 in exon 7 to thymine is a mutated SMN gene, whereas an SMN2 gene with a conversion mutation of the nucleotide at position 6 in exon 7 to cytosine is the normal SMN gene. It should be noted that the normal SMN gene may be any gene that can express an SMN mRNA containing the nucleotide sequence corresponding to exon 7 and may have a mutation different from the one found in a wild-type SMN1 gene, as long as it has the function of the wild-type gene. Furthermore, the normal SMN gene as well as the mutated SMN gene may have any SNPs as long as the definitions mentioned above are satisfied.

[Formulation and Administration of Medicaments]

Medicaments in the embodiment of the present invention contain one of the above-mentioned compounds or a salt thereof as an active ingredient; however, they may contain substances other than the active ingredient for various purposes, such as one or more of pharmaceutically acceptable vehicles, disintegrants, diluents, lubricants, flavoring agents, colorants, sweeteners, acidifiers, corrigents, suspending agents, humectants, emulsifiers, dispersants, auxiliary agents, preservatives, buffers, binders, stabilizers, coating agents, local anesthetics, and isotonisants. Specifically, examples of the vehicle include lactose, refined sugar, sodium chloride, glucose, starch, calcium carbonate, kaolin, microcrystalline cellulose, and silicic acid; examples of the binder include water, ethanol, propanol, simple syrup, glucose solutions, starch solutions, gelatin solutions, carboxymethyl cellulose, hydroxypropyl cellulose, hydroxypropyl starch, methyl cellulose, ethyl cellulose, shellac, calcium phosphate, and polyvinyl pyrrolidone; examples of the disintegrant include dry starch, sodium alginate, agar powder, sodium hydrogen carbonate, calcium carbonate, sodium lauryl sulfate, monoglyceride stearate, and lactose; examples of the lubricant include purified talc, stearate, borax, and polyethylene glycol; examples of the sweetener, acidifier, and corrigent include refined sugar, peel of Citrus aurantium Linne, citric acid, and tartaric acid; examples of the buffer include sodium citrate, sodium acetate, and sodium phosphate; examples of the stabilizer include tragacanth, gum arabic, gelatin, sodium pyrosulfite, ethylenediaminetetraacetic acid (EDTA), thioglycolic acid, and thiolactic acid; examples of the local anesthetics include procaine hydrochloride and lidocain hydrochloride; and examples of the isotonisant include sodium chloride and glucose.

For each of the above-mentioned medicaments, the choice of route of administration can be either of systemic or topical. In either cases, each medicament can be administered either orally or parenterally. The parenteral administration may be, for example, intravenous administration, intra-arterial administration, dermal administration, subcutaneous administration, intradermal administration, intramuscular administration, intraperitoneal administration, and transmucosal administration. The topical routes are preferably those to the central nervous system, and examples include injections into the subarachnoid space, injections into the ventricle, and injections into the cerebrospinal fluid.

Any dosage form can be used as long as the dosage form used is suitable for the choice of route of administration. By way of example, for oral administrations, tablets, capsules, powders, granules, pills, liquids, emulsions, suspensions, solutions, spirits, syrups, extracts, and elixirs may be used. For parenteral drugs, examples include injections such as subcutaneous injections, intravenous injections, intramuscular injections, and intraperitoneal injections; transdermal therapeutic systems or patches, ointments or lotions; sublingual preparations and oral patches for buccal administrations; aerosols for nasal administrations; and suppositories. These pharmaceutical formulations can be manufactured using a known method that is commonly used in drug formulation processes. In addition, drugs according to the present invention may be in an extended- or sustained-release dosage form.

For preparing a liquid formulation for oral administrations, oral liquids, syrups, and elixirs can be manufactured using an ordinary process by adding, for example, a corrigent, a buffer, a stabilizer and/or an odor masking agent to the active ingredient. Applicable examples of the corrigent include those mentioned above. Sodium citrate is an example of the buffer, and tragacanth, gum arabic, and gelatin are examples of the stabilizer.

The amount of the active ingredient contained in each of the above-mentioned medicaments can appropriately be determined depending on, for example, the range of doses and frequency of administration of the active ingredient. The range of doses is not limited and can appropriately be selected depending on, for example, the efficacy of the ingredient(s) contained, the administration process, the route of administration, the type of disease, the information associated with a subject (such as body weight, age, medical condition, and the use of other medicament(s)), and the decision of an attending physician. Generally, a suitable dose is, for example, about 0.01 µg to about 100 mg, preferably about 0.1 µg to about 1 mg per 1 kg of the body weight of the subject. The above dose can be administered once a day or several times a day.

Formulation Examples

A medicament containing one of the above-mentioned compounds or a salt thereof as an active ingredient can be manufactured using, for example, the following formulation.

| 1. Capsules | |
|---|---|
| (1) Compound or salt thereof | 40 mg |
| (2) Lactose | 70 mg |
| (3) Microcrystalline cellulose | 9 mg |
| (4) Stearic acid, magnesium salt | 1 mg |
| per capsule | 120 mg |

The ingredients (1), (2), and (3), and one half of the ingredient (4) are kneaded and then granulated. The remaining (4) is added to the granules and the entire mixture is encapsulated into gelatin capsules.

| 2. Tablets | |
|---|---|
| (1) Compound or salt thereof | 40 mg |
| (2) Lactose | 58 mg |
| (3) Corn starch | 18 mg |
| (4) Microcrystalline cellulose | 3.5 mg |
| (5) Stearic acid, magnesium salt | 0.5 mg |
| per tablet | 120 mg |

The ingredients (1), (2), and (3), two thirds of the ingredient (4), and one half of the ingredient (5) are kneaded and then granulated. The remaining (4) and (5) are added to the granules, and the granules are compressed into tablets.

3. Injections

One of the above-mentioned compounds or a salt thereof is dissolved in 50 mL of distilled water for injection described in Japanese Pharmacopoeia, and another distilled water for injection described in Japanese Pharmacopoeia is added to a final volume of 100 mL. This solution is filtered under sterile conditions. Subsequently, this solution is aliquoted into 1 mL volumes, filled in injection vials under sterile conditions, lyophilized, and sealed.

[Method Used for Examining Enhancement of Expression]

Any method can be used to examine whether each of the above-mentioned compounds or a salt thereof can enhance the expression of the normal SMN mRNA and/or the normal SMN protein.

Specifically, it is possible to bring one of the compounds or a salt thereof just mentioned above into contact with cells with a mutated SMN gene having thymine at nucleotide position 6 in exon 7 to examine whether the amount of the normal SMN mRNA and/or the normal SMN protein in the cells is increased by the compound or its salt. For example, cells (such as fibroblasts) derived from a patient with SMA are cultured, and the compound or its salt is added to the culture medium. Subsequently, mRNA or protein is isolated from the cells, and it is examined whether the amount of the mRNA or protein is increased, compared, as a control, with that in cells cultured in medium without the compound or its salt or in the cells prior to culture in the medium containing the compound or its salt. Any method can be used for this type of examination. For mRNA, Northern blotting and dot blotting can be used, but a method involving the generation of cDNA by reverse transcription and the measurement of the amount of the normal SMN cDNA using PCR is preferable because of its convenience. For protein, Western blotting and dot blotting can be used, but the measurement of the amount of normal protein using ELISA is preferable because of its convenience.

Working Examples

[Experimental Example 1] Method Used for Producing Compounds

The term "room temperature" in the following Examples generally refer to about 10° C. to about 35° C. The ratio used in terms of a mixed solvent is expressed as volume ratio, unless otherwise specified. The percentage is expressed as weight percent, unless otherwise specified.

Column chromatography in the Examples was performed while analyzing fractions of eluate by thin layer chromatography (TLC), unless otherwise specified. Specifically, a 60F$_{254}$ plate (Merck) was used as a TLC plate, and a solvent used as the eluent for column chromatography was used as the eluent for TLC. An ultraviolet detector was used for detection. For silica gel column chromatography, the denotation "NH" indicates that aminopropylsilane bound to silica gel was used, and the denotation "Diol" indicates that 3-(2,3-dihydroxypropoxy)propylsilane bound to silica gel was used. For preparative high-performance liquid chromatography (HPLC), the denotation "C18" indicates the use of octadecyl bound to silica gel. The ratio for an eluent is indicated by volume ratio, unless otherwise specified.

For $^1$H-NMR analysis, software such as ACD/SpecManager (trade name) was used. Peaks which are quite broad such as a peak of hydroxyl or amino protons are sometimes omitted.

Mass spectra were measured by LC/MS. For ionization, an ESI or APCI technique was used. Data is indicated as measured values (Found). Typically, molecular ion peaks are observed; however, fragment ion peaks may be observed in some cases. For salts, peaks from free ions are usually observed as molecular or fragment ion peaks.

Concentration of a sample (c) with specific rotation ([α]p) is expressed in g/100 mL.

Results of elemental analysis (Anal.) are indicated as calculated (Calcd.) and measured (Found) values.

Peaks by x-ray powder diffraction in the Examples are those recorded at room temperature by an Ultima IV instrument (Rigaku Corporation, Japan) using Cu Kα radiation as a radiation source. Measurement conditions are as follows.

Electric pressure/Electric current: 40 kV/50 mA
Scan speed: 6 degree/min
Scan range of 2 Theta: 2-35 degrees The degree of crystallinity from x-ray powder diffraction patterns in the Examples was calculated according to the Hermans theory.

In the Examples below, the following abbreviations are used.

mp: melting point
MS: mass spectrum
M: molarity
CDCl$_3$: deuterated chloroform
CD$_3$OD: deuterated methanol
DMSO-d$_6$: deuterated dimethyl sulfoxide
$^1$H NMR: proton nuclear magnetic resonance
J: J-coupling
s: singlet
d: doublet
t: triplet
q: quartet
quin: quintet
brs: broad singlet
LC/MS: liquid chromatograph mass spectrometer
HPLC: high-performance liquid chromatogram
ESI: electrospray ionization
APCI: atmospheric pressure chemical ionization
DMA: N,N-dimethylacetamide
DMF: N,N-dimethylformamide
THF: tetrahydrofuran
Ac: acetyl
tert: tertiary Working Example 1

2-(4,6-Dimethylpyrazolo[1,5-a]pyrazin-2-yl)-7-fluoro-6-(1-methylpiperidin-4-yl)quinazolin-4(3H)-one (A) 2-Amino-4-fluoro-5-(1-methylpiperidin-4-yl)benzamide

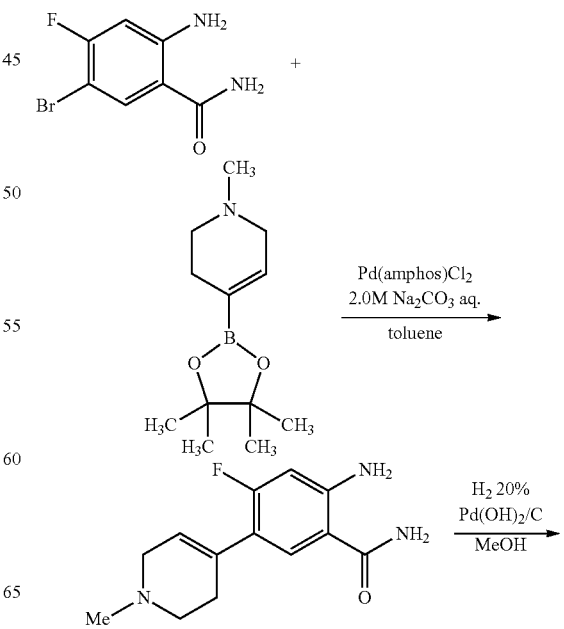

-continued

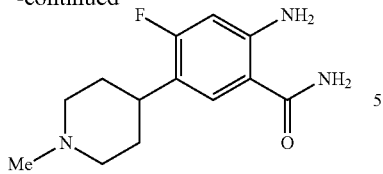

A mixture of 2-amino-5-bromo-4-fluorobenzamide (820 mg), 1-methyl-4-(4,4,5,5-tetramethyl-1,3,2-dioxaborolan-2-yl)-1,2,3,6-tetrahydropyridine (942 mg), bis[di-tert-butyl(4-dimethylaminophenyl)phosphine]dichloropalladium(II) (237 mg), a 2.0 M aqueous sodium carbonate solution (5.28 mL) and toluene (15 mL) was stirred at 100° C. overnight. To the obtained mixture was added water at room temperature and the mixture was extracted with ethyl acetate. The organic layer was separated, washed with saturated brine and dried over anhydrous magnesium sulfate, and then the volatile components were distilled off under reduced pressure. The remaining solid was purified by silica gel column chromatography (NH, methanol/ethyl acetate). To the obtained solid were added palladium hydroxide on activated carbon (20% palladium) (100 mg) and methanol, and then the obtained mixture was stirred under normal pressure and hydrogen atmosphere at room temperature overnight. Then, the catalyst was removed by filtration and the volatile components were distilled off from the filtrate under reduced pressure to obtain the title compound (716 mg).

$^1$H-NMR (300 MHz, DMSO-$d_6$) δ: 1.84-1.98 (2H, m), 2.18 (3H, s), 2.29 (1H, dd, J=10.6, 4.9 Hz), 2.84 (2H, d, J=11.2 Hz), 3.17 (3H, d, J=5.2 Hz), 4.10 (1H, q, J=5.2 Hz), 6.27 (2H, s), 7.04 (1H, d, J=12.6 Hz), 7.20 (1H, brs), 7.29 (1H, s), 7.86 (1H, brs). MS: [M+H]$^+$252.2.

(B) Diethyl 1-(2-oxopropyl)-1H-pyrazole-3,5-dicarboxylate

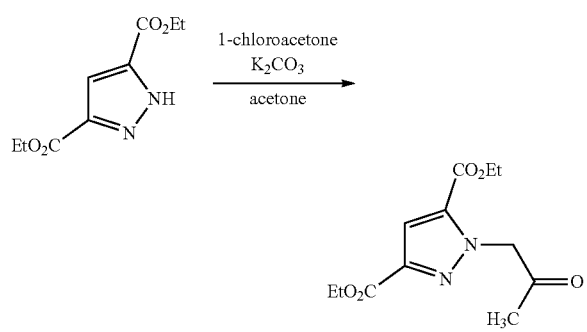

To a mixture of diethyl 1H-pyrazole-3,5-dicarboxylate (300 g) and acetone (1.5 L) was added potassium carbonate (216 g) with ice-cooling. The mixture was stirred at room temperature for 30 minutes and 1-chloroacetone (140 g) was added dropwise thereto at room temperature over 10 minutes. After the mixture was stirred at room temperature for 13 hours, water was added to the mixture at room temperature and the mixture was extracted with ethyl acetate. The organic layer was separated, washed with saturated brine and dried over anhydrous magnesium sulfate, and then the volatile components were distilled off under reduced pressure to obtain the title compound (367 g).

$^1$H-NMR (300 MHz, DMSO-$d_6$) δ: 1.24-1.33 (6H, m), 2.22 (3H, s), 4.21-4.36 (4H, m), 5.55 (2H, s), 7.29 (1H, s). MS: [M+H]$^+$269.2.

(C) Ethyl 4-hydroxy-6-methylpyrazolo[1,5-α]pyrazine-2-carboxylate

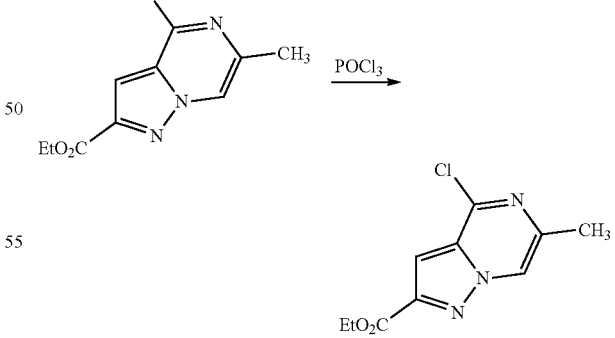

To a mixture of diethyl 1-(2-oxopropyl)-1H-pyrazole-3,5-dicarboxylate (367 g) and acetic acid (2.0 L) was added ammonium acetate (1.09 kg) at room temperature. The mixture was heated under reflux for 24 hours and ice-cooled, and then water (1.0 L) was added dropwise thereto. After the mixture was stirred at room temperature overnight, the precipitate was isolated by filtration and washed with water. After a mixture solution of the obtained solid and a 5% aqueous sodium hydrogen carbonate solution (1.0 L) was stirred at room temperature for 1 hour, the precipitate was isolated by filtration and washed with water to obtain the title compound (200 g).

$^1$H-NMR (300 MHz, DMSO-$d_6$) δ: 1.32 (3H, t, J=7.2 Hz), 2.14 (3H, d, J=1.1 Hz), 4.33 (2H, q, J=7.2 Hz), 7.32 (1H, d, J=0.8 Hz), 7.62 (1H, s), 11.51 (1H, brs). MS: [M+H]$^+$222.2.

(D) Ethyl 4-chloro-6-methylpyrazolo[1,5-a]pyrazine-2-carboxylate

A mixture of ethyl 4-hydroxy-6-methylpyrazolo[1,5-α]pyrazine-2-carboxylate (200 g) and phosphoryl chloride (1.0 L) was heated under reflux for 1 hour. After the mixture was ice-cooled, diisopropyl ether (2.5 L) was added thereto and the mixture was stirred at room temperature overnight. The precipitate isolated by filtration of the mixture was washed with diisopropyl ether to obtain the title compound (202 g).

¹H-NMR (300 MHz, DMSO-d₆) δ: 1.35 (3H, t, J=6.9 Hz), 2.46 (3H, d, J=1.1 Hz), 4.38 (2H, q, J=6.9 Hz), 7.41 (1H, d, J=1.1 Hz), 8.75-8.83 (1H, m). MS: [M+H]⁺240.2.

(E) Ethyl 4,6-dimethylpyrazolo[1,5-a]pyrazine-2-carboxylate

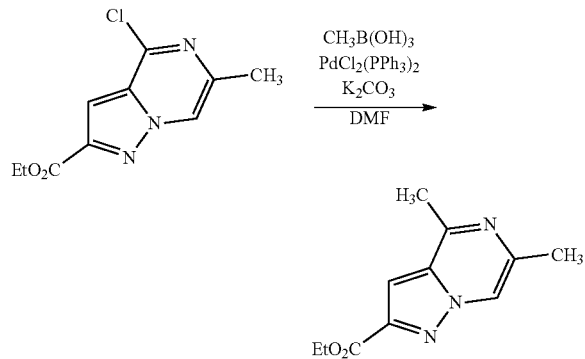

After a mixture of ethyl 4-chloro-6-methylpyrazolo[1,5-a]pyrazine-2-carboxylate (202 g), potassium carbonate (350 g) and DMF (2.0 L) was heated to 60° C., bi s(triphenylphosphine)palladium(II) dichloride (18.4 g) and methylboronic acid (104 g) were added thereto, and then the mixture was stirred under nitrogen atmosphere at 105-123° C. for 7 hours. The mixture was ice-cooled and 5% brine (1.5 L) and ethyl acetate (1.0 L) were added thereto. The mixture was filtered and the residue was washed with THF. Then, the generated liquid was added to the filtrate. After the obtained filtrate was extracted with ethyl acetate, the organic layer was separated and then washed with a 5% ammonium hydroxide solution and 5% brine. To the obtained organic layer was added activated carbon (20 g) and the mixture was stirred at room temperature for 30 minutes. The mixture was filtered and the activated carbon was washed with ethyl acetate. Then, the generated liquid was added to the filtrate. The volatile components were distilled off from the obtained filtrate under reduced pressure. To the remaining solid was added diethyl ether (800 mL) and the mixture was stirred at 60° C. for 1 hour, ice-cooled and then stirred again at the same temperature for 30 minutes. Then, the precipitate was isolated by filtration to obtain the title compound (130 g).

¹H-NMR (300 MHz, DMSO-d₆) δ: 1.34 (3H, t, J=7.1 Hz), 2.43 (3H, d, J=1.1 Hz), 2.70 (3H, s), 4.36 (2H, q, J=7.1 Hz), 7.48 (1H, d, J=0.8 Hz), 8.54 (1H, d, J=0.8 Hz). MS: [M+H]⁺220.2.

(F) (4,6-Dimethylpyrazolo[1,5-α]pyrazin-2-yl)methanol

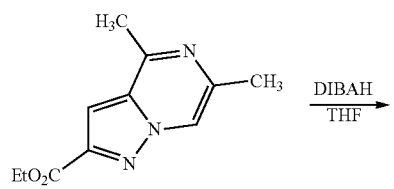

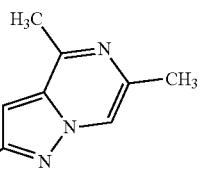

After a mixture of ethyl 4,6-dimethylpyrazolo[1,5-a]pyrazine-2-carboxylate (101 g) and THF (1.7 L) was ice-cooled, a 1.5 M diisobutylaluminium hydride/toluene solution (820 mL) was added dropwise thereto over 30 minutes. The mixture was stirred at the same temperature for 30 minutes. To the mixture was added dropwise a 2.0 M aqueous potassium sodium tartrate solution (1.38 L) with ice-cooling over 30 minutes and the mixture was stirred at room temperature for 2 hours. The mixture was filtered through Celite and the filtrate was extracted with ethyl acetate. The organic layer containing ethyl acetate was washed with 5% brine and the volatile components were distilled off under reduced pressure to obtain a solid A (57 g). To the aqueous layer containing the filtrate was added ethyl acetate (1.0 L) again, followed by mixing, and the mixture was stirred at room temperature for 12 hours. The organic layer was separated and the volatile components were distilled off under reduced pressure to obtain a solid B (8.0 g). To the solid A (57 g) and the solid B (8.0 g) was added diisopropyl ether (500 mL) and the obtained mixture was stirred at 70° C. for 1 hour and for 30 minutes with ice-cooling. Then, the precipitate was isolated by filtration to obtain the title compound (54.4 g).

¹H-NMR (300 MHz, DMSO-d₆) δ: 2.38 (3H, d, J=0.8 Hz), 2.64 (3H, s), 4.64 (2H, d, J=6.0 Hz), 5.27-5.38 (1H, m), 6.81 (1H, s), 8.35 (1H, d, J=0.8 Hz). MS: [M+H]⁺178.3.

(G) 4,6-Dimethylpyrazolo[1,5-a]pyrazine-2-carb aldehyde

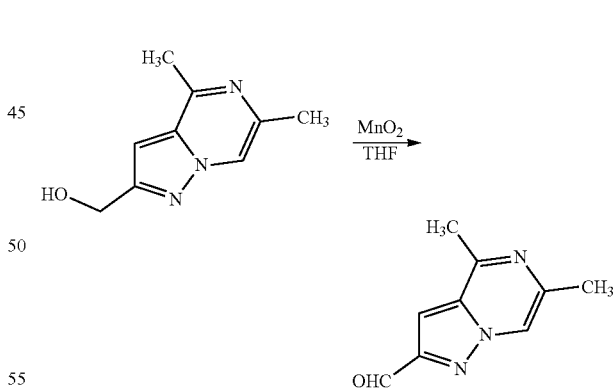

To a mixture of (4,6-dimethylpyrazolo[1,5-α]pyrazin-2-yl)methanol (54.5 g) and THF (800 mL) was added manganese dioxide (269 g) at room temperature and the mixture was stirred at room temperature for 3 days. The mixture was filtered through Celite and the residue was washed with THF. Then, the generated liquid was added to the filtrate and the volatile components were distilled off from the obtained filtrate under reduced pressure. To the resulting solid was added diisopropyl ether (500 mL) and the mixture was incubated at 70° C. for 1 hour and then stirred for 1 hour

43 with ice-cooling. Then, the mixture was filtered to obtain the title compound as a solid (44.3 g).

$^1$H-NMR (300 MHz, DMSO-d$_6$) δ: 2.44 (3H, d, J=1.1 Hz), 2.72 (3H, s), 7.53 (1H, d, J=0.8 Hz), 8.59 (1H, d, J=0.8 Hz), 10.15 (1H, s). MS: [M+H]$^+$176.1.

(H) 2-(4,6-Dimethylpyrazolo[1,5-a]pyrazin-2-yl)-7-fluoro-6-(1-methylpiperidin-4-yl)quinazolin-4(3H)-one

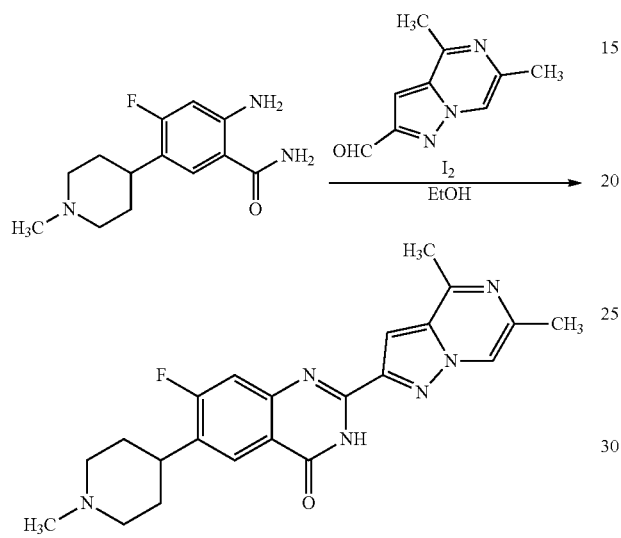

A mixture of 2-amino-4-fluoro-5-(1-methylpiperidin-4-yl)benzamide (110 mg), 4,6-dimethylpyrazolo[1,5-a]pyrazine-2-carbaldehyde (77.0 mg), iodine (222 mg) and ethanol (10 mL) was stirred at 80° C. overnight. The volatile components were distilled off under reduced pressure and the obtained solid was purified by silica gel column chromatography (NH, methanol/ethyl acetate). The obtained solid was washed with diethyl ether to obtain the title compound (56 mg). $^1$H-NMR (300 MHz, CDCl$_3$) δ: 1.78-1.98 (4H, m), 2.03-2.15 (2H, m), 2.34 (3H, s), 2.55 (3H, s), 2.58-2.72 (1H, m), 2.80 (3H, s), 3.01 (2H, d, J=11.4 Hz), 7.43 (1H, d, J=11.3 Hz), 7.59 (1H, s), 7.98 (1H, s), 8.06 (1H, s), 9.59-10.62 (1H, m). MS: [M+H]$^+$407.2.

Working Example 2

2-(4,6-Dimethylpyrazolo[1,5-a]pyrazin-2-yl)-6-(1-methylpiperidin-4-yl)quinazolin-4(3H)-one (A) 2-Amino-5-(1-methylpiperidin-4-yl)benzamide

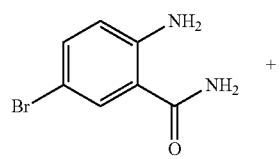

44

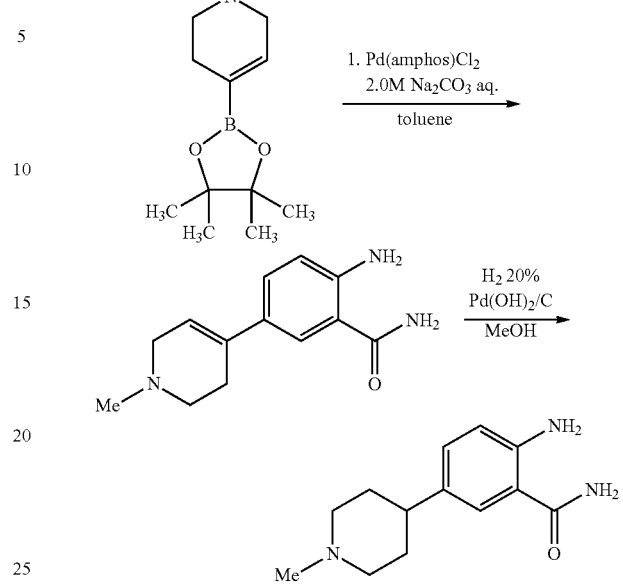

A mixture of 2-amino-5-bromobenzamide (2.7 g), 1-methyl-4-(4,4,5,5-tetramethyl-1,3,2-dioxaborolan-2-yl)-1,2,3,6-tetrahydropyridine (3.36 g), bis[di-tert-butyl(4-dimethylaminophenyl)phosphine]dichloropalladium(II) (845 mg), a 2.0 M aqueous sodium carbonate solution (18.8 mL) and toluene (50 mL) was stirred at 100° C. overnight. To the mixture was added water at room temperature and the mixture was extracted with ethyl acetate. The organic layer was separated, washed with saturated brine and dried over anhydrous magnesium sulfate, and then the volatile components were distilled off under reduced pressure. The remaining solid was purified by silica gel column chromatography (NH, ethyl acetate/hexane and NH, methanol/ethyl acetate), and then palladium hydroxide-activated carbon (20% palladium) (160 mg) and methanol were added to the obtained solid. Then, the mixture was stirred under normal pressure and hydrogen atmosphere at room temperature overnight. After the obtained mixture was filtered to remove the catalyst and the volatile components were distilled off from the filtrate under reduced pressure, the resulting solid was washed with diethyl ether to obtain the title compound (1.40 g). $^1$H-NMR (300 MHz, DMSO-d$_6$) δ: 1.55-1.71 (4H, m), 1.84-1.98 (2H, m), 2.17 (3H, s), 2.21-2.32 (1H, m), 2.84 (2H, d, J=10.9 Hz), 6.36 (2H, s), 6.60 (1H, d, J=8.3 Hz), 7.01 (2H, d, J=8.6 Hz), 7.38 (1H, s), 7.71 (brs, 1H). MS: [M+H]$^+$234.2.

(B) 2-(4,6-Dimethylpyrazolo[1,5-α]pyrazin-2-yl)-6-(1-methylpiperidin-4-yl)quinazolin-4(3H)-one

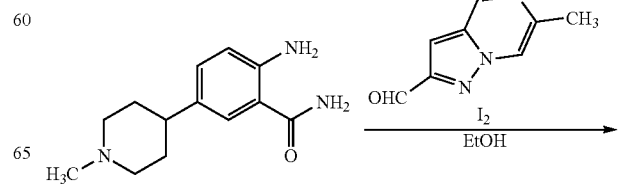

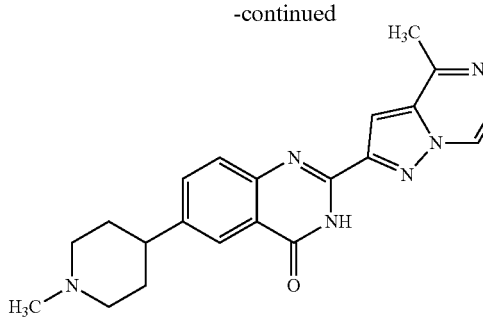

A mixture of 2-amino-5-(1-methylpiperidin-4-yl)benzamide (110 mg), 4,6-dimethylpyrazolo[1,5-α]pyrazine-2-carbaldehyde (83 mg), iodine (144 mg) and ethanol (10 mL) was stirred at 80° C. overnight. After the volatile components were distilled off from the mixture under reduced pressure, the remaining solid was purified by silica gel column chromatography (NH, methanol/ethyl acetate). The obtained solid was washed with diethyl ether to obtain the title compound (32.0 mg). $^1$H-NMR (300 MHz, CDCl$_3$) δ: 1.91 (4H, d, J=5.8 Hz), 2.03-2.17 (2H, m), 2.34 (3H, s), 2.55 (3H, s), 2.66 (1H, brs), 2.80 (3H, s), 3.02 (2H, d, J=10.6 Hz), 7.51 (1H, s), 7.65-7.81 (2H, m), 8.07 (1H, s), 8.19 (1H, s), 10.07 (1H, brs). MS: [M+H]$^+$389.2.

Working Example 3

2-(4,6-Dimethylpyrazolo[1,5-α]pyrazin-2-yl)-8-fluoro-6-(1-methylpiperidin-4-yl)quinazolin-4(3H)-one (A) 2-Amino-5-chloro-3-fluorobenzamide

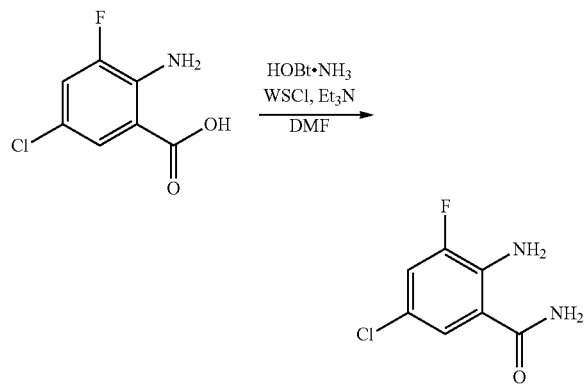

After a mixture of 2-amino-5-chloro-3-fluorobenzoic acid (2.00 g), 1-(3-dimethyl aminopropyl)-3-ethyl carbodiimide hydrochloride (3.03 g), ammonium 1H-benzo[d][1,2,3]triazol-1-olate (1/1) (2.09 g), triethyl amine (4.41 mL) and DMF (30 mL) was stirred at room temperature overnight, water was added thereto at room temperature and the mixture was extracted with ethyl acetate. The organic layer was separated, washed with a saturated aqueous sodium hydrogen carbonate solution and saturated brine and then dried over anhydrous magnesium sulfate, and the volatile components were distilled off under reduced pressure. The resulting solid was washed with diethyl ether to obtain the title compound (699 mg). $^1$H-NMR (300 MHz, DMSO-d$_6$) δ: 6.62 (2H, brs), 7.29-7.46 (2H, m), 7.52 (1H, s), 7.97 (1H, brs). MS: [M+H]$^+$190.1.

(B) 2-Amino-3-fluoro-5-(1-methylpiperidin-4-yl)benzamide

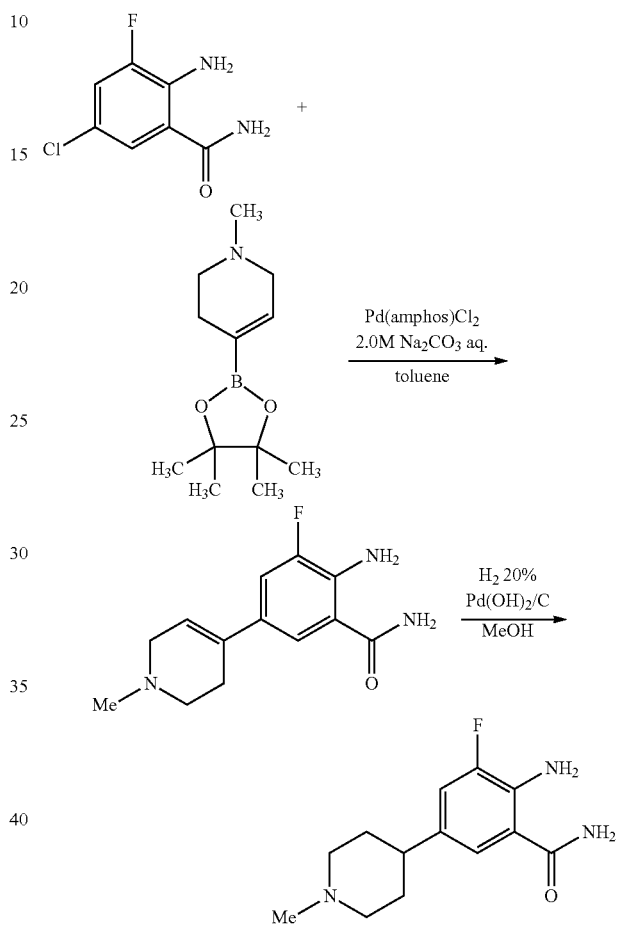

After a mixture of 2-amino-5-chloro-3-fluorobenzamide (660 mg), 1-methyl-4-(4,4,5,5-tetramethyl-1,3,2-dioxaborolan-2-yl)-1,2,3,6-tetrahydropyridine (1.02 g), bis[di-tert-butyl(4-dimethylaminophenyl)phosphine]dichloropalladium(II) (235 mg), a 2.0 M aqueous sodium carbonate solution (5.25 mL) and toluene (15 mL) was stirred at 100° C. overnight, water was added thereto at room temperature and the mixture was extracted with ethyl acetate. The organic layer was separated, washed with saturated brine and dried over anhydrous magnesium sulfate, and then the volatile components were distilled off under reduced pressure. The remaining solid was purified by silica gel column chromatography (NH, ethyl acetate/hexane) and a mixture of the obtained solid (800 mg), palladium hydroxide-activated carbon (20% palladium) (70 mg) and methanol (20 mL) was stirred under normal pressure and hydrogen atmosphere at room temperature overnight. Then, the catalyst was removed by filtration and the volatile components were distilled off from the filtrate under reduced pressure to obtain the title compound (580 mg).

MS: [M+H]$^+$252.2.

(C) 2-(4,6-Dimethylpyrazolo[1,5-α]pyrazin-2-yl)-8-fluoro-6-(1-methylpiperidin-4-yl)quinazolin-4(3H)-one

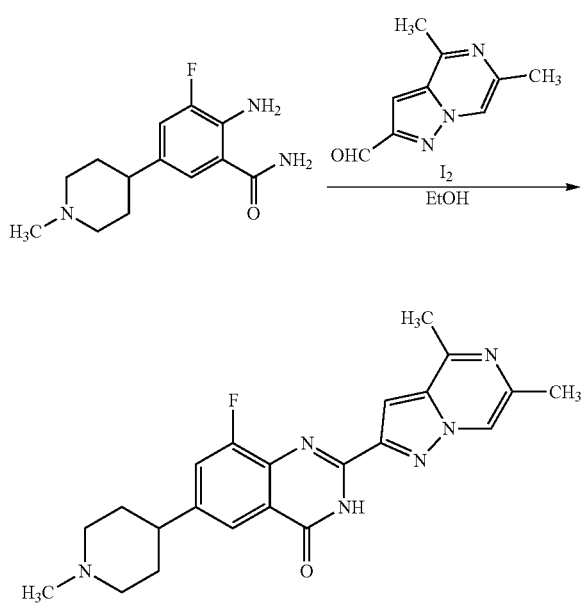

After a mixture of 2-amino-3-fluoro-5-(1-methylpiperidin-4-yl)benzamide (120 mg), 4,6-dimethylpyrazolo[1,5-α]pyrazine-2-carbaldehyde (92.0 mg), iodine (242 mg) and ethanol (10 mL) was stirred at 80° C. overnight, the volatile components were distilled off under reduced pressure and the remaining solid was purified by silica gel column chromatography (NH, methanol/ethyl acetate). The obtained solid was washed with diethyl ether to obtain the title compound (50.0 mg).

¹H-NMR (300 MHz, CDCl₃) δ: 1.80-1.99 (4H, m), 2.03-2.15 (2H, m), 2.34 (3H, s), 2.55 (3H, s), 2.58-2.72 (1H, m), 2.80 (3H, s), 3.01 (2H, d, J=11.1 Hz), 7.43 (1H, d, J=11.5 Hz), 7.59 (1H, s), 7.99 (1H, s), 8.07 (1H, s), 9.94-10.33 (1H, m). MS: [M+H]⁺407.2.

Working Example 4

2-(4,6-Dimethylpyrazolo[1,5-α]pyrazin-2-yl)-5-fluoro-6-(1-methylpiperidin-4-yl)quinazolin-4(3H)-one

(A) 6-Amino-2-fluoro-3-(1-methyl-1,2,3,6-tetrahydropyridin-4-yl)benzamide

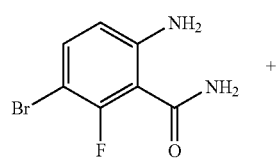 +

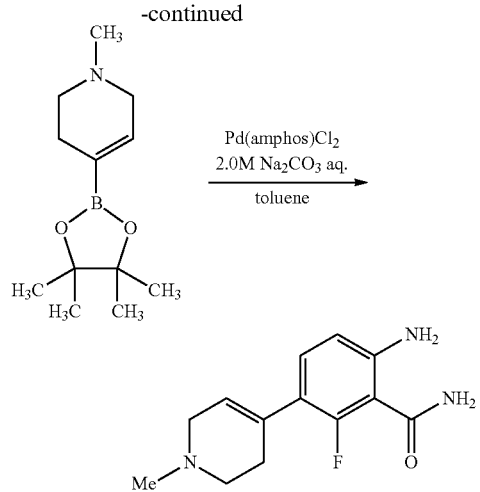

A mixture of 6-amino-3-bromo-2-fluorobenzamide (640 mg), 1-methyl-4-(4,4,5,5-tetramethyl-1,3,2-dioxaborolan-2-yl)-1,2,3,6-tetrahydropyridine (758 mg), 4[di-tert-butylphosphino]-N, N-dimethylaniline-dichloropalladium (2:1) (II) (188 mg), a 2.0 M aqueous sodium carbonate solution (4.12 mL) and toluene (20 mL) was stirred under nitrogen atmosphere at 100° C. overnight. To the mixture was added water at room temperature and the mixture was extracted with ethyl acetate. The organic layer was separated and dried over anhydrous magnesium sulfate, and then the volatile components were distilled off under reduced pressure. The resulting solid was purified by silica gel column chromatography (NH, ethyl acetate/hexane) to obtain the title compound (184 mg).

¹H-NMR (300 MHz, DMSO-d₆) δ: 2.25 (3H, s), 2.37 (2H, brs), 2.46-2.50 (2H, m), 2.93-2.96 (2H, m), 5.77 (1H, brs), 5.93 (2H, s), 6.47 (1H, d, J=8.5 Hz), 6.97-7.09 (1H, m), 7.41-7.71 (2H, m). MS: [M+H]⁺250.1.

(B) 6-Amino-2-fluoro-3-(1-methylpiperidin-4-yl)benzamide

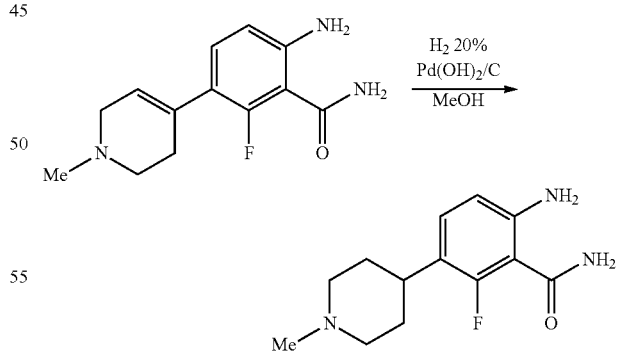

A mixture of 6-amino-2-fluoro-3-(1-methyl-1,2,3,6-tetrahydropyridin-4-yl)benzamide (180 mg), palladium hydroxide-activated carbon (20% palladium) (101 mg) and methanol (20 mL) was stirred under normal pressure and hydrogen atmosphere at room temperature overnight. The obtained mixture was filtered to remove the catalyst and the volatile components were distilled off under reduced pressure to obtain the title compound (63.1 mg).

¹H-NMR (300 MHz, DMSO-d₆) δ: 1.53-1.72 (4H, m), 1.86-2.03 (2H, m), 2.18 (3H, s), 2.52-2.65 (1H, m), 2.78-2.92 (2H, m), 5.82 (2H, s), 6.47 (1H, d, J=8.5 Hz), 7.00 (1H, t, J=8.5 Hz), 7.51 (2H, brs). MS: [M+H]⁺252.2.

(C) 2-(4,6-Dimethylpyrazolo[1,5-α]pyrazin-2-yl)-5-fluoro-6-(1-methylpiperidin-4-yl)quinazolin-4(3H)-one

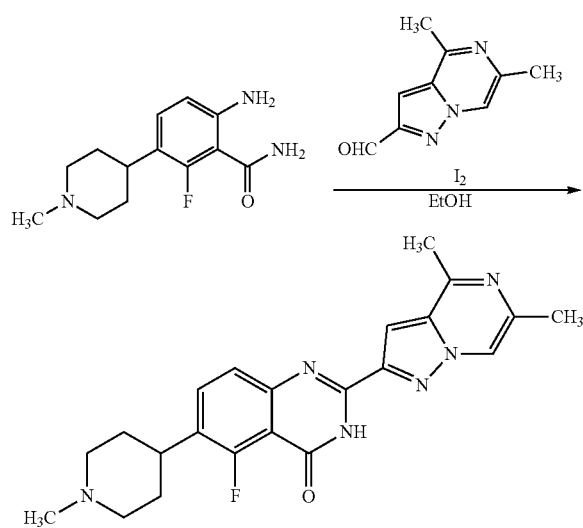

To a mixture of 6-amino-2-fluoro-3-(1-methylpiperidin-4-yl)benzamide (60.0 mg) and ethanol (10 mL) were added 4,6-dimethylpyrazolo[1,5-α]pyrazine-2-carbaldehyde (46 mg) and iodine (121 mg) at room temperature. After the mixture was stirred under nitrogen atmosphere at 80° C. overnight, the volatile components were distilled off under reduced pressure. The remaining solid was purified by silica gel column chromatography (NH, methanol/ethyl acetate) and the obtained solid was washed with ethyl acetate to obtain the title compound (56.3 mg).
¹H-NMR (300 MHz, DMSO-d₆) δ: 1.63-1.87 (4H, m), 1.93-2.09 (2H, m), 2.21 (3H, s), 2.46 (3H, s), 2.74 (3H, s), 2.84-3.00 (3H, m), 7.53 (1H, d, J=8.9 Hz), 7.70 (1H, s), 7.73-7.84 (1H, m), 8.52 (1H, s), 12.21 (1H, brs). MS: [M+H]⁺407.2.

Working Example 5

2-(4-Ethyl-6-methylpyrazolo[1,5-α]pyrazin-2-yl)-6-(4-methylpiperazin-1-yl)quinazolin-4(3H)-on e (A) Ethyl 4-ethyl-6-methylpyrazolo[1,5-α]pyrazine-2-carboxylate

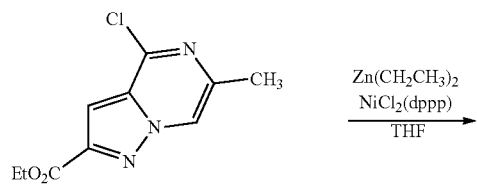

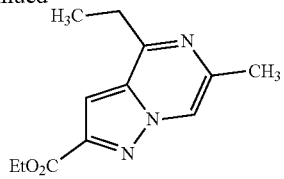

To a mixture of ethyl 4-chloro-6-methylpyrazolo[1,5-α]pyrazine-2-carboxylate (500 mg) and THF (10 mL) was added dichloro[1,3-bis(diphenylphosphino)propane]nickel (II) (56.5 mg) at room temperature. After the mixture was ice-cooled, a 1.0 M diethylzinc/toluene solution (4.17 mL) was added dropwise thereto and the mixture was stirred with ice-cooling for 1 hour and at room temperature for 2 hours. After the mixture was ice-cooled again, a 1.0 M diethylzinc/toluene solution (4.17 mL) was added dropwise thereto and the mixture was stirred at room temperature for 1 hour. Then, water was added thereto at room temperature. After the mixture was extracted with ethyl acetate, the organic layer was washed with saturated brine and dried over anhydrous magnesium sulfate, and then the volatile components were distilled off under reduced pressure. The resulting solid was purified by silica gel column chromatography (NH, ethyl acetate/hexane) to obtain the title compound (335 mg).
¹H-NMR (300 MHz, DMSO-d₆) δ: 1.27-1.39 (6H, m), 2.44 (3H, d, J=0.8 Hz), 3.06 (2H, q, J=7.3 Hz), 4.36 (2H, q, J=7.1 Hz), 7.50 (1H, d, J=1.1 Hz), 8.54 (1H, s). MS: [M+H]⁺234.2.

(B) (4-Ethyl-6-methylpyrazolo[1,5-α]pyrazin-2-yl)methanol

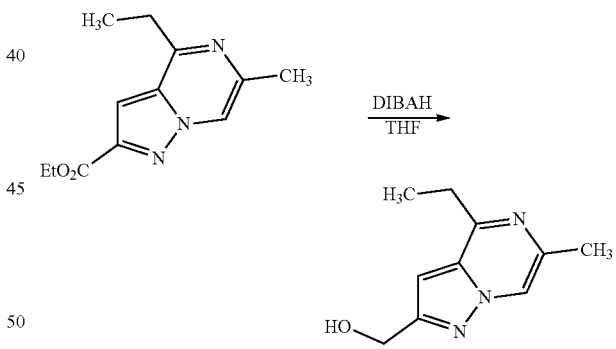

To a mixture of ethyl 4-ethyl-6-methylpyrazolo[1,5-α]pyrazine-2-carboxylate (330 mg) and THF (10 mL) was added dropwise a 1.0 M diisobutylaluminium hydride/toluene solution (4.24 mL) at room temperature and the mixture was stirred under nitrogen atmosphere at room temperature for 4 hours. To the obtained mixture was added dropwise a 1.0 M diisobutylaluminium hydride/toluene solution (4.24 mL) at room temperature and the mixture was stirred under nitrogen atmosphere at room temperature for 30 minutes. Then, a saturated aqueous Rochelle salt solution (10 mL) and ethyl acetate (20 mL) were added thereto at room temperature and the mixture was stirred at the same temperature overnight. After the obtained mixture was extracted with ethyl acetate, the organic layer was washed with saturated brine and dried over anhydrous magnesium sulfate, and then the volatile components were distilled off under reduced pressure. The remaining solid was purified by silica gel column chromatography (ethyl acetate/hexane) to obtain the title compound (219 mg).

$^1$H-NMR (300 MHz, DMSO-$d_6$) δ: 1.30 (3H, t, J=7.6 Hz), 2.40 (3H, d, J=0.8 Hz), 2.98 (2H, q, J=7.6 Hz), 4.65 (2H, d, J=5.7 Hz), 5.33 (1H, t, J=5.7 Hz), 6.83 (1H, s), 8.36 (1H, s). MS: [M+H]$^+$192.2.

(C) 4-Ethyl-6-methylpyrazolo[1,5-a]pyrazine-2-carbaldehyde

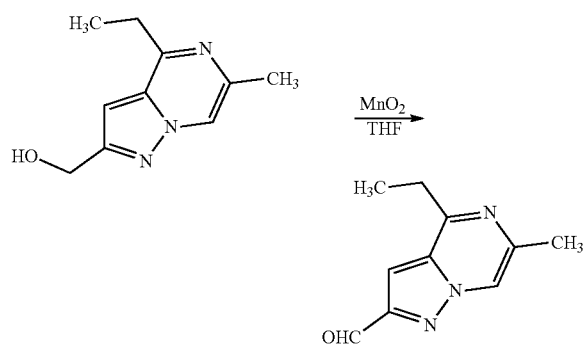

To a mixture of (4-ethyl-6-methylpyrazolo[1,5-α]pyrazin-2-yl)methanol (210 mg) and THF (5 mL) was added manganese dioxide (955 mg) at room temperature and the mixture was stirred at room temperature overnight. After the obtained mixture was filtered through Celite, the volatile components were distilled off from the filtrate under reduced pressure to obtain the title compound (199 mg).

$^1$H-NMR (300 MHz, DMSO-$d_6$) δ: 1.31 (3H, t, J=7.6 Hz), 2.46 (3H, d, J=1.1 Hz), 3.08 (2H, q, J=7.6 Hz), 7.55 (1H, d, J=1.1 Hz), 8.59 (1H, s), 10.15 (1H, s). MS: [M+H]$^+$190.2.

(D) 2-(4-Ethyl-6-methylpyrazolo[1,5-α]pyrazin-2-yl)-6-(4-methylpiperazin-1-yl)quinazolin-4(3H)-one

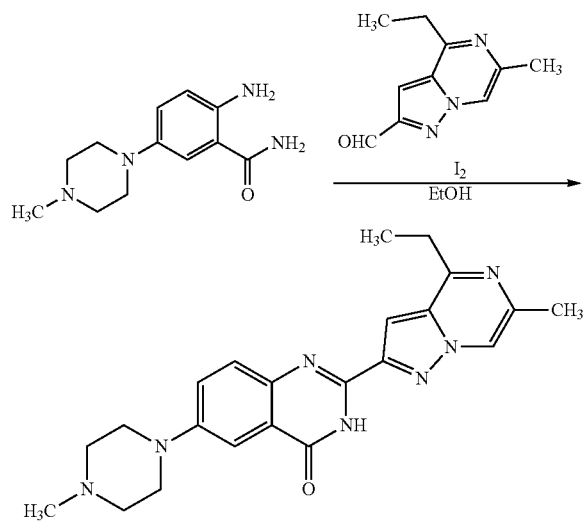

To a mixture of 2-amino-5-(4-methylpiperazin-1-yl)benzamide (150 mg) and ethanol (5 mL) were added 4-ethyl-6-methylpyrazolo[1,5-α]pyrazine-2-carbaldehyde (133 mg) and iodine (325 mg) at room temperature and the mixture was stirred under nitrogen atmosphere at 80° C. for 1 hour. Then, the volatile components were distilled off under reduced pressure. The resulting solid was purified by silica gel column chromatography (NH, methanol/ethyl acetate) to obtain the title compound (16.5 mg).

$^1$H-NMR (300 MHz, DMSO-$d_6$) δ: 1.34 (3H, t, J=7.6 Hz), 2.24 (3H, s), 2.45-2.49 (7H, m), 3.08 (2H, q, J=7.6 Hz), 3.25-3.30 (4H, m), 7.46 (1H, d, J=2.6 Hz), 7.55-7.61 (1H, m), 7.61-7.68 (2H, m), 8.50 (1H, s), 12.09 (1H, brs). MS: [M+H]$^+$404.3.

Example 6

2-(4,6-Dimethylpyrazolo[1,5-α]pyrazin-2-yl)-6-(4-methylpiperazin-1-yl)quinazolin-4(3H)-one dihydrochloride

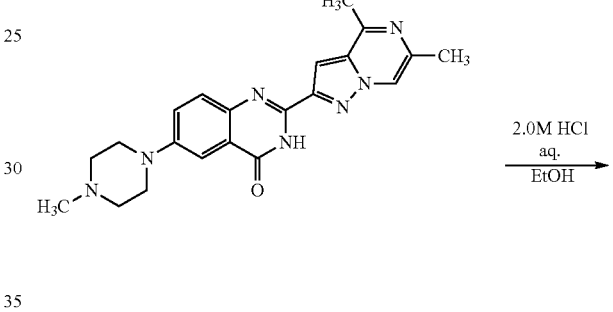

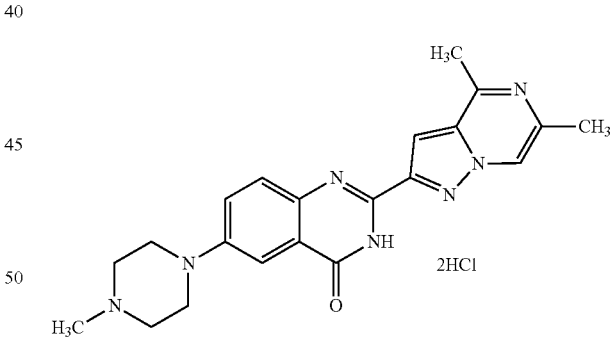

After 2-(4,6-dimethylpyrazolo[1,5-a]pyrazin-2-yl)-6-(4-methylpiperazin-1-yl)quinazolin-4(3H)-one (500 mg) was dissolved in 2.0 M hydrochloric acid (4 mL) at 70° C., ethanol (4 mL) was added dropwise thereto. The mixture was stirred at 60-70° C. for 30 minutes and at room temperature overnight, and then the solid obtained by filtration was washed with ethanol/water (1/1) to obtain the title compound (440 mg).

$^1$H-NMR (300 MHz, DMSO-$d_6$) δ: 2.46 (3H, s), 2.74 (3H, s), 2.84 (3H, d, J=4.2 Hz), 3.16-3.28 (4H, m), 3.52-3.57 (2H, m), 4.03 (2H, d, J=10.8 Hz), 7.55 (1H, d, J=2.3 Hz), 7.61-7.72 (3H, m), 8.52 (1H, s), 10.82 (1H, brs). MS: [M-2HCl+H]$^+$390.3.

Example 7

2-(4,6-Dimethylpyrazolo[1,5-α]pyrazin-2-yl)-7-fluoro-6-(4-methylpiperazin-1-yl)quinazolin-4(3H)-one (A) 4-Fluoro-5-(4-methylpiperazin-1-yl)-2-nitrobenzamide

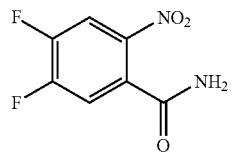

A mixture of 4,5-difluoro-2-nitrobenzamide (2.0 g), 1-methylpiperazine (1.49 g), triethyl amine (2.77 mL) and THF (20 mL) was stirred at room temperature overnight and diisopropyl ether (10 mL) was added thereto at room temperature. Then, the precipitate was isolated by filtration to obtain the title compound (3.50 g).

MS: [M+H]$^+$283.2.

(B) 2-Amino-4-fluoro-5-(4-methylpiperazin-1-yl)benzamide

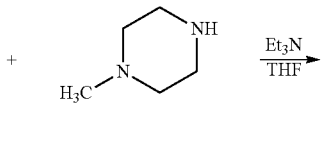

A mixture of 4-fluoro-5-(4-methylpiperazin-1-yl)-2-nitrobenzamide (3.50 g), palladium hydroxide-activated carbon (20% palladium) (348 mg) and methanol (70 mL) was stirred under normal pressure and hydrogen atmosphere at room temperature for 2 hours. The obtained mixture was filtered to remove the catalyst and the volatile components were distilled off from the filtrate under reduced pressure. Then, the remaining solid was purified by silica gel column chromatography (NH, methanol/ethyl acetate). The obtained solid was washed with diisopropyl ether to obtain the title compound (2.50 g).

MS: [M+H]$^+$253.2.

(C) 2-(4,6-Dimethylpyrazolo[1,5-α]pyrazin-2-yl)-7-fluoro-6-(4-methylpiperazin-1-yl)quinazolin-4(3H)-one

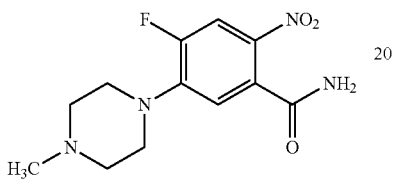

A mixture of 2-amino-4-fluoro-5-(4-methylpiperazin-1-yl)benzamide (165 mg), 4,6-dimethylpyrazolo[1,5-α]pyrazine-2-carbaldehyde (126 mg), iodine (183 mg) and ethanol (5 mL) was stirred at 70° C. for 3 hours and then purified by silica gel column chromatography (NH, methanol/ethyl acetate) to obtain the title compound (38.0 mg).

$^1$H-NMR (300 MHz, DMSO-d$_6$) δ: 2.38 (3H, s), 2.48 (3H, s), 2.64-2.71 (4H, m), 2.75 (3H, s), 3.19-3.27 (4H, m), 7.37 (1H, d, J=13.2 Hz), 7.50 (1H, s), 7.69 (1H, d, J=9.4 Hz), 8.33 (1H, s). MS: [M+H]$^+$408.1.

Example 8

2-(4,6-Dimethylpyrazolo[1,5-a]pyrazin-2-yl)-6-(4-methylpiperazin-1-yl)quinazolin-4(3H)-one (A) 5-Fluoro-2-nitrobenzamide To a mixture of 5-fluoro-2-nitrobenzoic acid (25.0 g), DMF (0.105 mL) and THF (125 mL) was added dropwise oxalyl chloride (17.7 mL) at room temperature and the mixture was stirred at room temperature for 1 hour. After the volatile components were distilled off from the obtained mixture under reduced pressure, the residue was azeotroped with THF to remove the volatile components. To the obtained solid was added THF (225 mL), followed by mixing, and a 7.0 M ammonia/methanol solution (38.6 mL) was added dropwise thereto with ice-cooling. Then, the mixture was stirred at the same temperature for 1 hour. Water was further added thereto at the same temperature and the mixture was extracted with ethyl acetate. After the organic layer was separated and washed with 1.0 M hydrochloric acid and water, the volatile components were distilled off under reduced pressure. To the remaining solid was added diisopropyl ether (150 mL) and the mixture was stirred at 60° C. for 30 minutes. The mixture was cooled to room temperature, and then the precipitate was isolated by filtration and washed with diisopropyl ether to obtain the title compound (20.0 g).

$^1$H-NMR (300 MHz, DMSO-$d_6$) δ: 7.38-7.61 (2H, m), 7.79 (1H, brs), 8.13 (2H, dd, J=9.8, 4.9 Hz).

(B) 5-(4-Methylpiperazin-1-yl)-2-nitrobenzamide

To a mixture of 5-fluoro-2-nitrobenzamide (20.0 g), 1-methylpiperazine (11.4 g) and THF (100 mL) was added triethyl amine (18.2 mL) at room temperature and the mixture was stirred at 60° C. overnight. The volatile components were distilled off under reduced pressure and the remaining solid was washed with diisopropyl ether/ethyl acetate to obtain the title compound (30.5 g).

$^1$H-NMR (300 MHz, DMSO-$d_6$) δ: 2.21-2.24 (3H, m), 2.38-2.46 (4H, m), 3.40-3.48 (4H, m), 6.86 (1H, d, J=2.6 Hz), 7.01 (1H, dd, J=9.4, 2.6 Hz), 7.50 (1H, brs), 7.85 (1H, brs), 7.94 (1H, d, J=9.1 Hz). MS: [M+H]$^+$265.3.

(C) 2-Amino-5-(4-methylpiperazin-1-yl)benzamide

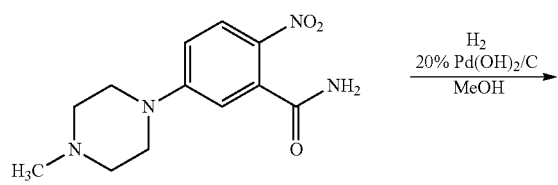

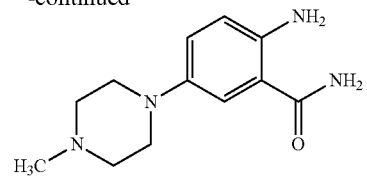

A mixture of 5-(4-methylpiperazin-1-yl)-2-nitrobenzamide (30.0 g), palladium hydroxide-activated carbon (20% palladium) (3.0 g) and methanol (600 mL) was stirred under normal pressure and hydrogen atmosphere at room temperature overnight. After the obtained mixture was filtered to remove the catalyst and the volatile components were distilled off from the filtrate under reduced pressure, the remaining solid was washed with ethyl acetate/diisopropyl ether to obtain the title compound (18.0 g).

$^1$H-NMR (300 MHz, DMSO-$d_6$) δ: 2.20 (3H, s), 2.44 (4H, d, J=4.9 Hz), 2.90-3.01 (4H, m), 6.04 (2H, s), 6.60 (1H, d, J=8.7 Hz), 6.89 (1H, dd, J=8.7, 2.6 Hz), 6.94-7.11 (2H, m), 7.72 (1H, brs). MS: [M+H]$^+$235.3.

(D) 2-(4,6-Dimethylpyrazolo[1,5-a]pyrazin-2-yl)-6-(4-methylpiperazin-1-yl)quinazolin-4(3H)-one

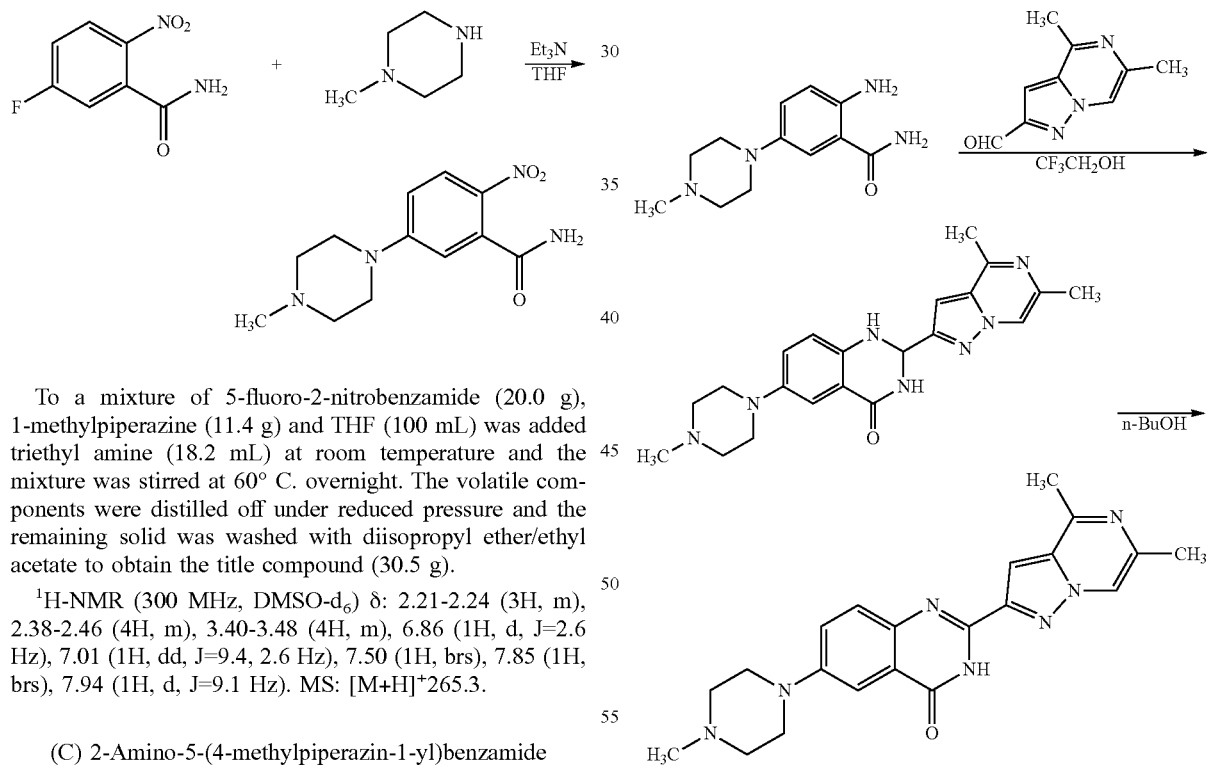

To a mixture of 2-amino-5-(4-methylpiperazin-1-yl)benzamide (3.00 g) and 2,2,2-trifluoroethanol (30 mL) was added 4,6-dimethylpyrazolo[1,5-α]pyrazine-2-carbaldehyde (2.24 g) at room temperature and the mixture was stirred at 80° C. for 16 hours. The volatile components were distilled off under reduced pressure and 1-butanol (30 mL) was added to the remaining solid. Then, the mixture was stirred at 130° C. for 59 hours. After the mixture was cooled to room temperature, ethanol (30 mL) was added thereto and the precipitate was isolated by filtration to obtain a solid (2.91 g). To the obtained solid was added 1-butanol (60 mL) and the mixture was stirred at 130° C. Then, ethyl acetate (60 mL) was added dropwise thereto at the same temperature. The mixture was cooled to room temperature and the precipitate was isolated by filtration to obtain the title compound (2.05 g).

$^1$H-NMR (300 MHz, DMSO-$d_6$) δ: 2.24 (3H, s), 2.45 (3H, s), 2.47-2.50 (4H, m), 3.24-3.31 (4H, m), 3.32 (3H, s), 7.44 (1H, d, J=2.3 Hz), 7.54-7.66 (3H, m), 8.48 (1H, s), 12.04 (1H, brs). MS: [M+H]$^+$390.3.

Example 9

6-(2-Methylimidazo[1,2-α]pyridin-6-yl)-2-(1-methylpiperidin-4-yl)quinazolin-4(3H)-one (A) N-(4-bromo-2-carbamoylphenyl)-1-methylpiperidine-4-carboxamide

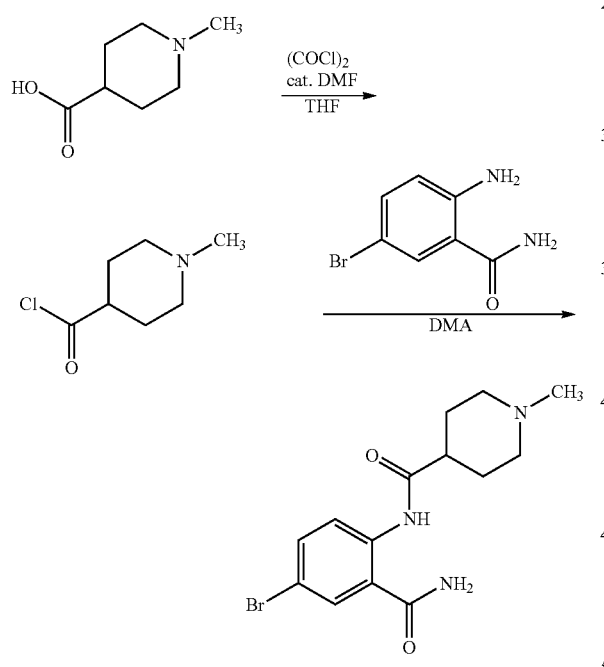

To a mixture of 1-methylpiperidine-4-carboxylic acid (519 mg), oxalyl chloride (0.977 mL) and THF (10 mL) was added DMF (0.216 mL) at room temperature. The mixture was stirred at room temperature for 1 hour and the volatile components were distilled off under reduced pressure. To the remaining solid was added DMA (5 mL) and then 2-amino-5-bromobenzamide (600 mg) was further added thereto at room temperature. After the mixture was stirred at room temperature for 1 hour, water was added thereto and the mixture was extracted with ethyl acetate. The organic layer was washed with saturated brine and dried over magnesium sulfate, and then the volatile components were distilled off under reduced pressure. The remaining solid was washed with diethyl ether to obtain the title compound (430 mg).

MS: [M+H]$^+$340.1.

(B) 6-Bromo-2-(1-methylpiperidin-4-yl)quinazolin-4(3H)-one

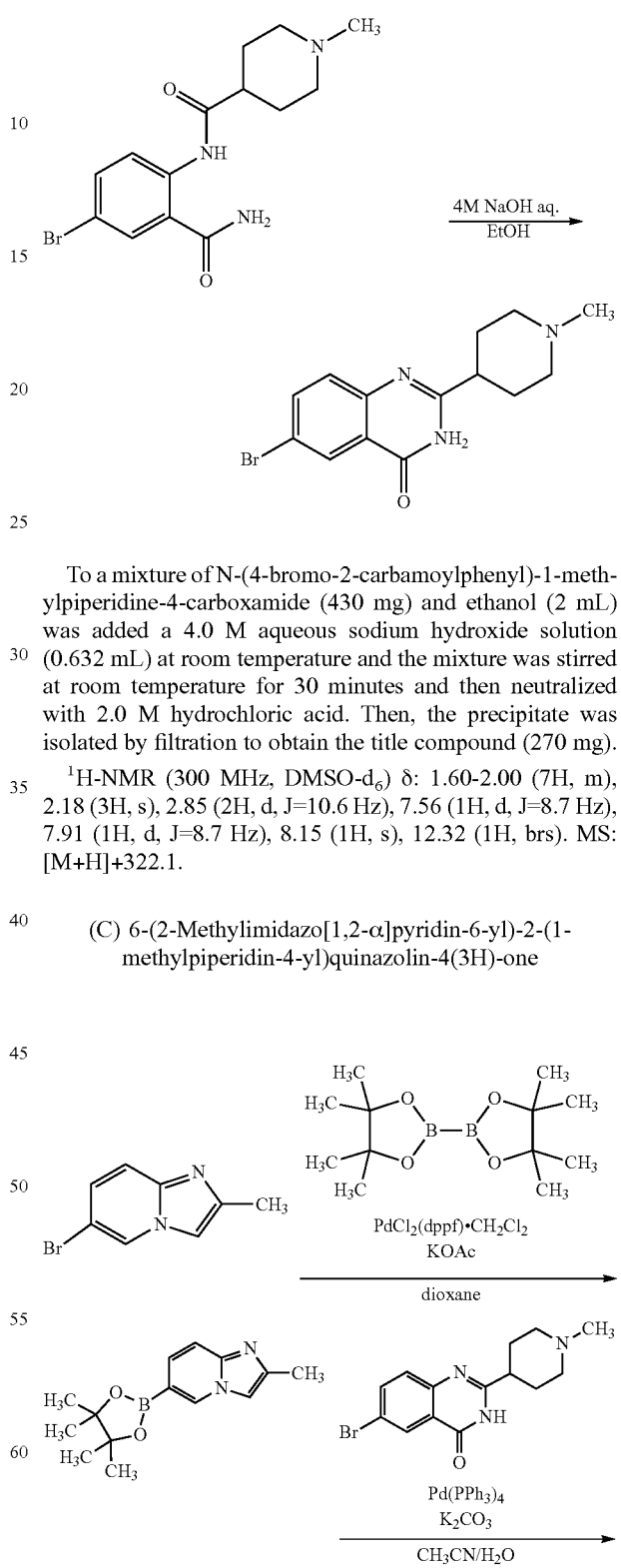

To a mixture of N-(4-bromo-2-carbamoylphenyl)-1-methylpiperidine-4-carboxamide (430 mg) and ethanol (2 mL) was added a 4.0 M aqueous sodium hydroxide solution (0.632 mL) at room temperature and the mixture was stirred at room temperature for 30 minutes and then neutralized with 2.0 M hydrochloric acid. Then, the precipitate was isolated by filtration to obtain the title compound (270 mg).

$^1$H-NMR (300 MHz, DMSO-$d_6$) δ: 1.60-2.00 (7H, m), 2.18 (3H, s), 2.85 (2H, d, J=10.6 Hz), 7.56 (1H, d, J=8.7 Hz), 7.91 (1H, d, J=8.7 Hz), 8.15 (1H, s), 12.32 (1H, brs). MS: [M+H]+322.1.

(C) 6-(2-Methylimidazo[1,2-α]pyridin-6-yl)-2-(1-methylpiperidin-4-yl)quinazolin-4(3H)-one -continued

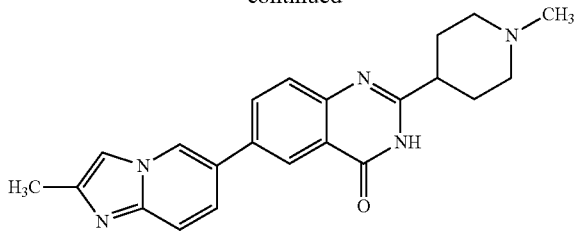

To a mixture of 6-bromo-2-methylimidazo[1,2-α]pyridine (100 mg) and dioxane (10 mL) was added bis(pinacolato)diboron (144 mg), followed by mixing, and the mixture was degassed with nitrogen for 10 minutes. To the mixture were further added dichloro[1,1'-bis(diphenylphosphino)ferrocene]palladium(II) dichloromethane adduct (19.4 mg) and potassium acetate (140 mg), and then the mixture was stirred at 100° C. overnight. The obtained mixture was cooled to room temperature and THF (15 mL) was added thereto. Then, the mixture was filtered and the volatile components were distilled off from the obtained filtrate under reduced pressure. To the remaining solid were added 6-bromo-2-(1-methylpiperidin-4-yl)quinazolin-4(3H)-one (150 mg), acetonitrile (12 mL) and water (0.5 mL), followed by mixing, and then potassium carbonate (130 mg) was further added thereto. The mixture was degassed with argon for 20 minutes and tetrakis(triphenylphosphine)palladium(0) (53.8 mg) was further added thereto. Then, the mixture was stirred at 90° C. for 16 hours, cooled to room temperature and filtered through Celite. The volatile components were distilled off from the obtained filtrate under reduced pressure and the remaining solid was purified by silica gel column chromatography (methanol/dichloromethane) to obtain the title compound (50.0 mg).

$^1$H-NMR (400 MHz, DMSO-$d_6$) δ: 1.78-1.95 (7H, m), 2.19 (3H, s), 2.36 (3H, s), 2.83-2.91 (2H, m), 7.53 (1H, d, J=8.8 Hz), 7.61 (1H, d, J=9.5 Hz), 7.71 (2H, d, J=8.0 Hz), 8.12 (1H, d, J=10.6 Hz), 8.35 (1H, s), 9.00 (1H, s), 12.25 (1H, brs). MS: [M+H]$^+$374.2.

Example 10

6-(8-Fluoro-2-methylimidazo[1,2-α]pyridin-6-yl)-2-(1-methylpiperidin-4-yl)quinazolin-4(3H)-one

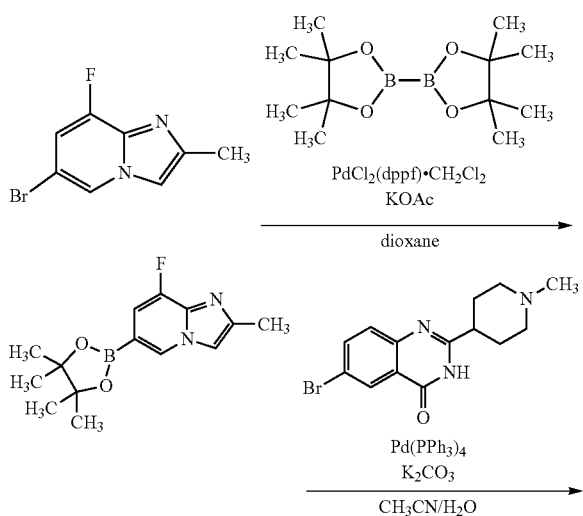

-continued

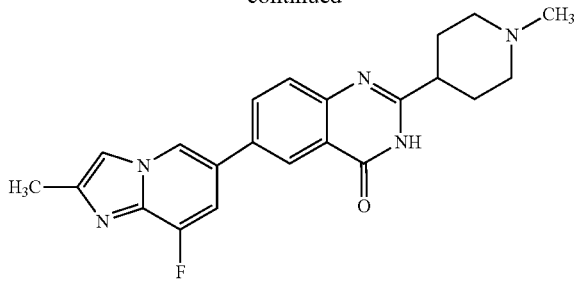

To a mixture of 6-bromo-8-fluoro-2-methylimidazo[1,2-α]pyridine (300 mg) and dioxane (20 mL) was added bis(pinacolato)diboron (665 mg), followed by mixing, and the mixture was degassed with argon for 10 minutes. To the mixture were added dichloro[1,1'-bis(diphenylphosphino)ferrocene]palladium(II) dichloromethane adduct (53.5 mg) and potassium acetate (386 mg), followed by mixing, and then the mixture was stirred at 100° C. overnight. After the obtained mixture was cooled to room temperature, THF (15 mL) was added thereto and the mixture was filtered. Then, the volatile components were distilled off from the obtained filtrate under reduced pressure. To a mixture of the remaining solid, 6-bromo-2-(1-methylpiperidin-4-yl)quinazolin-4(3H)-one (100 mg), acetonitrile (12 mL) and water (0.5 mL) was added potassium carbonate (86.3 mg) and the mixture was degassed with argon for 20 minutes. Then, tetrakis(triphenylphosphine)palladium(0) (35.9 mg) was added thereto. After the obtained mixture was stirred at 90° C. for 16 hours, cooled to room temperature and filtered through Celite, the volatile components were distilled off from the obtained filtrate under reduced pressure and then the resulting solid was purified by silica gel column chromatography (methanol/dichloromethane) to obtain the title compound (50.0 mg).

$^1$H-NMR (400 MHz, DMSO-$d_6$) δ: 1.85-2.06 (4H, m), 2.38 (3H, s), 2.45-2.60 (5H, m), 2.67-2.70 (1H, m), 3.15 (2H, d, J=10.7 Hz), 7.61 (1H, d, J=12.4 Hz), 7.72 (1H, d, J=8.5 Hz), 7.84 (1H, d, J=2.4 Hz), 8.14 (1H, dd, J=8.5, 2.0 Hz), 8.38 (1H, d, J=1.7 Hz), 8.93 (1H, s), 12.31 (1H, brs). MS: [M+H]$^+$392.1.

Example 11

2-(4,6-Dimethylfuro[3,2-c]pyridin-2-yl)-6-(4-methylpiperazin-1-yl)quinazolin-4(3H)-one (A) 3-Iodo-2,6-4-hydroxypyridine

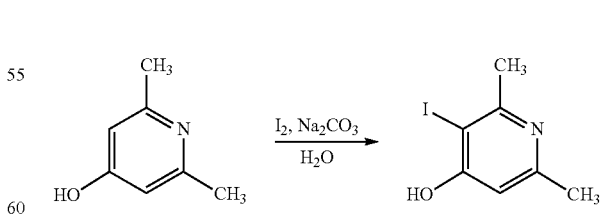

To a mixture of 2,6-dimethyl-4-hydroxypyridine (6.5 g), sodium carbonate (11.2 g) and water (100 mL) was added iodine (13.4 g) and the reaction mixture was stirred at room temperature for 16 hours. Then, concentrated hydrochloric acid was added thereto to adjust the pH to 4-5. To the solid obtained by filtration was added methanol (60 mL), followed by mixing, and the mixture was heated. The mixture was filtered and the volatile components were distilled off from the obtained filtrate under reduced pressure to obtain the title compound (4.5 g).

$^1$H-NMR (400 MHz, DMSO-d$_6$) δ: 2.17 (3H, s), 2.44 (3H, s), 5.85 (1H, s), 11.52 (1H, brs). MS: [M+H]$^+$249.9.

(B) (4,6-Dimethylfuro[3,2-c]pyridin-2-yl)methanol

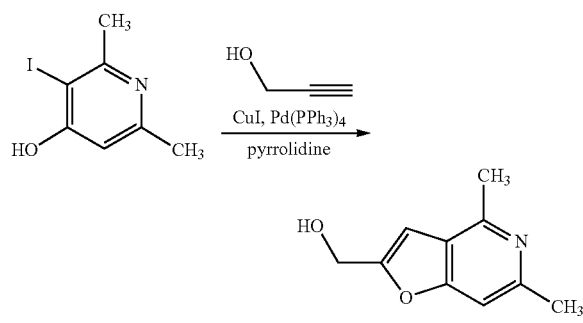

After a mixture of 3-iodo-2,6-4-hydroxypyridine (4.5 g) and pyrrolidine (50 mL) was degassed with argon for 10 minutes, tetrakis(triphenylphosphine)palladium(0) (1.05 g) and copper iodide (0.35 g) were added to the mixture and the mixture was stirred at room temperature for 20 minutes. Propargylalcohol (1.52 g) was further added thereto and the mixture was stirred at room temperature for 48 hours. Then, the volatile components were distilled off under reduced pressure. To the remaining solid was added THF (100 mL), followed by mixing, and the mixture was heated under reflux for 2 hours. After the volatile components were distilled off under reduced pressure, ethyl acetate and a saturated potassium hydrogen carbonate solution were added to the remaining solid. The organic layer was separated, washed with saturated brine and dried over anhydrous sodium sulfate, and then the volatile components were distilled off under reduced pressure. The remaining solid was purified by silica gel column chromatography (ethyl acetate/hexane) to obtain the title compound (2.2 g).

$^1$H-NMR (400 MHz, DMSO-d$_6$) δ: 2.59 (3H, s), 4.55 (2H, d, J=5.5 Hz), 5.51 (1H, t, J=5.6 Hz), 6.84 (1H, s), 7.27 (1H, s). MS: [M+H]$^+$178.1.

(C) 4,6-Dimethylfuro[3,2-c]pyridine-2-carbaldehyde

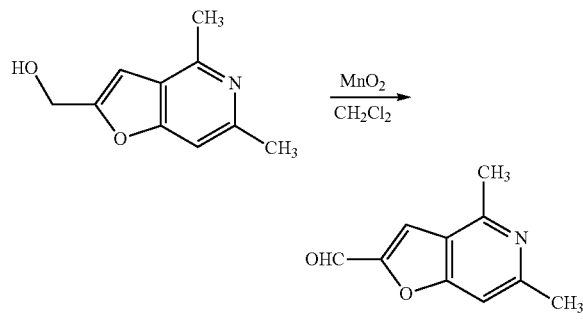

To (4,6-dimethylfuro[3,2-c]pyridin-2-yl)methanol (2.2 g) and dichloromethane (100 mL) was added manganese dioxide (16.2 g) at room temperature and the mixture was stirred at room temperature for 32 hours. After the obtained mixture was filtered through Celite, the volatile components were distilled off from the filtrate under reduced pressure. The remaining solid was purified by silica gel column chromatography (ethyl acetate/hexane) to obtain the title compound (1.2 g).

$^1$H-NMR (400 MHz, CDCl$_3$) δ: 2.66 (3H, s), 2.76 (3H, s), 7.20 (1H, s), 7.56 (1H, s), 9.85 (1H, s). MS: [M+H]$^+$175.8.

(D) 6-Bromo-2-(4,6-dimethylfuro[3,2-c]pyridin-2-yl)quinazolin-4(3H)-one

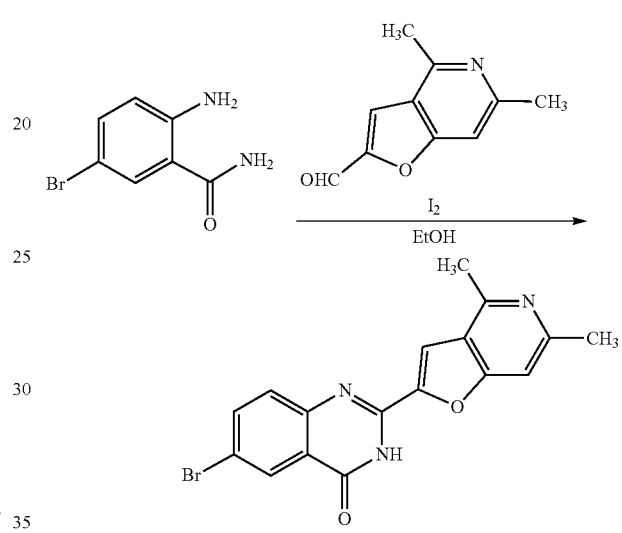

To 2-amino-5-bromobenzamide (1.5 g), 4,6-dimethylfuro[3,2-c]pyridine-2-carbaldehyde (1.22 g) and ethanol (50 mL) was added iodine (1.86 g) at room temperature and the mixture was heated under reflux for 40 hours. The solid obtained by filtration after the obtained mixture was cooled to room temperature was washed with ethyl acetate, a 10% aqueous sodium thiosulfate solution, water and methanol to obtain the title compound (1.5 g).

$^1$H-NMR (400 MHz, DMSO-d$_6$) δ: 2.79 (3H, s), 2.95 (3H, s), 7.73 (1H, d, J=8.6 Hz), 8.02 (1H, d, J=6.7 Hz), 8.15 (1H, s), 8.23 (1H, d, J=1.6 Hz), 8.44 (1H, s), 13.17 (1H, brs). MS: [M+H]$^+$369.9.

(E) 2-(4,6-Dimethylfuro[3,2-c]pyridin-2-yl)-6-(4-methylpiperazin-1-yl)quinazolin-4(3H)-one

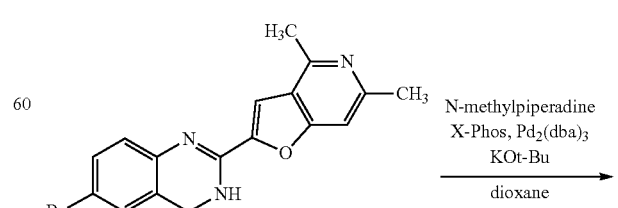

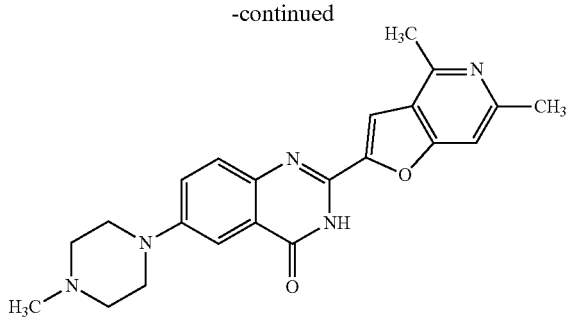

To a sealed tube were added 6-bromo-2-(4,6-dimethylfuro[3,2-c]pyridin-2-yl)quinazolin-4(3H)-one (150 mg), 1-methylpiperazine (81.9 mg) and dioxane (10 mL), and then potassium tert-butoxide (136 mg) was added to the mixture. Then, the mixture was degassed with argon for 10 minutes. 2-Dicyclohexylphosphino-2',4',6'-triisopropylbiphenyl (23.4 mg) and tris(dibenzylideneacetone)dipalladium(0) (18.5 mg) were further added thereto, and then the mixture was sealed in a sealed tube and stirred at 110° C. for 18 hours. After being cooled to room temperature, the mixture was filtered through Celite and the volatile components were distilled off from the filtrate under reduced pressure. The remaining solid was purified by silica gel column chromatography (methanol/dichloromethane) to obtain the title compound (70.0 mg).

$^1$H-NMR (400 MHz, DMSO-$d_6$) δ: 2.57 (3H, s), 2.67 (3H, s), 2.83-3.11 (4H, m), 3.36-3.72 (4H, m), 7.45 (1H, s), 7.51 (1H, s), 7.58-7.66 (1H, m), 7.69 (1H, d, J=8.8 Hz), 8.10 (1H, s), 12.61 (1H, brs). MS: [M+H]$^+$390.0.

Example 12

2-(4,6-Dimethylpyrazolo[1,5-a]pyrazin-2-yl)-6-(4-ethylpiperazin-1-yl)quinazolin-4(3H)-one

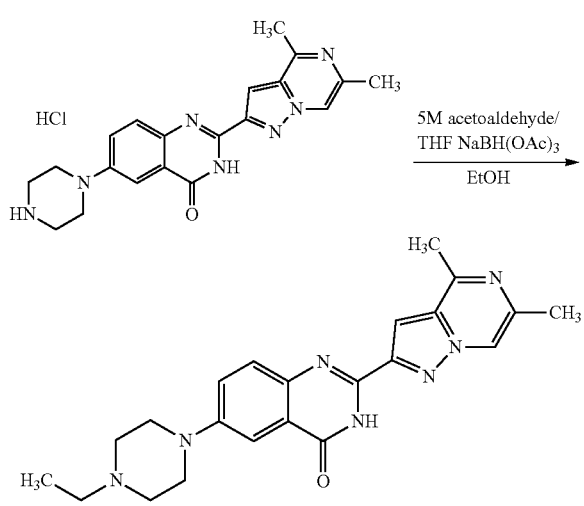

To a mixture of 2-(4,6-dimethylpyrazolo[1,5-a]pyrazin-2-yl)-6-(piperazin-1-yl)quinazolin-4(3H)-one dihydrochloride (100 mg) and ethanol (5 mL) were added a 5.0 M acetaldehyde/THF solution (0.466 mL) and sodium triacetoxyborohydride (284 mg) at room temperature, and then the mixture was stirred under nitrogen atmosphere at room temperature for 2 hours. After the volatile components were distilled off under reduced pressure, the remaining solid was purified by silica gel column chromatography (NH, methanol/ethyl acetate). The obtained solid was washed with ethanol and recrystallized from 1-butanol/ethyl acetate to obtain the title compound (18.1 mg).

$^1$H-NMR (300 MHz, DMSO-$d_6$) δ: 1.05 (3H, t, J=7.0 Hz), 2.39 (2H, q, J=7.0 Hz), 2.45 (3H, s), 2.52-2.58 (4H, m), 2.73 (3H, s), 3.25-3.31 (4H, m), 7.45 (1H, d, J=2.6 Hz), 7.53-7.70 (3H, m), 8.50 (1H, s), 12.09 (1H, brs). MS: [M+H]$^+$404.4.

Example 13

6-(2-Methyl-1,3-benzoxazol-6-yl)-2-(1-methylpiperidin-4-yl)quinazolin-4(3H)-one

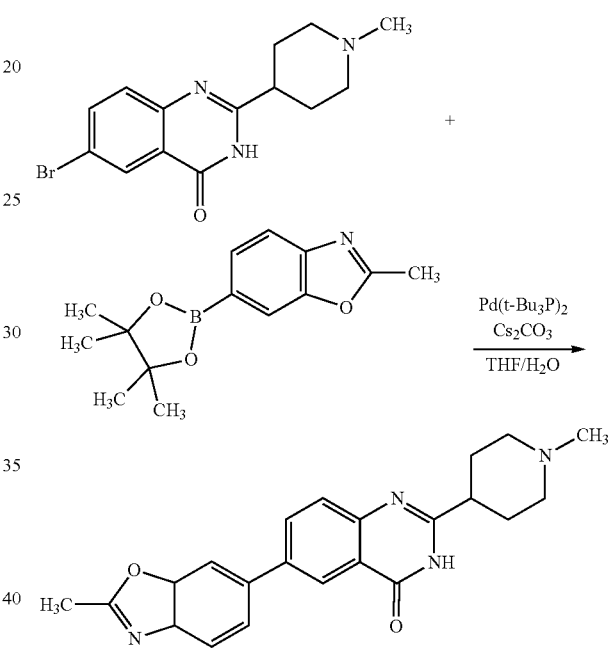

After a mixture of 6-bromo-2-(1-methylpiperidin-4-yl)quinazolin-4(3H)-one (180 mg), 2-methyl-6-(4,4,5,5-tetramethyl-1,3,2-dioxaborolan-2-yl)benzo[d]oxazole (184 mg), bis(tri-tert-butylphosphine)palladium(0) (14.3 mg), cesium carbonate (364 mg), THF (2 mL) and water (0.40 mL) was stirred under nitrogen atmosphere at 70° C. for 1 hour, water was added thereto at room temperature and the mixture was extracted with ethyl acetate/THF. The organic layer was separated and dried over anhydrous magnesium sulfate, and then the volatile components were distilled off under reduced pressure. After the remaining solid was purified by silica gel column chromatography (NH, methanol/ethyl acetate), the obtained solid was washed with ethyl acetate. Furthermore, dimethyl sulfoxide (2.0 mL) and ethanol (2.0 mL) were added to the solid and they were mixed, and the mixture was stirred at 70° C. for 1 hour. The solid obtained by filtration after cooling the mixture to room temperature was washed with dimethyl sulfoxide/ethanol (1/1) and ethanol to obtain the title compound (81 mg).

$^1$H-NMR (300 MHz, DMSO-$d_6$) δ: 1.75-1.97 (6H, m), 2.19 (3H, s), 2.52-2.60 (1H, m), 2.65 (3H, s), 2.87 (2H, d, J=10.2 Hz), 7.66-7.80 (3H, m), 8.07 (1H, s), 8.15 (1H, dd, J=8.5, 2.5 Hz), 8.35 (1H, d, J=2.3 Hz), 12.22 (1H, s). MS: [M+H]$^+$375.3.

Example 14

6-(2-Methyl-1,3-benzothiazol-6-yl)-2-(1-methylpiperidin-4-yl)quinazolin-4(3H)-one

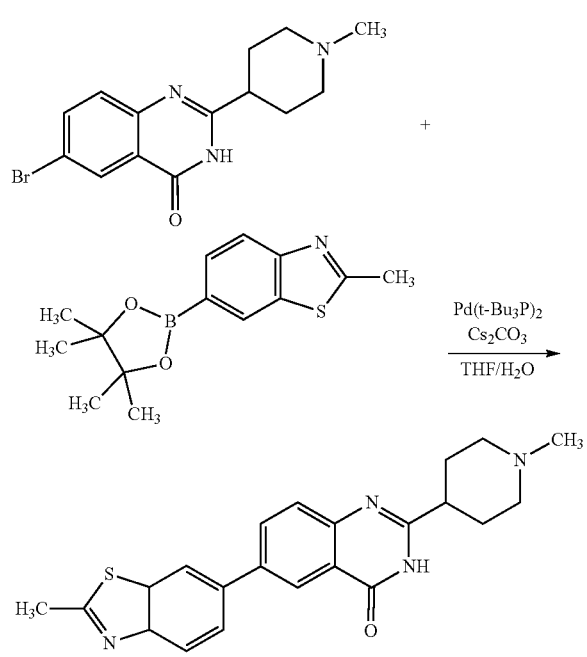

After a mixture of 6-bromo-2-(1-methylpiperidin-4-yl)quinazolin-4(3H)-one (170 mg), 2-methyl-6-(4,4,5,5-tetramethyl-1,3,2-dioxaborolan-2-yl)benzo[d]oxazole (182 mg), bis(tri-tert-butylphosphine)palladium(0) (13.5 mg), cesium carbonate (344 mg), THF (10 mL) and water (2.0 mL) was stirred under nitrogen atmosphere at 70° C. for 1 hour, water was added thereto at room temperature and the mixture was extracted with ethyl acetate/THF. The organic layer was separated and dried over anhydrous magnesium sulfate, and then the volatile components were distilled off under reduced pressure. After the remaining solid was purified by silica gel column chromatography (NH, methanol/ethyl acetate), the obtained solid was washed with ethyl acetate to obtain the title compound (11.8 mg).

$^1$H-NMR (300 MHz, DMSO-$d_6$) δ: 1.79-1.99 (7H, m), 2.19 (3H, s), 2.79-2.92 (5H, m), 7.71 (1H, d, J=8.7 Hz), 7.86 (1H, dd, J=8.7, 1.9 Hz), 8.00 (1H, d, J=8.7 Hz), 8.18 (1H, dd, J=8.7, 2.3 Hz), 8.39 (1H, d, J=2.3 Hz), 8.49 (1H, d, J=1.9 Hz), 12.21 (1H, brs). MS: [M+H]$^+$391.3.

Example 15

2-(1-Methylpiperidin-4-yl)-6-(3-methylpyrrolo[1,2-α]pyrazin-7-yl)quinazolin-4(3H)-one (A) 7-Bromo-3-methylpyrrolo[1,2-α]pyrazine

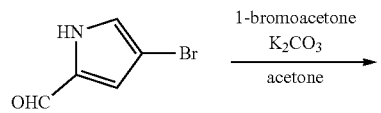

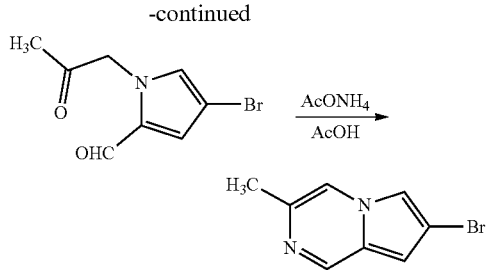

To a mixture of 6-bromo-1H-pyrrole-2-carbaldehyde (810 mg), potassium carbonate (965 mg) and acetonitrile (20 mL) was added 1-bromopropan-2-one (0.469 mL) at room temperature and the mixture was stirred under nitrogen atmosphere at room temperature for 6 hours while protected from light. Then, water was further added thereto and the mixture was extracted with ethyl acetate. The organic layer was washed with saturated brine and dried over anhydrous magnesium sulfate, and then the volatile components were distilled off under reduced pressure. To a mixture of the remaining solid and acetic acid (20 mL) was added ammonium acetate (7.18 g) at room temperature and the mixture was stirred at 120° C. for 3 hours. After the volatile components were distilled off under reduced pressure, a saturated aqueous sodium hydrogen carbonate solution was added to the remaining solid and the mixture was extracted with ethyl acetate. The organic layer was washed with saturated brine and dried over anhydrous magnesium sulfate, and then the volatile components were distilled off under reduced pressure. The remaining solid was purified by silica gel column chromatography (ethyl acetate/hexane) to obtain the title compound (470 mg).

MS: [M+H]$^+$211.1.

(B) 2-(1-Methylpiperidin-4-yl)-6-(3-methylpyrrolo[1,2-α]pyrazin-7-yl)quinazolin-4(3H)-one

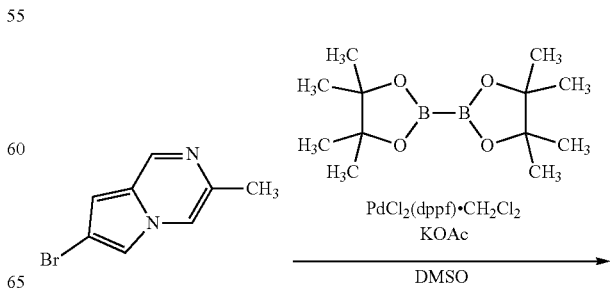

-continued

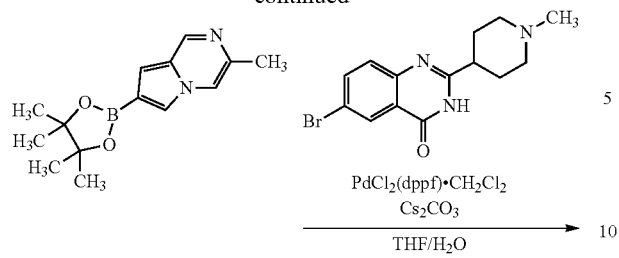

PdCl₂(dppf)·CH₂Cl₂
Cs₂CO₃
THF/H₂O

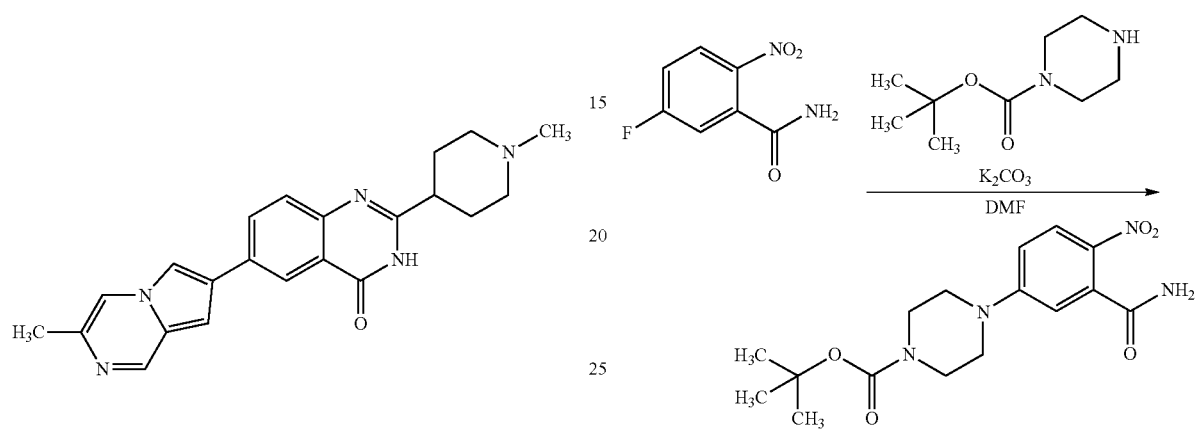

A mixture of 7-bromo-3-methylpyrrolo[1,2-α]pyrazine (200 mg), bis(pinacolato)diboron (265 mg), di chloro[1,1'-bis(diphenylphosphino)ferrocene]palladium(II) dichloromethane adduct (38.7 mg), potassium acetate (279 mg) and dimethyl sulfoxide (3.0 mL) was stirred under nitrogen atmosphere at 90° C. overnight. To the obtained mixture was added water at room temperature and the mixture was filtered. Then, the filtrate was extracted with ethyl acetate and the organic layer was washed with water and saturated brine and then dried over anhydrous magnesium sulfate. Then, the volatile components were distilled off under reduced pressure. To the remaining solid were added 6-bromo-2-(1-methylpiperidin-4-yl)quinazolin-4(3H)-one (120 mg), dichloro[1,1'-bis(diphenylphosphino)ferrocene] palladium(II) dichloromethane adduct (15.2 mg), cesium carbonate (243 mg), 1,2-dimethoxyethane (1.5 mL) and water (0.30 mL), followed by mixing, and then the mixture was stirred under microwave irradiated conditions at 100° C. for 1 hour. Water was added thereto at room temperature and the debris was removed by filtration. Then, the filtrate was extracted with ethyl acetate/THF. The organic layer was separated, washed with water and dried over anhydrous magnesium sulfate, and then the volatile components were distilled off under reduced pressure. After the remaining solid was purified by silica gel column chromatography (NH, methanol/ethyl acetate), the purified product thus obtained was washed with ethyl acetate. To the obtained solid were added dimethyl sulfoxide (1.0 mL) and ethanol (1.0 mL), followed by mixing, and then the mixture was stirred at 70° C. for 1 hour and cooled to room temperature. The solid obtained by filtration was washed with dimethyl sulfoxide/ethanol (1/1) and ethanol to obtain the title compound (47.8 mg).

¹H-NMR (300 MHz, DMSO-d₆) δ: 1.78-1.96 (6H, m), 2.17-2.21 (3H, m), 2.32 (3H, s), 2.54 (1H, s), 2.82-2.92 (2H, m), 7.24 (1H, s), 7.65 (1H, d, J=8.7 Hz), 8.05 (1H, s), 8.16 (1H, dd, J=8.7, 2.3 Hz), 8.23 (1H, d, J=0.8 Hz), 8.37 (1H, d, J=2.3 Hz), 8.76 (1H, s), 12.16 (1H, brs). MS: [M+H]⁺374.3.

Example 16

2-(4,6-Dimethylpyrazolo[1,5-α]pyrazin-2-yl)-6-(piperazin-1-yl)quinazolin-4(3H)-one dihydrochloride (A) tert-Butyl 4-(3-carbamoyl-4-nitrophenyl)piperazine-1-carboxylate

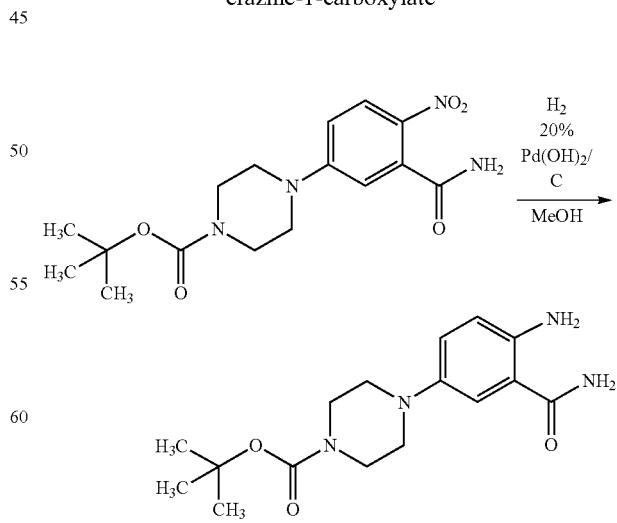

A mixture of 5-fluoro-2-nitrobenzamide (3.00 g), potassium carbonate (4.50 g), tert-butyl piperazine-1-carboxylate (3.34 g) and DMF (15 mL) was stirred at 50° C. overnight and water was added thereto at room temperature. Then, the mixture was extracted with ethyl acetate. The organic layer was separated, washed with saturated brine, and dried over anhydrous magnesium sulfate, and then the volatile components were distilled off under reduced pressure. The remaining solid was washed with diisopropyl ether to obtain the title compound (4.55 g).

¹H-NMR (400 MHz, DMSO-d₆) δ: 1.49 (9H, s), 3.44 (4H, dd, J=6.2, 4.0 Hz), 3.60 (4H, dd, J=6.4, 4.2 Hz), 5.76 (2H, brs), 6.78-6.86 (2H, m), 8.07-8.14 (1H, m).

(B) tert-Butyl 4-(4-amino-3-carbamoylphenyl)piperazine-1-carboxylate

After a mixture of tert-butyl 4-(3-carbamoyl-4-nitrophenyl)piperazine-1-carboxylate (4.5 g), palladium hydroxide-activated carbon (20% palladium) (450 mg) and methanol (90 mL) was stirred under normal pressure and hydrogen atmosphere at room temperature overnight, the catalyst was removed by filtration and the volatile components were distilled off from the filtrate under reduced pressure to obtain the title compound (3.27 g).

MS: [M+H]⁺321.2.

(C) tert-Butyl 4-[2-(4,6-dimethylpyrazolo[1,5-α]pyrazin-2-yl)-4-oxo-3,4-dihydroquinazolin-6-yl]piperazine-1-carboxylate

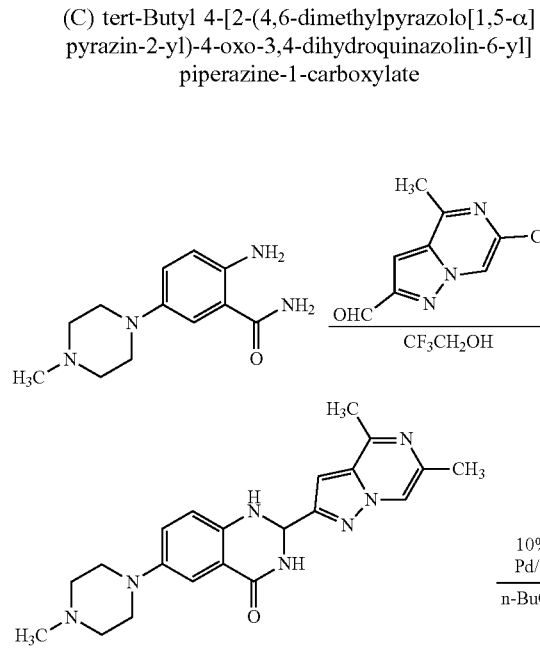

To a mixture of tert-butyl 4-(4-amino-3-carbamoylphenyl)piperazine-1-carboxylate (1.00 g) and 2,2,2-trifluoroethanol (20 mL) was added 4,6-dimethylpyrazolo[1,5-α]pyrazine-2-carbaldehyde (547 mg) at room temperature and the mixture was stirred at 80° C. overnight. Then, the volatile components were distilled off under reduced pressure. Then, 1-butanol (20 mL) was added to the remaining solid and they were mixed, and palladium-activated carbon (10% palladium) (100 mg) was added thereto. Then, the mixture was stirred at 130° C. for 4 hours. The obtained mixture was filtered through Celite to remove the catalyst and washed with THF, and then the volatile components were distilled off from the filtrate under reduced pressure. Then, the remaining solid was washed with ethanol to obtain the title compound (839 mg).

¹H-NMR (300 MHz, DMSO-d₆) δ: 1.44 (9H, s), 2.45 (3H, s), 2.73 (3H, s), 3.23-3.30 (4H, m), 3.47-3.55 (4H, m), 7.48 (1H, d, J=2.6 Hz), 7.54-7.72 (3H, m), 8.50 (1H, s), 12.10 (1H, brs). MS: [M+H]⁺476.4.

(D) 2-(4,6-Dimethylpyrazolo[1,5-α]pyrazin-2-yl)-6-(piperazin-1-yl)quinazolin-4(3H)-one dihydrochloride

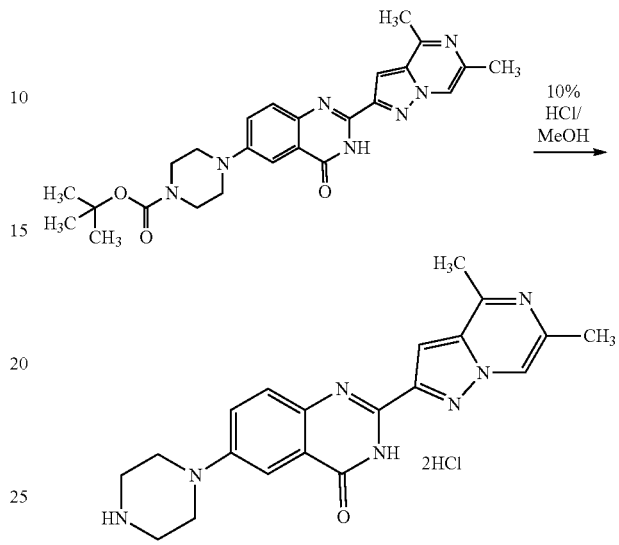

After a mixture of tert-butyl 4-[2-(4,6-dimethylpyrazolo[1,5-α]pyrazin-2-yl)-4-oxo-3,4-dihydroquinazolin-6-yl]piperazine-1-carboxylate (300 mg) and 10% hydrogen chloride/methanol (10 mL) was stirred at room temperature for 6 hours and at 60° C. for 3 hours. Then, the volatile components were distilled off under reduced pressure and the remaining solid was washed with ethanol to obtain the title compound (175 mg).

¹H-NMR (300 MHz, DMSO-d₆) δ: 2.46 (3H, s), 2.75 (3H, s), 3.28 (4H, brs), 3.53-3.56 (4H, m), 7.55 (1H, d, J=3.0 Hz), 7.60-7.76 (3H, m), 8.52 (1H, s), 9.00 (2H, brs). MS: [M-2HCl+H]⁺376.3

Example 17

6-(8-Chloro-2-methylimidazo[1,2-α]pyridin-6-yl)-2-(1-methylpiperidin-4-yl)quinazolin-4(3H)-one (A) 6-Bromo-8-chloro-2-methylimidazo[1,2-α]pyridine

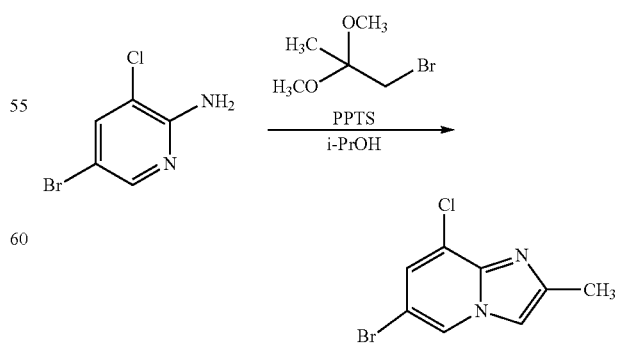

After a mixture of 5-bromo-3-chloropyridin-2-amine (1.5 g), 1-bromo-2,2-dimethoxypropane (2.15 mL), pyridinium p-toluenesulfonate (363 mg) and 2-propanol (20 mL) was heated under reflux overnight and a saturated aqueous potassium hydrogen carbonate solution was added thereto at room temperature, the mixture was extracted with ethyl acetate. The organic layer was washed with saturated brine and dried over anhydrous magnesium sulfate, and then the volatile components were distilled off under reduced pressure. After the remaining solid was purified by silica gel column chromatography (NH, ethyl acetate/hexane), the obtained solid was washed with diisopropyl ether to obtain the title compound (1.23 g).

$^1$H-NMR (300 MHz, DMSO-d$_6$) δ: 2.35 (3H, d, J=0.8 Hz), 7.59 (1H, d, J=1.5 Hz), 7.78 (1H, d, J=0.8 Hz), 8.84 (1H, d, J=1.9 Hz). MS: [M+H]$^+$247.1.

(B) tert-Butyl 4-(6-bromo-4-oxo-3,4-dihydroquinazolin-2-yl)piperidine-1-carboxylate

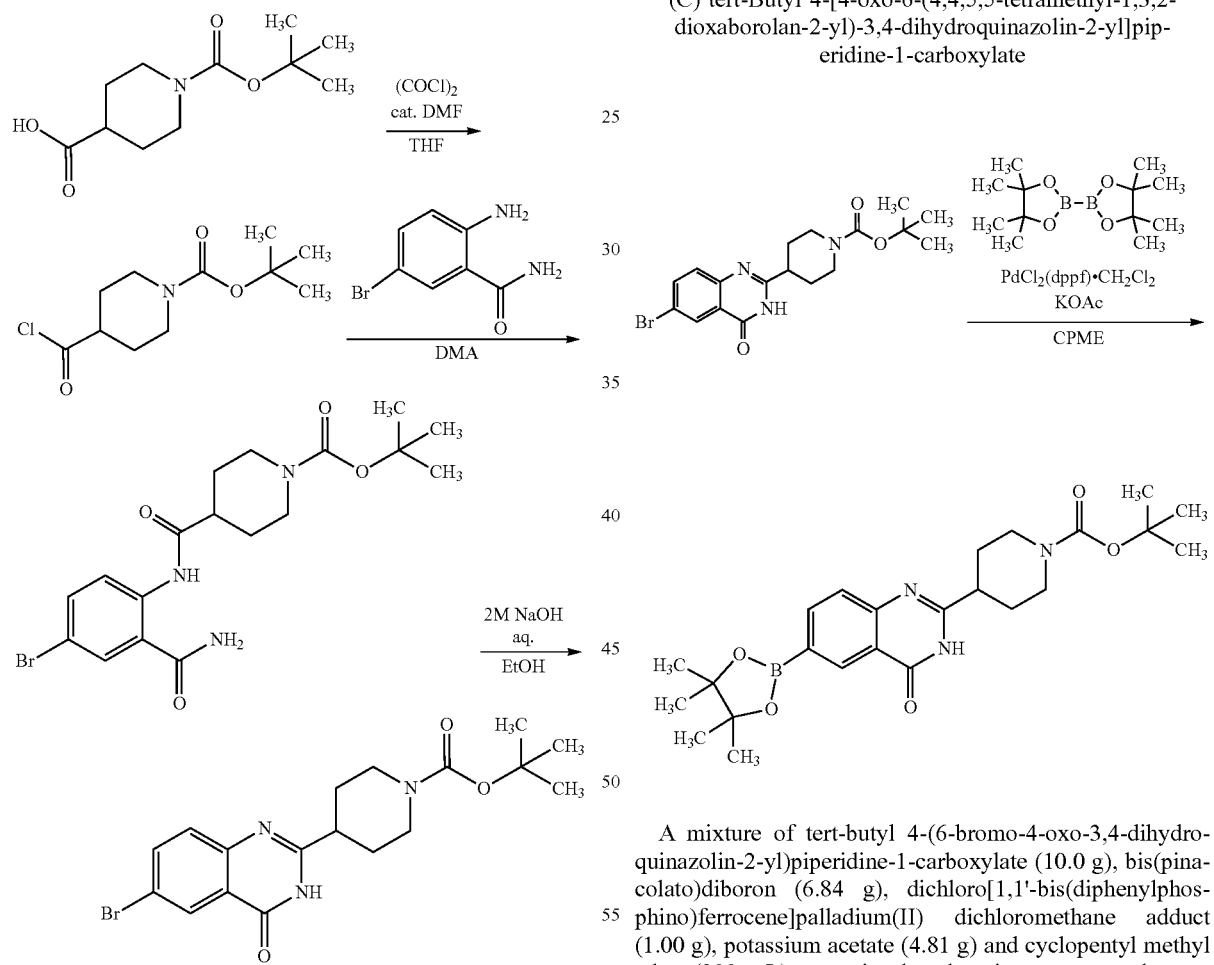

To a mixture of 1-(tert-butoxycarbonyl)piperidine-4-carboxylic acid (25.6 g), oxalyl chloride (24.4 mL) and THF (200 mL) was added DMF (0.072 mL) at room temperature and the mixture was stirred at room temperature for 2 hours. Then, the volatile components were distilled off under reduced pressure. To the remaining solid was added DMA (60 mL) and a mixture of 2-amino-5-bromobenzamide (20.0 g) and DMA (60 mL) was added thereto. Then, the mixture was stirred at room temperature for 1 hour. A saturated aqueous sodium hydrogen carbonate solution (200 mL) was further added thereto at room temperature and the mixture was extracted with ethyl acetate. The organic layer was washed with saturated brine and dried over anhydrous magnesium sulfate, and then the volatile components were distilled off under reduced pressure. To the remaining solid was added ethanol (300 mL), followed by mixing, and a 2.0 M aqueous sodium hydroxide solution (93 mL) was further added thereto at room temperature. Then, the mixture was stirred for 1 hour and neutralized with 2.0 M hydrochloric acid (90 mL). The precipitate was isolated by filtration and washed with ethanol/water (1/1, 120 mL) to obtain the title compound (32.9 g).

$^1$H-NMR (300 MHz, DMSO-d$_6$) δ: 1.41 (9H, s), 1.55-1.73 (2H, m), 1.89 (2H, d, J=9.8 Hz), 2.70-2.90 (3H, m), 4.05 (2H, d, J=12.8 Hz), 7.56 (1H, d, J=8.7 Hz), 7.92 (1H, dd, J=8.7, 2.6 Hz), 8.15 (1H, d, J=2.3 Hz), 12.37 (1H, brs).

(C) tert-Butyl 4-[4-oxo-6-(4,4,5,5-tetramethyl-1,3,2-dioxaborolan-2-yl)-3,4-dihydroquinazolin-2-yl]piperidine-1-carboxylate

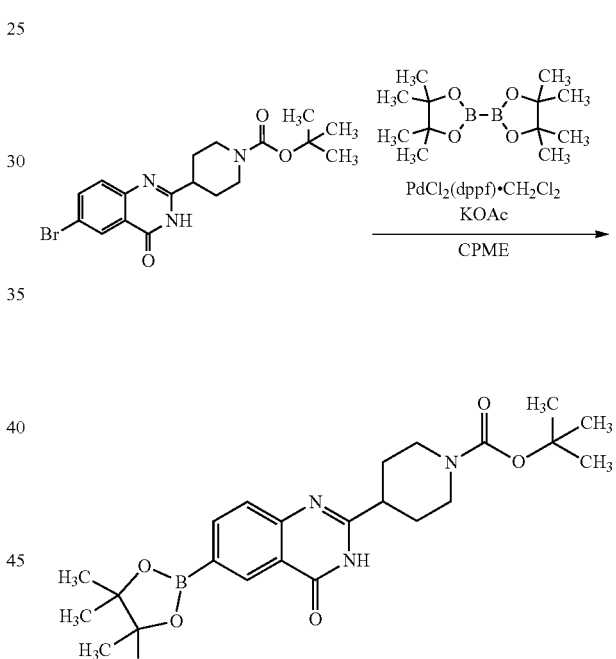

A mixture of tert-butyl 4-(6-bromo-4-oxo-3,4-dihydroquinazolin-2-yl)piperidine-1-carboxylate (10.0 g), bis(pinacolato)diboron (6.84 g), dichloro[1,1'-bis(diphenylphosphino)ferrocene]palladium(II) dichloromethane adduct (1.00 g), potassium acetate (4.81 g) and cyclopentyl methyl ether (200 mL) was stirred under nitrogen atmosphere at 120° C. overnight and cooled to room temperature, and then the mixture was purified by silica gel column chromatography (ethyl acetate). The obtained solid was washed with water to obtain the title compound (5.4 g).

$^1$H-NMR (300 MHz, DMSO-d$_6$) δ: 1.32 (12H, s), 1.42 (9H, s), 1.57-1.73 (2H, m), 1.89 (2H, d, J=11.0 Hz), 2.77 (3H, ddd, J=11.4, 7.8, 3.8 Hz), 4.05 (2H, d, J=12.8 Hz), 7.55 (1H, d, J=7.9 Hz), 7.95 (1H, dd, J=7.9, 1.5 Hz), 8.41 (1H, d, J=1.1 Hz). MS: [M+H]$^+$456.4.

(D) tert-Butyl 4-[6-(8-chloro-2-methylimidazo[1,2-α]pyridin-6-yl)-4-oxo-3,4-dihydroquinazolin-2-yl]piperidine-1-carboxylate

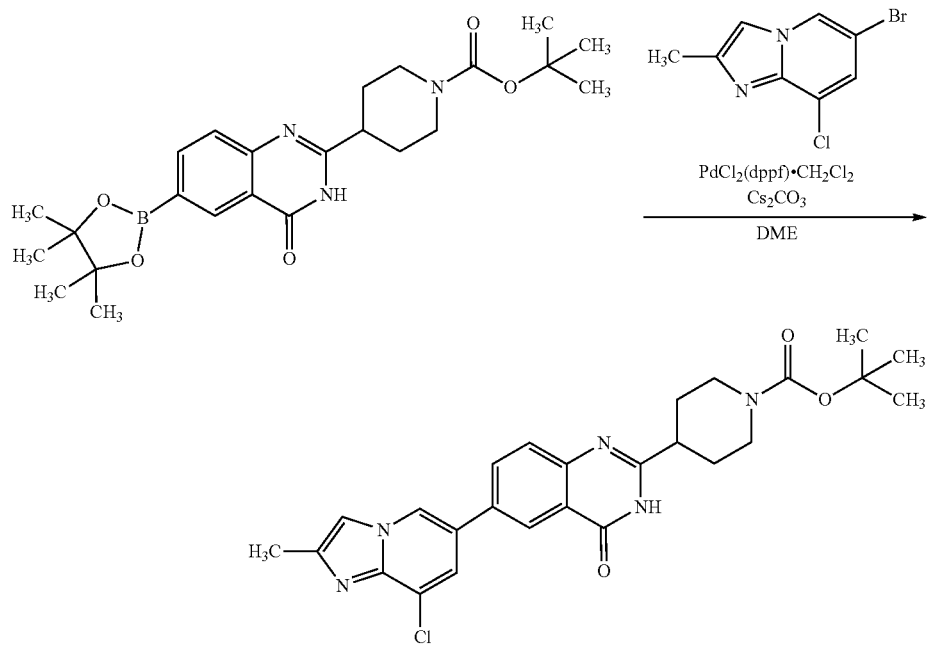

A mixture of tert-butyl 4-[4-oxo-6-(4,4,5,5-tetramethyl-1,3,2-dioxaborolan-2-yl)-3,4-dihydroquinazolin-2-yl]piperidine-1-carboxylate (400 mg), 6-bromo-8-chloro-2-methylimidazo[1,2-α]pyridine (216 mg), dichloro[1,1'-bis(diphenylphosphino)ferrocene]palladium(II) dichloromethane adduct (35.9 mg), cesium carbonate (572 mg) and 1,2-dimethoxyethane (4 mL) was stirred under microwave irradiated conditions at 130° C. for 30 minutes and purified by silica gel column chromatography (NH, methanol/ethyl acetate). The obtained solid was washed with ethyl acetate to obtain the title compound (152 mg).

$^1$H-NMR (300 MHz, DMSO-d$_6$) δ: 1.42 (9H, s), 1.59-1.77 (2H, m), 1.92 (2H, d, J=11.7 Hz), 2.39 (3H, s), 2.69-2.91 (3H, m), 4.00-4.13 (2H, m), 7.71 (1H, d, J=8.7 Hz), 7.82-7.88 (2H, m), 8.15 (1H, dd, J=8.7, 2.3 Hz), 8.37 (1H, d, J=2.3 Hz), 9.04 (1H, d, J=1.9 Hz), 12.29 (1H, s). MS: [M+H]$^+$ 494.3.

(E) 6-(8-Chloro-2-methylimidazo[1,2-α]pyridin-6-yl)-2-(1-methylpiperidin-4-yl)quinazolin-4(3H)-one

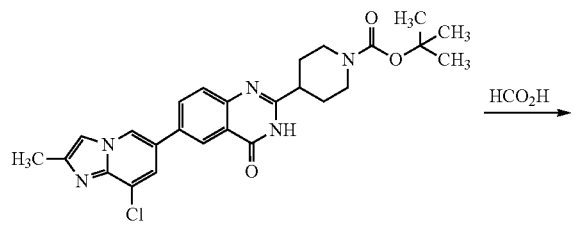

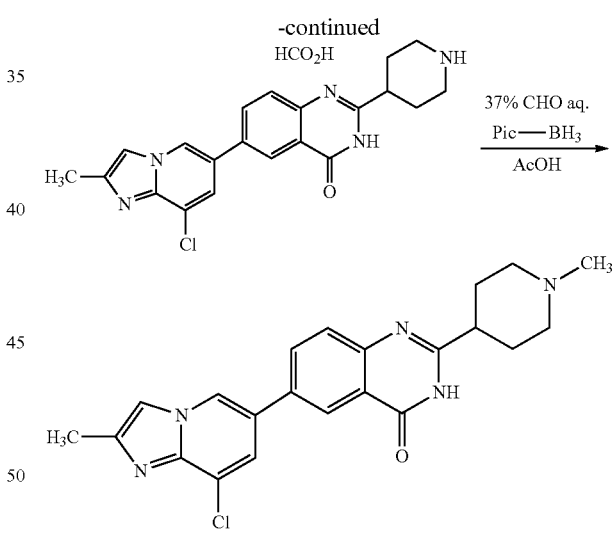

After a mixture of tert-butyl 4-[6-(8-chloro-2-methylimidazo[1,2-α]pyridin-6-yl)-4-oxo-3,4-dihydroquinazolin-2-yl]piperidine-1-carboxylate (150 mg) and formic acid (2 mL) was stirred at 60° C. for 10 minutes, the volatile components were distilled off under reduced pressure. To a mixture of the remaining solid, methanol (1 mL) and acetic acid (0.5 mL) were added a 37% aqueous formaldehyde solution (0.099 mL) and borane-2-methylpyridine complex (81 mg), and the mixture was stirred at room temperature for 1 hour. Then, the volatile components were distilled off under reduced pressure. After the remaining solid was purified by silica gel column chromatography (NH, methanol/ethyl acetate), the obtained solid was washed with diisopropyl ether to obtain the title compound (94 mg).

$^1$H-NMR (300 MHz, DMSO-$d_6$) δ: 1.78-1.97 (6H, m), 2.19 (3H, s), 2.39 (3H, s), 2.53-2.60 (1H, m), 2.87 (2H, d, J=10.6 Hz), 7.71 (1H, d, J=8.3 Hz), 7.84 (2H, s), 8.14 (1H, dd, J=8.5, 2.5 Hz), 8.36 (1H, d, J=2.3 Hz), 9.03 (1H, d, J=1.5 Hz), 12.23 (1H, brs). MS: [M+H]$^+$408.3.

Example 18

6-(4-Fluoro-2-methyl-1,3-benzoxazol-6-yl)-2-(1-methylpiperidin-4-yl)quinazolin-4(3H)-one (A) 6-Bromo-4-fluoro-2-methyl-1,3-benzoxazole

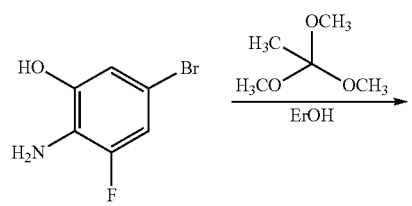

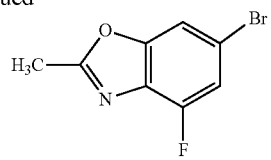

A mixture of 2-amino-5-bromo-3-fluorophenol (6.8 g), 1,1,1-trimethoxyethane (13.9 g) and ethanol (60 mL) was heated under reflux overnight. After the volatile components were distilled off from the mixture under reduced pressure, the remaining solid was purified by silica gel column chromatography (ethyl acetate/hexane) to obtain the title compound (5.9 g).

$^1$H-NMR (300 MHz, DMSO-$d_6$) δ: 2.63 (3H, s), 7.55 (1H, dd, J=9.6, 1.7 Hz), 7.91 (1H, d, J=1.5 Hz). MS: [M+H]$^+$ 230.1.

(B) tert-Butyl 4-[6-(4-fluoro-2-methyl-1,3-benzoxazol-6-yl)-4-oxo-3,4-dihydroquinazolin-2-yl]piperidine-1-car

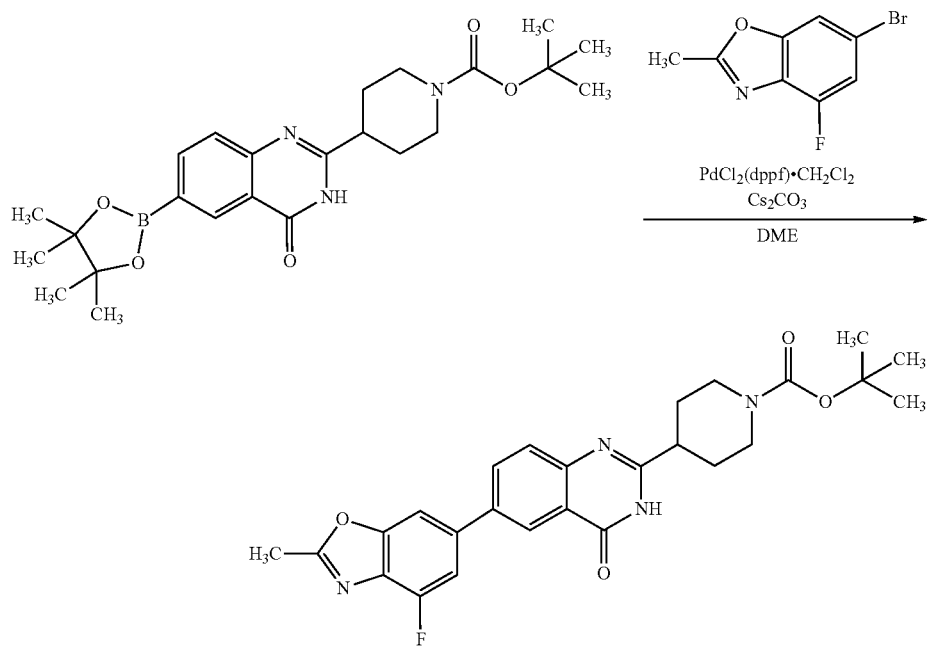

A mixture of tert-butyl 4-[4-oxo-6-(4,4,5,5-tetramethyl-1,3,2-dioxaborolan-2-yl)-3,4-dihydroquinazolin-2-yl]piperidine-1-carboxylate (400 mg), 6-bromo-4-fluoro-2-methyl-1,3-benzoxazole (202 mg), dichloro[1,1'-bis(diphenylphosphino)ferrocene]palladium(II) dichloromethane adduct (35.9 mg), cesium carbonate (572 mg) and 1,2-dimethoxyethane (4 mL) was stirred under microwave irradiated conditions at 130° C. for 30 minutes and purified by silica gel column chromatography (NH, ethyl acetate). The obtained solid was washed with diisopropyl ether to obtain the title compound (180 mg).

$^1$H-NMR (300 MHz, DMSO-$d_6$) δ: 1.42 (9H, s), 1.58-1.77 (2H, m), 1.92 (2H, d, J=10.6 Hz), 2.67 (3H, s), 2.73-2.91 (3H, m), 4.07 (2H, d, J=14.0 Hz), 7.63-7.72 (2H, m), 7.99 (1H, d, J=1.5 Hz), 8.18 (1H, dd, J=8.5, 2.5 Hz), 8.38 (1H, d, J=2.3 Hz), 12.29 (1H, brs). MS: [M+H]$^+$479.3.

(C) 6-(4-Fluoro-2-methyl-1,3-benzoxazol-6-yl)-2-(1-methylpiperidin-4-yl)quinazolin-4(3H)-one

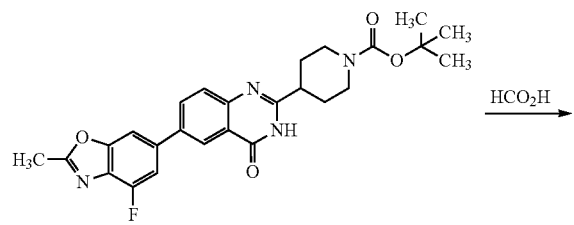

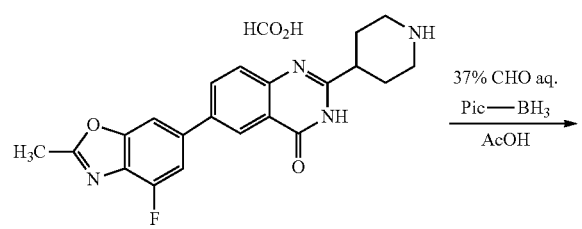

After a mixture of tert-butyl 4-[6-(4-fluoro-2-methyl-1,3-benzoxazol-6-yl)-4-oxo-3,4-dihydroquinazolin-2-yl]piperidine-1-carboxylate (180 mg) and formic acid (2 mL) was stirred at 60° C. for 10 minutes, the volatile components were distilled off under reduced pressure. To a mixture of the remaining solid, methanol (1 mL) and acetic acid (0.5 mL) were added a 37% aqueous formaldehyde solution (0.122 mL) and borane-2-methylpyridine complex (101 mg). Then, the mixture was stirred at room temperature for 1 hour and the volatile components were distilled off under reduced pressure. After the remaining solid was purified by silica gel column chromatography (NH, methanol/ethyl acetate), the obtained solid was washed with diisopropyl ether to obtain the title compound (70 mg).

$^1$H-NMR (300 MHz, DMSO-$d_6$) δ: 1.82-1.96 (6H, m), 2.19 (3H, s), 2.67 (3H, s), 2.85 (2H, brs), 7.70 (2H, d, J=8.7 Hz), 7.99 (1H, d, J=1.1 Hz), 8.17 (1H, dd, J=8.7, 2.3 Hz), 8.37 (1H, d, J=2.3 Hz), 12.24 (1H, brs). MS: [M+H]$^+$393.3.

Working Example 19

8-Methyl-6-(2-methylimidazo[1,2-α]pyridin-6-yl)-2-(1-methylpiperidin-4-yl)quinazolin-4(3H)-one (A) tert-Butyl 4-(6-bromo-8-methyl-4-oxo-3,4-dihydroquinazolin-2-yl)piperidine-1-carboxylate

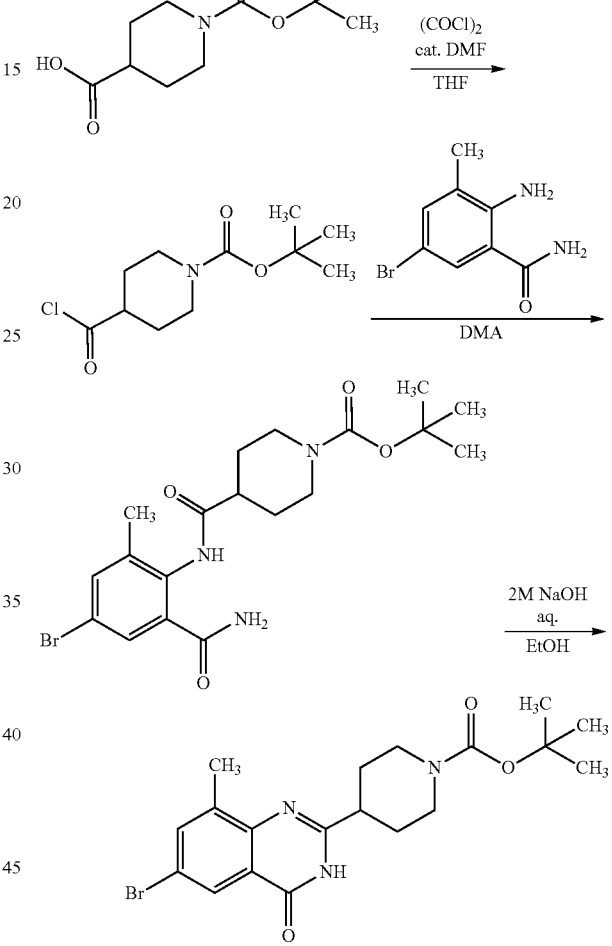

To a mixture of 1-(tert-butoxycarbonyl)piperidine-4-carboxylic acid (270 mg), oxalyl chloride (0.258 mL) and THF (2 mL) was added DMF (catalytic amount) and the mixture was stirred at room temperature for 1 hour. Then, the volatile components were distilled off under reduced pressure. To the remaining solid were sequentially added DMA (2 mL) and 2-amino-5-bromo-3-methylbenzamide (225 mg), and then the mixture was stirred at room temperature for 10 minutes. Then, a saturated aqueous sodium hydrogen carbonate solution was further added thereto and they were mixed, and the mixture was extracted with ethyl acetate. The organic layer was washed with saturated brine and dried over anhydrous magnesium sulfate, and then the volatile components were distilled off under reduced pressure. To the remaining solid were sequentially added ethanol (10 mL) and a 2.0 M aqueous sodium hydroxide solution (0.982 mL) and then the mixture was stirred at room temperature for 1 hour and neutralized with 2.0 M hydrochloric acid (0.98 mL) and water (5 mL). The precipitate was isolated by filtration and washed with ethanol/water (1/1, 30 mL) to obtain the title compound (341 mg).

¹H-NMR (300 MHz, DMSO-d₆) δ: 1.41 (9H, s), 1.56-1.78 (2H, m), 1.90 (2H, d, J=11.0 Hz), 2.50 (3H, quin, J=1.8 Hz), 2.68-2.95 (3H, m), 4.03 (2H, d, J=13.2 Hz), 7.83 (1H, dd, J=2.3, 0.8 Hz), 7.99 (1H, d, J=3.0 Hz), 12.33 (1H, s). MS: [M+H]⁺424.2.

(B) tert-Butyl 4-[8-methyl-6-(2-methylimidazo[1,2-α]pyridin-6-yl)-4-oxo-3,4-dihydroquinazolin-2-yl]piperidin e-1-carboxylate (251 mg), dichloro[1,1'-bis(diphenylphosphino)ferrocene]palladium(II) dichloromethane adduct (33.1 mg), cesium carbonate (528 mg), 1,2-dimethoxyethane (10 mL) and water (2 mL), and then the mixture was stirred under microwave irradiated conditions at 130° C. for 30 minutes and purified by silica gel column chromatography (NH, methanol/ethyl acetate). Then, the obtained solid was recrystallized from ethyl acetate/diisopropyl ether (2/1) to obtain the title compound (233 mg).

MS: [M+H]⁺474.4.

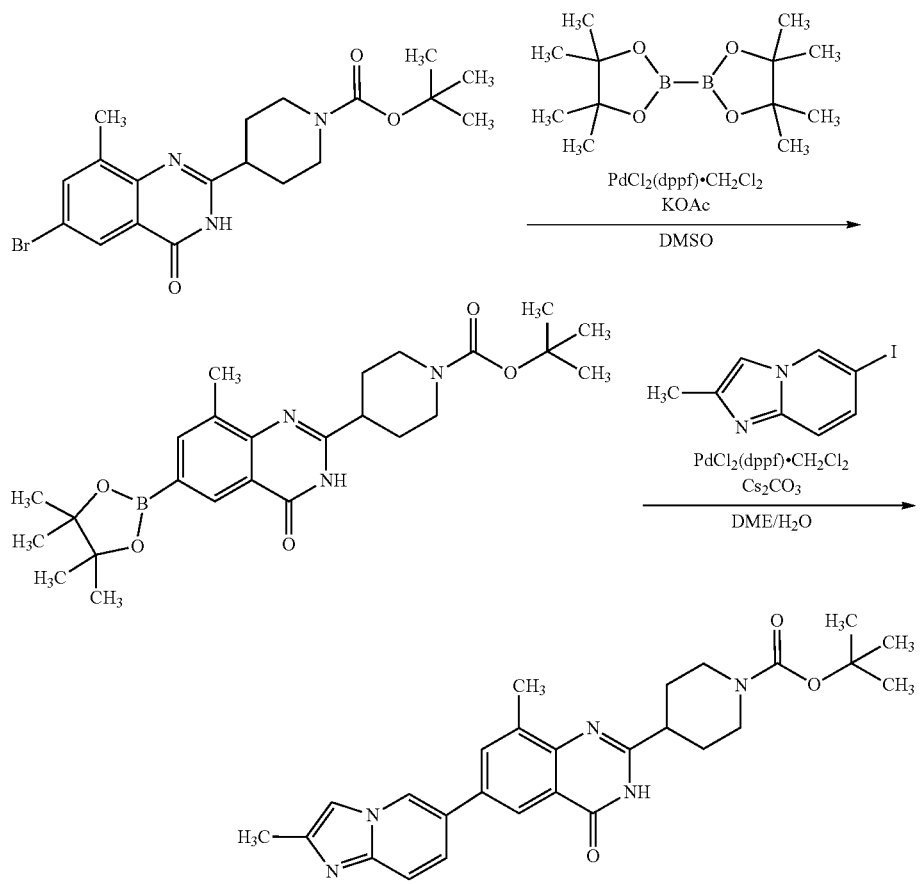

After a mixture of tert-butyl 4-(6-bromo-8-methyl-4-oxo-3,4-dihydroquinazolin-2-yl)piperidine-1-carboxylate (341 mg), bi s(pinacolato)diboron (225 mg), di chloro[1,1'-bi s(diphenylphosphino)ferrocene]palladium(II) dichloromethane adduct (32.9 mg), potassium acetate (158 mg) and dimethyl sulfoxide (4 mL) was stirred under microwave irradiated conditions at 130° C. for 30 minutes and cooled to room temperature, water and ethyl acetate were added thereto and the debris was removed by filtration. The filtrate was extracted with ethyl acetate and the organic layer was washed with water and saturated brine and then purified by silica gel column chromatography (ethyl acetate) to give a crude product (480 mg). To the obtained crude product (380 mg) were added 6-iodo-2-methylimidazo[1,2-α]pyridine (C) 8-Methyl-6-(2-methylimidazo[1,2-α]pyridin-6-yl)-2-(1-methylpiperidin-4-yl)quinazolin-4(3H)-one

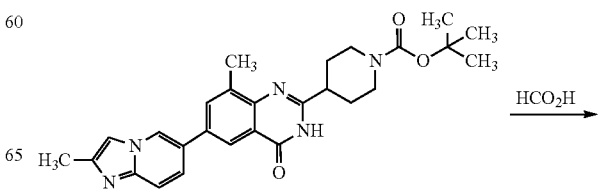

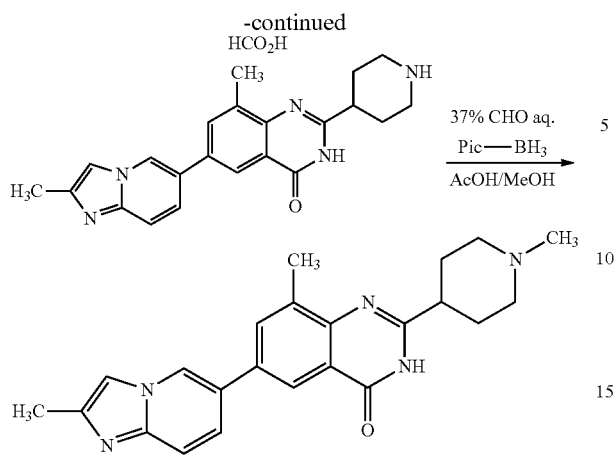

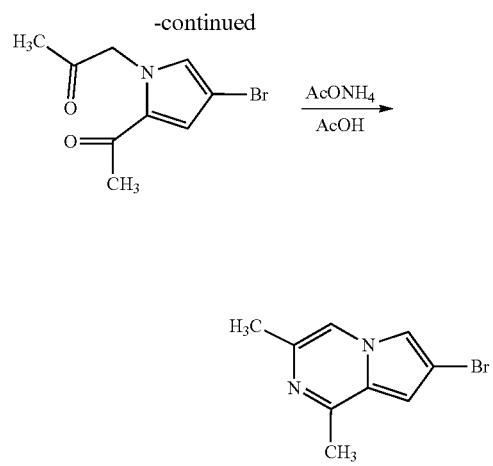

After a mixture of tert-butyl 4-[8-methyl-6-(2-methylimidazo[1,2-α]pyridin-6-yl)-4-oxo-3,4-dihydroquinazolin-2-yl]piperidin e-1-carboxylate (233 mg) and formic acid (2 mL) was stirred at 70° C. for 10 minutes, the volatile components were distilled off under reduced pressure. To the remaining solid were added methanol (1.5 mL) and acetic acid (0.1 mL), and then a 37% aqueous formaldehyde solution (0.120 mL) and borane-2-methylpyridine complex (79 mg) were further added thereto at room temperature. Then, the mixture was stirred at room temperature for 30 minutes and the volatile components were distilled off under reduced pressure. After the remaining solid was purified by silica gel column chromatography (NH, methanol/ethyl acetate), the obtained solid was recrystallized from ethyl acetate to obtain the title compound (137 mg).

$^1$H-NMR (300 MHz, DMSO-$d_6$) δ: 1.80-2.00 (6H, m), 2.19 (3H, s), 2.35 (3H, s), 2.52-2.64 (4H, m), 2.80-2.95 (2H, m), 7.49-7.55 (1H, m), 7.56-7.64 (1H, m), 7.72 (1H, s), 8.02 (1H, d, J=1.5 Hz), 8.19 (1H, d, J=2.3 Hz), 8.97 (1H, d, J=0.8 Hz), 12.19 (1H, s). MS: [M+H]$^+$388.3.

Example 20

6-(1,3-Dimethylpyrrolo[1,2-α]pyrazin-7-yl)-2-(1-methylpiperidin-4-yl)quinazolin-4(3H)-one (A) 7-Bromo-1,3-dimethyl pyrrolo[1,2-α]pyrazine

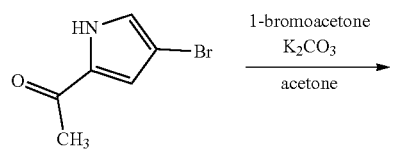

To a mixture of 1-(4-bromo-1H-pyrrol-2-yl)ethanone (2.90 g), potassium carbonate (3.20 g) and acetonitrile (50 mL) was added 1-chloropropan-2-one (1.84 mL) at room temperature and the mixture was stirred under nitrogen atmosphere at room temperature overnight while protected from light. Then, the volatile components were distilled off under reduced pressure. To the obtained solid was added water and the mixture was extracted with ethyl acetate. Then, the organic layer was washed with saturated brine and purified by silica gel column chromatography (ethyl acetate) to obtain a crude product. To the obtained crude product were added acetic acid (50 mL) and ammonium acetate (23.8 g) at room temperature and the mixture was stirred at 120° C. for 4 hours. After the volatile components were distilled off under reduced pressure, a 1.0 M aqueous sodium hydroxide solution and ethyl acetate were added to the remaining solid and the debris was removed by filtration. The filtrate was extracted with ethyl acetate and the organic layer was washed with saturated brine and then dried over anhydrous magnesium sulfate. Then, the volatile components were distilled off under reduced pressure. The remaining solid was purified by silica gel column chromatography (ethyl acetate/hexane) to obtain the title compound (2.29 g).

$^1$H-NMR (300 MHz, DMSO-$d_6$) δ: 2.26 (3H, d, J=1.1 Hz), 2.48-2.54 (3H, m), 6.92 (1H, t, J=1.1 Hz), 7.76 (1H, d, J=1.5 Hz), 7.91 (1H, s). MS: [M+H]$^+$225.2.

(B) tert-Butyl 4-[6-(1,3-dimethylpyrrolo[1,2-α]pyrazin-7-yl)-4-oxo-3,4-dihydroquinazolin-2-yl]piperidine-1-car

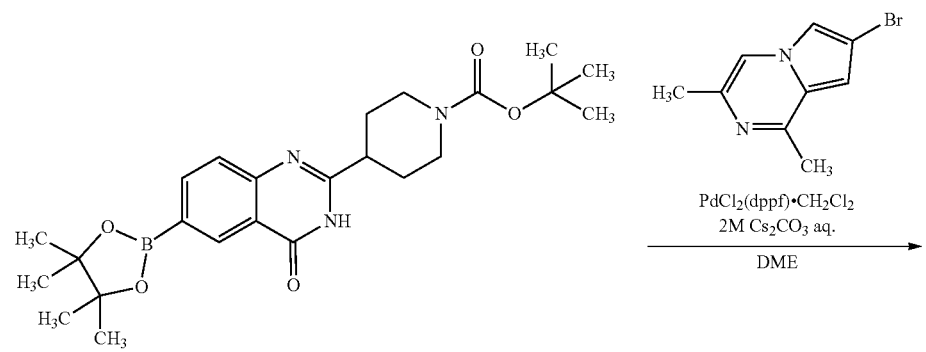

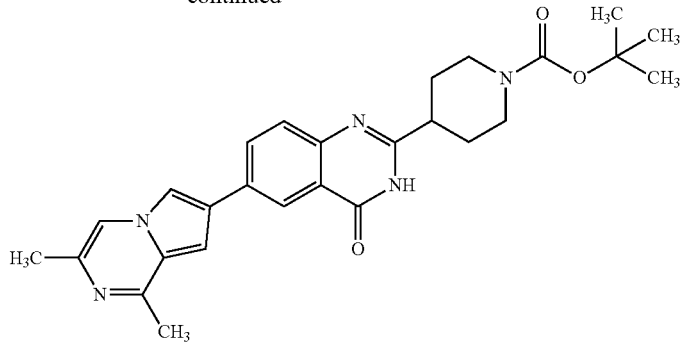

After a mixture of tert-butyl 4-[4-oxo-6-(4,4,5,5-tetramethyl-1,3,2-dioxaborolan-2-yl)-3,4-dihydroquinazolin-2-yl]piperidine-1-carboxylate (346 mg), 7-bromo-1,3-dimethylpyrrolo[1,2-α]pyrazine (205 mg), dichloro[1,1'-bis(diphenylphosphino)ferrocene]palladium(II) dichloromethane adduct (31.1 mg), a 2.0 M aqueous cesium carbonate solution (0.761 mL) and 1,2-dimethoxyethane (4 mL) was stirred under microwave irradiated conditions at 130° C. for 30 minutes and purified by silica gel column chromatography (NH, ethyl acetate/methanol), the obtained solid was washed with ethyl acetate/diisopropyl ether (1/1) to obtain the title compound (168 mg).

MS: [M+H]⁺474.4.

(C) 6-(1,3-Dimethylpyrrolo[1,2-α]pyrazin-7-yl)-2-(1-methylpiperidin-4-yl)quinazolin-4(3H)-one

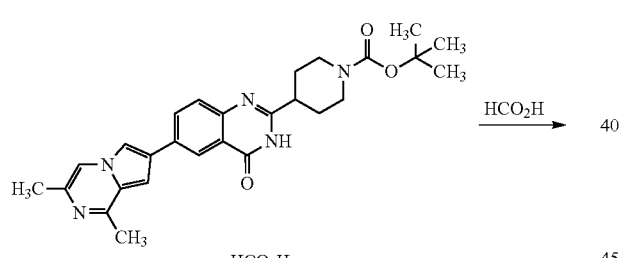

After a mixture of tert-butyl 4-[6-(1,3-dimethylpyrrolo[1,2-α]pyrazin-7-yl)-4-oxo-3,4-dihydroquinazolin-2-yl]piperidine-1-car boxylate (168 mg) and formic acid (3 mL) was stirred at 70° C. for 10 minutes, the volatile components were distilled off under reduced pressure. To the remaining solid were added methanol (3 mL) and acetic acid (0.2 mL), followed by mixing, and then a 37% aqueous formaldehyde solution (0.086 mL) and borane-2-methylpyridine complex (56.8 mg) were added thereto. Then, the mixture was stirred at room temperature for 30 minutes and the volatile components were distilled off under reduced pressure. After the remaining solid was purified by silica gel column chromatography (NH, methanol/ethyl acetate), the obtained solid was recrystallized from ethyl acetate to obtain the title compound (42.6 mg).

¹H-NMR (300 MHz, DMSO-d₆) δ: 1.76-1.98 (6H, m), 2.19 (3H, s), 2.28 (3H, s), 2.50 (1H, dt, J=3.7, 1.7 Hz), 2.59 (3H, s), 2.87 (2H, d, J=11.0 Hz), 7.32 (1H, s), 7.64 (1H, d, J=8.3 Hz), 7.91 (1H, s), 8.12-8.23 (2H, m), 8.39 (1H, d, J=2.3 Hz), 12.14 (1H, brs). MS: [M+H]⁺388.3.

Working Example 21

2-(4,6-Dimethylpyrazolo[1,5-α]pyrazin-2-yl)-8-methyl-6-(4-methylpiperazin-1-yl)quinazolin-4(3H)-one (A) 5-Fluoro-3-methyl-2-nitrobenzamide

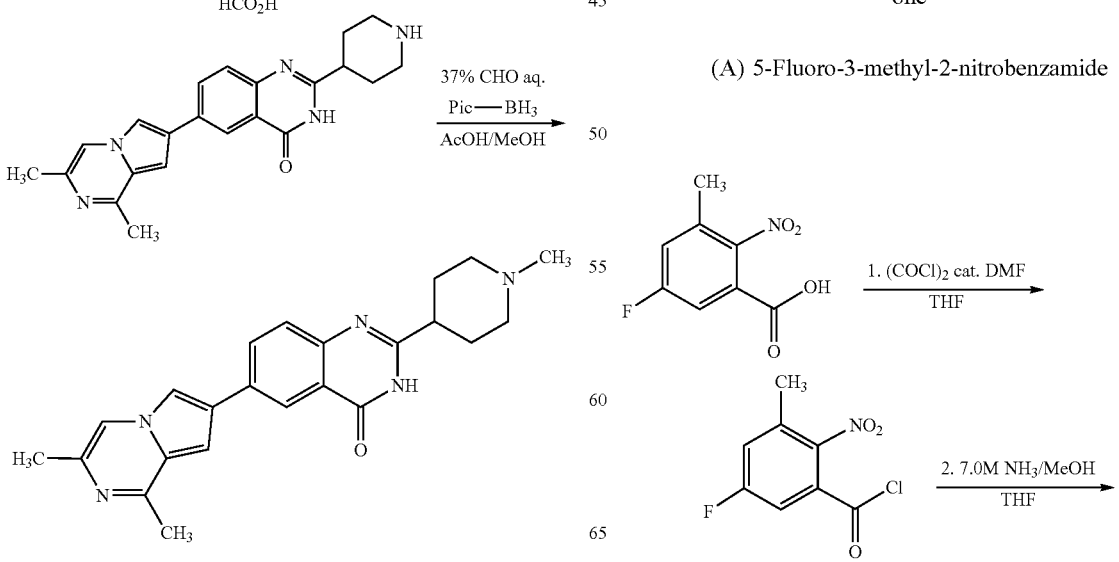

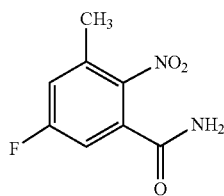

To a mixture of 5-fluoro-3-methyl-2-nitrobenzoic acid (2.0 g) and THF (50 mL) were added dropwise oxalyl chloride (1.38 mL) and DMF (0.078 mL) at room temperature, and then the reaction mixture was stirred under nitrogen atmosphere at room temperature for 1 hour. Then, the volatile components were distilled off under reduced pressure. To the remaining solid was added THF (50 mL), followed by mixing, and a 7.0 M ammonia/methanol solution (2.87 mL) was added dropwise thereto with ice cooling. Then, the obtained mixture was stirred under nitrogen atmosphere at room temperature for 2 hours. The volatile components were distilled off under reduced pressure and the remaining solid was purified by silica gel column chromatography (NH, hexane/ethyl acetate) to obtain the title compound (1.18 g).

$^1$H-NMR (300 MHz, DMSO-$d_6$) δ: 2.30 (3H, s), 7.46 (1H, dd, J=8.3, 2.5 Hz), 7.51 (1H, dd, J=8.9, 2.5 Hz), 7.80 (1H, brs), 8.23 (1H, brs).

(B) 3-Methyl-5-(4-methylpiperazin-1-yl)-2-nitrobenzamide

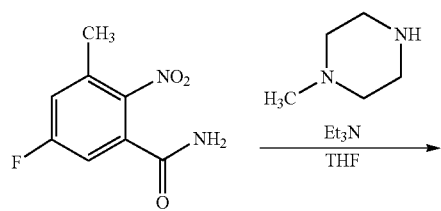

To a mixture of 5-fluoro-3-methyl-2-nitrobenzamide (1.18 g) and THF (50 mL) were added 1-methylpiperazine (0.701 mL) and triethylamine (1.00 mL) at room temperature, and then the mixture was stirred at 80° C. overnight. Then, the obtained mixture was purified by silica gel column chromatography (NH, hexane/ethyl acetate) to obtain the title compound (740 mg).

$^1$H-NMR (300 MHz, DMSO-$d_6$) δ: 2.22 (3H, s), 2.25-2.32 (3H, m), 2.38-2.47 (4H, m), 3.34 (4H, d, J=4.9 Hz), 6.87-6.97 (2H, m), 7.51 (1H, s), 7.99 (1H, brs). MS: [M+H]$^+$ 279.3.

(C) 2-Aamino-3-methyl-5-(4-methylpiperazin-1-yl)benzamide

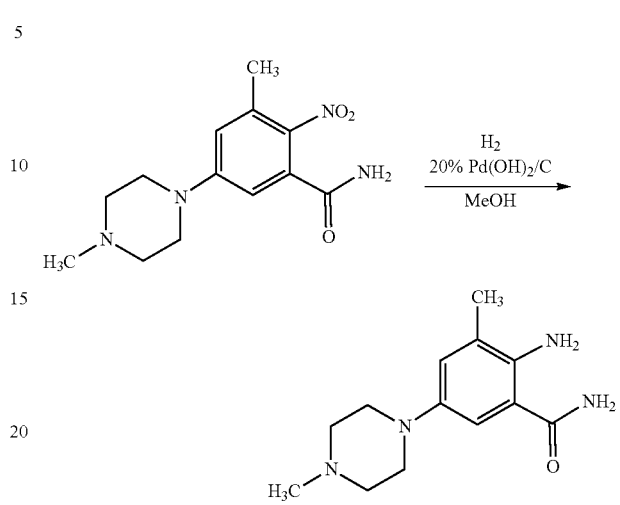

After a mixture of 3-methyl-5-(4-methylpiperazin-1-yl)-2-nitrobenzamide (740 mg), palladium hydroxide-activated carbon (20% palladium) (74 mg) and methanol (20 mL) was stirred under normal pressure and hydrogen atmosphere at room temperature overnight, the catalyst was removed by filtration and the volatile components were distilled off from the filtrate under reduced pressure. Then, the remaining solid was washed with diisopropyl ether to obtain the title compound (570 mg).

$^1$H-NMR (300 MHz, DMSO-$d_6$) δ: 2.06 (3H, s), 2.20 (3H, s), 2.37-2.47 (4H, m), 2.90-3.01 (4H, m), 5.88 (2H, s), 6.85 (1H, d, J=2.3 Hz), 6.94 (1H, d, J=2.3 Hz), 7.00 (1H, brs), 7.73 (1H, brs). MS: [M+H]$^+$249.3.

(D) 2-(4,6-Dimethylpyrazolo[1,5-α]pyrazin-2-yl)-8-methyl-6-(4-methylpiperazin-1-yl)quinazolin-4(3H)-one

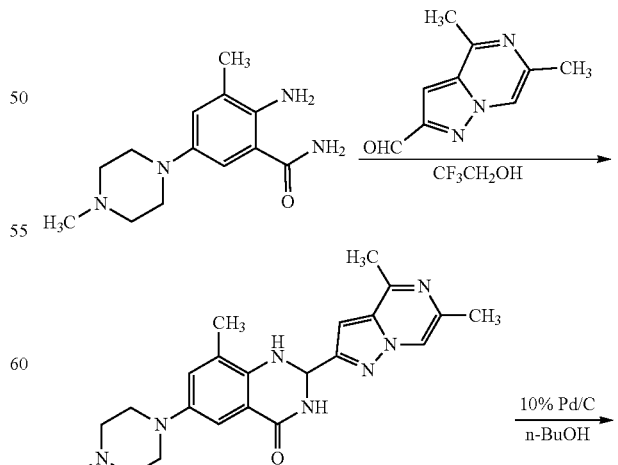

-continued

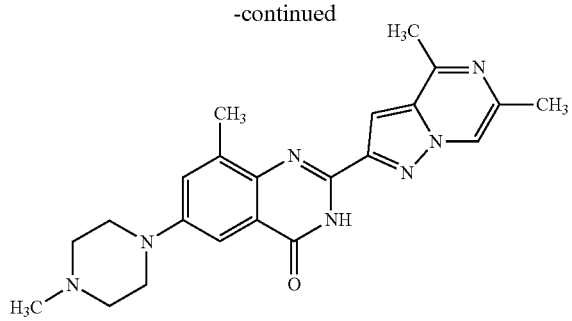

To a mixture of 2-amino-3-methyl-5-(4-methylpiperazin-1-yl)benzamide (200 mg) and 2,2,2-trifluoroethanol (5 mL) was added 4,6-dimethylpyrazolo[1,5-α]pyrazine-2-carbaldehyde (141 mg) at room temperature and the mixture was stirred at 80° C. overnight. Then, the volatile components were distilled off under reduced pressure. To the remaining solid was added 1-butanol (5 mL), followed by mixing, and palladium-activated carbon (10% palladium) (40 mg) was further added thereto. Then, the resulting mixture was stirred at 130° C. overnight and the catalyst was removed by filtration. Then, the volatile components were distilled off from the filtrate under reduced pressure. The remaining solid was washed with ethanol and recrystallized from 1-butanol/ethyl acetate to obtain the title compound (18.8 mg).

$^1$H-NMR (300 MHz, DMSO-$d_6$) δ:2.24 (3H, s), 2.45 (3H, s), 2.46-2.49 (4H, m), 2.60 (3H), s), 2. 74 (3H, s), 3. 23-3. 29 (4H, m), 7.3 1 (1H, d, J=2.6 Hz), 7.47 (1H, d, J=2.3 Hz), 7. 60 (1H, d, J=O. 8 Hz), 8. 50 (1H, s), 11.99 (1H, brs). MS: [M+H]$^+$404.4.

Working Example 22

6-(8-methoxy-2-methylimidazo[1,2-a]pyridine-6-yl)-2-(1-methylpiperidine-4-yl) kinazoline-4 (3H)-one (A) 6-bromo-8-methoxy-2-methylimidazo[1,2-a]pyridine

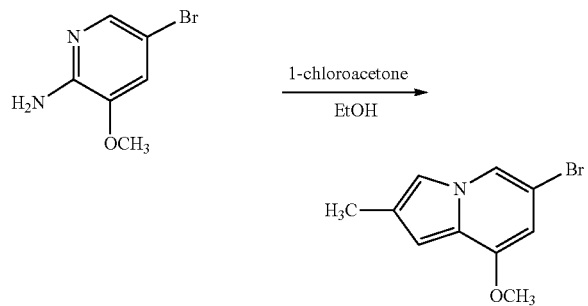

A mixture of 4-bromo-2-methoxy-2-aminopyridine (2.0 g), chloroacetone (2.3 7 ml) and ethanol (15 ml) was heated to reflux for 48 hours, and then the volatile components were distilled off under reduced pressure. Ethyl acetate and saturated aqueous sodium hydrogen carbonate solution were added to the remaining solid. After separating the organic layer, dehydrating it with anhydrous sodium sulfate, and distilling off volatile components under reduced pressure, the remaining solid was purified by silica gel column chromatography (ethyl acetate/hexane) to obtain the title compound (1.3 g).

$^1$H-NMR (400 MHz, CDCl-$_3$) δ: 2.41 (3H, s), 3.97 (3H, s), 6.47 (1H, s), 7.23 (1H, s), 7.79 (1H, s). MS: [M+H]$^+$ 241.0.

(B) 6-(8-methoxy-2-methylimidazo[1,2-a]pyridine-6-yl)-2-(1-methylpiperidin-4-yl) quinazoline-4-(3H)—one

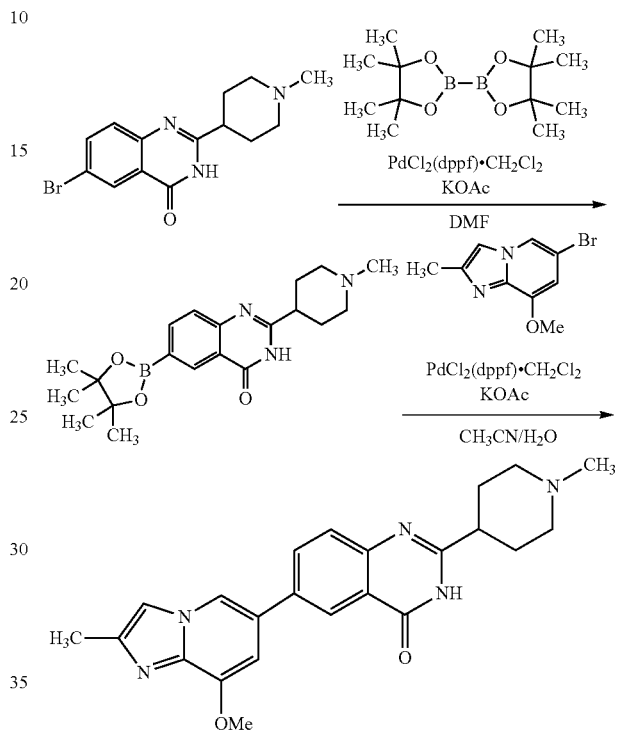

After adding bis (pinacolato) diboron (316 mg) to a mixture of 6-bromo-2-(1-methylpiperidin-4-yl) quinazoline-4 (3H)-one (200 mg) and DMF (8 ml), degassing was performed with nitrogen for 10 minutes, [1, 1'-bis (diphenylphosphino) ferrocene]palladium (II) dichloride dichloromethane adduct (25.3 mg) and potassium acetate (183 mg) were added, and the mixture was stirred at 90° C. for 3 hours. After cooling the resulting mixture to room temperature, THF (15 ml) was added and mixed, the solid matter was removed by filtration, and the volatile components were distilled off from the filtrate under reduced pressure. To the remaining solid, 6-bromo-8-methoxy-2-methylimidazo[1,2-a]pyridine (183 mg) and acetonitrile/water (12.5 ml) were added and mixed. Further, potassium carbonate (148 mg) was added, and after degassing with argon for 20 minutes, tetrakis (triphenylphosphine) palladium (0) (62 mg) was further added and mixed. After stirring the resulting mixture at 100° C. for 16 hours, it was cooled to room temperature and filtered through Celite to remove solids. Volatile components were distilled off from the obtained filtrate under reduced pressure. The remaining solid was purified by preparative HPLC (C18, mobile phase: 20 mM ammonium carbonate aqueous solution/acetonitrile) to obtain the title compound (25 mg).

$^1$H-NMR (400 MHz, CD-$_3$OD) 6: 1.95-2.05 (4H, m), 2.15-2.20 (2H, m), 2.34 (3H, s), 2.40 (3H, s), 2.59-2.68 (1H, m), 3.04 (2H), d, J=11.5 Hz), 4.08 (3H, s), 6.97 (1H, s), 7.60 (1H, s), 7.75 (1H, d, J=8.6 Hz), 8.09 (1H, d, J=7.4 Hz), 8.33 (1H, s), 8.41 (1H, s). MS: [M+H]$^+$40 4.3.

Working Example 23

6-(2,8-dimethylimidazo[1, 2-a]pyridine-6-yl)-2-(1-methylpiperidin-4-yl) kinazoline-4 (3H)—one

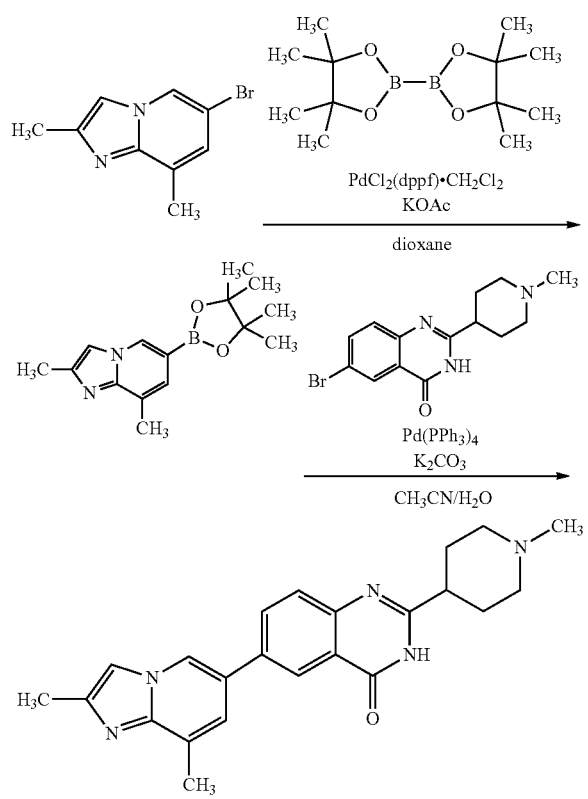

Bis (pinacolato) diboron (339 mg) was added to a mixture of 6-bromo-2,8-dimethylimidazole[1, 2-a]pyridine (150 mg) and 1,4-dioxane (5 mL); after degassing with nitrogen for 10 minutes, [1'1'-bis (diphenylphosphino) ferrocene]palladium (II) dichloride dichloromethane adduct (27.2 mg) and potassium acetate (197 mg) were further added, and the mixture stirred overnight at 100° C. After cooling the resulting mixture to room temperature, THF (15 ml) was added, the solids were removed by filtration, and the volatile components were distilled off from the filtrate under reduced pressure. to the remaining solid, 6-bromo-2-(1-methylpiperidin-4-yl) quinazoline-4-(3H)-one (183 mg), acetonitrile (1 2 ml) and water (0.5 ml) were added and mixed. After adding potassium carbonate (1 55 mg) and degassing with argon for 20 minutes, tetrakis (triphenylphosphine) palladium (0) (65 mg) was further added. The resulting mixture was stirred at 90° C. for 16 hours, cooled to room temperature and filtered through Celite to remove the solids. Volatile components were distilled off from the obtained filtrate under reduced pressure, and the remaining solid was purified by preparative HPLC (C18, mobile phase: 20 mM aqueous ammonium carbonate solution/acetonitrile) to obtain the title compound (40 mg).

$^1$H-NMR (400 MHz, CD 3 0D) δ: 1.97-2.02 (4H, m), 2.11-2.23 (2H, m), 2.34 (3H, s), 2.42 (3H, s), 2.58-2.61 (4H, m), 3.03 (2H, d, J=11.5 Hz), 7.40 (1H, s), 7.61 (1H, s), 7.72 (1H, d, J=8.5 Hz), 8.04 (1H, dd, J=8.6, 22 Hz), 8.35 (1H, d, J=2.1 Hz), 8.54 (1H, s), MS: [M+H]$^+$388.1.

Working Example 24

8-Fluoro-6-(4-fluoro-2-methyl-1,3-benzoxazole 6-yl)-2-(1-methylpiperidin-4-yl) quinazoline 4-(3H)-one (A) 2-Amino-5-Bromo-3-fluorobenzamide

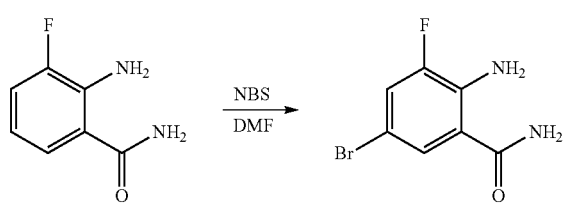

N-Bromosuccinimide (4.9 g) was added to a mixture of 2-amino-3-fluorobenzamide (4.0 g) and DMF (24 mL). After stirring at room temperature for 1 hour, water was added and the mixture was extracted with ethyl acetate. The organic layer was washed with aqueous sodium thiosulfate solution and then saturated brine, in order the product was then dehydrated with anhydrous magnesium sulfate, and volatile components were distilled off under reduced pressure. The remaining solid was washed with diisopropyl ether to obtain the title compound (4.24 g).

$^1$H-NMR (300 MHz, DMSO-d$_6$) δ: 6.64 (2H, s), 7.31-7.49 (2H, m), 7.62 (1H, t, J=1.7 Hz), 7.97 (1H, brs). MS: [M+H]$^+$233. 1.

(B) tert-butyl 4-(6-bromo-8-fluoro-4-oxo-3,4-dihydroquinazoline-2-yl) piperidin-1-carboxylate

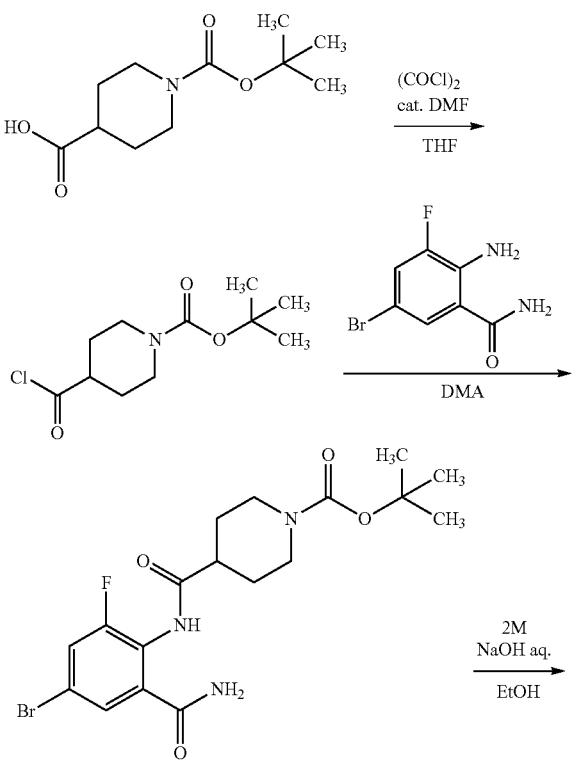

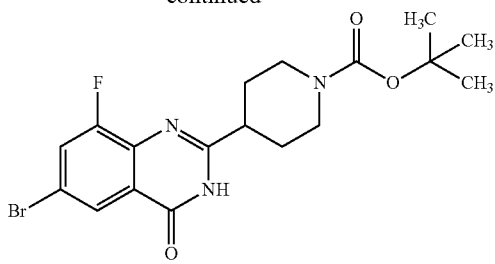

DMF (9.97 μL) was added to a mixture of 1-(tert-butoxycarbonyl) piperidin-4-carboxylic acid (3. 5 4 g), oxalyl chloride (3.3 8 ml) and THF (30 ml). After stirring at room temperature for 2 hours, the volatile components were distilled off under reduced pressure. 2-amino-5-bromo-3-fluorobenzamide (3.0 g) was added to the remaining solid and the mixture of DMA (30 ml), the mixture was stirred at room temperature for 1 hour, saturated aqueous sodium hydrogen carbonate solution was added at room temperature, and the mixture was extracted with ethyl acetate/THF (2/1). The organic layer was washed with saturated brine, dehydrated with anhydrous magnesium sulfate, and volatile components were distilled off under reduced pressure. The remaining solid was washed with diisopropyl ether, ethanol (60 mL) was added to the obtained solid, the mixture was mixed, 2.0 M sodium hydroxide aqueous solution (12.9 ml) was added at room temperature, and the mixture was stirred at room temperature for 1 hour. Neutralization was performed by adding 2.0 M hydrochloric acid (10 ml), the precipitate was isolated by filtration, and washed with ethanol/water (1/1, 10 ml) to obtain the title compound (4.80 g).

¹H-NMR (300 MHz, DMSO-d₆) δ: 1.41 (9H, s), 1.64 (2H, d, J=9.1 Hz), 1.89 (2H, d, J=11.7 Hz), 2.68-2.92 (3H, m), 4.05 (2H, d, J)=11.7 Hz), 7. 9 1-8.0 8 (2H, m), 1 2.5 5 (1H, brs). MS: [M+H]⁺448. 2.

(C) tert-butyl 4-(8-fluoro-6-(4-fluoro-2-methyl-1,3-benzoxazole-6-yl)-4-oxo-3,4-dihydroquinazoline-2-yl) piperidine-1-carboxylate

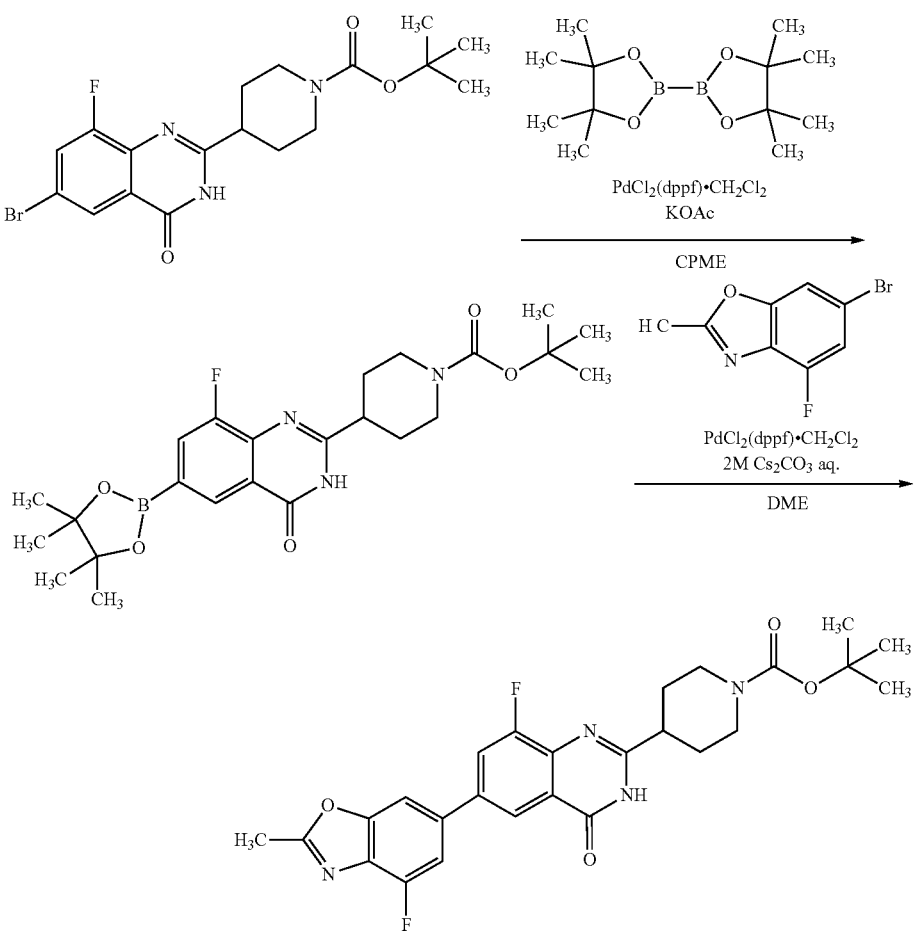

A mixture of tert-butyl 4-(6-bromo-8-fluoro-4-oxo-3,4-dihydroquinazoline-2-yl) piperidin-1-carboxylate (800 mg), bis (pinacolato) diboron (572 mg), [1, 1'¬bis (diphenylphosphino) ferrocene]palladium (I I) dichloride dichloromethane adduct (77 mg), potassium acetate (368 mg) and cyclopropylmethyl ether (5 mL) was stirred under microwave irradiation at 130° C. for 40 minutes. After cooling to room temperature, THF was added, and the mixture was filtered through Celite to remove solids, and then volatile components were distilled off from the filtrate under reduced pressure. To the remaining solid, 6-bromo-4-fluoro-2-methylbenzo[d]oxazol (432 mg), [1, 1'-bis (diphenylphosphino) ferrocene]palladium (I I) dichloride dichloromethane adduct (77 mg), 2.0M cesium carbonate aqueous solution (1.8 8 ml) and 1,2-dimethoxyethane (18 ml) were added, and mixed. The mixture was then stirred at 130° C. for 30 minutes under microwave irradiation. After purifying the mixture by silica gel column chromatography (NH, methanol/ethyl acetate), the obtained solid was washed with diisopropyl ether to obtain the title compound (690 mg).

$^1$H-NMR (300 MHz, DMSO-d$_6$) δ: 1.43 (9H, s), 1.59-1.76 (2H, m), 1.87-1.97 (2H, m), 2.68 (3H, s), 2.73-2. 90 (3H, m), 4.00-4.12 (2H, m)), 7.72 (1H, dd, J=11. 7, 1.1 Hz), 8.06 (1H, d, J=1.1 Hz), 8.14 (1H, dd, J=11.9, 2.1 Hz), 8.22 (1H, d, J=1.9 Hz), 12.49 (1H, brs). MS: [M+H]+497.3.

(D) 8-Methyl-6-(4-fluoro-2-methyl-1,3-benzooxazole-6-yl)-2-(piperidin-4-yl) quinazoline-4-(3H)one formate

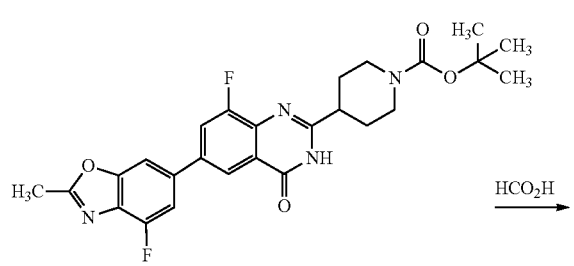

A mixture of tert-butyl 4-(8-fluoro-6-(4-fluoro-2-methyl-1,3-benzoxazole-6-yl)-4-oxo-3,4-dihydroquinazoline-2-yl) piperidine-1-carboxylate (690 mg) and formic acid (3 mL) was stirred at 70° C. for 10 minutes, and then the volatile components were distilled off under reduced pressure. The remaining solid was washed with ethyl acetate to obtain the title compound (615 mg). 1-H-NMR (300 MHz, DMSO-d$_6$) δ: 1.90-2.09 (4H, m), 2.68 (3H, s), 2.78-2.93 (3H, m), 3.30 (2H, d, J=12.5 Hz), 7.73 (1H, dd, J=11. 5, 1.3 Hz), 8. 06 (1H, d, J=1.5 Hz), 8. 16 (1H, dd, J=11.9, 2.1 Hz), 8.23 (1H, d, J=1.9) Hz), 8.30 (2H, s). MS: [M−HCOOH+H]⁺397.3

(E) 8-Fluoro-6-(4-fluoro-2-methyl-1,3-benzooxazole-6-yl)-2-(1-methylpiperidin-4-yl) quinazoline-4-(3H)—one

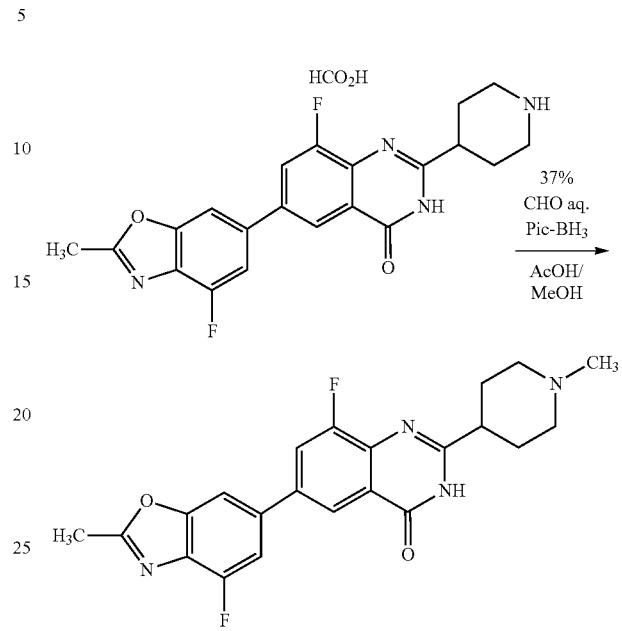

Bolan-2-picolin complex (121 mg) was added to a mixture of 8-Methyl-6-(4-fluoro-2-methyl-1,3-benzoxazolu 6-yl)-2-(piperidin-4-yl) quinazoline-4 (3H)-on formate (200 mg), 37% formaldehyde aqueous solution (0.147 mL), methanol (1.0 ml) and acetic acid (0.5 ml); after stirring at room temperature for 1 hour, the volatile components were distilled off under reduced pressure. After purifying the remaining solid with silica gel column chromatography (NH, methanol/ethyl acetate), the obtained solid was washed with ethyl acetate/diisopropyl ether to obtain the title compound (100 mg).

$^1$H-NMR (300 MHz, DMSO-d$_6$) δ: 1.79-1.96 (6H, m), 2.19 (3H, s), 2.54-2.62 (1H, m), 2.67 (3H, s), 2.87 (2H, d, J=10.6 Hz), 7.72 (1H, dd, J=11.7, 1.5 Hz), 8.05 (1H, d, J=1.5 Hz), 8.14 (1H, dd, J=11.9, 2.1 Hz), 8.21 (1H, d, J=1.9 Hz), 12.42 (1H, brs). MS: [M+H]⁺411.3.

Working Example 25

2-(1-ethylpiperidin-4-yl)-6-(4-fluoro-2-methylu 1,3-benzoxazole-6-yl) kinazoline-4 (3H)-one

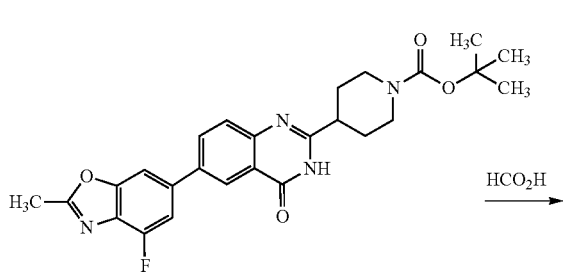

-continued

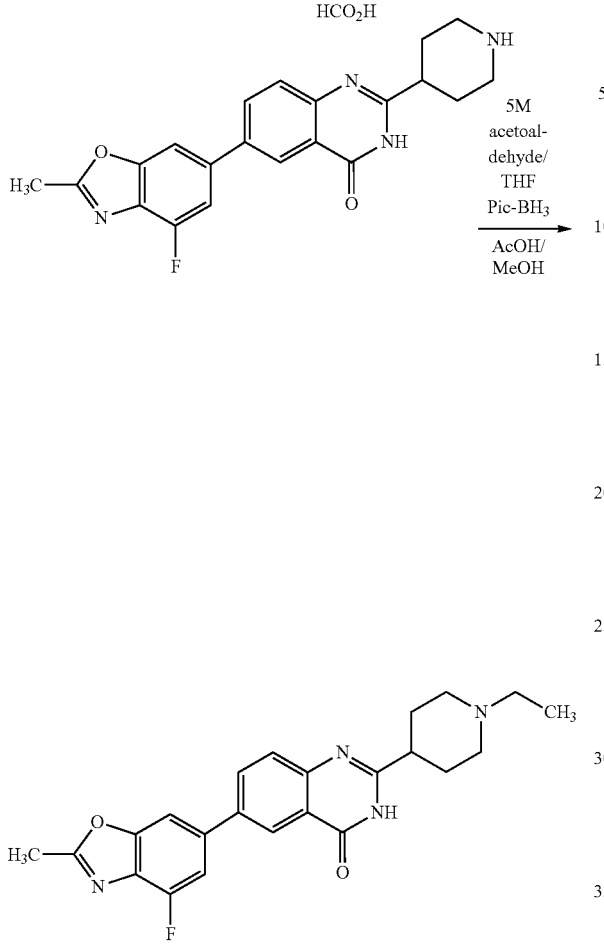

A mixture of tert-butyl 4-(6-(4-fluoro-2-methyl-1,3-benzooxazole-6-yl)-4-oxo-3,4-dihydroquinazoline-2-yl) piperidin-1-carboxylate (149 mg) and formic acid (2 mL) was stirred at 70° C. for 20 minutes, and then the volatile components were distilled off under reduced pressure. To the remaining solid, methanol (1.5 ml) and acetic acid (0.1 ml) were added, and mixed; further, 2-picolinboran complex (50 mg) and 5.0 M acetaldehyde/THF solution (0.19 ml) were added, and the mixture was stirred overnight at room temperature. Volatile components were distilled off under reduced pressure, and the remaining solid was purified by silica gel column chromatography (NH, methanol/ethyl acetate). The obtained solid was washed with ethanol/diisopropyl ether (1/1) to obtain the title compound (17.5 mg).

$^1$H-NMR (300 MHz, DMSO-$d_6$) δ: 1.02 (3H, t, J=7.2 Hz), 1.70-1.99 (6H, m), 2.34 (2H, q, J=7.2 Hz), 2.67 (4H, s), 2.97 (2H, d, J=1 0.2 Hz), 7.62-7.74 (2H, m), 8.00 (1H, d, J=1.5 Hz), 8.18 (1H, dd, J=8. 5, 2.5 Hz), 8.37 (1H, d, J=2.3 Hz), 12.24 (1H, b rs), MS: [M+H]$^+$407. 3.

Working Example 26

7-(2-methylimidazo[1, 2-a]pyridine-6-yl)-3-(1-methylpiperidin-4-yl) kinazoline-4 (3H)-one (A) 7-bromo-3-(1-methylpiperidin-4-yl) kinazoline 4-(3H)-one

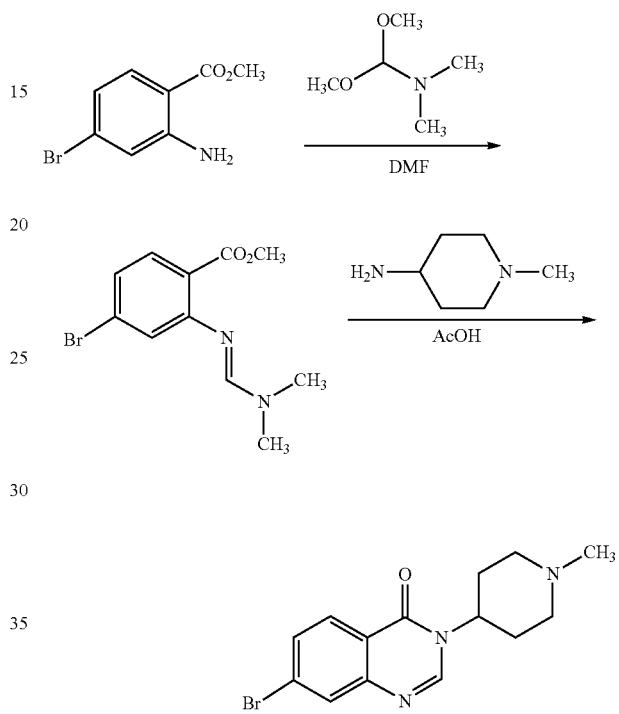

A mixture of 2-Amino-4-bromomethyl benzoate (2.0 g), 1,1-dimethoxy N, N-dimethylmethaneamine (3.2 ml) and DMF (10 ml) were stirred at 110° C. for 2 hours; water was then added at room temperature, and the mixture was extracted with ethyl acetate. The organic layer was separated, washed with saturated brine, drained over anhydrous sodium sulfate, and volatile components were evaporated under reduced pressure. Acetic acid (15 ml) and 1-methylpiperidine-4-amine (1.2 g) were added to the remaining solid, the mixture was heated under reflux for 2 hours, and then the volatile components were distilled off under reduced pressure. A saturated aqueous solution of sodium hydrogen carbonate was added to the remaining solid under ice-cooling, and the mixture was extracted with 10% methanol/dichloromethane. The organic layer was separated, washed with saturated brine, dehydrated with anhydrous sodium sulfate, and volatile components were distilled off under reduced pressure. The remaining solid was purified by silica gel column chromatography (dichloromethane/methanol) to obtain the title compound (1.0 g).

$^1$H-NMR (300 MHz, DMSO-$d_6$) δ: 1.76-1.79 (2H, m), 2.00-2.10 (4H, m), 2.21 (3H, s), 2.89-2.92 (2H, m), 4.51-4.57 (1H, m), 7.71 (1H, dd, J=8.5, 1.8 Hz), 7.89 (1H, d, J=1.7 Hz), 8.07 (1H, d, J=8.5 Hz), 8.51 (1H, s), MS: [M+H]$^+$322.2.

(B) 7-(2-methylimidazo[1, 2-a]pyridine-6-yl)-3-(1-methylpiperidin-4-yl) kinazoline-4 (3H)-one

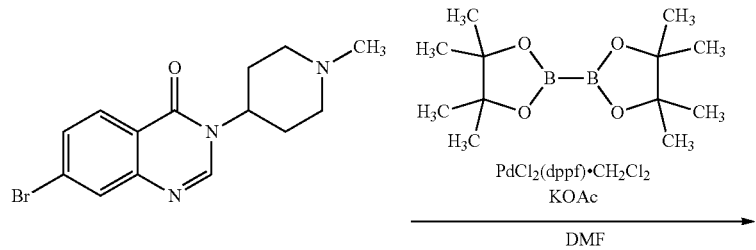

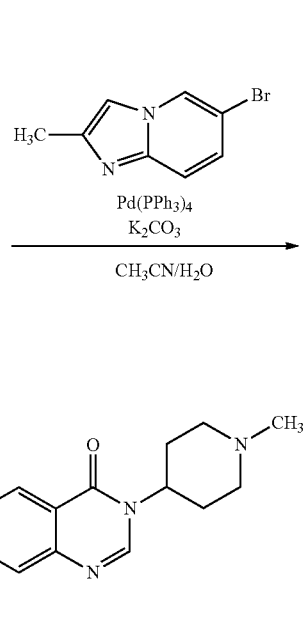

Potassium acetate (274 mg) was added to a mixture of 7-bromo-3-(1-methylpiperidin-4-yl) quinazoline-4-(3H)-one (300 mg), bis (pinacolato) diboron (473 mg) and DMF (10 ml), and the mixture was degassed with argon for 15 minutes. In addition, dichloro[1, 1'-bis (diphenylphosphino) ferrocene]palladium dichloromethane adduct (38 mg) was added, the mixture was stirred at 90° C. for 3 hours and filtered through Celite to remove solids, and then the filtrate was evaporated under reduced pressure to obtain a crude product. To the obtained crude product, 6-bromo-2-methylimidazole[1, 2-a]pyridine (296 mg), acetonitrile (1 2 ml) and water (0.5 ml) were added and mixed. Further, potassium carbonate (260 mg) was added, and the mixture was degassed with argon for 20 minutes. Tetrakis (triphenylphosphine) palladium (0) (108 mg) was added to the obtained mixture, and the mixture was stirred at 90° C. for 16 hours. After filtering with Celite to remove solids, volatile components were distilled off from the filtrate under reduced pressure. The remaining solid was purified by silica gel column chromatography (dichloromethane/methanol) to obtain the title compound (70 mg).

$^1$H-NMR (400 MHz, DMSO-d$_6$) δ: 1.80-1.84 (2H, m), 2.05-2.15 (4H, m), 2.25 (3H, s), 2.36 (3H, s), 2.94-2.97 (2H, m), 4.54-4. 65 (1H, m), 7.55 (1H, d, J=9.3 Hz), 7.67 (1H, d, J=9. 0 Hz), 7.73 (1H, s), 7.90 (1H, d, J=8.2 Hz), 7.99 (1H, s), 8.23 (1H, d, J=8.3 Hz), 8.51 (1H, s), 9.07 (1H, s). MS: [M+H]$^+$374.2.

Working Example 27

2-(1-cyclopropylpiperidin-4-yl)-6-(4-fluoro-2-methyl-1,3-benzoxazole-6-yl) quinazoline-4-(3H) one (A) 4-Fluoro-2-methyl-6-(4, 4, 5, 5-tetramethyl-1, 3, 2-dioxaborolan-2-yl)-1,3-benzoxazole

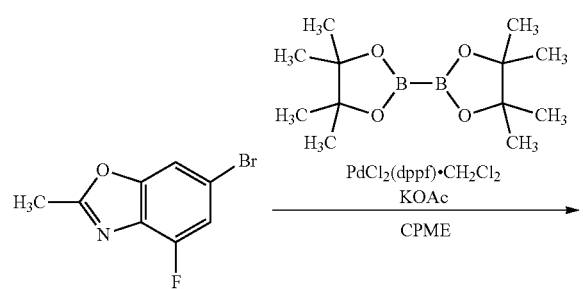

-continued

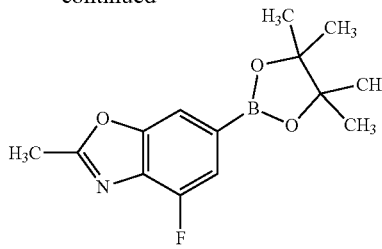

A mixture of 6-bromo-4-fluoro-2-methyl-1,3-benzoxazole (3.00 g), bis (pinacolato) diboron (3.97 g), potassium acetate (2.56 g), dichloro[1, 1'-bis (diphenylphosphino) ferrocene]palladium dichloromethane adduct (0.533 g) and cyclopentylmethyl ether (30 ml) was stirred at 120° C. for 3 hours under a nitrogen atmosphere, water was added, the mixture was filtered to remove solids, and then the filtrate was extracted with ethyl acetate. The organic layer was separated, washed with saturated brine, dehydrated with anhydrous magnesium sulfate, and volatile components were distilled off under reduced pressure. The remaining solid was purified by silica gel column chromatography (ethyl acetate/hexane), and the obtained solid was washed with ethanol/water (1/1) to obtain the title compound (3.60 g).

$^1$H-NMR (300 MHz, DMSO-$d_6$) δ: 1.32 (1 2H, s), 2.66 (3H, s), 7.36 (1H, d, J=10.2 Hz), 7.72 (1H, s). MS: [M+H]$^+$ 278.0.

(B) 6-Bromo-2-(1-cyclopropylpiperidin-4-yl) kinazoline-4-(3H)-one

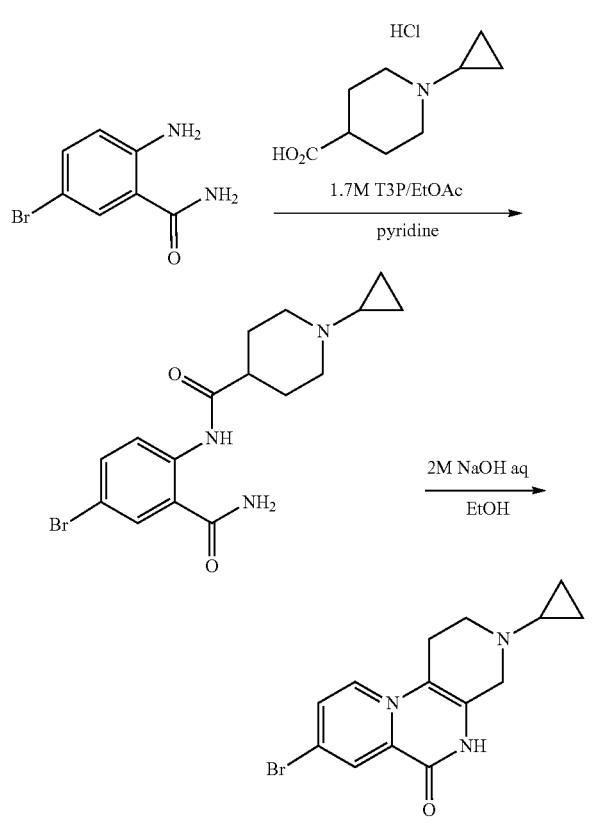

1.7 M propylphosphonate anhydride/ethyl acetate solution (3.56 mL) was added to a mixture of 2-amino-5-bromobenzamide (1.00 g), 1-cyclopropylpiperidin-4-carboxylate (1.15 g) and pyridine (8 mL); after stirring at room temperature for 5 hours, the volatile components were distilled off under reduced pressure, and ethyl acetate and saturated aqueous sodium hydrogen carbonate solution were added to the remaining solid. After separating the organic layer, it was washed with saturated brine, dehydrated with anhydrous magnesium sulfate, and volatile components were distilled off under reduced pressure. Ethanol (20 ml) was added to the remaining solid and mixed; then 2.0M sodium hydroxide aqueous solution (4.65 ml) was further added, the mixture stirred at room temperature for 1 hour, then neutralized with 2.0 M hydrochloric acid and filtered to isolate the precipitate to obtain the title compound (1.14 g).

$^1$H-NMR (300 MHz, DMSO-$d_6$) δ: 0.20-0.50 (4H, m), 1.59-1.79 (3H, m), 1.80-1.92 (2H, m), 2.20 (2H, t, J=1 0.6 Hz), 3.01 (2H, d, J=11.3) Hz), 7.53 (1H, d, J=9.1 Hz), 7.90 (1H, dd, J=8.7, 2.3 Hz), 8.14 (1H, d, J=2.3 Hz), 12.32 (1H, brs). MS: [M+H]$^+$348. 2.

(C) 2-(1-cyclopropylpiperidin-4-yl)-6-(4-fluoro-2-methyl-1,3-benzoxazole-6-yl) quinazoline 4-(3H)-one

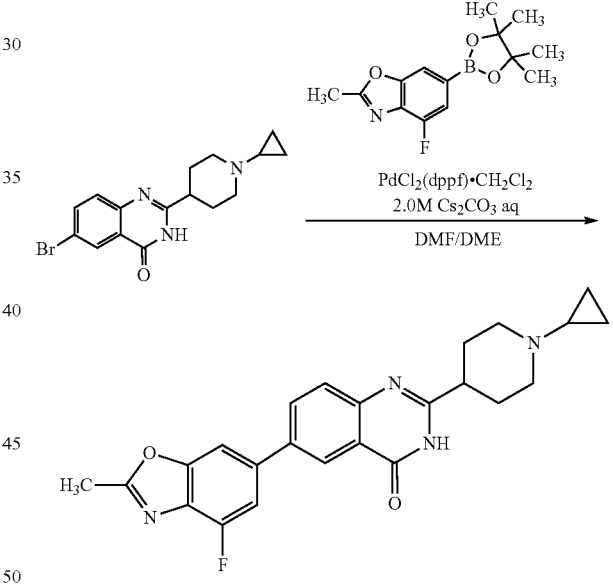

A mixture of 6-Bromo-2-(1-cyclopropylpiperidine-4-yl)-quinazoline-4-(3H)-one (100 mg), 4-fluoro-2-methyl-6-(4, 4, 5, 5-tetramethyl-1, 3, 2-dioxaborolan-2-yl)-1,3-benzoxazole (95 mg), dichloro[1, 1'-bis (diphenylphosphino) ferrocene]palladium dichloromethane adduct (1 2 mg), 2.0M cesium carbonate aqueous solution (0.29 ml), DME (3 mL) and DMF (3 ml) was stirred under microwave irradiation at 130° C. for 90 minutes; after cooling to room temperature, the precipitate was isolated by filtration and washed with water. The obtained solid was dissolved in acetic acid/methanol, filtered through Celite to remove the solid, and the volatile components were distilled off from the filtrate under reduced pressure. The remaining solid was washed with metanol to obtain the title compound (50 mg).

$^1$H-NMR (300 MHz, DMSO-$d_6$) δ: 0.31 (2H, d, J=3.0 Hz), 0.43 (2H, d, J=4.2 Hz), 1.60-1.89 (5H, m), 2.14-2.31

(2H, m), 2.55-2.73 (4H, m), 3.04 (2H, d, J=11.7 Hz), 7.59-7.74 (2H, m), 7.99 (1H, s), 8.17 (1H, dd, J=87, 2.3 Hz), 8.37 (1H, d), J=1.9 Hz), 12.21 (1H, brs). MS: [M+H]⁺419.3.

Working Example 28

2-(1-cyclopropylpiperidin-4-yl)-8-fluoro-6-(4-fluoro-2-methyl-1,3-benzoxazole-6-yl)quinazoline-4-(3H)-one (A) N-(4-bromo-2-carbamoyl-6-fluorophenyl)-1-cyclopropylpiperidin-4-carboxamide

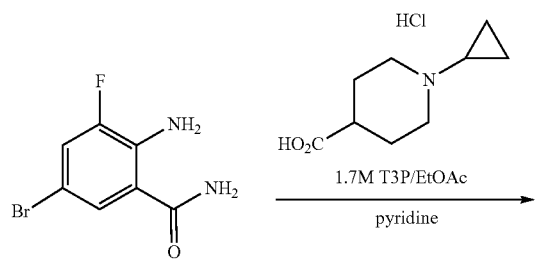

A mixture of 2-amino-5-Bromo-3-fluorobenzamide (2.3 g), 1-cyclopropylpiperidin-4-carboxylic acid hydrochloride (3.05 g), 1.7 M propylphosphonic anhydride/ethyl acetate solution (23.2 ml) and pyridine (48 ml) was stirred at room temperature for 5 hours; after distilling off the volatile components under reduced pressure, ethyl acetate and saturated aqueous sodium hydrogen carbonate solution were added to the remaining solid. After separating the organic layer, the mixture was washed with water, the volatile components were distilled off under reduced pressure, and the remaining solid was washed with ethyl acetate to obtain the title compound (1.84 g).

¹H-NMR (400 MHz, DMSO-d₆) δ: 0.24-0.32 (2H, m), 0.36-0.44 (2H, m), 1.43-1.63 (3H, m), 1.74 (2H, d, J=11.7 Hz), 2.15 (2H, t, J=11.1) Hz), 2.30-2.42 (1H, m), 2.94 (2H, d, J=11.5 Hz), 7.53 (1H, s), 7.57 (1H, brs), 7.69 (1H, d, J=9.4 Hz), 7.88 (1H, brs), 9.53 (1H, brs). MS: [M+H]+384. 2.

(B) 6-bromo-2-(1-cyclopropylpiperidin-4-yl)-quinazoline-4-(3H)—one

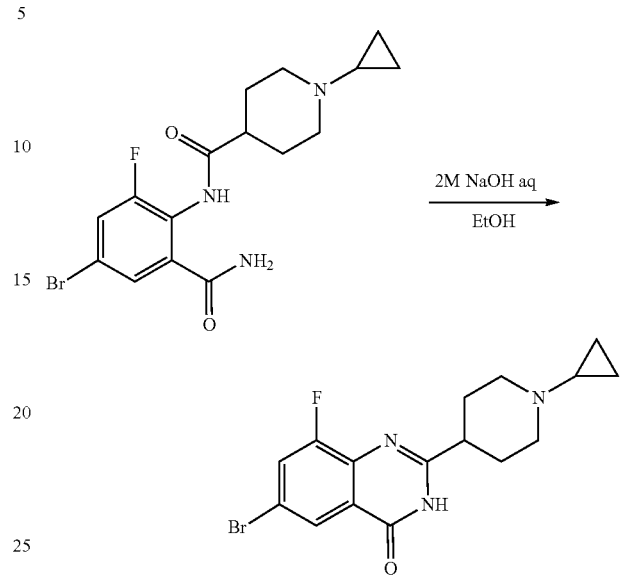

2.0M Sodium hydroxide aqueous solution (4.79 mL) was added to a mixture of N-(4-bromo-2-carbamoyl-6-fluorophenyl)-1-cyclopropylpiperidin-4-carboxamide (1.84 g) and ethanol (20 ml) at room temperature; after stirring at room temperature for 1 hour, the mixture was neutralized with 1.0 M hydrochloric acid. The precipitate was isolated by filtration to obtain the title compound (1.50 g).

MS: [M+H]⁺366.2.

(C) 2-(1-cyclopropylpiperidin-4-yl)-8-fluoro-6-(4-fluoro-2-methyl-1,3-benzoxazole-6-yl) quinazoline-4-(3H)-one

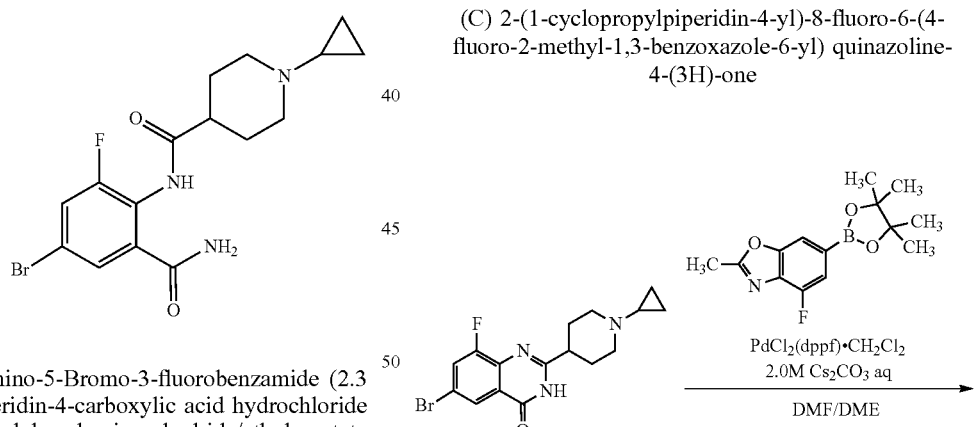

A mixture of 6-bromo-2-(1-cyclopropylpiperidin-4-yl)-8-fluoroquinazoline-4 (3H)one (100 mg), 4-fluoro-2-methyl- 6-(4, 4, 5, 5-tetramethyl-1, 3, 2-dioxaborolane-2-yl)-1,3-benzoxazole (91 mg), dichloro[1, 1'-bis (diphenylphosphino) ferrocene]palladium dichloromethane adduct (11 mg), 2.0M cesium carbonate aqueous solution (0.27 mL), DME (3 ml) and DMF (3 ml) was stirred under microwave irradiation at 130° C. for 50 minutes; after cooling to room temperature, the precipitate was isolated by filtration and washed with water. The obtained solid was dissolved in acetic acid/methanol, filtered through Celite to remove the solid, and the volatile components were distilled off from the filtrate under reduced pressure. The remaining solid was washed with methanol to obtain the title compound (50 mg).

$^1$H-NMR (300 MHz, DMSO-$d_6$) δ: 0.2 6-0.35 (2H, m), 0.39-0.48 (2H, m), 1.59-1.94 (5H, m), 2.15-2.29 (2H, m), 2.55-2.72 (4H, m), 3.04 (2H, d, J=11.3 Hz), 7.71 (1H, dd, J=11.5, 1.3 Hz), 8.04 (1H, d, J=1.1 Hz), 8.12 (1H, dd, J=11. 7, 2.3 Hz)), 8.20 (1H, d, J=1.9 Hz), 12.41 (1H, brs). MS: [M+H]$^+$437.3

Working Example 29

7-(4-fluoro-2-methyl-1,3-benzoxazole-6-yl)-3-(1-methylpiperidin-4-yl) quinazoline-4 (3H)-one

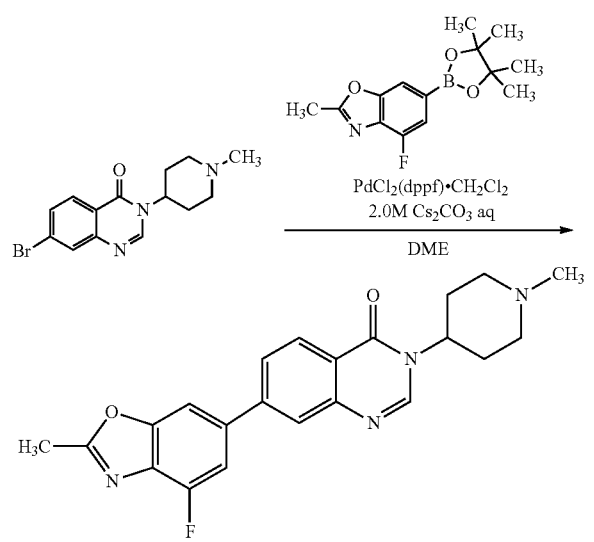

A mixture of 7-bromo-3-(1-methylpiperidin-4-yl) quinazoline-4 (3H)-one (1 50 mg), 4-fluoro-2-methyl-6-(4, 4, 5, 5-tetramethyl-1, 3, 2-dioxaborolan-2-yl)-1,3-benzoxazole (155 mg), dichloro[1, 1'-bis (diphenylphosphino) ferrocene] palladium dichloromethane adduct (19 mg), 2.0M cesium carbonate aqueous solution (0.466 ml) and DME (4 mL) were stirred at 130° C. for 50 minutes under microwave irradiation, and the mixture purified by silica gel column chromatography (NH, ethyl acetate/hexane). The obtained solid was washed with diisopropyl ether to obtain the title compound (87 mg).

$^1$H-NMR (300 MHz, DMSO-$d_6$) δ: 1.81 (2H, d, J=11.0 Hz), 2.00-2.17 (4H, m), 2.23 (3H, d, J=1.1 Hz), 2.68 (3H, d, J=1.5 Hz), 2.93 (2H), d, J=9.4 Hz), 4.51-4.66 (1H, m), 7.72-7.79 (1H, m), 7.93-7.99 (1H, m), 8.06 (1H, s), 8.09 (1H, t, J)=1.5 Hz), 8.22 (1H, dd, J=8. 3, 1.1 Hz), 8.52 (1H, d, J=1.5 Hz). MS: [M+H]$^+$393.3.

Working Example 30

8-fluoro-6-(2-methyl-1,3-benzoxazole-6-yl)-2-(1-methylpiperidine-4-yl) kinazoline-4 (3H)-one (A) tert-butyl 4-(6-bromo-8-fluoro-4-oxo-3,4-dihydroquinazoline-2-yl) piperidine-1-carboxylate

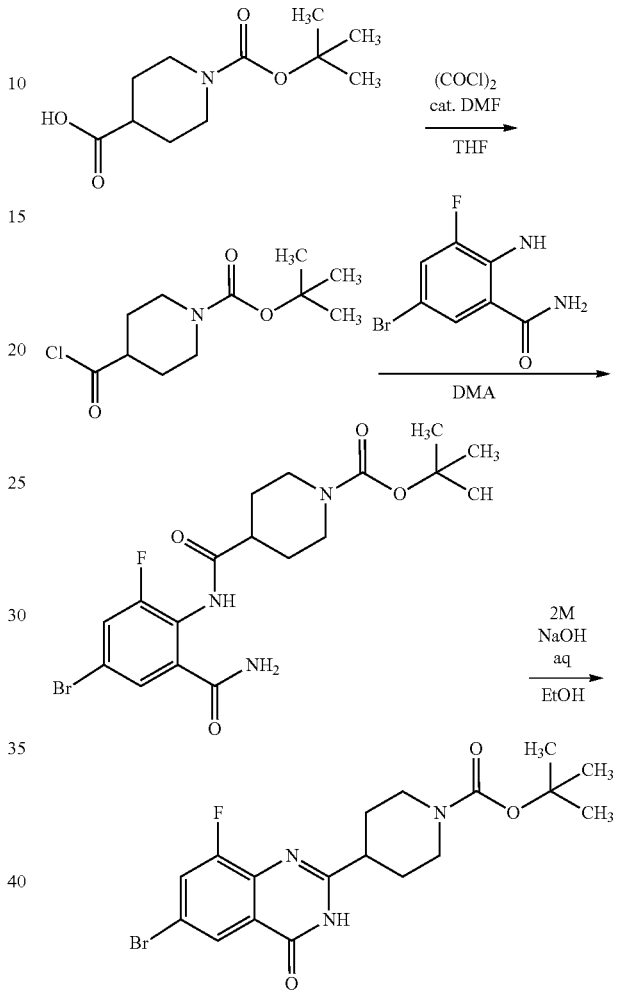

DMF (9.97 µL) was added to a mixture of 1-(tert-butyloxycarbonyl) piperidin-4-carboxylic acid (3. 5 4 g), oxalyl chloride (3.3 8 ml) and THF (30 ml) at room temperature; after stirring for 2 hours, the volatile components were distilled off under reduced pressure. DMA (30 ml) was added to the remaining solid and mixed; further, 2-amino-5-bromo-3-fluorobenzamide (3.0 g) was added at room temperature, and the mixture was stirred for 1 hour. A saturated aqueous solution of sodium hydrogen carbonate was added to the obtained mixture, and the mixture was extracted with ethyl acetate/THF. The organic layer was separated, washed with saturated brine, dehydrated with anhydrous magnesium sulfate, and volatile components were distilled off under reduced pressure. The remaining solid was washed with diisopropyl ether, ethanol (60 mL) added and mixed. 2.0M aqueous sodium hydroxide solution (12.9 ml) was added, and the mixture was stirred at room temperature for 1 hour. Further, 2.0M hydrochloric acid (10 ml) was added to neutralize the mixture, and the mixture was filtered to isolate the precipitate. The obtained solid was washed with ethanol/water (1/1) to obtain the title com $^1$H-NMR (300 MHz, DMSO-$d_6$) δ: 1.41 (9H, s), 1.64 (2H, d, J=9.1 Hz), 1.89 (2H, d, J=11.7 Hz), 2.68-2.92 (3H, m), 4.05 (2H, d, J=1 7 Hz), 7.9 1-8.0 8 (2H, m), 1 2.5 5 (1H, brs) pound (4.8 g).

(B) tert-butyl 4-(8-fluoro-6-(2-methyl-1,3-benzoxazole-6-yl)-4-oxo-3,4-dihydroquinazolin-2-yl) piperidine-1-carboxylate

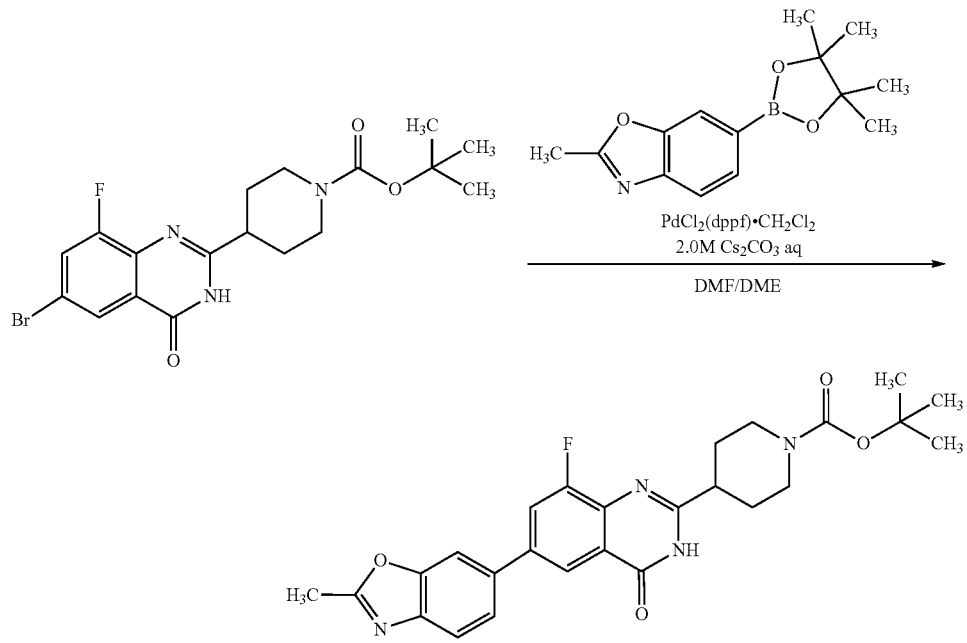

After stirring a mixture of tert-butyl 4-(6-bromo-8-fluoro-4-oxo-3,4-dihydroquinazoline-2-yl) piperidin-1-carboxylate (400 mg), 2-Methyl-6-(4, 4, 5, 5-tetramethyl-1, 3, 2-dioxaborolan-2-yl)-1,3-benzoxazole (292 mg), dichloro[1, 1'-bis (diphenylphosphino) ferrocene]palladium dichloromethane adduct (38 mg), 2.0M aqueous solution of cesium carbonate (0.94 ml), DME (3 ml) and DMF (3 ml) at 130° C. for 50 minutes under microwave irradiation, water was added and filtered to isolate the precipitate. After dissolving the obtained solid in acetic acid/methanol and filtering with Celite to remove the solid, volatile components were distilled off from the obtained filtrate under reduced pressure, and the remaining solid was washed with ethyl acetate to obtain the title compound (122 mg).

$^1$H-NMR (300 MHz, DMSO-$d_6$) δ: 1.43 (9H, s), 1.58-1.79 (2H, m), 1.87-1.99 (2H, m), 2.65 (3H, s), 2.72-2.94 (3H, m), 4.07 (2H, d, J=11. 3 Hz), 7.76 (2H, s), 8.02-8.29 (3H, m). 12.45 (1H, brs). MS: [M+H]$^+$479.3.

(C) 8-fluoro-6-(2-methyl-1,3-benzoxazole-6-yl)-2-(1-methylpiperidine-4-yl) kinazoline-4 (3H)-one

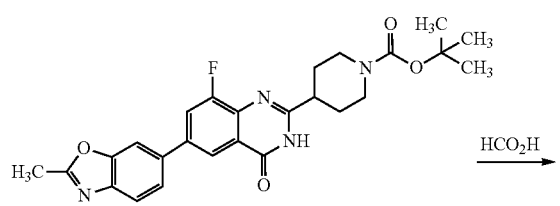

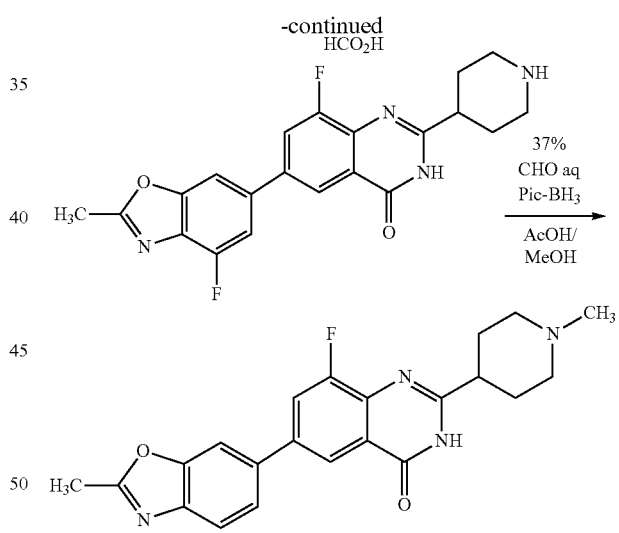

A mixture of tert-butyl 4-(8-fluoro-6-(2-methyl-1,3-benzooxazole-6-yl)-4-oxo-3,4-dihydroquinazoline-2-yl) piperidin-1-carboxylate (120 mg) and formic acid (2 mL) was stirred at 60° C. for 10 minutes, and then the volatile components were distilled off under reduced pressure. Methanol (1.0 ml), acetic acid (0.5 ml) and a 37% aqueous formaldehyde solution (0.081 ml) were added to the remaining solid and mixed. Further, bis-picolin borane complex (67 mg) was added, and the mixture was stirred overnight at room temperature. Volatile components were distilled off under reduced pressure, and the remaining solid was purified by silica gel column chromatography (NH, methanol/ethyl acetate). The obtained solid was washed with diisopropyl ether to obtain the title compound (70 mg).

¹H-NMR (300 MHz, DMSO-d₆) δ: 1.78-1.97 (6H, m), 2.19 (3H, s), 2.53-2.61 (1H, m), 2.65 (3H, s), 2.87 (2H, d, J=10.2 Hz), 7.74-777 (2H, s) m), 8.06-8. 15 (2H, m), 8.19 (1H, d, J=1.9 Hz), 12.43 (1H, brs). MS: [M+H]⁺393.3.

Working Example 31

2-(1-Cyclopropylpiperidin-4-yl)-8-fluoro-6-(2-methyl-1,3-benzoxazole-6-yl) quinazoline-4 (3H) one

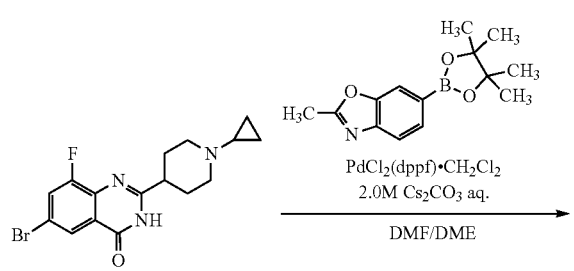

A mixture of 6-bromo-2-(1-cyclopropylpiperidine-4-yl)-8-fluoroquinazoline-4-(3H)-one (200 mg), 2-methyl-6-(4,4,5,5-tetramethyl-1,3,2-dioxaborolan-2-yl)-1,3-benzoxazole (156 mg), dichloro[1, 1'-bis (diphenylphosphino) ferrocene] palladium dichloromethane adduct (22 mg), 2.0M cesium carbonate aqueous solution (0.55 ml), DME (2 mL) and DMF (2 ml) was stirred under microwave irradiation at 130° C. for 30 minutes; after cooling to room temperature, water (1.5 ml) was added, and the precipitate was isolated by filtration and washed with ethanol/water (1/1). The obtained solid was dissolved in acetic acid (1 mL), activated carbon (90 mg) was added, and the solid was filtered to remove the solid. The obtained filtrate was extracted with acetic acid/methanol (1/1), and volatile components were distilled off from the obtained organic layer under reduced pressure. The remaining solid was washed with ethanol to obtain the title compound (1 44 mg).

¹H-NMR (300 MHz, DMSO-d₆) δ: 0.26-0.36 (2H, m), 0.36-0.48 (2H, m), 1.58-1.97 (5H, m), 2.14-2.30 (2H, m), 2.55-2.76 (4H, m), 3.04 (2H, d, J=11.0 Hz), 7.75 (2H, s), 8.06-8.15 (2H, m), 8.18 (1H, d), J=1.9 Hz), 12.38 (1H, brs). MS: [M+H]⁺4 1 9. 3.

Working Example 32

2-(1-Cyclopropylpiperidin-4-yl)-6-(3-methylpyrro mouth[1, 2-a]pyrazine-7-yl) quinazoline-4-(3H)-one acetate

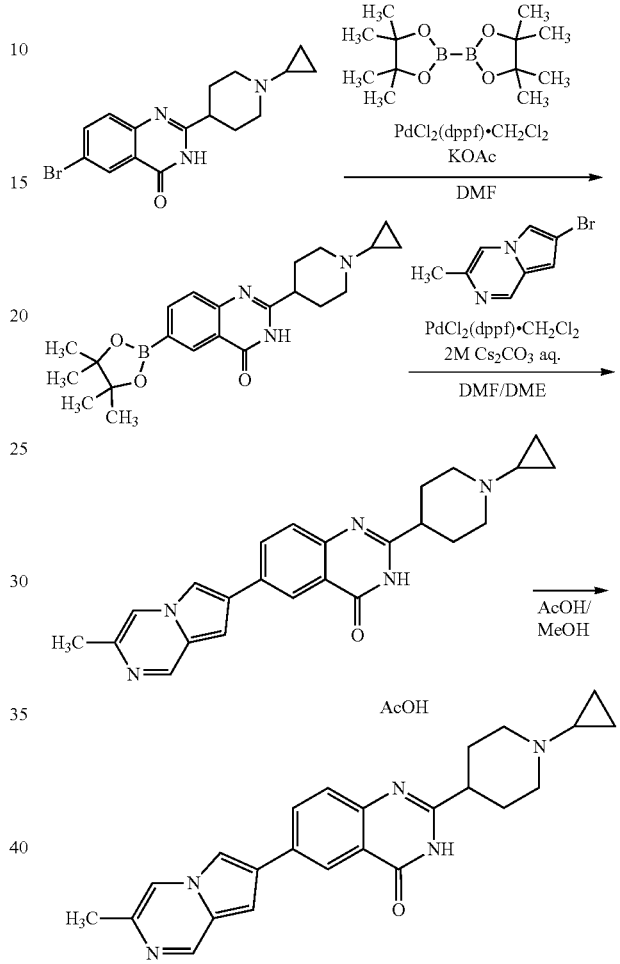

A mixture of 6-bromo-2-(1-cyclopropylpiperidine-4-yl)-quinazoline-4-(3H)-one (200 mg), bis (Pinacolato) diboron (175 mg), potassium acetate (113 mg), dichloro[1, 1'-bis (diphenylphosphino) ferrocene]palladium dichloromethane adduct (2 3 mg), cyclopentyl methyl ether (3 mL) and DMF (2 ml) was stirred at 130° C. for 1 hour under microwave irradiation. The solid obtained by filtering with Celite was washed with ethyl acetate, the washing solution was mixed with the filtrate, and the volatile components were distilled off under reduced pressure. To the remaining solid, 7-bromo-3-methylpyrrolo[1, 2-a]pyrazine (1 20 mg), dichloro[1, 1'-bis (diphenylphosphino) ferrocene]palladium dichloromethane adduct (23 mg), 2.0 M aqueous cesium carbonate solution (0.57 ml), DME (3 mL) and DMF (3 ml) were added and mixed. The mixture was stirred at 130° C. for 50 minutes under microwave irradiation, water was added to the mixture at room temperature and the resulting precipitate was filtered to isolate and dissolved in acetic acid/methanol. The solid was removed by filtration through Celite, volatile components were distilled off from the filtrate under reduced pressure, and the remaining solid was washed with ethyl acetate to obtain the title compound (2 mg).

MS: [M-CH₃COOH+H]⁺400.4.

Working Example 33

2-(1-cyclopropyl piperidin-4-yl)-8-fluoro-6-(3-methylpyrrolo[1, 2-a]pyrazine-7-yl) quinazoline-4 (3H) one acetate

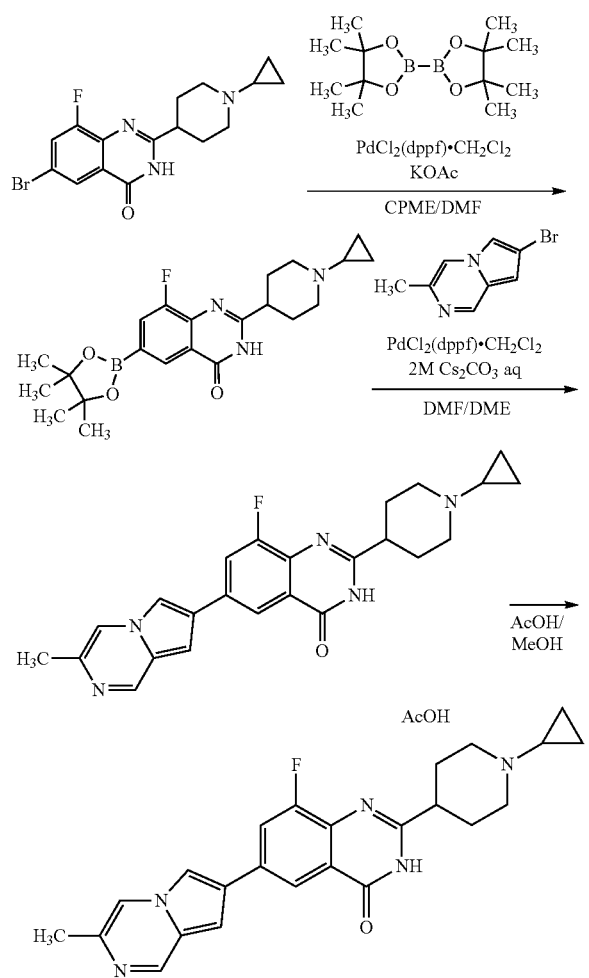

A mixture of 6-bromo-2-(1-cyclopropylpiperidine-4-yl)-8-fluoroquinazoline-4-(3H)-one (250 mg), bis (Pinacolato) diboron (208 mg), potassium acetate (1 34 mg), dichloro[1, 1'-bis (diphenylphosphino) ferrocene]palladium dichloromethane adduct (28 mg), cyclopentyl methyl ether (3 mL) and DMF (2 ml) was stirred at 130° C. for 1 hour under microwave irradiation. The solid obtained by filtering with Celite was washed with ethyl acetate, the washing solution was mixed with the filtrate, and the volatile components were distilled off under reduced pressure. To the remaining solid, 7-Bromo-3-methylpyrrolo[1, 2-a]pyrazine (144 mg), dichloro[1, 1'-bis (diphenylphosphino) ferrocene]palladium dichloromethan adduct (28 mg), 2.0M cesium carbonate aqueous solution (0.68 ml), DME (3 ml) and DMF (3 ml) were added and mixed, and the mixture was stirred at 130° C. for 50 minutes under microwave irradiation. Water was added to the obtained mixture at room temperature, and the mixture was filtered to isolate the precipitate. The obtained solid was dissolved in acetic acid/methanol, filtered through Celite to remove the solid, and the volatile components were distilled off from the filtrate under reduced pressure. The remaining solid was purified by silica gel column chromatography (NH, methanol/ethyl acetate). The obtained solid was washed with diisopropyl ether to obtain the title compound (21 mg).

$^1$H-NMR (300 MHz, DMSO-$d_6$) δ: 0.27-0.35 (2H, m), 0.40-0.47 (2H, m), 1.63 (1H, d, J=34 Hz), 1.71-1.82 (2H, m), 1.82-1.92 (5H, m), 2.22 (2H, s), 2.32 (3H, s), 2.54-2.68 (1H, m), 3.03 (2H, d, J=11.3 Hz), 7.29 (1H, s), 8.04 (1H, s), 8.09 (1H), dd, J=11.7, 1.9 Hz), 8.19 (1H, d, J=1.5 Hz), 8.28 (1H, s), 8. 77 (1H, s). MS: [M-CH 3 COOH+H]$^+$41 8. 3.

Working Example 34

3-(1-cyclopropylpiperidin-4-yl)-7-(4-fluoro-2-methyl-1,3-benzoxazole-6-yl) quinazoline-4-(3H) one (A) 7-bromo-3-(1-cyclopropylpiperidin-4-yl) kinazoline-4-(3H)-one

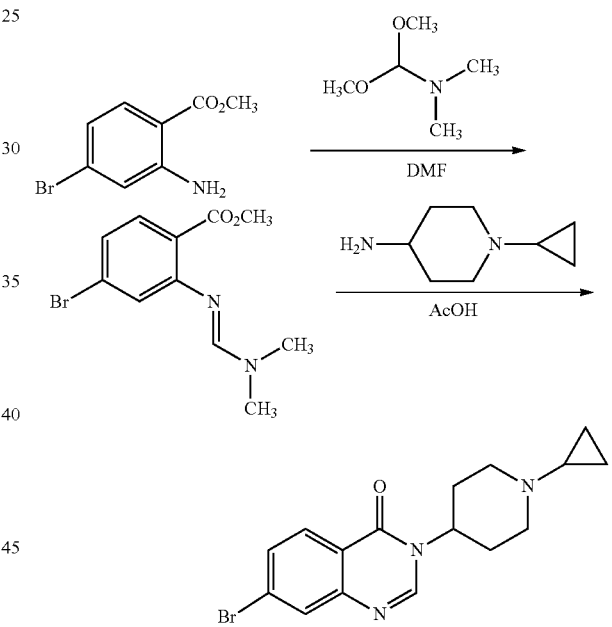

A mixture of 2-amino-4-bromobenzoate (530 mg), 1,1-dimethoxy-N, N-dimethylmethaneamine (755 mg) and DMF (5 ml) was stirred at 100° C. for 2 hours, water was added at room temperature and the mixture extracted with ethyl acetate. The organic layer was separated, washed with saturated brine, dehydrated with anhydrous magnesium sulfate, and volatile components were evaporated under reduced pressure. Acetic acid (10 ml) and 1-cyclopropylpiperidin-4-amine (485 mg) were added to the remaining solid, the mixture was stirred at 120° C. for 1 hour, and then the volatile components were distilled off under reduced pressure. The remaining solid was purified by silica gel column chromatography (ethyl acetate/hexane). The obtained solid was washed with diisopropyl ether to obtain the title compound (360 mg).

$^1$H-NMR (300 MHz, DMSO-$d_6$) δ: 0.28-0.35 (2H, m), 0.41-0.49 (2H, m), 1.69 (1H, dt, J=6.6, 3.1 Hz), 1.78 (2H, d, J=11. 3 Hz), 1.92-2.07 (2H, m), 2.27-2.39 (2H, m), 3.08 (2H, d, J=11. 3 Hz), 4.60 (1H, tt, J=12.2, 3.8 Hz), 7.71 (1H, dd, J=8. 5, 2.1 Hz), 7.89 (1H, d, J=1.9 Hz), 8.07 (1H, d, J=8.3 Hz), 8.49 (1H, s). MS: [M+H]⁺348. 2.

(B) 3-(1-Cyclopropylpiperidin-4-yl)-7-(4-full-year-old low 2-methyl-1,3-benzoxazole-6-yl) quinazoline 1 4 (3H)-one

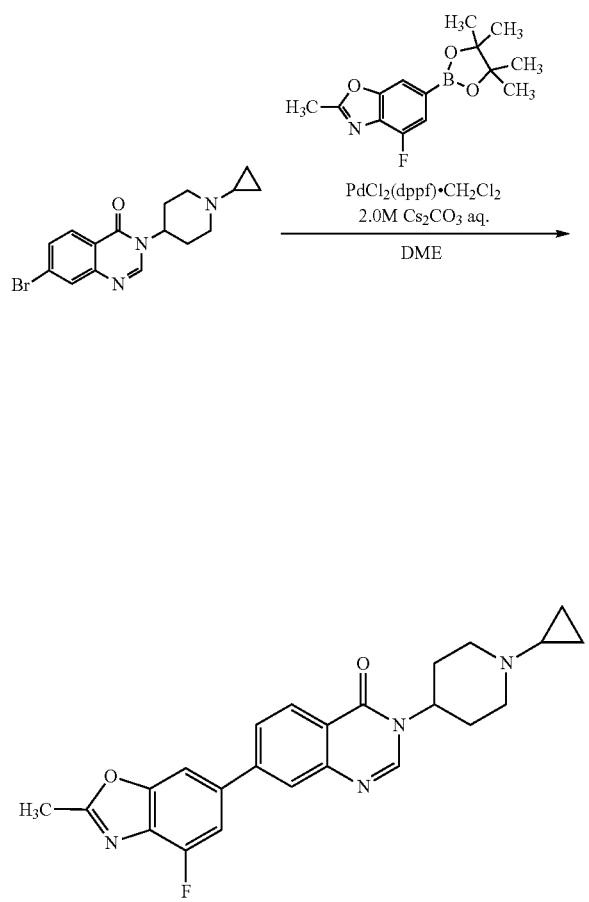

A mixture of (7-bromo-3-(1-cyclopropylpiperidin-4-yl) kinazolin-4-(3H)-one (200 mg), 4-fluoro-2-methyl-6-(4, 4, 5, 5-tetramethyl-1, 3, 2-dioxaborolan-2-yl)-1,3-benzoxazole (191 mg), dichloro[1, 1'¬bis (diphenylphosphino) ferrocene]palladium with dichloromethane (23. 45 mg), 2.0M cesium carbonate aqueous solution (0.574 ml) and DME (5 ml) was stirred under microwave irradiation at 130° C. for 30 minutes; then after cooling to room temperature, the precipitate was isolated by filtration and washed with water. The obtained solid was dissolved in acetic acid/methanol and filtered through Celite to remove the solid. Volatile components were distilled off from the filtrate under reduced pressure, and the remaining solid was washed with ethyl acetate to obtain the title compound (1 23 mg).
¹H-NMR (300 MHz, DMSO-d₆) δ: 0.29-0.37 (2H, m), 0.42-0.50 (2H, m), 1.66-1.75 (1H, m), 1.81 (2H, d, J=10.2 Hz), 1.94-2.11 (2H, m), 2.30-2.42 (2H, m), 2.68 (3H, s), 3.10 (2H, d, J=11.7 Hz), 4.58-4.73 (1H, m), 7.75 (1H, dd, J=11. 5, 1.3 Hz), 7. 95 (1H, dd, J=8.3, 1.9 Hz), 8.06 (2H, dd, J=11.7, 15 Hz), 8.22 (1H, d, J=8.3 Hz), 8.50 (1H, s). MS: [M+H]⁺419.3.

Working Example 35

2-(1-cyclopropylpiperidin-4-yl)-8-fluoro-6-(3-fluoro-4-methoxyphenyl) quinazoline-4-(3H)—one

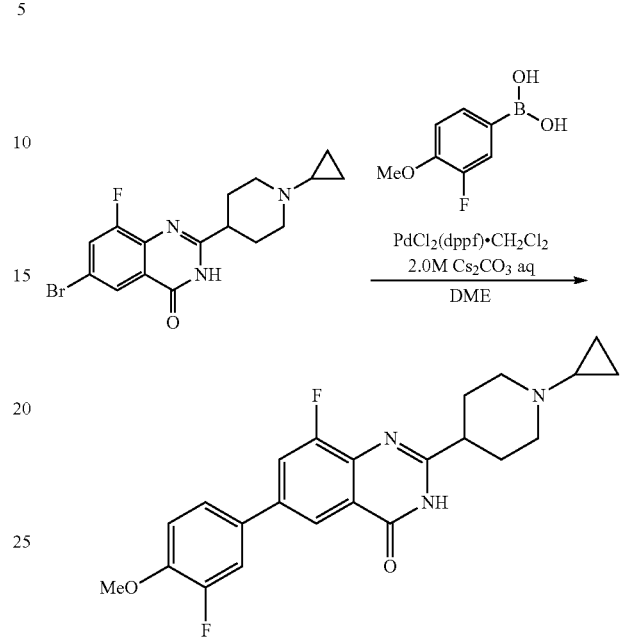

A mixture of 6-bromo-2-(1-cyclopropylpiperidin-4-yl)-8-fluolocinazoline-4 (3H)-one (100 mg), (3-fluoro-4-methoxyphenyl) boronic acid (56 mg), dichloro[1, 1'-bis (diphenylphosphino) ferrocene]palladium dichloromethane adduct (11 mg), 2.0M cesium carbonate aqueous solution (0.27 ml) and DME (4 mL) was stirred under microwave irradiation at 130° C. for 30 minutes; then after cooling to room temperature, the precipitate was isolated by filtration and washed with water. The obtained solid was dissolved in acetic acid/methanol, filtered through Celite to remove the solid, and the volatile components were distilled off from the filtrate under reduced pressure. The remaining solid was washed with ethyl acetate to obtain the title compound (54 mg).
¹H-NMR (300 MHz, DMSO-d₆) δ: 0.26-0.34 (2H, m), 0.38-0.46 (2H, m), 1.59-1.93 (5H, m), 2.15-2.29 (2H, m), 2.54-2.67 (1H, m), 3.03 (2H, m) d, J=11. 3 Hz), 3.90 (3H, s), 7.27 (1H, t, J=8.9 Hz), 7.57-7.64 (1H, m), 7.72 (1H, dd, J=13. 2, 2.3 Hz), 8.01 (1H, dd, J=11. 9, 2.1 Hz), 8.10 (1H, d, J=1.9 Hz), 12.30 (1H, brs). MS: [M+H]⁺412.3.

Working Example 36

6-(4-Cyclopropylpiperazin-1-yl)-2-(4, 6-dimethylpyrazolo[1,5-α]piperazine-2-yl) Kinazolin-4 (3H)-One (A)
5-(4-Cyclopropylpiperazin-1-yl)-2-nitrobenzamide

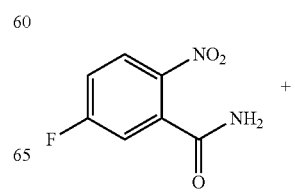

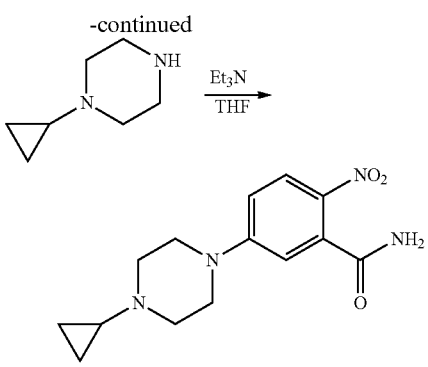

A mixture of 5-Fluoro-2-nitrobenzamide (2.00 g), 1-cyclopropylpiperazine (1.44 g), triethylamine (5.00 ml) and THF (10 ml) was stirred at 60° C. overnight; then after distilling off the volatile components under reduced pressure and washing the remaining solid with ethyl acetate, the obtained solid was purified by silica gel column chromatography (NH, hexane/ethyl acetate) to obtain the title compound (2.96 g).

$^1$H-NMR (300 MHz, DMSO-$d_6$) δ: 0.31-0.40 (2H, m), 0.41-0.50 (2H, m), 1.59-1.73 (1H, m), 2.56-2.69 (4H, m), 3.36-3.47 (4H, m), 6.85 (1H, d, J=2.6 Hz), 7.00 (1H, dd, J=9.4, 2.6 Hz), 7.51 (1H, s), 7.86 (1H, s), 7.94 (1H, d, J=9.4 Hz). MS: [M+H]$^+$291.3.

(B)
2-Amino-5-(4-cyclopropylpiperadin-1-yl)benzamide

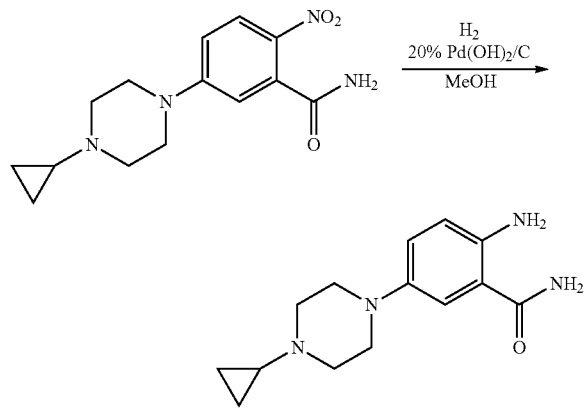

A mixture of 5-(4-cyclopropylpiperadin-1-yl)-2-nitrobenzamide (2.96 g), palladium hydroxide-activated carbon (20% palladium) (300 mg) and methanol (100 mL) was stirred under normal pressure and hydrogen atmosphere at room temperature overnight, and then the catalyst was removed by filtration. Then, the volatile components were distilled off from the filtrate under reduced pressure and the remaining solid was washed with diisopropyl ether to obtain the title compound (2.03 g)

$^1$H-NMR (300 MHz, DMSO-$d_6$) δ: 0.27-0.36 (2H, m), 0.38-0.47 (2H, m), 1.59-1.69 (1H, m), 2.60-2.73 (4H, m), 2.83-2.99 (4H, m), 6.05 (2H, s), 6.60 (1H, d, J=9.1 Hz), 6.88 (1H, dd, J=9.1, 3.0 Hz), 7.00 (1H, brs), 7.04 (1H, d, J=3.0 Hz), 7.72 (1H, brs). MS: [M+H]$^+$261.3.

(C) 6-(4-Cyclopropylpiperazin-1-yl)-2-(4,6-dimethylpyrazolo[1,5-α]pyrazin-2-yl)quinazolin-4(3H)-one

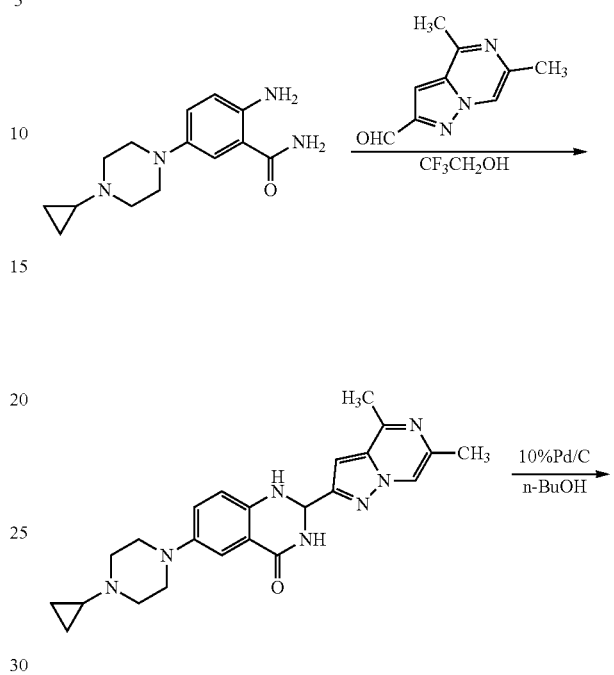

To a mixture of 2-amino-5-(4-cyclopropylpiperadin-1-yl)benzamide (200 mg) and 2,2,2-trifluoroethanol (5 mL) was added 4,6-dimethylpyrazolo[1,5-α]pyrazine-2-carbaldehyde (135 mg) at room temperature and the mixture was stirred at 80° C. overnight. The volatile components were distilled off under reduced pressure and 1-butanol (5 mL) was added to the remaining solid, followed by mixing. Then, palladium-activated carbon (10% palladium) (40 mg) was further added thereto and the mixture was stirred at 130° C. for 1 day. The catalyst was removed from the obtained mixture by filtration through Celite and the volatile components were distilled off from the filtrate under reduced pressure. Then, the remaining solid was washed with ethanol. The obtained solid was recrystallized from 1-butanol/ethyl acetate to obtain the title compound (16.4 mg).

$^1$H-NMR (300 MHz, DMSO-$d_6$) δ: 0.33-0.41 (2H, m), 0.41-0.51 (2H, m), 1.62-1.73 (1H, m), 2.45 (3H, s), 2.67-2.77 (7H, m), 3.19-3.30 (4H, m), 7.44 (1H, d, J=2.6 Hz), 7.53-7.74 (3H, m), 8.49 (1H, s), 12.06 (1H, brs). MS: [M+H]$^+$416.4.

Working Example 37

2-(4-Fluoro-1-methylpiperidin-4-yl)-6-(2-methylimidazo[1,2-α]pyridin-6-yl)quinazolin-4(3H)-one

(A) tert-Butyl 4-[(4-bromo-2-carbamoylphenyl)carbamoyl]-4-fluoropiperidine-1-carboxylate

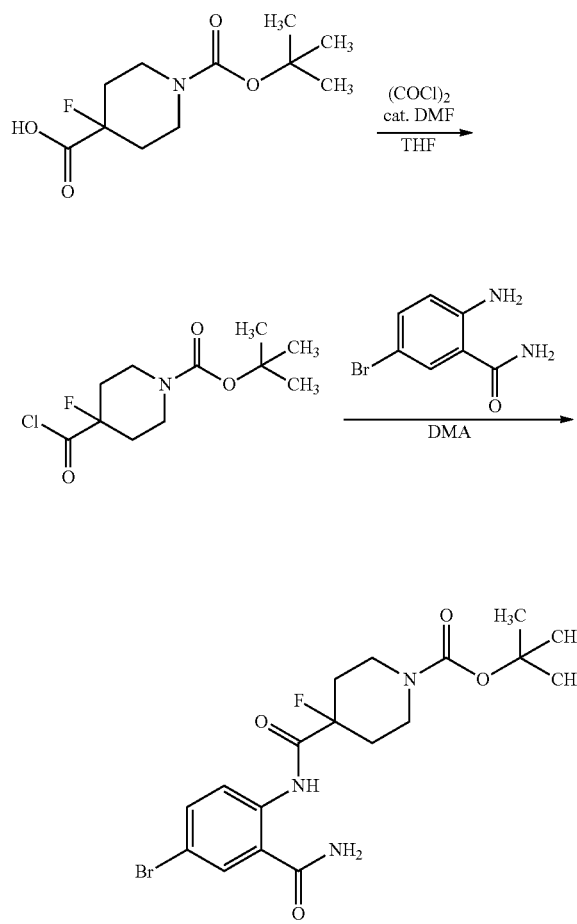

To a mixture of 1-(tert-butoxycarbonyl)-4-fluoropiperidine-4-carboxylic acid (2.0 g) and THF (40 mL) were added oxalyl chloride (2.1 mL) and DMF (0.57 mL), and then the mixture was stirred at room temperature for 1 hour. Then, the volatile components were distilled off under reduced pressure. To the remaining solid was added DMA (25 mL), followed by mixing, and 2-amino-5-bromobenzamide (1.56 g) was further added thereto at room temperature. The obtained mixture was stirred at room temperature for 2 hours and ethyl acetate (50 mL) was further added thereto. The precipitate was isolated by filtration and washed with diethyl ether, and then the obtained solid was purified by silica gel column chromatography (methanol/dichloromethane) to obtain the title compound (2.25 g).

$^1$H-NMR (400 MHz, DMSO-$d_6$) δ: 1.42 (9H, s), 1.80-2.09 (4H, m), 2.88-3.13 (2H, m), 3.90-3.99 (2H, m), 7.73 (1H, dd, J=8.9, 1.8 Hz), 7.89 (1H, s), 8.04 (1H, d, J=1.9 Hz), 8.43 (1H, s), 8.49 (1H, d, J=8.9 Hz), 12.49 (1H, d, J=5.1 Hz). MS: [M+H]$^+$443. 9.

(B) tert-Butyl 4-(6-Bromo-4-oxo-3,4-dihydroquinazoline-2-yl)-4-fluoropiperidine-1-carboxylate

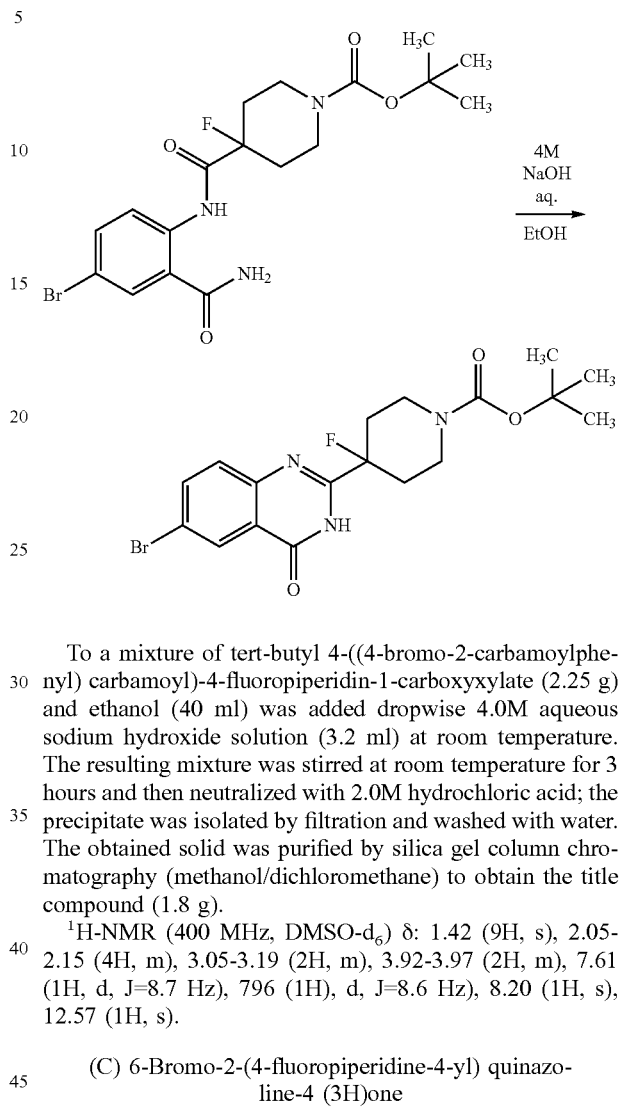

To a mixture of tert-butyl 4-((4-bromo-2-carbamoylphenyl) carbamoyl)-4-fluoropiperidin-1-carboxyxylate (2.25 g) and ethanol (40 ml) was added dropwise 4.0M aqueous sodium hydroxide solution (3.2 ml) at room temperature. The resulting mixture was stirred at room temperature for 3 hours and then neutralized with 2.0M hydrochloric acid; the precipitate was isolated by filtration and washed with water. The obtained solid was purified by silica gel column chromatography (methanol/dichloromethane) to obtain the title compound (1.8 g).

$^1$H-NMR (400 MHz, DMSO-$d_6$) δ: 1.42 (9H, s), 2.05-2.15 (4H, m), 3.05-3.19 (2H, m), 3.92-3.97 (2H, m), 7.61 (1H, d, J=8.7 Hz), 796 (1H), d, J=8.6 Hz), 8.20 (1H, s), 12.57 (1H, s).

(C) 6-Bromo-2-(4-fluoropiperidine-4-yl) quinazoline-4 (3H)one

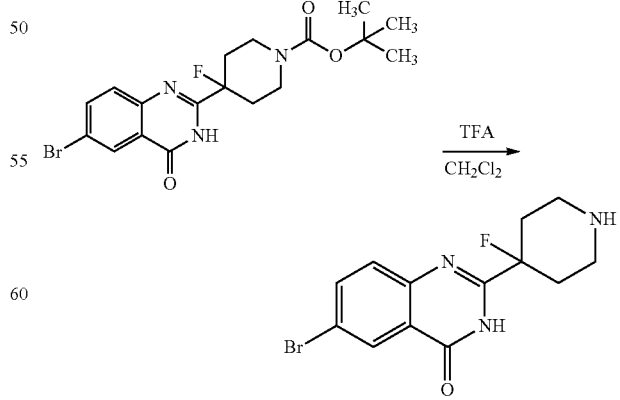

Trifluoroacetic acid (2.5 ml) was added to a mixture of tert-butyl 4-(6-bromo-4-oxo-3, 4-dihydroquinazoline-2-yl)-

4-fluoropiperidine-1-carboxylate (1.8 g) and dichloromethane (15 ml) under ice-cooling, and the mixture was stirred at room temperature for 2 hours. The volatile components were distilled off under reduced pressure, a saturated aqueous sodium hydrogen carbonate solution was added to the remaining solid, and the mixture was extracted with dichloromethane. After dehydrating the organic layer with anhydrous sodium sulfate, the volatile components were distilled off under reduced pressure to obtain the title compound (1.2 g).

$^1$H-NMR (400 MHz, DMSO-$d_6$) δ: 1.96-2.24 (4H, m), 2.81-2.86 (2H, m), 2.94-3.02 (2H, m), 7.59 (1H, d, J=8.6 Hz), 7.90-7.96 (1H, m), 8.18 (1H, d, J=2.0 Hz). MS: [M+H]$^+$326 2.

(D) 6-bromo-2-(4-fluoro-1-methylpiperidine-4-yl) quinazoline-4-(3H)-one

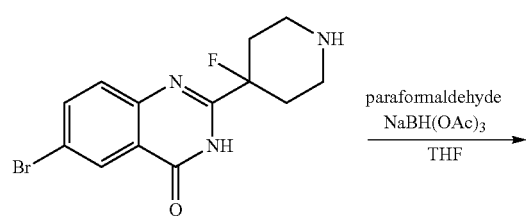

Paraformaldehyde (1.38 g) was added to a mixture of 6-bromo-2-(4-fluoropiperidine-4-yl) quinazoline-4 (3H)-one (1.0 g) and THF (20 ml); the mixture was stirred at room temperature for 2 hours, sodium borohydride (975 mg) was added, and the mixture was stirred overnight at room temperature. A cleaning solution in which the separated solids were washed with a 10% methanol/dichloromethane solution was added to the filtrate obtained by filtering the obtained mixture with Celite. The obtained filtrate was washed with saturated aqueous sodium hydrogen carbonate solution, dehydrated with anhydrous sodium sulfate, and volatile components were distilled off under reduced pressure. The remaining solid was purified by silica gel column chromatography (methanol/dichloromethane) to obtain the title compound (400 mg).

$^1$H-NMR (300 MHz, DMSO-$d_6$) δ: 2.03-2.27 (9H, m), 2.71-2.80 (2H, m), 7.62 (1H, d, J=8.6 Hz), 7.97 (1H, dd, J=8.6, 2.1 Hz), 8.20 (1H, d, J=1.9 Hz), 12.47 (1H, brs). MS: [M+H]$^+$340.1.

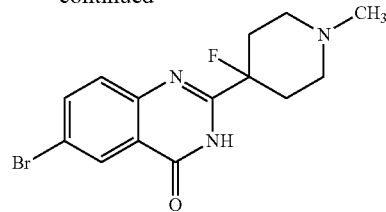

(E) 2-(4-fluoro-1-methylpiperidin-4-yl)-6-(2-methyl-imidazole[1, 2-a]pyridin-6-yl) quinazoline-4-(3H)-one

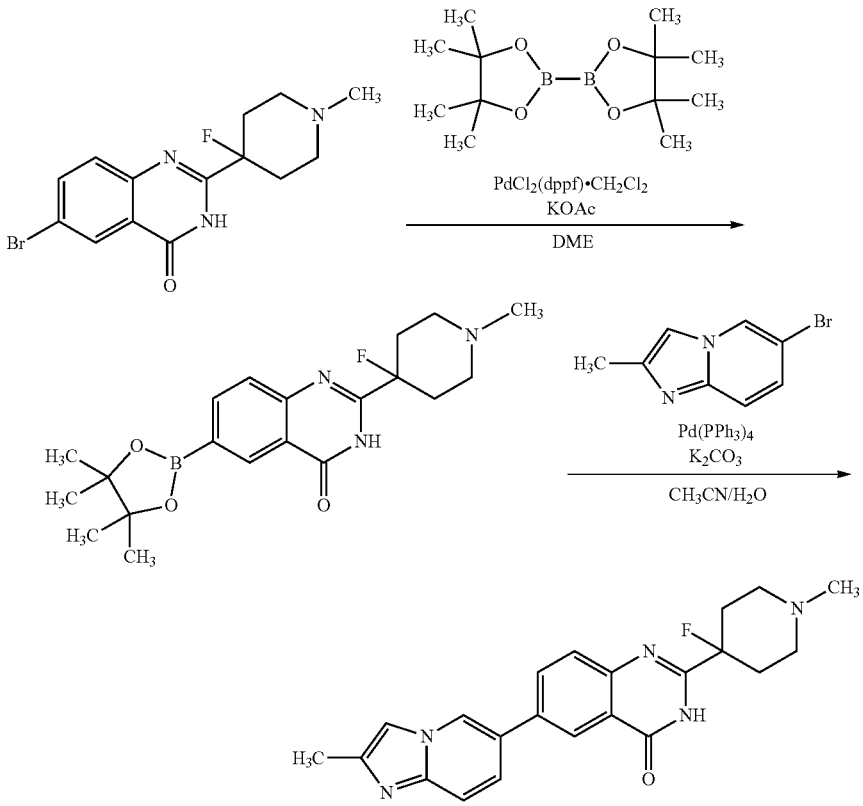

Potassium acetate (173 mg) was added to a mixture of 6-bromo-2-(4-fluoro-1-methylpiperidine-4-yl) quinazoline-4-(3H)-one (200 mg), bis (pinacolato) diboron (299 mg) and DMF (8 ml); after degassing with argon for 15 minutes, an additive containing dichloro[1, 1'-bis (diphenylphosphino) ferrocene]palladium dichloromethane (24.0 mg) was further added, and the mixture was stirred at 90° C. for 3 hours. After adding THF (15 ml) to the obtained mixture at room temperature, the solid was removed by filtration, and the volatile components were distilled off from the filtrate under reduced pressure. To the remaining solid, 6-bromo-2-amethylimidazole[1, 2-a]pyridine (150 mg), acetonitrile (10 ml) and water (0.5 ml) were added and mixed, and potassium carbonate (198 mg) was further added. The resulting mixture was degassed with argon for 20 minutes, and then tetrakis (triphenylphosphine) palladium (0) (82.2 mg) was added. The mixture was stirred at 90° C. for 16 hours, cooled to room temperature, and then filtered through Celite to remove solids. Volatile components were distilled off from the obtained filtrate under reduced pressure, and the remaining solid was purified by silicon gel column chromatography (dichloromethane/methanol) to obtain the title compound (27.0 mg).

$^1$H-NMR (400 MHz, CD$_3$OD) 6: 2.17-2.23 (2H, m), 2.35-2.61 (10H, m) 2.98-3.02 (2H, m), 7.56 (1H, d, J=9.3 Hz), 7.64-7.68 (2H, m), 7.81 (1H, d, J=8.5 Hz), 8.11-8.16 (1H, m), 8.4 6 (1H, s), 8.77 (1H, s). MS: [M+H]$^+$392.2.

Working Example 38

6-(4-fluoro-2-methyl-1,3-benzoxazole-6-yl)-2-(1-isopropylpiperidin-4-yl) quinazoline-4 (3H)-one

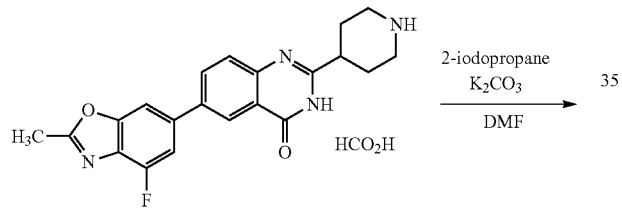

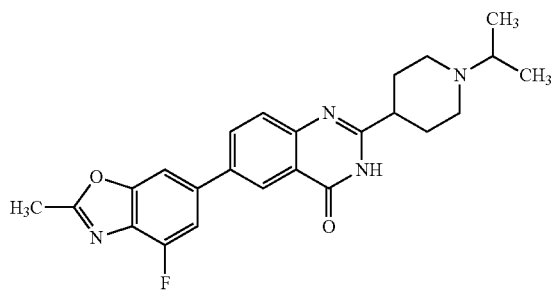

A mixture of 6-(4-fluoro-2-methyl-1,3-benzoxazole-6-yl)-2-(piperidin-4-yl) quinazoline-4-(3H)-one formic acid salt (150 mg), 2-iodopropane (0.106 ml), potassium carbonate (122 mg) and DMF (5 ml) was stirred at 60° C. for 3 hours, water (2.5 ml) was further added, the mixture was stirred at room temperature for 30 minutes and then filtered to isolate the precipitate. The obtained solid was washed with ethanol/water (1/1) and dimethylsulfoxide/ethanol (1/1) to obtain the title compound (74.5 mg).

$^1$H-NMR (400 MHz, DMSO-d$_6$) δ: 0.99 (6H, d, J=6.5 Hz), 1.69-1.85 (2H, m), 1.87-1.97 (2H, m), 2.16 (2H, t, J=10.8 Hz), 2.53-2.60 (1H, m)), 2.64-2.77 (4H, m), 2.84-2.95 (2H, m), 7.62-7.73 (2H, m), 7.99 (1H, s), 8.18 (1H, dd, J=8.4, 2.1 Hz)), 8.37 (1H, d, J=2.1 Hz), 12.20 (1H, brs). MS: [M+H]$^+$4 2 1. 3.

Working Example 39

3-(1-cyclopropylpiperidin-4-yl)-7 (8-fluoro-2-methylimidazo[1, 2-a]pyridin-6-yl) quinazoline-4-(3H)-one

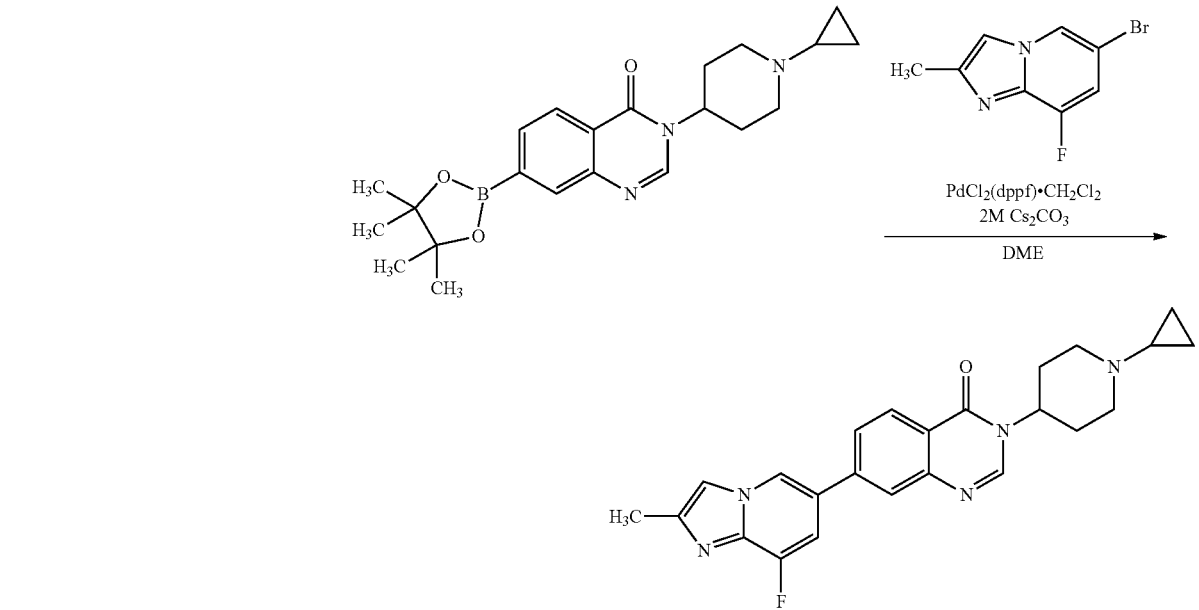

A mixture of 3-(1-cyclopropylpiperidin-4-yl)-7-(4, 4, 5, 5-tetramethyl-1, 3, 2-dioxaborolan-2-yl) quinazoline-4 (3H) one (170 mg), 6-bromo-8-fluoro-2-methilumidazo[1, 2-a]pyridine (108 mg), dichloro[1, 1'¬bis (diphenylphosphino) ferrocene]palladium with dichloromethane (17.6 mg), 2.0M cesium carbonate aqueous solution (0.43 ml) and DME (4 ml) was stirred under microwave irradiation at 130° C. for 30 minutes, then purified by silica gel column chromatography (NH, ethyl acetate and silica gel, methanol/ethyl acetate) to obtain the title compound (27.9 mg).

$^1$H-NMR (400 MHz, DMSO-d$_6$) δ: 0.33 (2H, d, J=2.4 Hz), 0.46 (2H, d, J=4.9 Hz), 1.65-1.75 (1H, m), 1.81 (2H, d, J=11.5 Hz), 1.95-2.11 (2H, m), 2.27-2.42 (5H, m), 3.09 (2H, d, J=11.1 Hz), 4.55-4.74 (1H, m), 7.68 (1H, d, J=12.7 Hz), 7.85 (1H, d, J=2.3 Hz), 7.91 (1H, d, J=8.3 Hz), 8.02 (1H, s), 8.23 (1H, d, J=8.3 Hz), 8.50 (1H, s), 8.99 (1H, s). MS: [M+H]$^+$418.3.

Working Example 40

2-(1-Cyclopropylpiperidin-4-yl)-6-(8-fluoro-2-methylimidazo[1, 2-a]pyridin-6-yl)-8-methylquinazoline-4-(3H)-one (A) tert-butyl 4-(6-(8-fluoro-2-methylimidazo[1, 2-a]pyridin-6-yl)-8-methyl-4-oxo-3,4-dihydroquinazoline-2-yl) piperidine-1-carboxylate A mixture of tert-butyl 4-(6-bromo-8-methyl-4-oxo-3,4-dihydroquinazoline-2-yl) piperidin-1-carboxylate (629 mg), bis (pinacolato) diboron (416 mg), [1,1'-bis (diphenylphosphino) ferrocene]palladium (I I) dichloride dichloromethane adduct (61 mg), potassium acetate (292 mg) and cyclopropyl methyl ether (5 mL) was stirred under microwave irradiation at 130° C. for 30 minutes; after cooling to room temperature, THF was further added, the mixture was filtered through Celite to remove solids, and volatile components were distilled off from the filtrate under reduced pressure to obtain a crude product (1.02 g). To the obtained crude product (699 mg), 2.0M aqueous solution of cesium carbonate (1.49 ml), dichloro[1, 1'-bis (diphenylphosphino) ferrocene]palladium dichloromethane adduct (61 mg) and DME (10 ml) were added, and the mixture was heated under reflux for 8 hours in a nitrogen atmosphere. Water, ethyl acetate and THF were added to the mixture at room temperature, and after filtration to remove insolubles, the obtained filtrate was extracted with ethyl acetate. The organic layer was separated and purified by silica gel column chromatography (NH, ethyl acetate), and the obtained solid was washed with diisopropyl ether to obtain the title compound (632 mg).

$^1$H-NMR (400 MHz, DMSO-d$_6$) δ: 1.43 (9H, s), 1.64-1.79 (2H, m), 1.93 (2H, d, J=10.6 Hz), 2.38 (3H, s), 2.59 (3H, s), 2.71-2.99 (3H, m)), 3.99-4.13 (2H, m), 7.59 (1H, d, J=12.6 Hz), 7.84 (1H, d, J=2.8 Hz), 8.04 (1H, s), 8.22 (1H, s), 8.91 (1H, s), 12. 26 (1H, s). MS: [M+H]$^+$492.4.

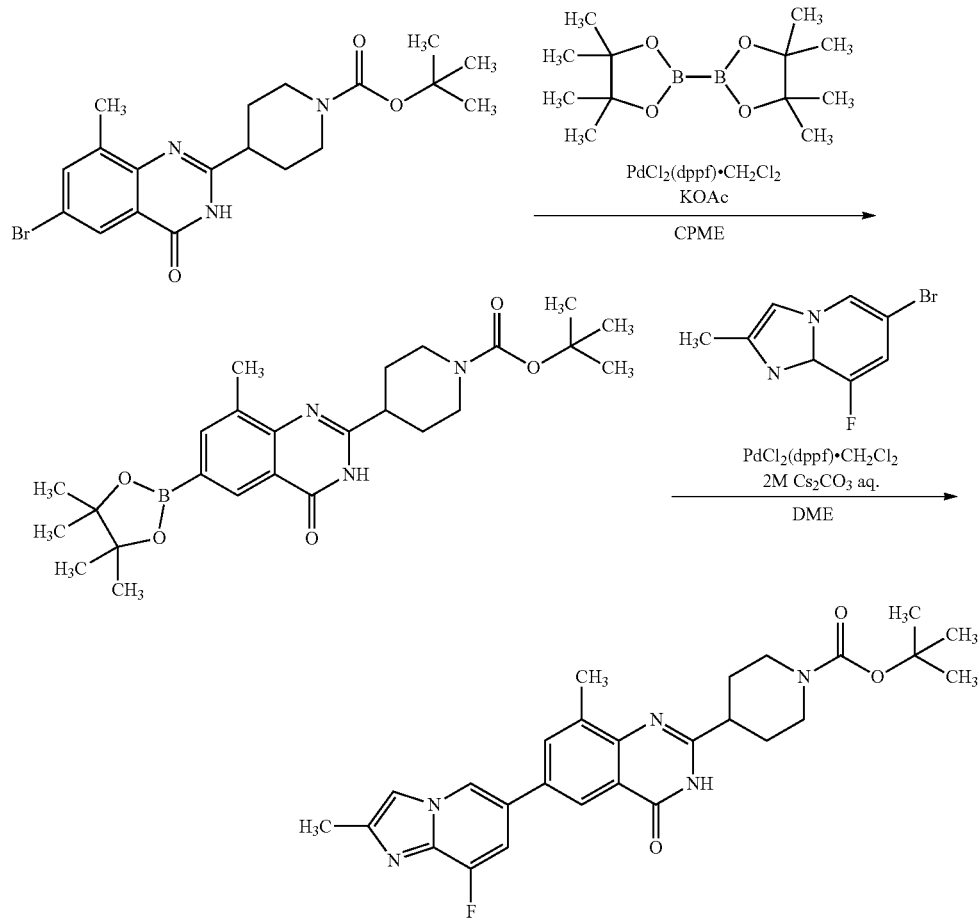

(B) 6-(8-Fluoro-2-methylimidazo[1,2-a]Pyridine-6-yl)-8-Methyl-2-(piperidin-4-yl) Kinazoline-4-(3H)-one

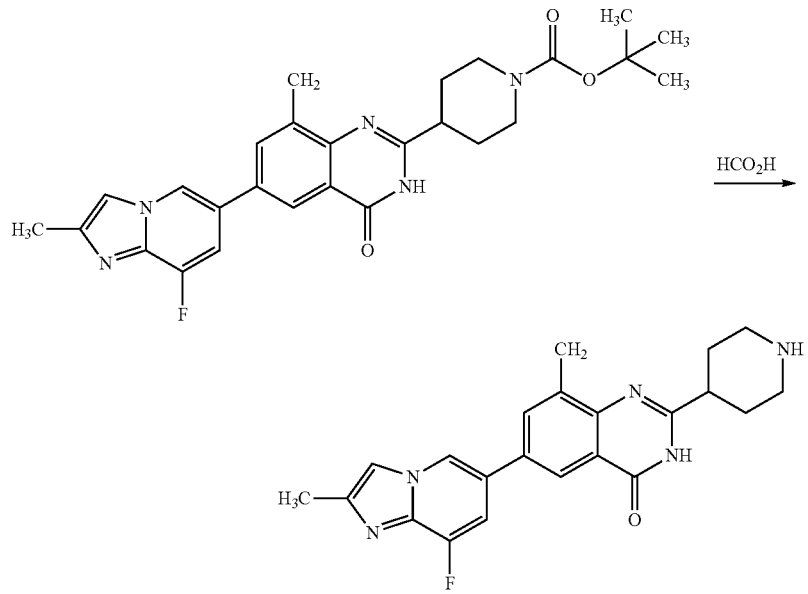

A mixture of tert-butyl 4-(6-(8-fluoro-2-methylimidazo[1,2-a]pyrididine-6-yl)-8-methyl-4-oxo-3,4-dihydroquinazoline-2-yl) piperidine-1-carboxylate (632 mg) and formic acid (5 mL) was stirred at 70° C. for 20 minutes, and the volatilizing components were distilled off under reduced pressure. The remaining solid was purified by silica gel column chromatography (NH, methanol/ethyl acetate) to obtain the title compound (432 mg).

$^1$H-NMR (400 MHz, DMSO-$d_6$) δ: 1.64-1.79 (2H, m), 1.80-1.91 (2H, m), 2.38 (3H, s), 2.52-2. 64 (5H, m), 2.64-2.77 (1H, m), 3.05 (2H, m) d, J=1 2.1 Hz), 7.59 (1H, d, J=12.6 Hz), 7.84 (1H, d, J=2.6 Hz), 8.04 (1H, s), 8.21 (1H, s), 8.90 (1H, s). MS: [M+H]$^+$392. 3.

(C) 2-(1-cyclopropylpiperidin-4-yl)-6-(8-fluoro-2-methylimidazo[1,2-a]pyridin-6-yl)-8-methylquinazoline-4-(3H)-one

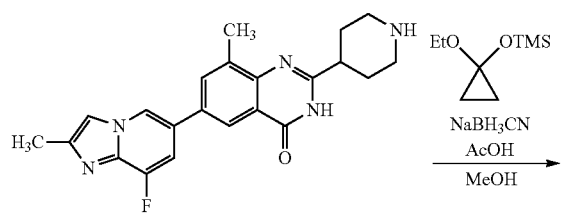

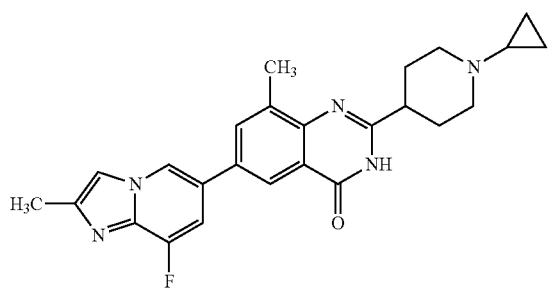

Sodium cyanoborohydride (128 mg) was added to a mixture of 6-(8-Fluoro-2-methylimidazo[1, 2-a]Pyridine-6-yl)-8-Methyl-2-(piperidin-4-yl) Kinazolin-4-(3H)-one (200 mg), ((1-ethoxycyclopropyl) oxy) (trimethyl) silane (514 ml), acetic acid (0.29 ml) and methanol (4 mL), and the mixture was stirred at 60° C. for 5 hours. After filtering to isolate the precipitate and washing with methanol, The obtained solid was purified by silica gel column chromatography (NH, ethyl acetate/hexane). Further, the obtained solid was washed with a mixed solution of ethanol/water (1/1) to obtain the title compound (21 mg).

$^1$H-NMR (400 MHz, DMSO-$d_6$) δ: 0.31 (2H, brs), 0.43 (2H, d, J=5.0 Hz), 1.64 (1H, d, J=35 Hz), 1.70-1.84 (2H, m), 1.85-1.94 (2H), m), 2.23 (2H, t, J=1 0.7 Hz), 2.38 (3H, s), 2.58 (4H, s), 3.04 (2H, d, J=11.6 Hz), 7.59 (1H, d, J=12.6 Hz), 7.84 (1H, d, J=2.2 Hz), 8.03 (1H, s), 8.21 (1H, s), 8.90 (1H, s), 12.20 (1H, s). MS: [M+H]$^+$432.3.

Working Example 85

2-(4-Fluoro-1-cyclopropylpiperidin-4-yl)-6-(8-fluoro-2-methylimidazo[1, 2-a]pyridin-6-yl) quinazoline-4-(3H)-one (A) tert-butyl 4-fluoro-4-(6-(8-fluoro-2-methylimidazole[1, 2-a]pyridin-6-yl)-4-oxo-3,4-dihydroquinazoline-2-yl) piperidine-1-carboxylate

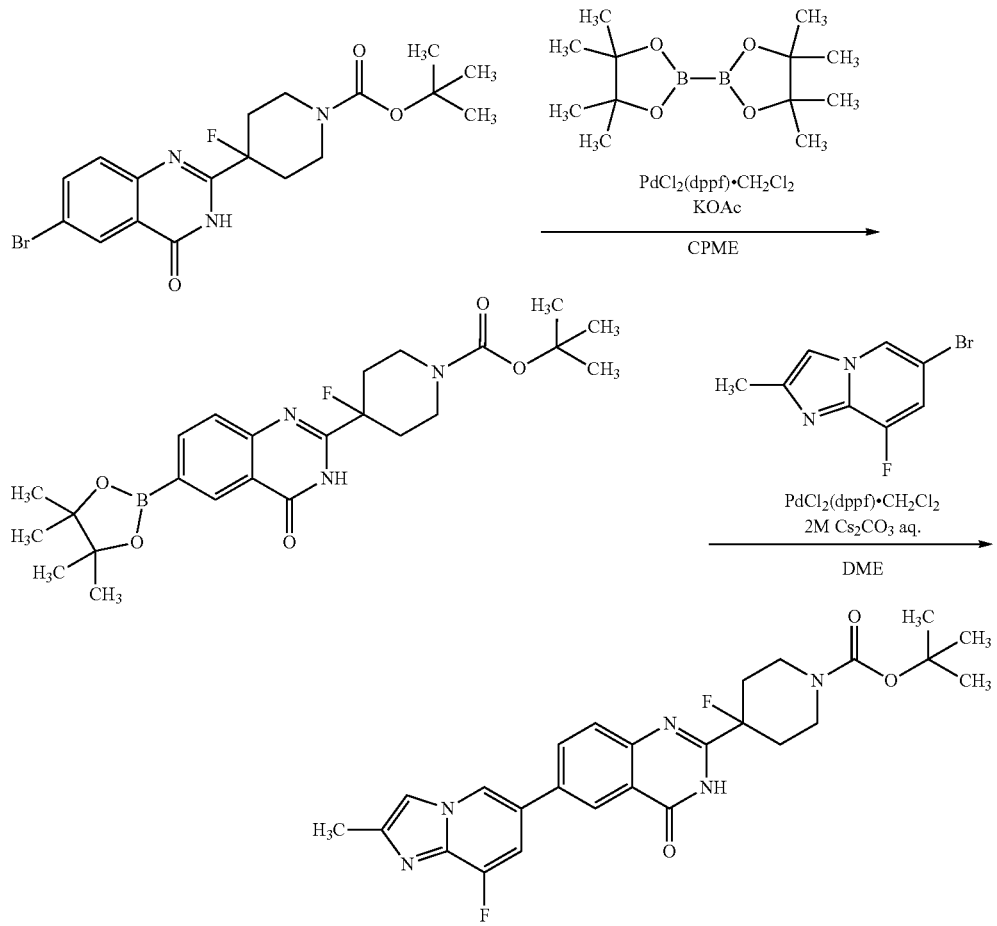

A mixture of tert-butyl 4-(6-bromo-4-oxo-3, 4-dihydroquinazoline-2-yl)-4-fluoropiperidine-1-carboxylate (2.77 g), bis (pinacolato) diboron (1.82 g), potassium acetate (1.28 g), [1, 1'-bis (diphenylphosphino) ferrocene]palladium (I I) dichloride dichloromethane adduct (0.265 g) and cyclopentyl methyl ether (50 ml) was stirred under a nitrogen atmosphere at 120° C. overnight, and purified by silica gel column chromatography (Dio I, ethyl acetate) to obtain a crude product (4.28 g). To the obtained crude product (3.08 g) were added 6-bromo-8-fluoro-2-methylimidazo[1,2-α]pyridine (1.79 g), dichloro[1, 1'-bis (diphenylphosphino) ferrocene]palladium dichloromethane adduct (0.27 g), 2.0 M aqueous cesium carbonate solution (6.5 ml) and DME (60 ml), the mixture mixed, and then heated under reflux in a nitrogen atmosphere for 4.5 hours. Water, ethyl acetate and THF were added to the obtained mixture at room temperature, and the mixture was filtered to remove insoluble matter. The obtained filtrate was extracted with ethyl acetate, the organic layer was separated, purified by silica gel column chromatography (NH, methanol/ethyl acetate), and the obtained solid was washed with ethanol/water (1/1) to obtain the title compound (2.59 g).

$^1$H-NMR (400 MHz, DMSO-$d_6$) δ: 1.44 (9H, s), 2.04-2.26 (4H, m), 2.38 (3H, s), 3.12 (2H, brs), 3.98 (2H, d, J=12.2 Hz), 7.64 (1H, d, J=12.5 Hz), 7.78 (1H, d, J=8.6 Hz), 7.85 (1H, brs), 8.19 (1H, d, J=8.6 Hz), 8.43 (1H, s), 8.97 (1H, s), 12.49 (1H, brs). MS: [M+H]$^+$496.3

(B) 6-(8-Fluoro-2-methylimidazo[1, 2-a]Pyridine-6-yl)-2-(4-Fluoropiperidine-4-yl) Kinazoline-4 (3H)-one

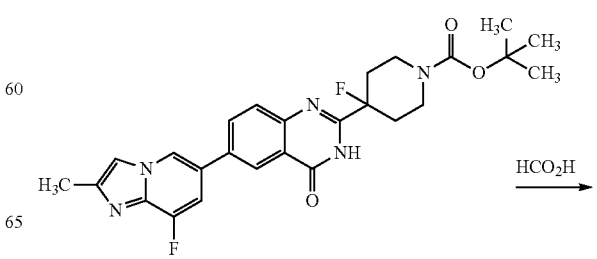

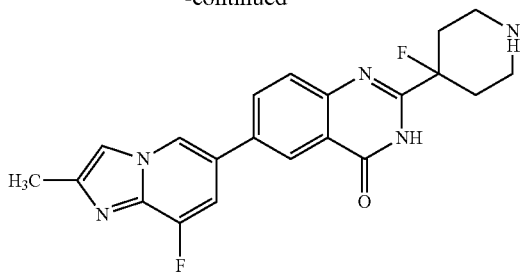
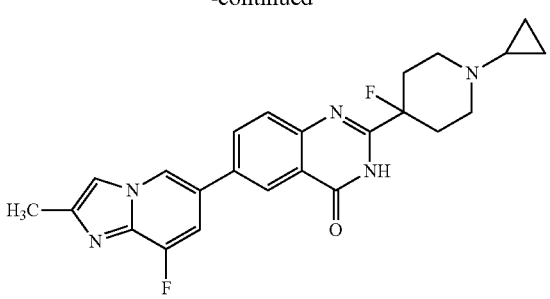

A mixture of tert-butyl 4-fluoro-4-(6-(8-fluoro-2-methilumidazo[1, 2-a]pyridin-6-yl)-4-oxo-3,4-dihydroquinazoline-2-yl) piperidine-1-carboxylate (1.25 g) and formic acid (12 ml) was stirred at 70° C. for 20 minutes and the volatile components were distilled off under reduced pressure. The remaining solid was purified by silica gel column chromatography (NH, methanol/ethyl acetate), and the obtained solid was recrystallized from ethyl acetate to obtain the title compound (820 mg).

$^1$H-NMR (400 MHz, DMSO-$d_6$) δ: 1.93-2.26 (4H, m), 2.38 (3H, s), 2.74-2.86 (2H, m), 2.89-2.99 (2H, m), 7.63 (1H, d, J=12.7 Hz), 7.76 (1H), d, J=8.7 Hz), 7.85 (1H, brs), 8.17 (1H, d, J=8.6 Hz), 8.42 (1H, s), 8.96 (1H, s). MS: [M+H]$^+$396.3.

(C) 2-(4-Fluoro-1-cyclopropylpiperidin-4-yl)-6-(8-fluoro-2-methylimidazo[1, 2-a]pyridin-6-yl) quinazoline-4-(3H)-one A mixture of 6-(8-fluoro-2-methylimidazo[1, 2-a]pyridine-6-yl)-2-(4-fluoropiperidine-4-yl) kinazoline-4 (3H)one (820 mg), ((1-ethoxycyclopropyl) oxy) (trimethyl) silane (2.09 ml), sodium cyanoborohydride (530 mg), acetic acid (1.2 ml) and methanol (20 ml) was stirred at 60° C. for 2 hours. Further, THF (50 ml) and an aqueous sodium hydrogen carbonate solution were added at room temperature, and the mixture was extracted with ethyl acetate. The organic layer was separated, washed with saturated brine, dehydrated with anhydrous magnesium sulfate, and volatile components were distilled off under reduced pressure. The remaining solid was purified by silica gel column chromatography (NH, methanol/ethyl acetate). The obtained solid was washed with ethanol/water (1/1) to obtain the title compound (497 mg).

$^1$H-NMR (400 MHz, DMSO-$d_6$) δ: 0.34 (2H, brs), 0.45 (2H, d, J=5.7 Hz), 1.72 (1H, brs), 2.04-2.28 (4H, m), 2.38 (3H, s), 2.45-2.57 (2H, m), 2.93 (2H, d, J=11.2 Hz), 7.63 (1H, d, J=12.5 Hz), 7.75 (1H, d, J=8.4 Hz), 7.85 (1H, brs), 8.18 (1H, d, J=8.8 Hz), 8.41 (1H, s), 8.95 (1H, s), 12.40 (1H, brs). MS: [M+H]$^+$436.3.

Working Example 86

2-(4-Fluoro-1-methylpiperidin-4-yl)-6-(8-full-year-old low 2-methylimidazo[1, 2-a]pyridin-6-yl) quinazoline-4 (3H)one

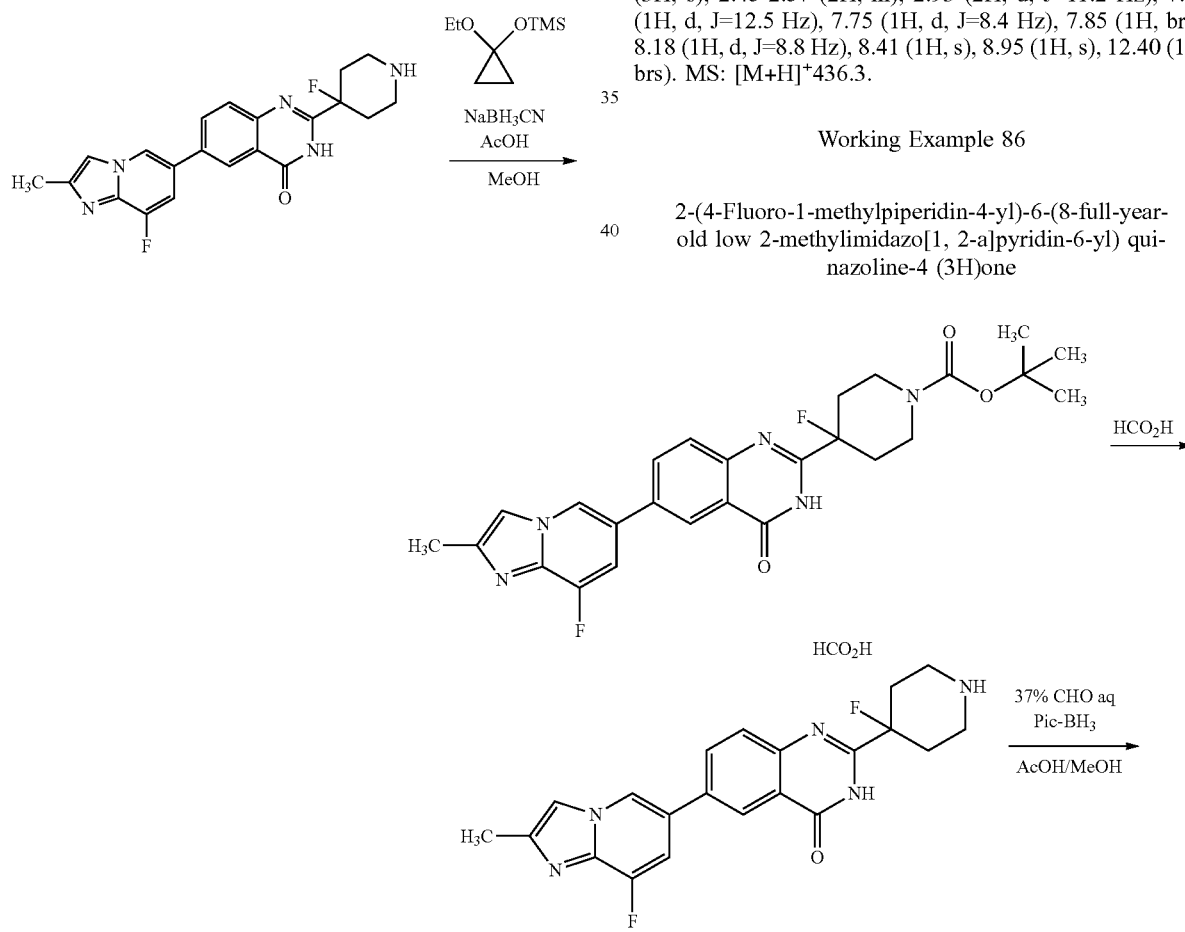

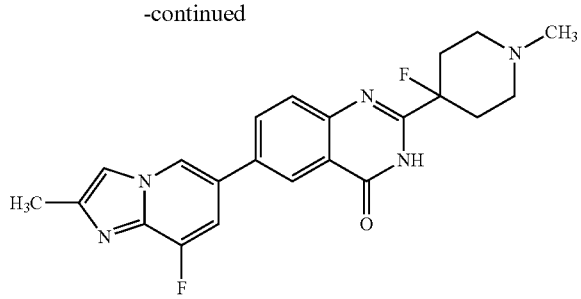

A mixture of tert-butyl 4-fluoro-4-(6-(8-fluoro-2-methilumidazo[1, 2-a]pyridine-6-yl)-4-oxo-3,4-dihydroquinazoline-2-yl) piperidine-1-carboxylate (1.2 g) and formic acid (6 mL) was stirred at 60° C. for 10 minutes, and then the volatile components were distilled off under reduced pressure. To the remaining solid, methanol (10 ml), acetic acid (2 mL) and 37% aqueous formaldehyde solution (0.79 ml) were added and mixed. Further, bolan-2-picolin complex (648 mg) was added, and the mixture was stirred overnight at room temperature. The volatile components were distilled off under reduced pressure, and THF, ethyl acetate, and saturated aqueous sodium hydrogen carbonate solution were added to the remaining solid to dissolve the solid. The aqueous layer was extracted with a mixed solution of THF and ethyl vinegar. The obtained organic layer was washed with saturated brine, dehydrated with anhydrous magnesium sulfate, and volatile components were distilled off under reduced pressure. The remaining solid was purified by silica gel column chromatography (NH, methanol/ethyl acetate), and the obtained solid was washed with diisopropyl ether and ethanol/water (4/1) to obtain the title compound (400 mg).

$^1$H-NMR (400 MHz, DMSO-$d_6$) δ: 2.06-2.17 (2H, m), 2.18-2.34 (7H, m), 2.38 (3H, s), 2.71-2.80 (2H, m), 7.63 (1H, d, J=12.6 Hz), 7.77 (1H), d, J=8.4 Hz), 7.85 (1H, d, J=1.5 Hz), 8.18 (1H, d, J=8.4 Hz), 8.42 (1H, s), 8.96 (1H, s), 12.41 (1H), brs). MS: [M+H]$^+$410.3.

Working Example 87

8-fluoro-6-(3-fluoro-4-methoxyphenyl)-2-(1-methylpiperidin-4-yl) kinazoline-4-(3H)-one (A) tert-butyl 4-(8-fluoro-6-(3-fluoro-4-methoxyphenyl)-4-oxo-3,4-dihydroquinazoline-2-yl) piperidine-1-carboxylate

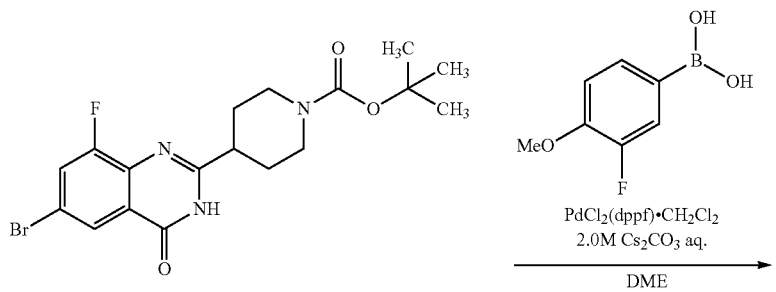

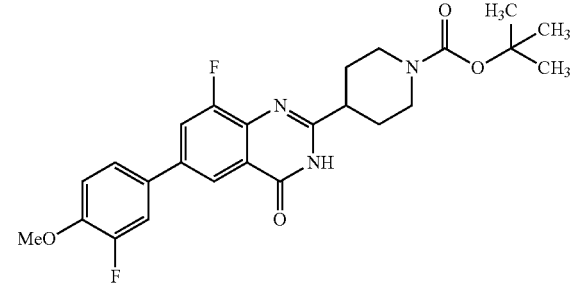

A mixture of tert-butyl 4-(6-bromo-8-fluoro-4-oxo-3,4-dihydroquinazoline-2-yl) piperidin-1-carboxylate (1.5 g), (3-fluoro-4-methoxyphenyl) boronic acid (718 mg), dichloro[1, 1'-bis (diphenylphosphino) ferrocene] radium dichloromethane adduct (144 mg), 2.0M aqueous cesium carbonate solution (3.52 ml) and DME (15 ml) was stirred under microwave irradiation at 130° C. for 30 minutes. After further adding ethyl acetate, THF and water at room temperature and mixing, the solids were removed by filtration through Celite. The organic layer of the obtained filtrate was separated, washed with saturated brine, and dehydrated with anhydrous magnesium sulfate. The volatile components were distilled off under reduced pressure, and the remaining solid was washed with methanol to obtain the title compound (1.5 g).

$^1$H-NMR (400 MHz, DMSO-$d_6$) δ: 1.42 (9H, s), 1.61-1.77 (2H, m), 1.87-1.97 (2H, m), 2.81 (3H, t, J=11.5 Hz), 3.90 (3H, s), 4.06 (2H, d, J=11.9 Hz), 7.28 (1H, t, J=8.8 Hz), 7.62 (1H, d, J=8.6 Hz), 7.73 (1H, d, J=13.0 Hz), 8.04 (1H, d, J=11.9 Hz), 8.11 (1H, s), 12.41 (1H, brs). MS: [M+H]$^+$ 472.3.

(B) 8-fluoro-6-(3-fluoro-4-methoxyphenyl)-2-(piperidin-4-yl) quinazoline-4-(3H)-one acetate

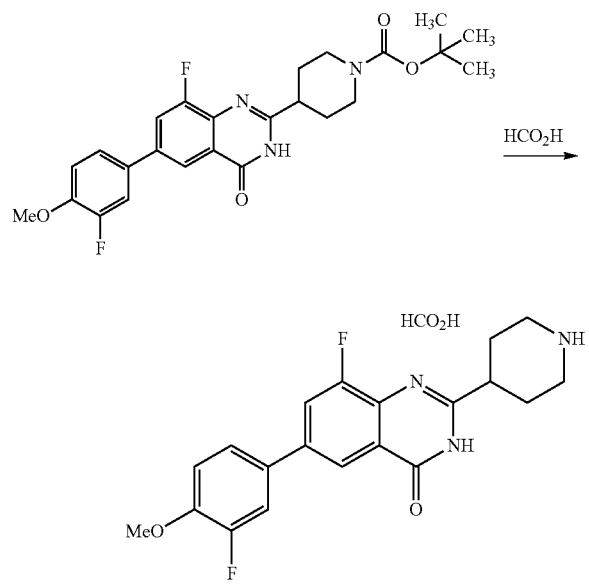 [SMILES: COc1ccc(-c2cc(F)c3nc(C4CCN(C(=O)OC(C)(C)C)CC4)[nH]c(=O)c3c2)cc1F ; "HCO2H" ; COc1ccc(-c2cc(F)c3nc(C4CCNCC4)[nH]c(=O)c3c2)cc1F ; "HCO2H"]

A mixture of tert-butyl 4-(8-fluoro-6-(3-fluoro-4-methoxyphenyl)-4-oxo-3,4-dihydroquinazoline-2-yl) piperidin-1-carboxylate (1.5 g) and formic acid (6 mL) was stirred at 70° C. for 20 minutes, and then the volatile components were distilled off under reduced pressure. The remaining solid was dissolved in acetic acid and purified by silica gel column chromatography (NH, methanol/ethyl acetate). The obtained solid was washed with ethyl acetate to obtain the title compound (1.28 g).

$^1$H-NMR (400 MHz, DMSO-$d_6$) δ: 1.68-1.81 (2H, m), 1.85-1.90 (7H, m), 2.54-2.65 (2H, m), 2.69-2.78 (1H, m), 3.09 (2H, d, J=12.2 Hz), 3.90 (3H, s), 7.28 (1H, t, J=8.9 Hz), 7.62 (1H, d, J=8.9 Hz), 7.72 (1H, d, J=144 Hz), 8.03 (1H, d, J)=12.0 Hz), 8.11 (1H, s). MS: [M+H]$^+$372.3.

(C) 8-fluoro-6-(3-fluoro-4-methoxyphenyl)-2-(1-methylpiperidin-4-yl) kinazoline-4 (3H)-one

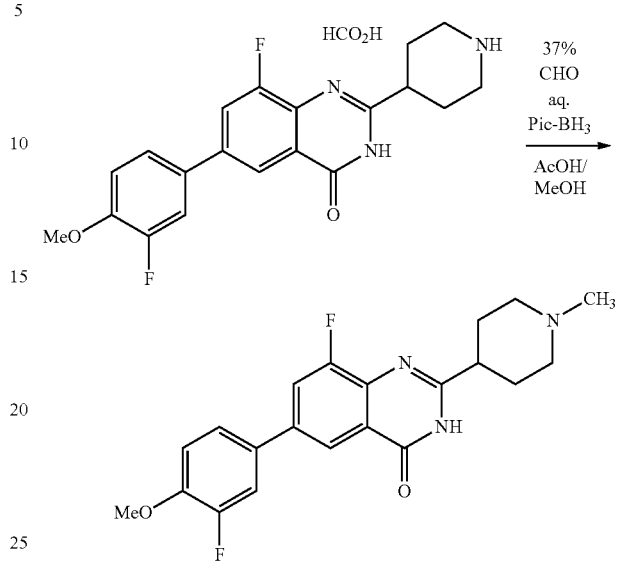

Bolan-2-picolin complex (428 mg) was added to a mixture of 8-fluoro-6-(3-fluoro-4-methoxyphenyl)-2-(piperidin-4-yl) quinazoline-4-(3H)-one acetate (1.15 g), methanol (20 ml), acetic acid (2 mL) and 37% aqueous formaldehyde solution (0.67 ml), the mixture was stirred overnight at room temperature, and the volatile components were distilled off under reduced pressure. The remaining solid was purified by silica gel column chromatography (NH, methanol/ethyl acetate), and the obtained solid was washed with ethanol/water (1/1) to obtain the title compound (510 mg).

$^1$H-NMR (400 MHz, DMSO-$d_6$) δ: : 1.75-1.98 (6H, m), 2.19 (3H, s), 2.52-2.61 (1H, m), 2.87 (2H, d, J=10.5 Hz), 3.90 (3H, s), 7.28 (1H, t), J=8.7 Hz), 7.62 (1H, d, J=8.7 Hz), 7.72 (1H, d, J=13.0 Hz), 8.03 (1H, d, J=12.0 Hz), 8.11 (1H, s), 12.36 (1H, brs). MS: [M+H]$^+$386.2

Working Example 85

2-(4, 6-dimethylpyrazolo[1,5-α]pyrazine-2-yl)-6-(4-methylpiperazin-1-yl) quinazoline-4 (3H)one succinate (A) 4, 6-Dimethylpyrazolo[1,5-α]pyrazine-2-carboxylic acid

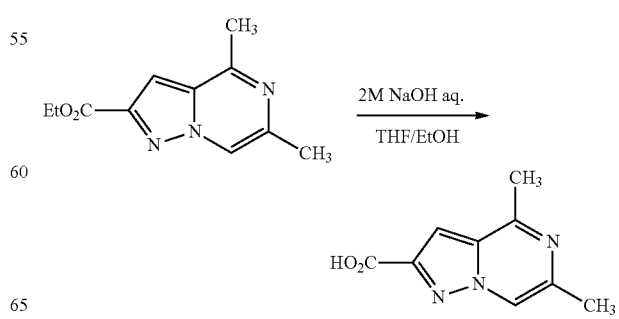

2.0M aqueous sodium hydroxide solution (135 ml) was added to a mixture of ethyl 4,6-dimethylpyrazolo[1,5-α]pyrazine-2-carboxylate (29.69) with ethanol (150 ml) and THF (300 mL); after stirring at room temperature for 3 hours, water (300 ml) and 2.0M hydrochloric acid (135 mL) were added at room temperature for neutralization. The resulting mixture was stirred under ice cooling for 1 hour and then the solid obtained by filtration was washed with water (100 ml) to obtain the title compound (23.6 g).

$^1$H-NMR (300 MHz, DMSO-$d_6$) δ: 2.37-2.45 (3H, m), 2.65-2.74 (3H, m), 7.35-7.46 (1H, m), 8.51 (1H, d, J=0.8 Hz), 13.25 (1H, brs). MS: [M+H]$^+$191.9

(B) N-(2-carbamoyl-4-(4-methylpiperazin-1-yl) phenyl)-4,6-dimethylpyrazolo[1,5-α]pyrazine-2-carboxamide

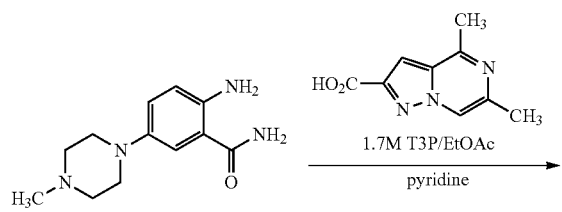

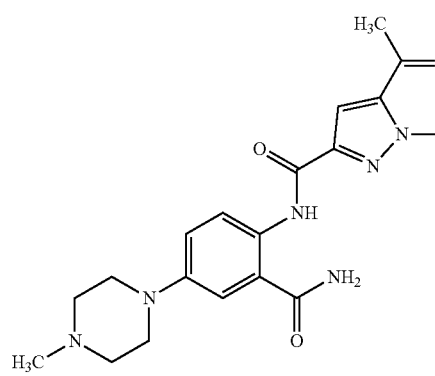

A mixture of 4, 6-dimethylpyrazolo[1,5-α]pyrazine-2-carboxylic acid (10.0 g), 1.7 M propylphosphonic anhydride/ethyl acetate solution (46.1 mL) and pyridine (200 ml) was stirred for 1 hour at room temperature; further, a mixture of 2-amino-5-(4-methylpiperidin-1-yl) benzamide (14.7 g) and pyridine (100 ml) was added, and the mixture was stirred at room temperature for 2 hours. After distilling off the volatile components under reduced pressure, water (300 ml) and a 10% aqueous potassium carbonate solution (300 ml) were added to the remaining solid, and the mixture was stirred at room temperature for 1 hour. The solid obtained by filtration was washed with water (300 ml), ethyl acetate (100 mL) and diisopropyl ether (100 ml) to obtain the title compound (20.0 g).

$^1$H-NMR (300 MHz, DMSO-$d_6$) δ: 2.16-2.29 (3H, m), 2.41-2.49 (7H, m), 2.72 (3H, s), 3.18 (4H, d, J=4.9 Hz), 7.16 (1H, dd, J=9.1, 2.3 Hz), 7.31 (1H, d, J=2.6 Hz), 7.43 (1H, s), 7.64 (1H, brs), 8.29 (1H, brs), 8.47-8.61 (2H, m), 12.48 (1H, b rs). MS: [M+H]$^+$408.1.

(C) 2-(4,6-dimethylpyrazolo[1,5-α]pyrazine-2-yl)-6-(4-methylpiperazin-1-yl) kinazoline-4 (3H)one

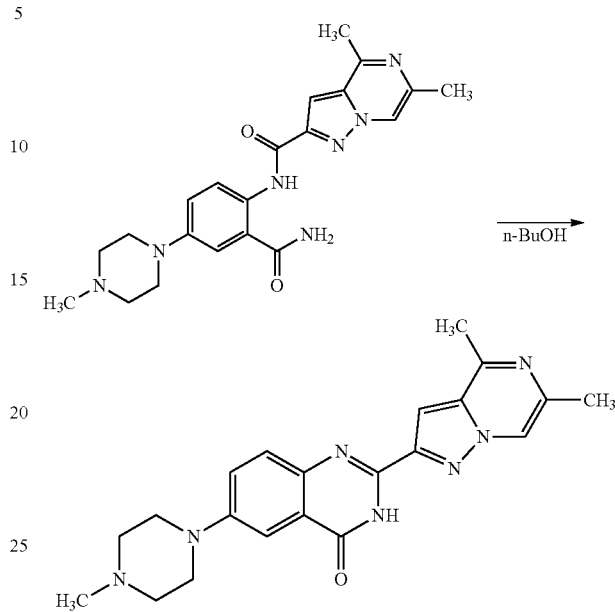

A mixture of N-(2-carbamoyl-4-(4-methylpiperazin-1-yl) phenyl)-4,6-dimethylpyrazolo[1, 5-a]pyrazine-2-carboxamide (35.5 g) and 1-butanol (1065 ml) was stirred at 120° C. overnight, and after distilling off the volatile components under reduced pressure, the remaining solid was washed with diisopropyl ether to obtain the title compound (31.2 g).

$^1$H-NMR (300 MHz, DMSO-$d_6$) δ: 2.24 (3H, s), 2.40-2.49 (7H, m), 2.65-2.77 (3H, m), 3.21-3.31 (4H, m), 7.45 (1H, d, J=2.3 Hz), 7.51-7.69 (3H, m), 8.49 (1H, s), 12.06 (1H, brs). MS: [M+H]$^+$390.1

(D) 2-(4,6-dimethylpyrazolo[1,5-α]pyrazine-2-yl)-6-(4-methylpiperazin-1-yl) kinazoline-4 (3H)one succinate

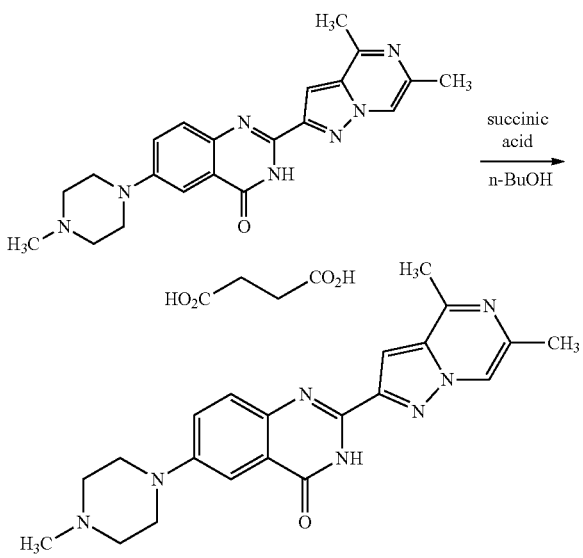

2-(4,6-dimethylpyrazolo[1,5-α]pyrazine-2-yl)-6-(4-methylpiperazin-1-yl) quinazoline-4-(3H)-one (40 g) 1-butanol (100 ml) succinic acid (12.6 g) was added to the mixture at 100° C., the mixture was stirred at the same temperature for 1 hour, and the filtrate obtained by filtration was mixed with a washing solution obtained by washing the separated solids with 1-butanol (100 ml). After stirring the obtained filtrate at 100° C. for 30 minutes, it was cooled to room temperature, and diisopropyl ether (200 ml) was added. The obtained mixture was stirred at room temperature overnight, and the solid obtained by filtration was washed with diisopropyl ether to obtain a solid (45.2 g). After stirring the mixture of the obtained solid (45.2 g) and ethyl acetate (900 ml) at 60° C. for 1 hour and at room temperature for 1 hour, the solid obtained by filtration was washed with ethyl acetate (200 ml) and dried under reduced pressure to obtain the title compound (44.0 g).

$^{1}$H-NMR (300 MHz, DMSO-$d_6$) δ: 2.28 (3H, s), 2.38-2.42 (5H, m), 2.46 (3H, s), 2.52-2.58 (3H, m), 2.54 (3H, d, J=4.5 Hz), 2.73 (3H, s)), 3.26-3.34 (4H, m), 7.46 (1H, d, J=2.3 Hz), 7.55-7.68 (3H, m), 8.50 (1H, s), 12.07 (2H, brs). MS: [M+H]$^+$386.2

Working Example 89

6-(8-Fluoro-2-methylimidazo[1, 2-a]pyridine-6-yl)-2-(4-fluoro-1-methylpiperidine-4-yl)-8-methylquinazoline-4-(3H)-one (A) tert-butyl 4-(6-bromo-8-methyl-4-oxo-3, 4-dihydroquinazoline-2-yl)-4-fluoropiperidine-1-calboxylate

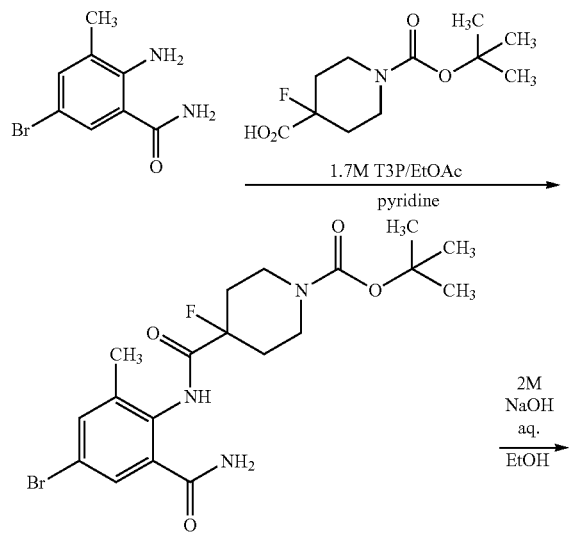

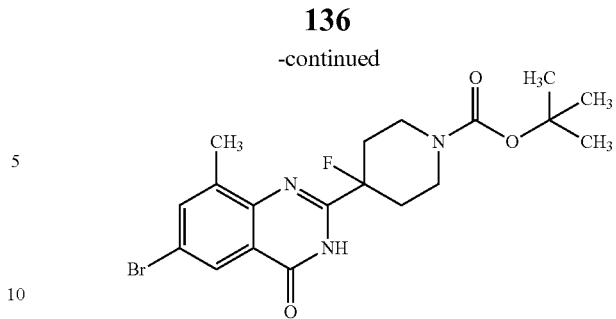

After stirring the mixture of 1-(tert-butoxycarbonyl)-4-fluoropiperidine-4-carboxylic acid (3.60 g), 1.7 M propylphosphonic anhydride/ethyl acetate solution (12.1 ml) and pyridine (25 ml) for 1 hour at room temperature, a pyridine solution (25 ml) of 2-amino-5-bromo-3-methylbenzamide (2.78 g) was added dropwise at room temperature and stirred at room temperature overnight. This was neutralized with 2.0 M aqueous sodium hydroxide solution (25 ml), and the volatile components were distilled off under reduced pressure. Ethyl acetate, THF and water were added to the remaining solid to separate the organic layer. After washing with saturated brine, dehydration was carried out with anhydrous magnesium sulfate, and volatile components were distilled off under reduced pressure. Ethanol (100 ml) was added to the remaining solid and mixed, and 2.0 M aqueous sodium hydroxide solution (24.3 ml) then added at room temperature. After stirring at room temperature for 30 minutes, 2.0 M hydrochloric acid (24 ml) was added to neutralize the mixture. The precipitate was isolated by filtration and washed with ethanol/water (1/1) to obtain the title compound (4.1 g).

$^{1}$H-NMR (300 MHz, DMSO-$d_6$) δ: 1.43 (9H, s), 2.04-2.26 (4H, m), 3.14 (2H, brs), 3.92 (2H, d, J=13.3 Hz), 7.89 (1H, dd, J=2.3, 0.8 Hz), 8.04 (1H, d, J=1.9 Hz), 12.57 (1H, brs). MS: [M+H]$^+$440.2

(B) tert-butyl 4-fluoro-4-(6-(8-fluoro-2-methylimidazole[1, 2-a]pyridin-6-yl)-8-methyl-4-oxo 3, 4-dihydroquinazoline-2-yl) piperidine-1-carboxylate

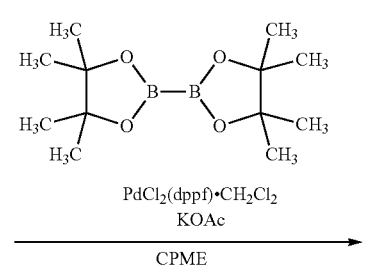

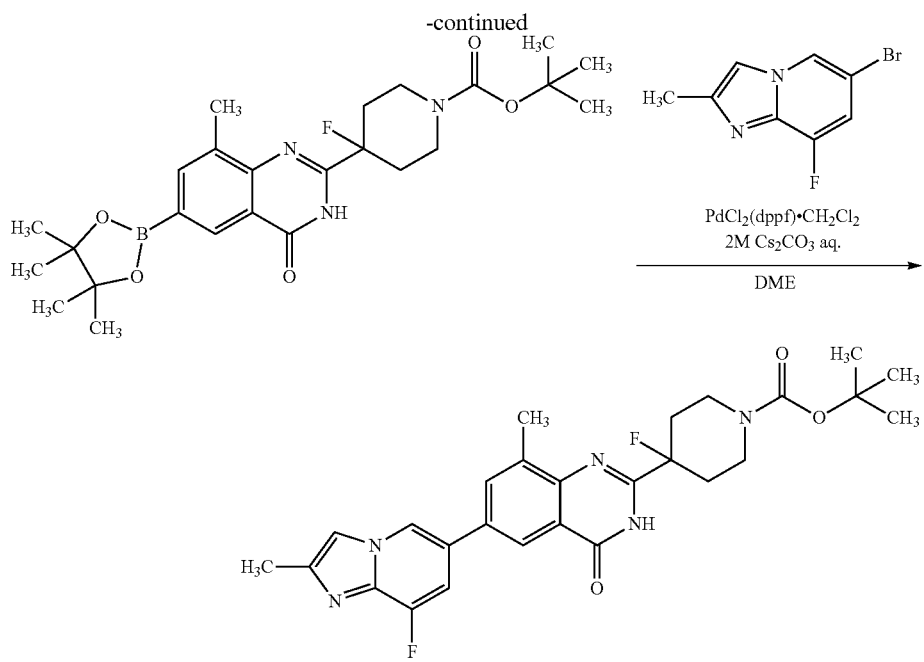

A mixture of tert-butyl 4-(6-bromo-8-methyl-4-oxo-3,4-dihydroquinazoline-2-yl)-4-fluoropiperidine-1-carboxylate (1.0 g), bis (pinacolato) diboron (692 mg), potassium vinegar (446 mg), [1,1'-Bis (diphenylphosphino) ferrocene] palladium (11) dichloride dichloromethane adduct (93 mg) and cyclopentyl methyl ether (5 mL) was stirred at 130° C. for 30 minutes under microwave irradiation, water was added and the mixture filtered at room temperature with Celite to remove solids; then the filtrate was extracted with ethyl acetate. After separating the organic layer, washing with saturated brine, and dehydrating with anhydrous magnesium sulfate, the volatile components were distilled off under reduced pressure to obtain a crude product. To the obtained crude product, 6-bromo-8-fluoro 2-methylimidazo [1, 2-a]pyridine (624 mg), fichloro[1, 1'-bis (diphenylphosphino) ferrocene]palladium dichloromethane adduct (93 mg), 2.0 M aqueous cesium carbonate solution (2.3 mL) and DME (10 ml) were added, and the mixture was stirred at 130° C. for 30 minutes under microwave irradiation. The obtained mixture was purified by silica gel column chromatography (NH, methanol/ethyl acetate) to obtain the title compound (440 mg).

MS: [M+H]$^+$510.4.

(C) 6-(8-Fluoro-2-methylimidazo[1, 2-a]Pyridine-6-yl)-2-(4-Fluoro-1-methylpiperidin-4-yl)-8-Methylquinazoline-4-(3H)-one

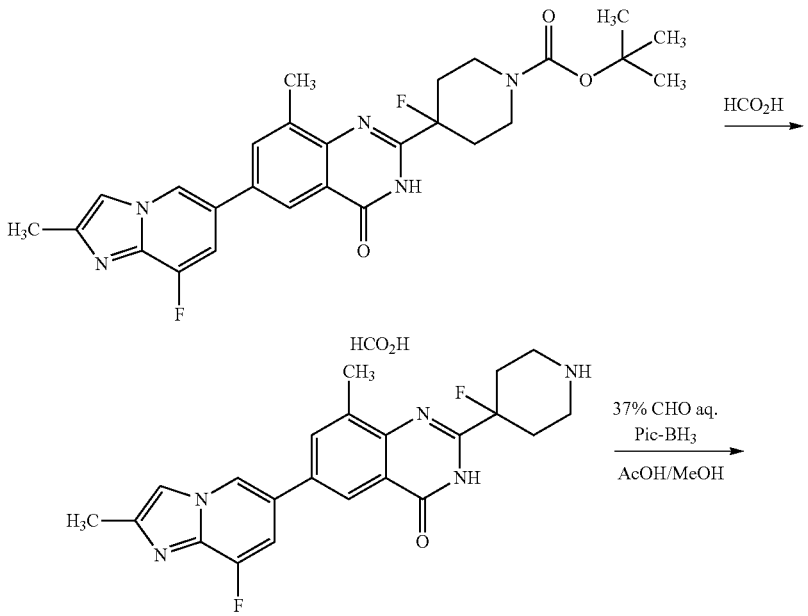

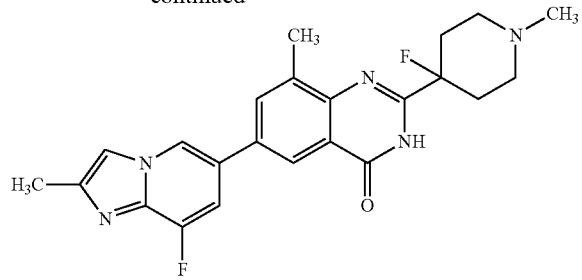

A mixture of tert-butyl 4-fluoro-4-(6-(8-fluoro-2-methyl-imidazole[1, 2-a]pyridin-6-yl)-8-methyl-4-oxo-3,4-dihydroquinazoline-2-yl) piperidin-1-carboxylate (114 mg) and formic acid (2 mL) was stirred at 60° C. for 10 minutes; after that, volatile components were distilled off under reduced pressure. Bolan-2-picolin complex (60 mg) was added to a mixture of the remaining solid, methanol (2 mL), acetic acid (0.2 ml) and 37% aqueous formaldehyde solution (0.073 ml), and the mixture was stirred overnight at room temperature. The volatile components of the mixture were distilled off under reduced pressure, the remaining solid was purified by silica gel column chromatography (NH, methanol/ethyl acetate), and the obtained solid was washed with ethyl acetate to obtain the title compound (28 mg).

$^1$H-NMR (300 MHz, DMSO-d$_6$) δ: 2.10-2.30 (8H, m), 2.38 (4H, s), 2.60 (3H, s), 2.69-2.82 (2H, m), 7.62 (1H, d, J=12.9 Hz), 7.85 (1H, s) brs), 8.08 (1H, s), 8.25 (1H, s), 8.93 (1H, s), 12.40 (1H, brs). MS: [M+H]$^+$424.3

Working Example 90

2-(1-ethyl-4-fluoropiperidine-4-yl)-6-(8-full-year-old low 2-methylimidazo[1, 2-a]pyridin-6-yl)-8-methylquinazoline-4-(3H)-one

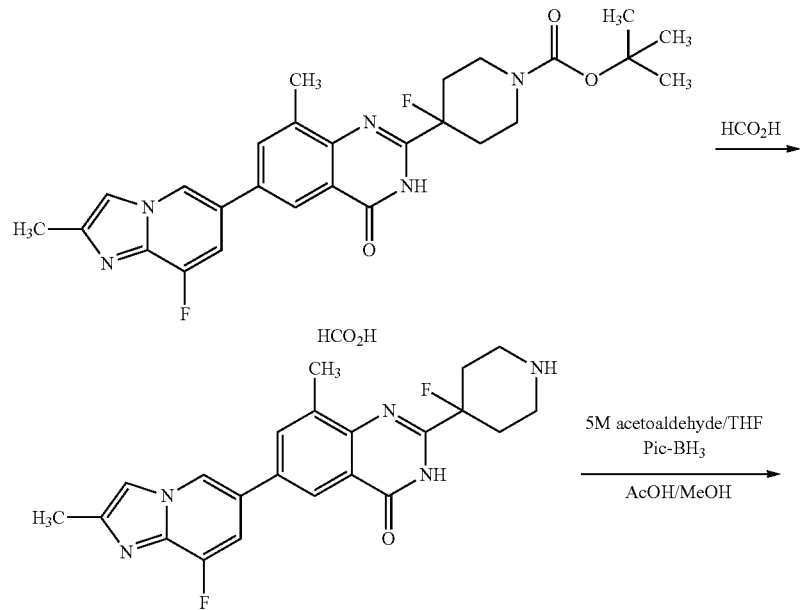

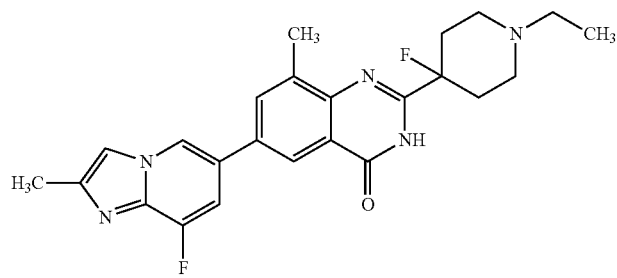

A mixture of tert-Butyl 4-fluoro-4-(6-(8-fluoro-2-methi-lumidazo[1, 2-a]pyridin-6-yl)-8-methyl-4-oxo-3,4-dihydroquinazoline-2-yl) piperidin-1-carboxylate (324 mg) and formic acid (2 mL) was stirred at 60° C. for 10 minutes, and then the volatile components were distilled off under reduced pressure. To the remaining solid, methanol (5 mL), acetic acid (1 mL) and 5.0 M acetaldehyde/THF solution (0.382 mL) were added and mixed; further, a bolan-2-picolin complex (102 mg) was added, and the mixture was stirred overnight at room temperature.

Volatile components were distilled off under reduced pressure, and the remaining solid was purified by silica gel column chromatography (NH, methanol/ethyl acetate). The obtained solid was washed with ethyl acetate and ethanol to obtain the title compound (120 mg).

$^1$H-NMR (300 MHz, DMSO-$d_6$) δ: 1.04 (3H, t, J=7.2 Hz), 2.08-2.45 (11H, m), 2.60 (3H, s), 2.80-2.89 (2H, m), 7.61 (1H, dd, J=12.5, 1.5 Hz), 7.84 (1H, dd, J=3.0, 0.8 Hz), 8.08 (1H, d, J=1.5 Hz), 8.25 (1H, d, J=1.9 Hz), 8.93 (1H, d, J=1.5 Hz), 12.39 (1H, brs). MS: [M+H]$^+$438. 3.

Working Example 91

2-(4-Fluoro-1-isopropylpiperidine-4-yl)-6-(8-fluoro-2-methylimidazo[1, 2-a]pyridin-6-yl) quinazoline-4-(3H)-one

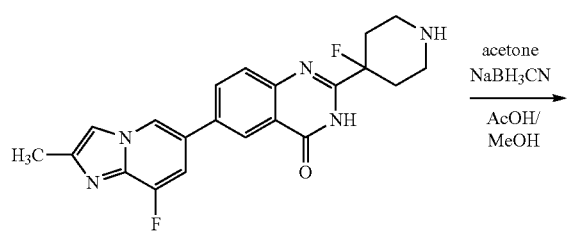

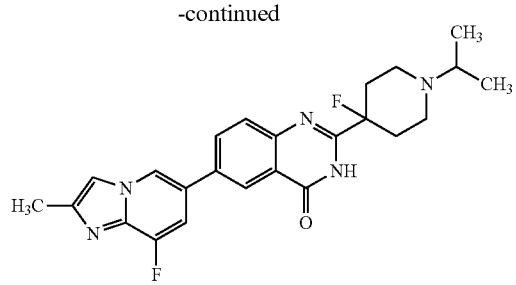

A mixture of 6-(8-Fluoro-2-methylimidazo[1, 2-a]Pyridine-6-yl)-2-(4-Fluoropiperidine-4-yl) Kinazoline-4 (3H) one (100 mg), acetone (0.093 ml), sodium cyanoborohydride (64 mg), acetic acid (0.15 ml) and methanol (3 mL) was stirred at 60° C. for 2 hours, and volatile components were distilled off under reduced pressure. The remaining solid was purified by silica gel column chromatography (NH, methanol/ethyl acetate), and the obtained solid was washed with ethanol/water (1/1) to obtain the title compound (45 mg).

$^1$H-NMR (300 MHz, DMSO-$d_6$) δ: 1.01 (6H, d, J=6.5 Hz), 2.06-2.47 (9H, m), 2.77 (3H, d, J=7.7 Hz), 7.63 (1H, d, J=12.6 Hz), 7.76 (1H, 1H, d, J=8.4 Hz), 7.85 (1H, brs), 8.18 (1H, d, J=8.4 Hz), 8.42 (1H, s), 8.96 (1H, s), 12.38 (1H, brs). MS: [M+H]$^+$438.3.

Working Example 92

2-(1-Ethyl-4-fluoropiperidine-4-yl)-6-(8-fluoro-2-methylimidazo[1, 2-a]pyridin-6-yl) quinazoline-4 (3H)one

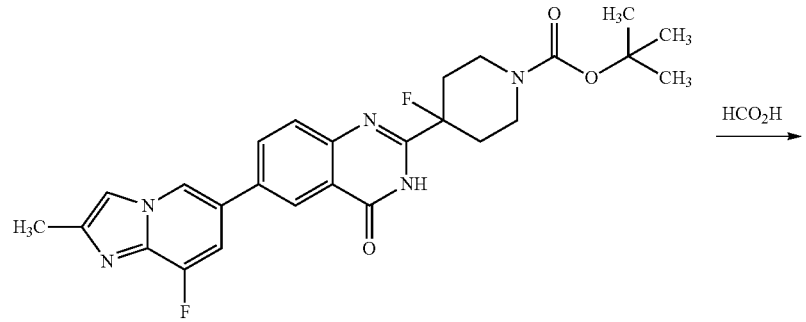

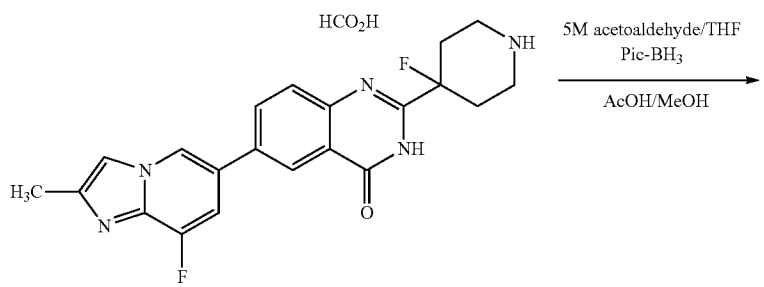

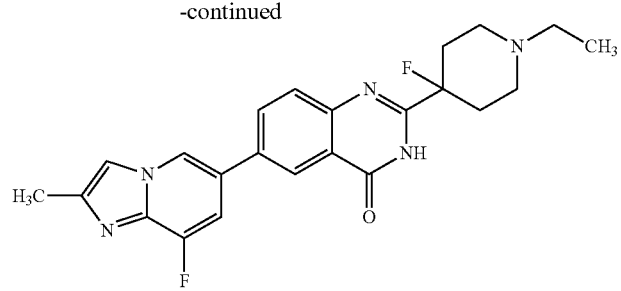

A mixture of tert-butyl 4-(6-(8-fluoro-2-methylimidazo[1,2-α]pyrididine-6-yl)-4-oxo-3,4-dihydroquinazoline-2-yl)piperidine-1-carboxylate (161 mg) and formic acid (2 mL) was stirred at 70° C. for 20 minutes, and then the volatile components were distilled off under reduced pressure. Methanol (1.5 ml), acetic acid (0.1 ml) and 5.0 M acetaldehyde/THF solution (0.195 ml) were mixed with the remaining solid, bolan-2-picolin complex (52 mg) was further added, and the mixture was stirred overnight at room temperature. Volatile components were distilled off under reduced pressure, and the remaining solid was purified by silica gel column chromatography (NH, methanol/ethyl acetate). The obtained solid was washed with ethanol/water (1/1) to obtain the title compound (32 mg).

$^1$H-NMR (400 MHz, DMSO-d$_6$) δ: 1.04 (3H, t, J=7.0 Hz), 2.05-2.45 (11H, m), 2.85 (2H, d, J=8.9 Hz), 7.64 (1H, d, J=12.5 Hz), 7.77 (1H, d, J=8.4 Hz), 7.85 (1H, brs), 8.19 (1H, d, J=8.4 Hz), 8.42 (1H, s), 8.96 (1H, s), 12.40 (1H, brs) MS: [M+H]$^+$424.3.

Working Example 93

2-(1-(2,2-difluoroethyl)-4-fluoropiperidine-4-yl)-6-(8-fluoro-2-methylimidazo[1, 2-a]pyridine-6-yl)quinazoline-4-(3H)-one

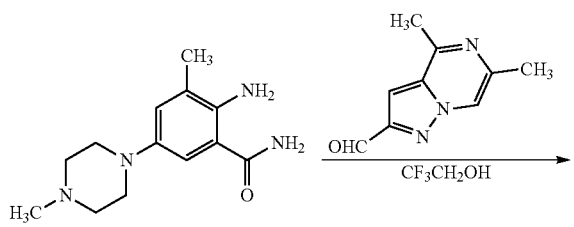

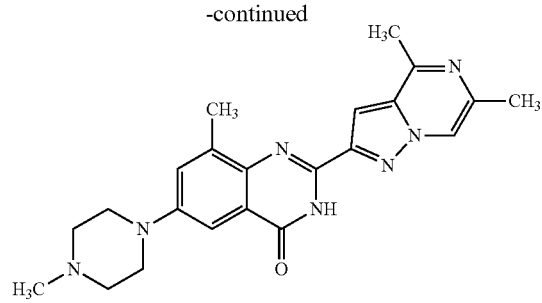

After stirring a mixture of 6-(8-fluoro-2-methylimidazo[1, 2-a]pyridine-1-yl)-2-(4-fluoropiperidine-4-yl) kinazoline-4 (3H)-one (200 mg), 2,2-difluoroethyltrifluoromethaneluhonate (0.201 ml), potassium carbonate (140 mg) and DMF (3 mL) at 60° C. overnight, water (4 mL) was added at room temperature and the mixture stirred at the same temperature for 3 hours. After filtering to isolate the precipitate and washing with ethanol/water (1/1), the product was purified by silica gel column chromatography (NH, methanol/ethyl acetate), and the obtained solid was washed with ethyl acetate to obtain the title compound (41 mg).

$^1$H-NMR (400 MHz, DMSO-d$_6$) δ: 2.06-2.35 (4H, m), 2.38 (3H, s), 2.52-2.59 (2H, m), 2.75-2.96 (4H, m), 6.00-6.36 (1H, m), 7.64 (1H, d, J=12.5 Hz), 7.77 (1H, d, J=8.4 Hz), 7.85 (1H, brs), 8.18 (1H, d, J=8.2 Hz), 8.42 (1H, s), 8.96 (1H, s), 12.42 (1H, brs). MS: [M+H]$^+$460.3.

Working Example 94

8-Fluoro-2-(4-fluoro-1-methylpiperidin-4-yl) 1-6-(2-methylimidazole[1, 2-a]pyridin-1-yl) quinazoline-4 (3H)one (A) tert-butyl 4-((4-bromo-2-carbamoyl-6-fluolophenyl)carbamoyl)-4-fluoropiperidin-1-carboxylate

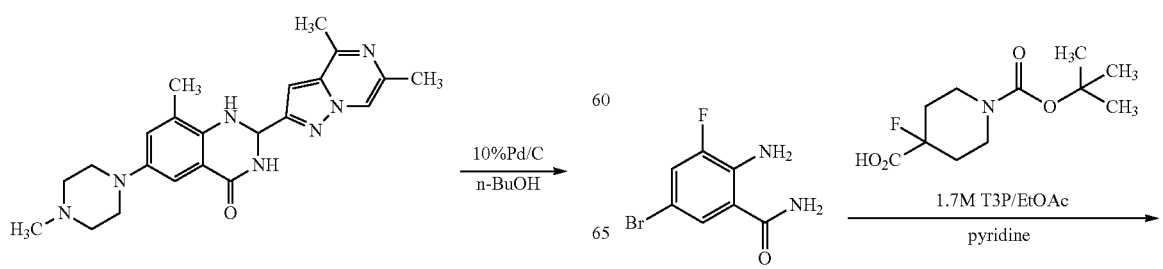

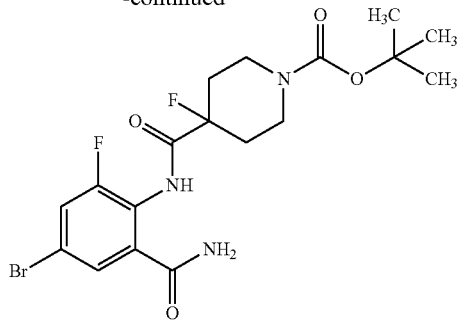
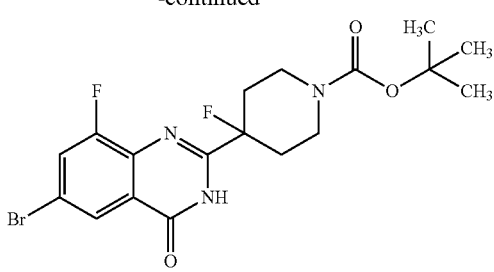

To a mixture of 2-amino-5-bromo-3-fluorobenzamide (4.0 g), 1-(tert-butoxycarbonyl)-4-fluoropiperidine-4-carboxylic acid (5.09 g) and pyridine (40 mL) was added a 1.7 M propylphosphonic acid anhydride/ethyl acetate solution (15 mL) at room temperature and the mixture was stirred at the same temperature for 16 hours. After the volatile components were distilled off under reduced pressure, the remaining solid was purified by silica gel column chromatography (ethyl acetate/hexane) to obtain the title compound (3.90 g).
MS: [M+Na]$^+$484.2.

(B) tert-Butyl 4-(6-bromo-8-fluoro-4-oxo-3,4-dihydroquinazolin-2-yl)-4-fluoropiperidine-1-carboxylate To a mixture of tert-butyl 4-[(4-bromo-2-carbamoyl-6-fluorophenyl)carbamoyl]-4-fluoropiperidine-1-carboxylate (3.9 g) and ethanol (78 mL) was added a 2.0 M aqueous sodium hydroxide solution (12.7 mL) at room temperature. After the mixture was stirred at room temperature for 1 hour, the mixture was neutralized with 2.0 M hydrochloric acid and the precipitate was isolated by filtration to obtain the title compound (3.4 g).

$^1$H-NMR (300 MHz, DMSO-d$_6$) δ: 1.43 (9H,$), 1.97-2.28 (4H, m), 3.09 (2H, brs), 3.96 (2H, d, J=13.6 Hz), 7.95-8.11 (2H, m), 12.76 (1H, s). MS: [M+Na]$^+$466.2.

(C) tert-Butyl 4-fluoro-4-[8-fluoro-6-(2-methylimidazo[1,2-α]pyridin-6-yl)-4-oxo-3,4-dihydroquinazolin-2-yl]piperidine -1-carboxylate

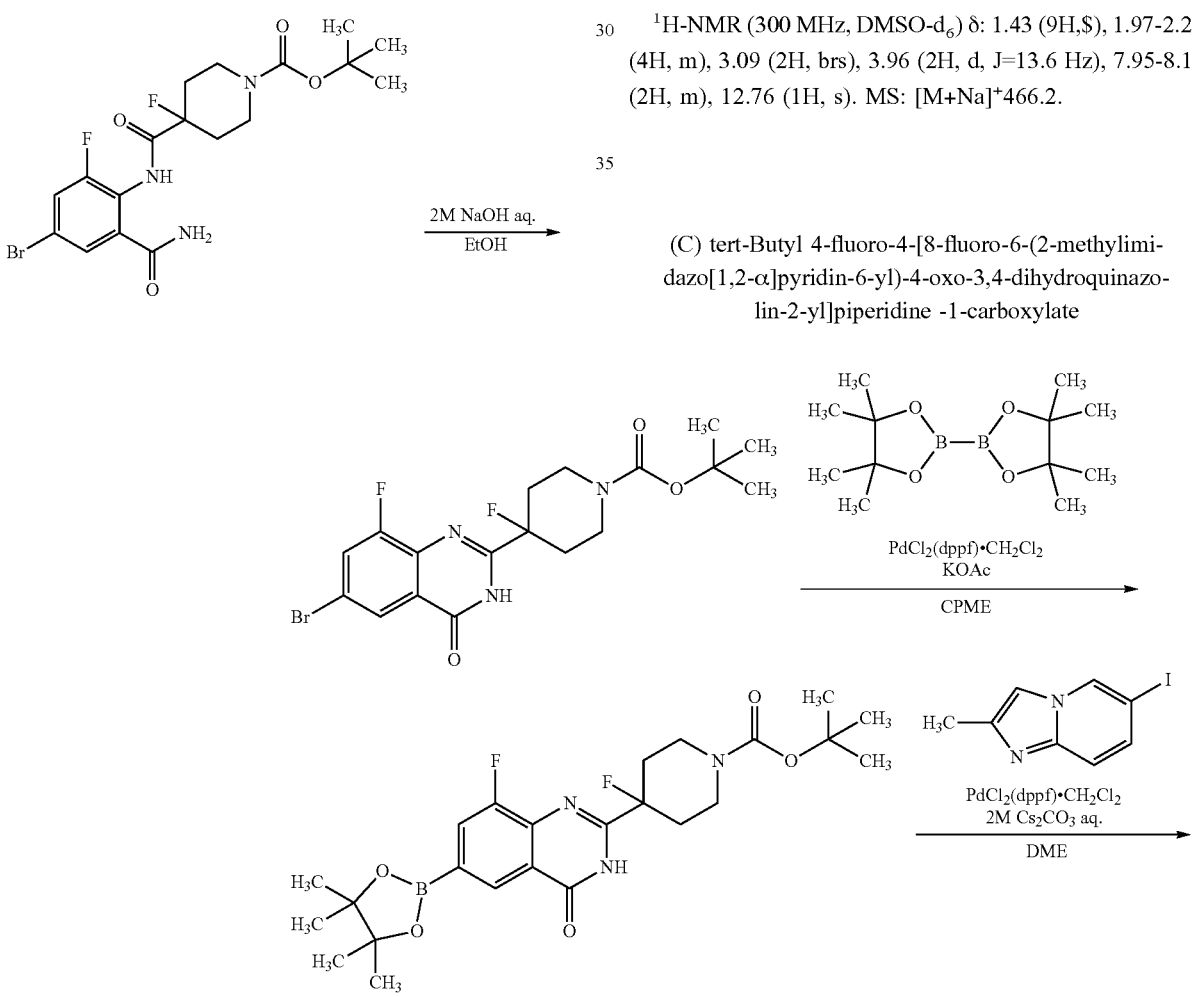

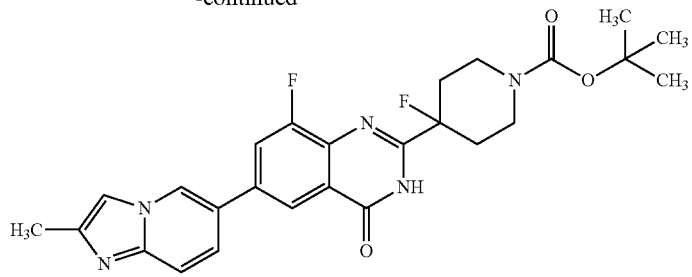

A mixture of tert-butyl 4-(6-bromo-8-fluoro-4-oxo-3,4-dihydroquinazolin-2-yl)-4-fluoropiperidine-1-carboxylate (254 mg), bis(pinacolato)diboron (174 mg), potassium acetate (112 mg), dichloro[1,1'-bis(diphenylphosphino)ferrocene]palladium(II) dichloromethane adduct (23.3 mg) and cyclopentyl methyl ether (5 mL) was stirred under microwave irradiated conditions at 130° C. for 30 minutes. After the mixture was filtered through Celite and washed with THF, the volatile components were distilled off from the filtrate under reduced pressure. The obtained solid was added to 6-iodo-2-methylimidazo[1,2-α]pyridine (177 mg), dichloro[1,1'-bis(diphenylphosphino)ferrocene]palladium (II) dichloromethane adduct (23.3 mg), a 2.0 M aqueous sodium carbonate solution (0.57 mL) and DME (12 mL), and the mixture was stirred under microwave irradiated conditions at 130° C. for 30 minutes. The mixture was purified by silica gel column chromatography (NH, methanol/ethyl acetate) and the obtained solid was washed with ethyl acetate to obtain the title compound (170 mg).

MS: [M+H]$^+$496.3.

(D) 8-Fluoro-2-(4-fluoro-1-methylpiperidin-4-yl)-6-(2-methylimidazo[1,2-α]pyridin-6-yl)quinazolin-4(3H)-one

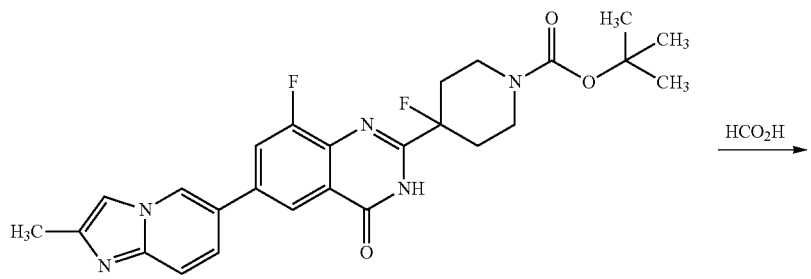

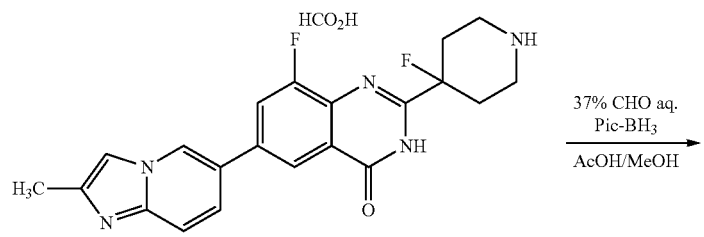

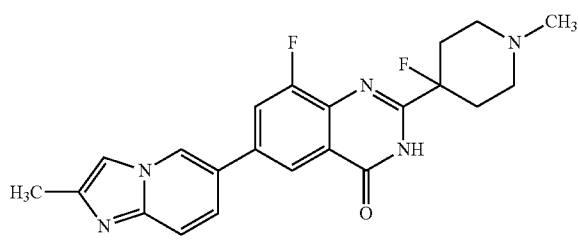

After a mixture of tert-butyl 4-fluoro-4-[8-fluoro-6-(2-methylimidazo[1,2-α]pyridin-6-yl)-4-oxo-3,4-dihydroquinazolin-2-yl]piperidine-1-carboxylate (170 mg) and formic acid (2 mL) was stirred at 60° C. for 10 minutes, the volatile components were distilled off under reduced pressure. To the remaining solid were added methanol (2 mL), acetic acid (0.5 mL) and an aqueous formaldehyde solution (0.10 mL), and then borane-2-methylpyridine complex (110 mg) was further added thereto. Then, the mixture was stirred at room temperature overnight. The volatile components were distilled off under reduced pressure and the remaining solid was purified by silica gel column chromatography (NH, methanol/ethyl acetate). Then, the obtained solid was washed with ethyl acetate to obtain the title compound (88 mg).

$^1$H-NMR (300 MHz, DMSO-$d_6$) δ: 2.05-2.29 (9H, m), 2.36 (3H, s), 2.74 (2H, brs), 7.51-7.56 (1H, m), 7.66 (1H, dd, J=9.4, 1.9 Hz), 7.72 (1H, s), 8.12 (1H, dd, J=11.7, 1.9 Hz), 8.23 (1H, d, J=1.5 Hz), 9.01-9.16 (1H, m), 12.56 (1H, brs). MS: [M+H]$^+$410.3.

Working Example 95

2-(1-Ethyl-4-fluoropiperidin-4-yl)-8-fluoro-6-(2-methylimidazo[1,2-α]pyridin-6-yl)quinazolin-4(3H)-one After a mixture of tert-butyl 4-fluoro-4-[8-fluoro-6-(2-methylimidazo[1,2-α]pyridin-6-yl)-4-oxo-3,4-dihydroquinazolin-2-yl]piperidine-1-carboxylate (224 mg) and formic acid (1 mL) was stirred at 60° C. for 10 minutes, the volatile components were distilled off under reduced pressure. To the remaining solid were added methanol (2 mL), acetic acid (0.2 mL) and acetaldehyde (0.27 mL), and then borane-2-methylpyridine complex (85 mg) was further added thereto. Then, the mixture was stirred at room temperature overnight. The volatile components were distilled off under reduced pressure and the remaining solid was purified by silica gel column chromatography (NH, methanol/ethyl acetate). Then, the obtained solid was recrystallized from ethanol/ethyl acetate/hexane to obtain the title compound (30 mg).

$^1$H-NMR (300 MHz, DMSO-$d_6$) δ: 1.04 (3H, t, J=7.2 Hz), 2.04-2.32 (6H, m), 2.35-2.46 (5H, m), 2.79-2.92 (2H, m), 7.48-7.58 (1H, m), 7.66 (1H, dd, J=9.4, 1.9 Hz), 7.72 (1H, s), 8.10 (1H, d, J=2.3 Hz), 8.23 (1H, d, J=1.5 Hz), 9.08 (1H, d, J=1.1 Hz), 12.56 (1H, brs). MS: [M+H]$^+$424.3.

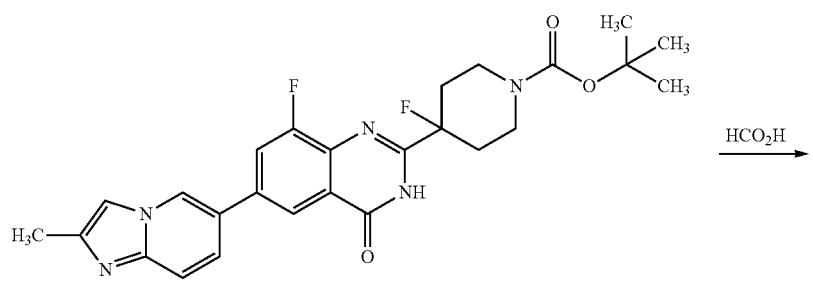

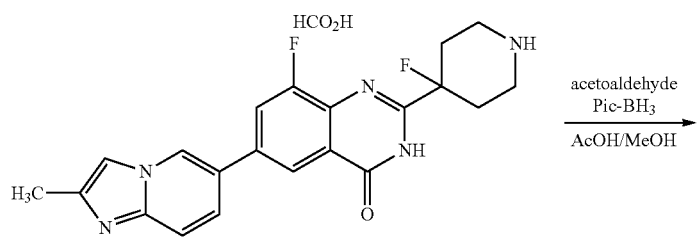

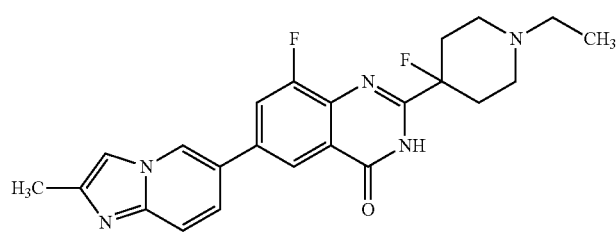

Working Example 96

8-Fluoro-2-(4-fluoro-1-isopropylpiperidin-4-yl)-6-(2-methylimidazo[1,2-α]pyridin-6-yl)quinazolin-4(3H)-one

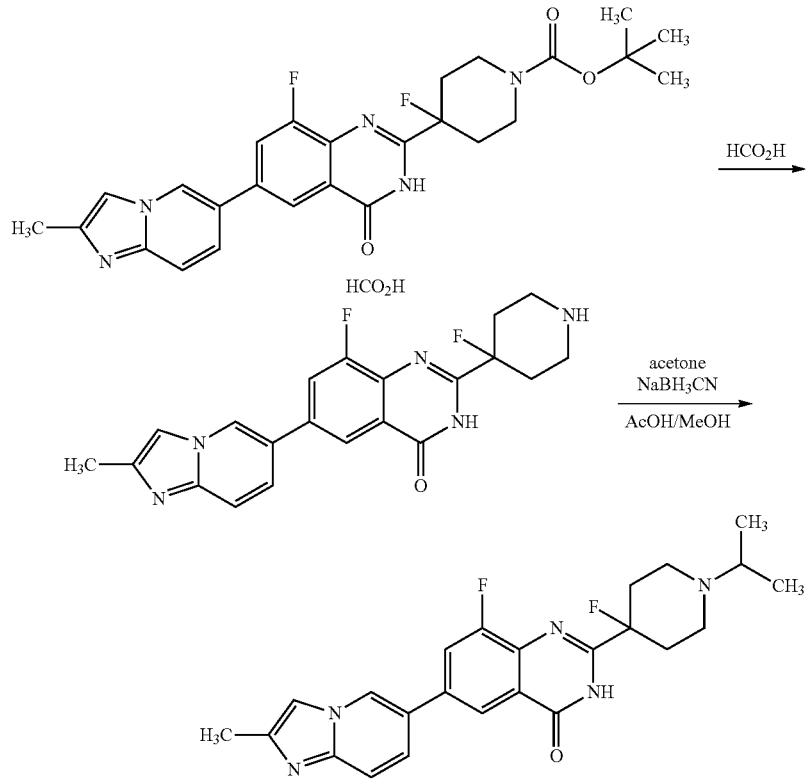

After a mixture of tert-butyl 4-fluoro-4-[8-fluoro-6-(2-methylimidazo[1,2-α]pyridin-6-yl)-4-oxo-3,4-dihydroquinazolin-2-yl]piperidine-1-carboxylate (115 mg) and formic acid (1.5 mL) was stirred at 60° C. for 10 minutes, the volatile components were distilled off under reduced pressure. To the remaining solid were added methanol (2 mL), acetic acid (0.13 mL) and acetone (0.086 mL), and then sodium cyanotrihydridoborate (58 mg) was further added thereto. Then, the mixture was stirred at 60° C. overnight. The volatile components were distilled off under reduced pressure and the remaining solid was purified by silica gel column chromatography (NH, methanol/ethyl acetate). Then, the obtained solid was washed with ethyl acetate to obtain the title compound (88 mg).

$^1$H-NMR (300 MHz, DMSO-d$_6$) δ: 1.01 (6H, d, J=6.8 Hz), 2.06-2.33 (4H, m), 2.36 (3H, s), 2.39-2.46 (2H, m), 2.71-2.84 (3H, m), 7.50-7.56 (1H, m), 7.62-7.68 (1H, m), 7.72 (1H, s), 8.09 (1H, dd, J=11.9, 2.1 Hz), 8.22 (1H, d, J=1.5 Hz), 9.07 (1H, d, J=0.8 Hz), 12.54 (1H, brs). MS: [M+H]$^+$438.3.

Working Example 97

8-Fluoro-6-(8-fluoro-2-methylimidazo[1,2-α]pyridin-6-yl)-2-(4-fluoro-1-methylpiperidin-4-yl)quinazolin-4(3H)-one (A) tert-Butyl 4-fluoro-4-[8-fluoro-6-(8-fluoro-2-methylimidazo[1,2-α]pyridin-6-yl)-4-oxo-3,4-dihydroquinazolin-2-yl]piperidine-1-carboxylate

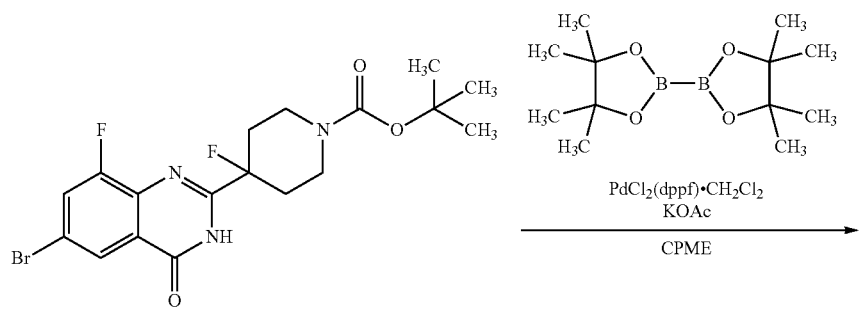

-continued

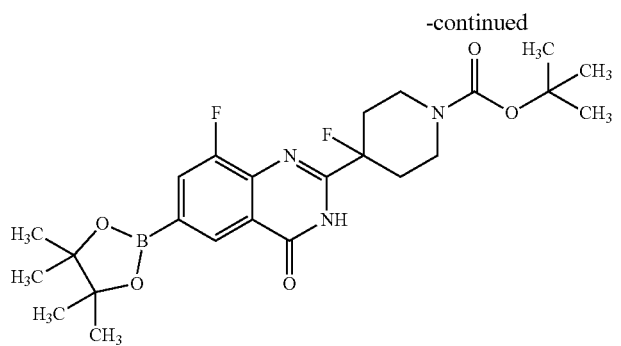
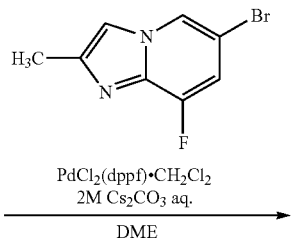

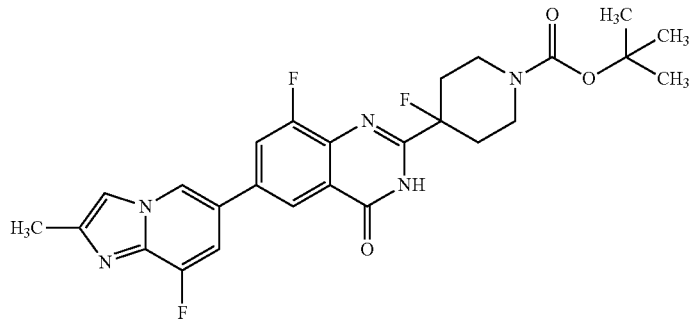

A mixture of tert-butyl 4-(6-bromo-8-fluoro-4-oxo-3,4-dihydroquinazolin-2-yl)-4-fluoropiperidine-1-carboxylate (500 mg), bis(pinacolato)diboron (343 mg), potassium acetate (221 mg), dichloro[1,1'-bis(diphenylphosphino)ferrocene]palladium(II) dichloromethane adduct (46.0 mg) and cyclopentyl methyl ether (5 mL) was stirred under microwave irradiated conditions at 130° C. for 30 minutes. After the mixture was filtered through Celite and washed with THF, the volatile components were distilled off from the filtrate under reduced pressure. A mixture of the obtained solid, tert-butyl 4-fluoro-4-[8-fluoro-4-oxo-6-(4,4,5,5-tetramethyl-1,3,2-dioxaborolan-2-yl)-3,4-di hydroquinazolin-2-yl]piperidine-1-carboxylate (553 mg), 6-bromo-8-fluoro-2-methylimidazo[1,2-α]pyridine (309 mg), dichloro[1,1'-bis(diphenylphosphino)ferrocene]palladium(II) dichloromethane adduct (46 mg), a 2.0 M aqueous sodium carbonate solution (1.13 mL) and DME (12 mL) was stirred under microwave irradiated conditions at 130° C. for 30 minutes. The mixture was purified by silica gel column chromatography (NH, methanol/ethyl acetate) and the obtained solid was washed with water and diisopropyl ether to obtain the title compound (344 mg).

MS: [M+H]⁺514.4.

(B) 8-Fluoro-6-(8-fluoro-2-methylimidazo[1,2-α]pyridin-6-yl)-2-(4-fluoro-1-methylpiperidin-4-yl)quinazolin-4(3H)-one

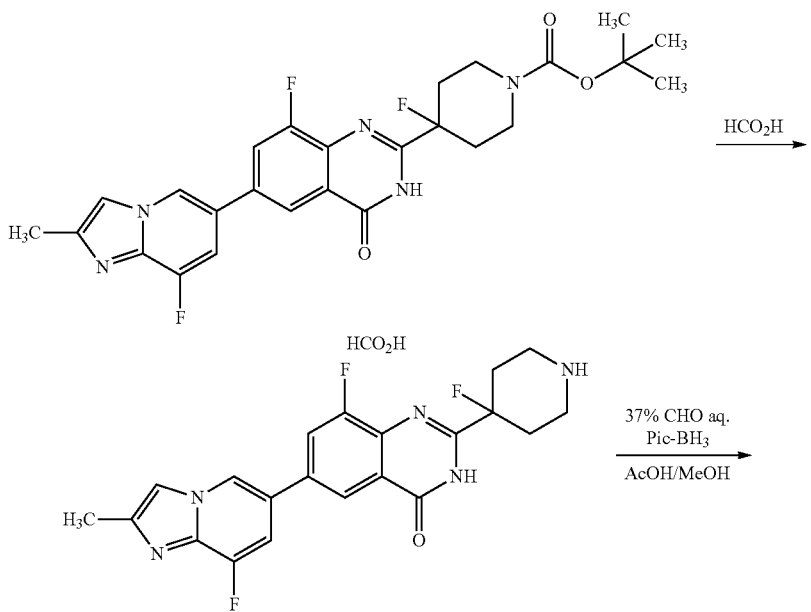

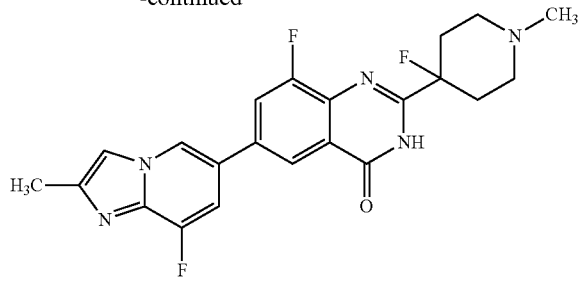

After a mixture of tert-butyl 4-fluoro-4-[8-fluoro-6-(8-fluoro-2-methylimidazo[1,2-α]pyridin-6-yl)-4-oxo-3,4-dihydroquinazolin-2-yl]piperidine-1-carboxylate (110 mg) and formic acid (2 mL) was stirred at 60° C. for 10 minutes, the volatile components were distilled off under reduced pressure. To the remaining solid were added methanol (2 mL), acetic acid (0.5 mL) and an aqueous formaldehyde solution (0.07 mL), and then borane-2-methylpyridine complex (69 mg) was further added thereto. Then, the mixture was stirred at room temperature overnight. The volatile components were distilled off under reduced pressure and the remaining solid was purified by silica gel column chromatography (NH, methanol/ethyl acetate). Then, the obtained solid was washed with ethyl acetate to obtain the title compound (50 mg).

$^1$H-NMR (300 MHz, DMSO-$d_6$) δ: 2.13-2.33 (9H, m), 2.38 (3H, s), 2.70-2.82 (2H, m), 7.68 (1H, dd, J=12.7, 1.3 Hz), 7.84 (1H, d, J=2.3 Hz), 8.14 (1H, dd, J=11.7, 1.9 Hz), 8.25 (1H, d, J=1.5 Hz), 9.02 (1H, d, J=1.5 Hz), 12.58 (1H, brs). MS: [M+H]$^+$428.3.

Working Example 98

2-(1-Ethyl-4-fluoropiperidin-4-yl)-8-fluoro-6-(8-fluoro-2-methylimidazo[1,2-α]pyridin-6-yl)quinazolin-4(3H)-one

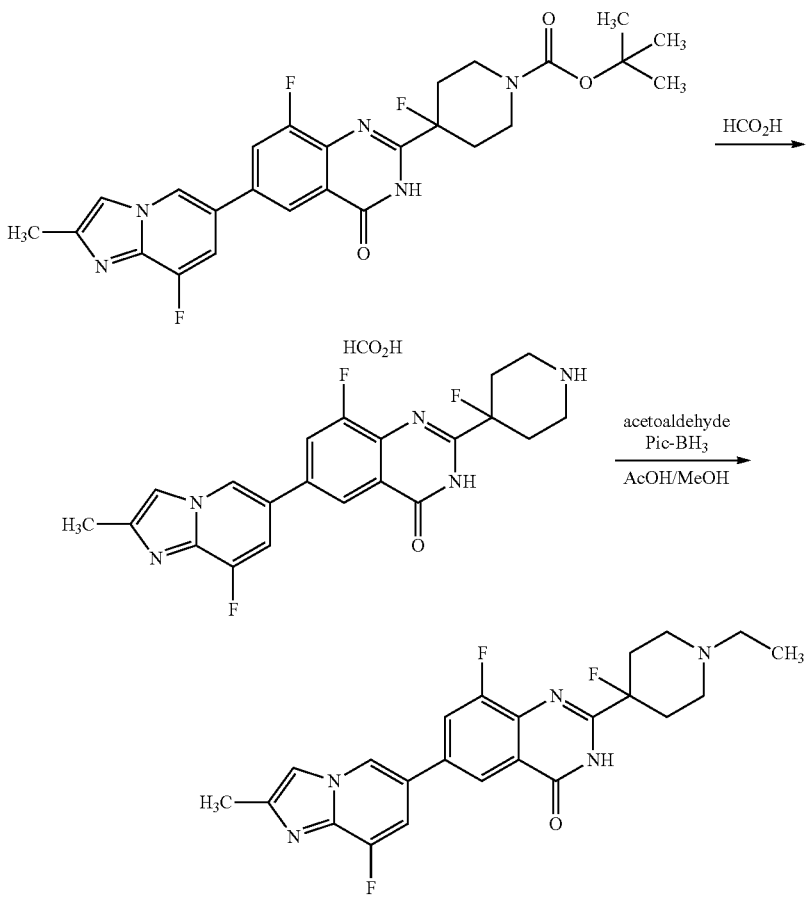

After a mixture of tert-butyl 4-fluoro-4-[8-fluoro-6-(8-fluoro-2-methylimidazo[1,2-α]pyridin-6-yl)-4-oxo-3,4-dihydroquinazolin-2-yl]piperidine-1-carboxylate (215 mg) and formic acid 2 mL) was stirred at 60° C. for 10 minutes, the volatile components were distilled off under reduced pressure. To the remaining solid were added methanol (2 mL), acetic acid (0.5 mL) and acetaldehyde (0.224 mL), and then borane-2-methylpyridine complex (134 mg) was further added thereto. Then, the mixture was stirred at room temperature overnight. The volatile components were distilled off under reduced pressure and the remaining solid was purified by silica gel column chromatography (NH, methanol/ethyl acetate). Then, the obtained solid was washed with ethyl acetate to obtain the title compound (62 mg).

¹H-NMR (300 MHz, DMSO-d₆) δ: 1.04 (3H, t, J=7.2 Hz), 2.07-2.32 (6H, m), 2.36-2.44 (5H, m), 2.84 (2H, d, J=10.6 Hz), 7.68 (1H, dd, J=12.7, 1.3 Hz), 7.84 (1H, d, J=2.6 Hz), 8.12 (1H, d, J=11.0 Hz), 8.25 (1H, s), 9.01 (1H, d, J=1.5 Hz), 12.60 (1H, brs). MS: [M+H]⁺442.3.

Working Example 99

8-Fluoro-2-(4-fluoro-1-isopropylpiperidin-4-yl)-6-(8-fluoro-2-methylimidazo[1,2-α]pyridin-6-yl) quinazolin-4(3H)-one

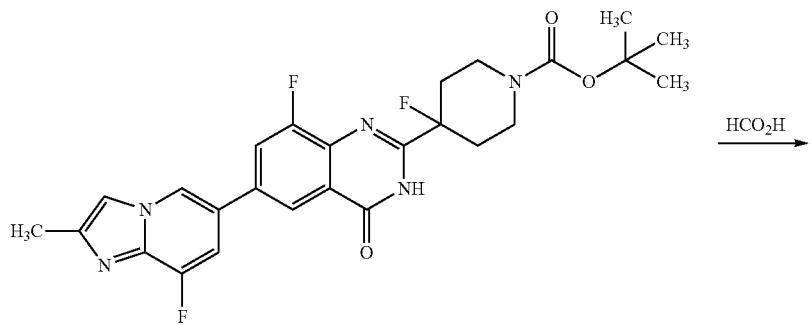

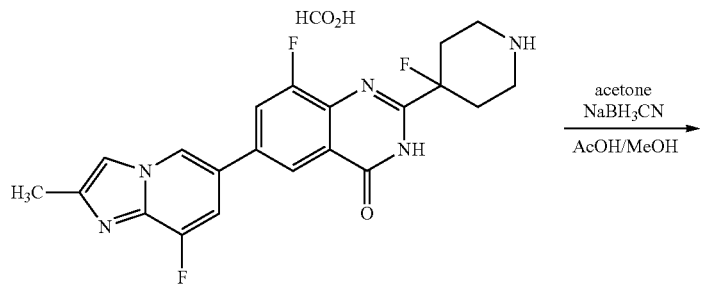

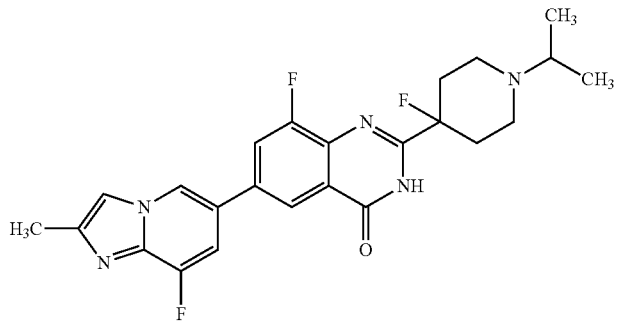

After a mixture of tert-butyl 4-fluoro-4-[8-fluoro-6-(8-fluoro-2-methylimidazo[1,2-α]pyridin-6-yl)-4-oxo-3,4-dihydroquinazolin-2-yl]piperidine-1-carboxylate (110 mg) and formic acid (2 mL) was stirred at 60° C. for 10 minutes, the volatile components were distilled off under reduced pressure. To the remaining solid were added methanol (2 mL), acetic acid (0.5 mL) and acetone (0.16 mL), and then sodium cyanotrihydridoborate (67.3 mg) was further added thereto. Then, the mixture was stirred at 60° C. overnight. The volatile components were distilled off under reduced pressure and the remaining solid was purified by silica gel column chromatography (NH, methanol/ethyl acetate). Then, the obtained solid was washed with ethyl acetate to obtain the title compound (62 mg).

$^1$H-NMR (300 MHz, DMSO-d$_6$) δ: 1.01 (6H, d, J=6.8 Hz), 2.06-2.30 (4H, m), 2.38 (3H, s), 2.41-2.47 (2H, m), 2.70-2.83 (3H, m), 7.67 (1H, dd, J=12.7, 1.3 Hz), 7.84 (1H, d, J=2.6 Hz), 8.12 (1H, dd, J=11.7, 1.9 Hz), 8.25 (1H, d, J=1.5 Hz), 9.00 (1H, d, J=1.5 Hz), 12.53 (1H, brs).

MS: [M+H]$^+$456.3.

Working Example 100

2-(1-Ethyl-4-fluoropiperidin-4-yl)-6-(8-fluoro-2-methylimidazo[1,2-α]pyridin-6-yl)-8-methylpyrido[3,2-d]pyrimidin-4(3H)-one (A) Methyl 3-amino-6-bromo-4-methylpicolinate

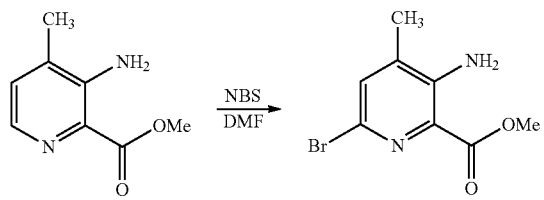

To a mixture of methyl 3-amino-4-methylpicolinate (8.0 g) and DMF (100 mL) was added N-bromosuccinimide (12.9 g) at room temperature and the mixture was stirred at the same temperature for 15 hours. Then, water was further added thereto and the mixture was extracted with ethyl acetate. The organic layer was separated, washed with water and saturated brine and dried over magnesium sulfate, and then the volatile components were distilled off under reduced pressure. The remaining solid was purified by silica gel column chromatography (NH, ethyl acetate/hexane) to obtain the title compound (11.3 g).

$^1$H-NMR (300 MHz, DMSO-d$_6$) δ: 2.17 (3H, d, J=0.8 Hz), 3.82 (3H, s), 6.75 (2H, s), 7.43 (1H, s). MS: [M+H]$^+$ 245.2.

(B) 3-Amino-6-bromo-4-methylpicolinamide

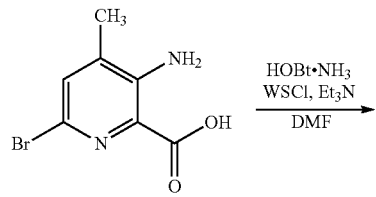

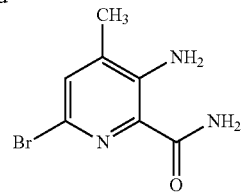

To a mixture of 3-amino-6-bromo-4-methylpicolinic acid (7.46 g), N-(3-dimethylaminopropyl)-N'-ethylcarbodiimide hydrochloride (1/1) (8.05 g), triethylamine (6.7 mL) and DMF (100 mL) was added 1H-benzotriazol-1-ol ammonium salt (1/1) (6.4 g) at room temperature and the mixture was stirred at the same temperature for 15 hours. Then, water was added thereto and the mixture was extracted with ethyl acetate. The organic layer was washed with a saturated aqueous sodium hydrogen carbonate solution and water and then dried over magnesium sulfate, and the volatile components were distilled off under reduced pressure. The obtained solid was washed with ethyl acetate/diisopropyl ether to obtain the title compound (3.71 g).

MS: [M+H]$^+$230.2.

(C) tert-Butyl 4-(6-bromo-8-methyl-4-oxo-3,4-dihydropyrido[3,2-d]pyrimidin-2-yl)-4-fluoropiperidine-1-carboxylate

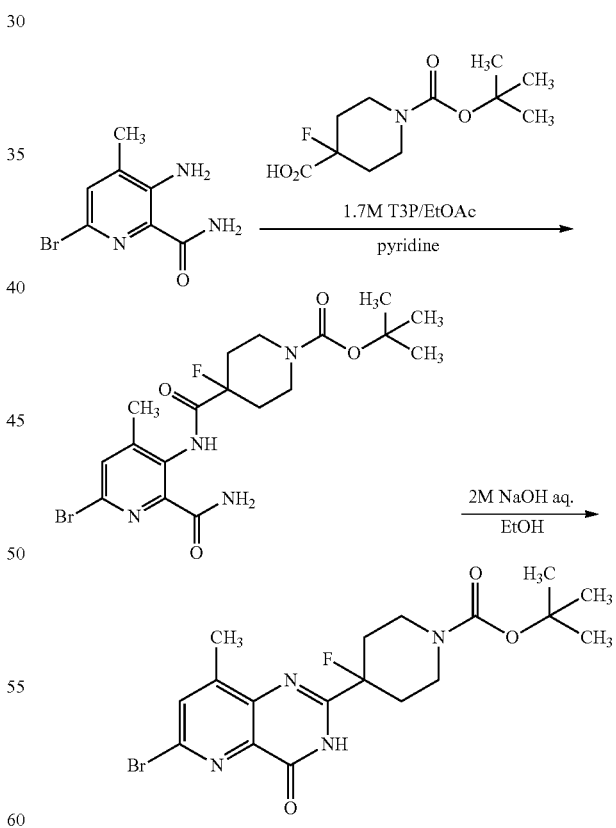

To a mixture of 3-amino-6-bromo-4-methylpicolinamide (0.96 g), 1-(tert-butoxycarbonyl)-4-fluoropiperidine-4-carboxylic acid (1.24 g) and pyridine (20 mL) was added a 1.7 M propylphosphonic acid anhydride/ethyl acetate solution (3.68 mL) at room temperature and the mixture was stirred at the same temperature for 15 hours. After the volatile components were distilled off under reduced pressure, 0.1 M hydrochloric acid was added to the remaining solid and the mixture was extracted with ethyl acetate. The organic layer was washed with water and saturated brine and then dried over magnesium sulfate, and the volatile components were distilled off under reduced pressure. After a 2.0 M aqueous sodium hydroxide solution (6.27 mL) was added to a mixture of the obtained solid and ethanol (15 mL) at room temperature and the mixture was stirred at the same temperature for 2 hours, the mixture was neutralized with 2.0 M hydrochloric acid and extracted with ethyl acetate. The organic layer was washed with water and saturated brine and then dried over magnesium sulfate, and the volatile components were distilled off under reduced pressure. Then, the obtained solid was purified by silica gel column chromatography (NH, ethyl acetate/hexane) to obtain the title compound (1.8 g).

MS: [M+H]$^+$441.2.

(D) 8-Fluoro-2-methyl-6-(4,4,5,5-tetramethyl-1,3,2-dioxaborolane-2-yl)imidazo[1,2-α]pyridine

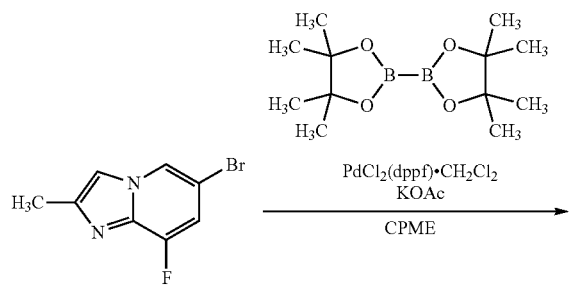

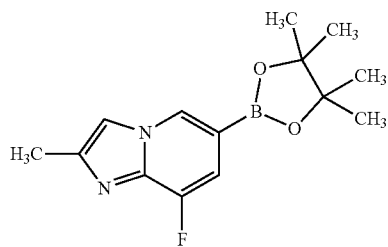

A mixture of 6-brome-8-fluoro-2-methylimidazo[1,2-α]pyridine (433 mg), bis(pinacolato)diboron (576 mg), potassium acetate (371 mg), dichloro[1,1'-bis(diphenylphosphino)ferrocene]palladium(II) dichloromethane adduct (77 mg) and cyclopentyl methyl ether (7 mL) was stirred under microwave irradiated conditions at 130° C. for 30 minutes. After the mixture was filtered through Celite, the volatile components were distilled off from the filtrate under reduced pressure to obtain the title compound (552 mg).

(E) tert-Butyl 4-fluoro-4-[6-(8-fluoro-2-methylimidazo[1,2-α]pyridin-6-yl)-8-methyl-4-oxo-3,4-dihydropyrido[3,2-d]pyrimidin-2-yl]piperidine-1-carboxylate

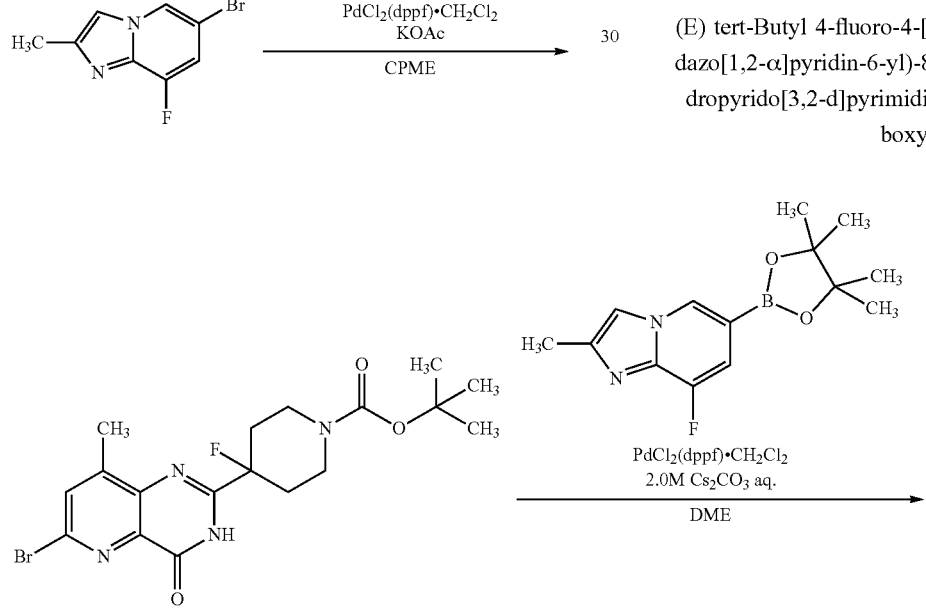

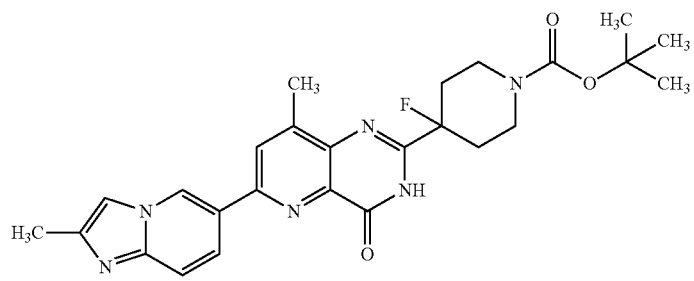

A mixture of 8-fluoro-2-methyl-6-(4,4, 5, 5-tetramethyl-1,3,2-dioxaborolane-2-yl)imidazo[1,2-α]pyridine (523 mg), tert-butyl 4-(6-bromo-8-methyl-4-oxo-3,4-dihydropyrido[3,2-d]pyrimidin-2-yl)-4-fluoropiperidine-1-carboxylate (760 mg), dichloro[1,1'-bis(diphenylphosphino)ferrocene]palladium(II) dichloromethane adduct (70.3 mg), a 2.0 M aqueous sodium carbonate solution (2.58 mL) and DME (13 mL) were stirred under microwave irradiated conditions at 130° C. for 30 minutes and water was further added thereto at room temperature. Then, the mixture was filtered. The filtrate was extracted with ethyl acetate and dried over magnesium sulfate and then purified by silica gel column chromatography (NH, ethyl acetate/hexane). Then, the obtained solid was washed with ethyl acetate/diisopropyl ether to obtain the title compound (650 mg).

$^1$H-NMR (300 MHz, DMSO-d$_6$) δ: 1.43 (9H, s), 2.05-2.31 (4H, m), 2.39 (3H, s), 2.58 (3H, s), 3.17 (2H, brs), 3.88 (2H, d, J=1 3.6 Hz), 7.83-8.01 (2H, m), 8.22 (1H, s), 9.22 (1H, d, J=1.1 Hz), 12.75 (1H, brs). MS: [M+H]$^+$511.4.

(F) 6-(8-Fluoro-2-methylimidazo[1,2-α]pyridin-6-yl)-2-(4-fluoropiperidin-4-yl)-8-methylpyrido[3,2-d]pyrimidin-4(3H)-one

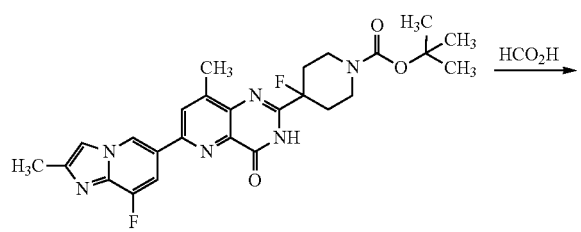

After a mixture of tert-butyl 4-fluoro-4-[6-(8-fluoro-2-methylimidazo[1,2-α]pyridin-6-yl)-8-methyl-4-oxo-3,4-dihydropyrido[3,2-d]pyrimidin-2-yl]piperidine-1-carboxylate (650 mg) and formic acid (2 mL) was stirred at 70° C. for 30 minutes, the volatile components were distilled off under reduced pressure. To the remaining solid were added methanol and an 8.0 M ammonia/methanol solution and the volatile components were distilled off under reduced pressure. Then, the remaining solid was washed with ethyl acetate to obtain the title compound (465 mg).

MS: [M+H]$^+$411.3.

(G) 2-(1-Ethyl-4-fluoropiperidin-4-yl)-6-(8-fluoro-2-methylimidazo[1,2-α]pyridin-6-yl)-8-methylpyrido[3,2-d]pyrimidin-4(3H)-one

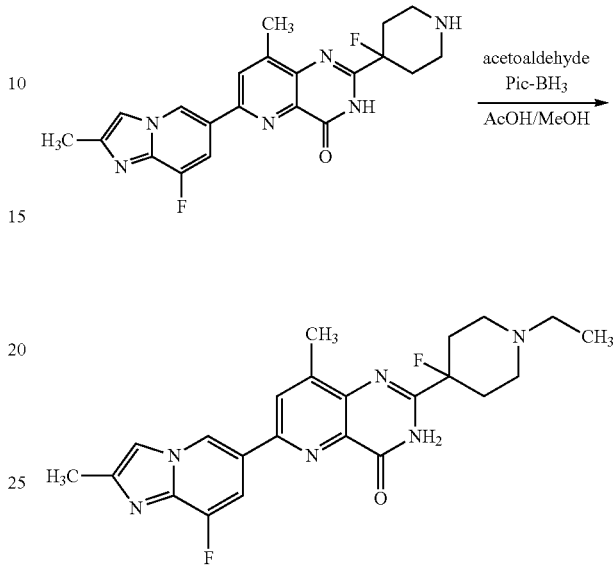

To a mixture of 6-(8-fluoro-2-methylimidazo[1,2-α]pyridin-6-yl)-2-(4-fluoropiperidin-4-yl)-8-methylpyrido[3,2-d]pyrimidin-4(3H)-one (148 mg), methanol (2 mL), acetic acid (0.2 mL) and acetaldehyde (0.201 mL) was added borane-2-methylpyridine complex (57.7 mg) and the mixture was stirred at room temperature for 15 hours. The volatile components were distilled off under reduced pressure and the remaining solid was purified by silica gel column chromatography (NH, methanol/ethyl acetate). Then, the obtained solid was washed with ethyl acetate to obtain the title compound (55 mg).

$^1$H-NMR (300 MHz, DMSO-d$_6$) δ: 1.04 (3H, t, J=7.2 Hz), 2.05-2.44 (11H, m), 2.62 (3H, s), 2.78-2.90 (2H, m), 7.89 (1H, dd, J=1 2.7, 1.3 Hz), 7.97 (1H, d, J=2.6 Hz), 8.34 (1H, s), 9.26 (1H, d, J=1.1 Hz), 12.65 (1H, brs). MS: [M+H]$^+$ 439.3.

Working Example 101

2-(4-Fluoro-1-isopropylpiperidin-4-yl)-6-(8-fluoro-2-methylimidazo[1,2-α]pyridin-6-yl)-8-methylpyrido[3,2-d]pyrimidin-4(3H)-one

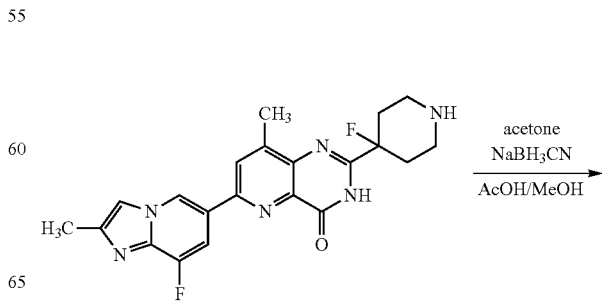

-continued

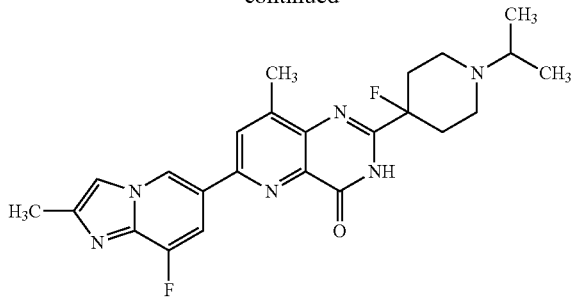

To a mixture of 6-(8-fluoro-2-methylimidazo[1,2-α]pyridin-6-yl)-2-(4-fluoropiperidin-4-yl)-8-methylpyrido[3,2-d]pyrimidin-4(3H)-one (168 mg), methanol (2 mL), acetic acid (0.2 mL) and acetone (0.301 mL) was added sodium cyanotrihydridoborate (38.5 mg) at room temperature and the mixture was stirred at the same temperature for 15 hours. Then, the volatile components were distilled off under reduced pressure. To the obtained solid was added a 5% ammonium hydroxide solution and the volatile components were distilled off under reduced pressure. The remaining solid was purified by silica gel column chromatography (NH, methanol/ethyl acetate) and the obtained solid was washed with ethyl acetate to obtain the title compound (35 mg).

$^1$H-NMR (300 MHz, DMSO-$d_6$) δ: 1.01 (6H, d, J=6.8 Hz), 2.07-2.46 (9H, m), 2.62 (3H, s), 2.70-2.84 (3H, m), 7.89 (1H, dd, J=12.7, 1.3 Hz), 7.97 (1H, d, J=2.3 Hz), 8.34 (1H, s), 9.26 (1H, d, J=1.1 Hz), 12.64 (1H, brs). MS: [M+H]$^+$453.4.

Working Example 102

2-(1-Cyclopropyl-4-fluoropiperidin-4-yl)-6-(8-fluoro-2-methylimidazo[1,2-α]pyridin-6-yl)pyrido[3,2-d]pyrimidin-4(3H)-one

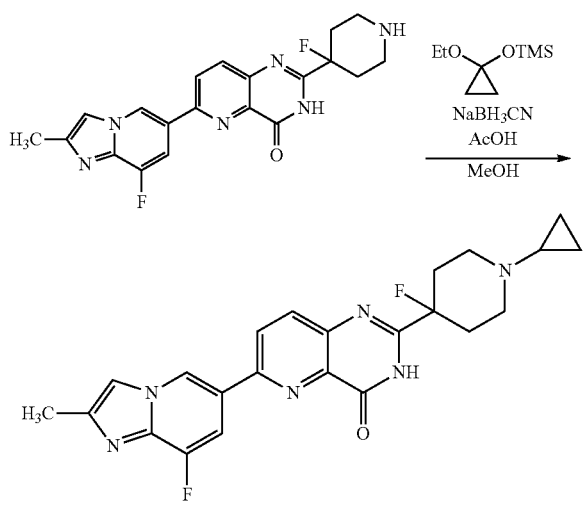

A mixture of 6-(8-fluoro-2-methylimidazo[1,2-α]pyridin-6-yl)-2-(4-fluoropiperidin-4-yl)pyrido[3,2-d]pyrimidin-4(3H)-one (180 mg), ((1-ethoxycyclopropoxy)oxy)(trimethyl)silane (0.274 mL), sodium cyanotrihydridoborate (57.1 mg), acetic acid (0.10 mL) and methanol (3.0 mL) was stirred at 60° C. for 3 hours and the volatile components were distilled off under reduced pressure. The remaining solid was purified by silica gel column chromatography (NH, methanol/ethyl acetate) and the obtained solid was washed with ethyl acetate to obtain the title compound (145 mg).

$^1$H-NMR (300 MHz, DMSO-$d_6$) δ: 0.28-0.47 (4H, m), 1.65 (1H, dt, J=6.9, 3.2 Hz), 1.93-2.32 (4H, m), 2.38 (3H, d, J=0.8 Hz), 2.52-2.59 (2H, m), 2.74-2.85 (2H, m), 7.84-7.93 (2H, m), 7.98 (1H, d, J=2.3 Hz), 8.06 (1H, d, J=8.7 Hz), 9.20 (1H, d, J=1.1 Hz). MS: [M+H]$^+$437.3.

Working Example 103

2-(1-Cyclopropyl-4-fluoropiperidin-4-yl)-6-(2-methylimidazo[1,2-α]pyrimidin-6-yl)-8-methyl quinazolin-4(3H)-one (A) 6-Bromo-2-(4-fluoropiperidin-4-yl)-8-methylquinazolin-4(3H)-one

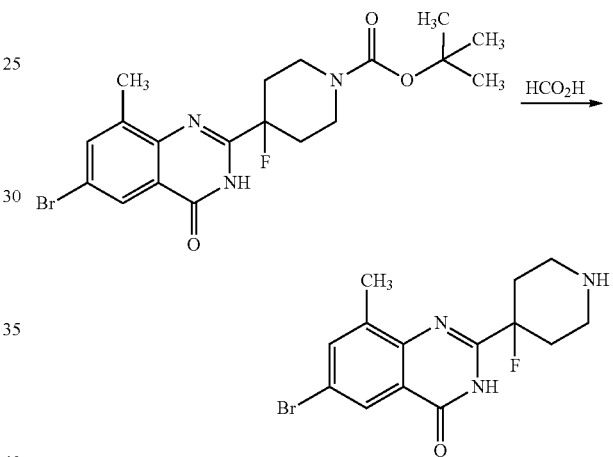

After a mixture of tert-butyl 4-(6-bromo-8-methyl-4-oxo-3,4-dihydroquinazolin-2-yl)-4-fluoropiperidin e-1-carboxylate (1.0 g) and formic acid (10 mL) was stirred at 60° C. for 10 minutes, the volatile components were distilled off under reduced pressure. The remaining solid was washed with a 5% ammonium hydroxide solution to obtain the title compound (720 mg).

$^1$H-NMR (300 MHz, DMSO-$d_6$) δ: 1.98-2.29 (4H, m), 2.51-2.53 (3H, m), 2.52 (1H, brs), 2.79-2.90 (2H, m), 2.92-3.02 (2H, m), 7.87 (1H, dd, J=2.3, 0.8 Hz), 8.03 (1H, d, J=1.9 Hz). MS: [M+H]$^+$340.2.

(B) 6-Bromo-2-(1-cyclopropyl-4-fluoropiperidin-4-yl)-8-methylquinazolin-4(3H)-one

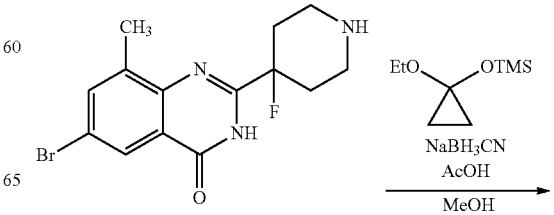

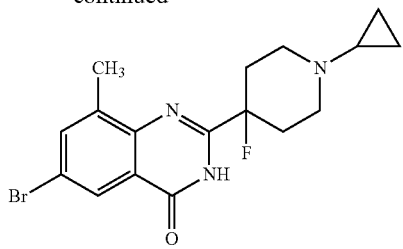

A mixture of 6-bromo-2-(4-fluoropiperidin-4-yl)-8-methylquinazolin-4(3H)-one (718 mg), (1-ethoxycyclopropoxy)trimethylsilane (2.12 mL), sodium cyanotrihydridoborate (265 mg), acetic acid (1.27 mL) and methanol (14 mL) was stirred at 60° C. for 3 hours and the volatile components were distilled off under reduced pressure. The remaining solid was purified by silica gel column chromatography (NH, methanol/ethyl acetate) and the obtained solid was washed with ethyl acetate to obtain the title compound (530 mg).
MS: [M+H]$^+$380.2.

(C) 2-(1-Cyclopropyl-4-fluoropiperidin-4-yl)-6-(2-methylimidazo[1,2-α]pyrimidin-6-yl)-8-methylquinazolin-4(3H)-one

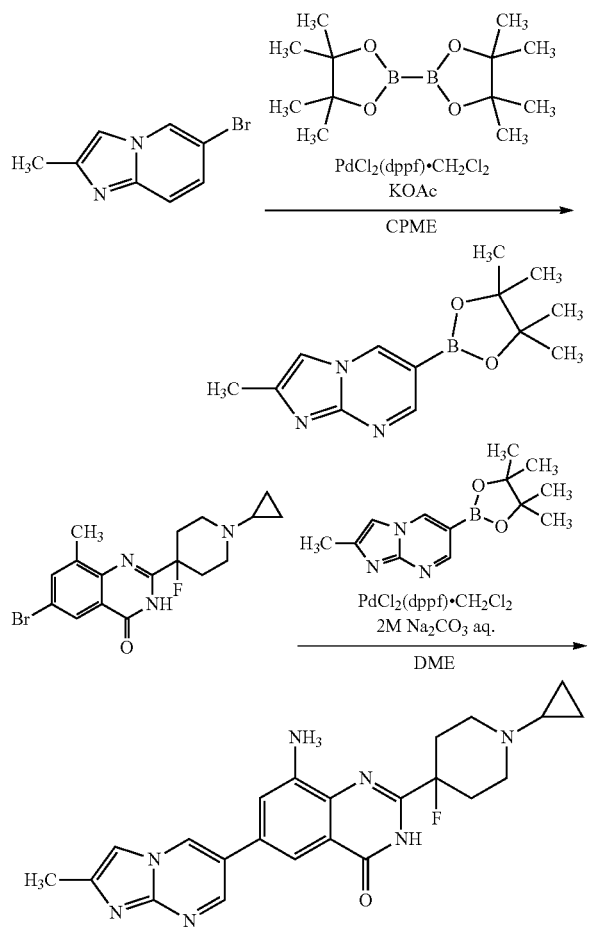

A mixture of 6-brome-2-methylimidazo[1,2-α]pyrimidine (170 mg), bis(pinacolato)diboron (265 mg), potassium acetate (236 mg), dichloro[1,1'-bis(diphenylphosphino)ferrocene]palladium(II) dichloromethane adduct (32.7 mg) and cyclopentyl methyl ether (2 mL) was stirred under microwave irradiated conditions at 130° C. for 4 hours. After the obtained mixture was filtered through Celite and washed with THF, the volatile components were distilled off from the filtrate under reduced pressure. A mixture of the obtained sub stance, 6-bromo-2-(4-cyclopropyl-1-fluoropiperidin-4-yl)-8-methyl quinazolin-4(3H)-one (250 mg), dichloro[1,1'-bis(diphenylphosphino)ferrocene]palladiumdichloromethane adduct (26.8 mg), a 2.0 M aqueous sodium carbonate solution (0.986 mL) and 1,2-dimethoxyethane (15 mL) was stirred under microwave irradiated conditions at 130° C. for 60 minutes. The obtained mixture was purified by silica gel column chromatography (NH, methanol/ethyl acetate) and the obtained solid was washed with ethyl acetate to obtain the title compound (19 mg).

$^1$H-NMR (300 MHz, DMSO-d$_6$) δ: 0.31-0.51 (4H, m), 1.66-1.77 (1H, m), 2.06-2.34 (4H, m), 2.40 (3H, s), 2.52-2.58 (2H, m), 2.60 (3H, s), 2.88-2.99 (2H, m), 7.68 (1H, d, J=0.8 Hz), 8.13 (1H, d, J=1.5 Hz), 8.29 (1H, d, J=1.9 Hz), 8.89 (1H, d, J=2.6 Hz), 9.34-9.46 (1H, m), 12.39 (1H, brs). MS: [M+H]$^+$433.3.

Working Example 104

2-(1-cyclopropyl-4-fluoropiperidin-4-yl)-6-(8-fluoro-2-methylimidazo[1,2-α]pyridin-6-yl)pyrido[3,4-d]pyrimidin-4(3H)-one (A) 5-amino-2-chloroisonicotinamide

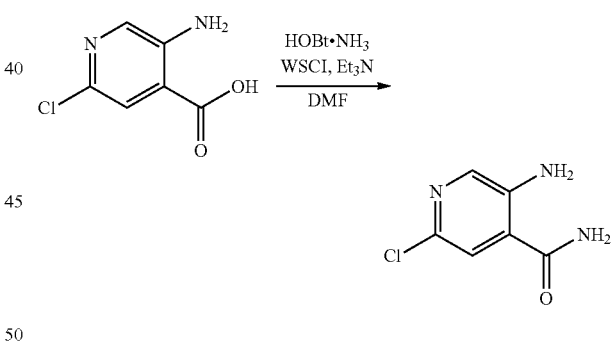

To a mixture of 5-amino-2-chloroisonicotinic acid (3.07 g), N-(3-dimethylaminopropyl)-N'-ethylcarbodiimide hydrochloride (1/1) (4.09 g), triethylamine (3.7 mL) and DMF (50 mL) was added 1H-benzotriazol-1-ol ammonium salt (1/1) (3.25 g) at room temperature and the mixture was stirred at the same temperature for 15 hours. Then, water was further added thereto and the mixture was extracted with ethyl acetate. The organic layer was washed with a saturated aqueous sodium hydrogen carbonate solution and saturated brine and then dried over magnesium sulfate, and the volatile components were distilled off under reduced pressure. The obtained solid was washed with ethyl acetate/diisopropyl ether to obtain the title compound (1.92 g).

$^1$H-NMR (300 MHz, DMSO-d$_6$) δ: 6.66 (2H, s), 7.46-7.65 (2H, m), 7.93 (1H, s), 8.10 (1H, brs). MS: [M+H]$^+$ 172.2.

(B) tert-Butyl 4-[(4-carbamoyl-6-chloropyridin-3-yl)carbamoyl-4-fluoropiperidine-1-carboxylate

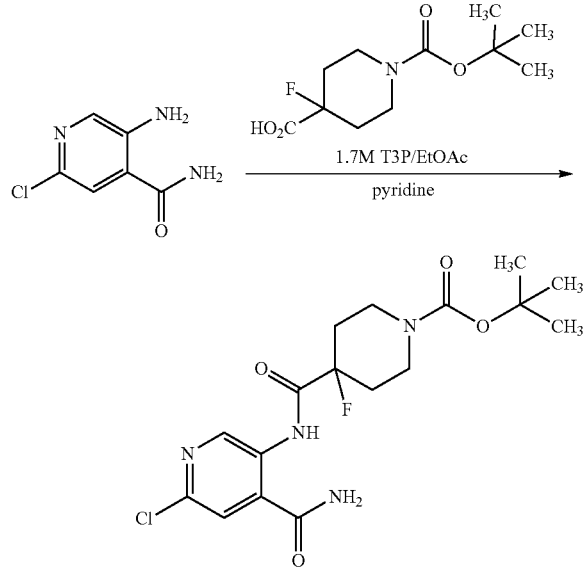

A mixture of 5-amino-2-chloroisonicotinamide (1.92 g), 1-(tert-butoxycarbonyl)-4-fluoropiperidine-4-carboxylic acid (2.77 g), a 1.7 M propylphosphonic acid anhydride/ethyl acetate solution (9.87 mL) and pyridine (20 mL) was stirred at room temperature overnight and the volatile components were distilled off under reduced pressure. After 0.1 M hydrochloric acid was further added thereto, the mixture was extracted with ethyl acetate. The obtained organic layer was washed with water and saturated brine and then dried over anhydrous magnesium sulfate, and the volatile components were distilled off under reduced pressure. The remaining solid was washed with diisopropyl ether to obtain the title compound (3.93 g).

$^1$H-NMR (300 MHz, DMSO-$d_6$) δ: 1.42 (9H, s), 1.85-2.09 (4H, m), 3.01 (2H, brs), 3.94 (2H, d, J=12.5 Hz), 7.91 (1H, s), 8.21 (1H, brs), 8.63 (1H, brs), 9.46 (1H, s), 11.99 (1H, d, J=5.3 Hz). MS: [M+Na]$^+$423.2.

(C) tert-Butyl 4-(6-chloro-4-oxo-3,4-dihydropyrido[3,4-d]pyrimidin-2-yl)-4-fluoropiperidine-1-carboxylate

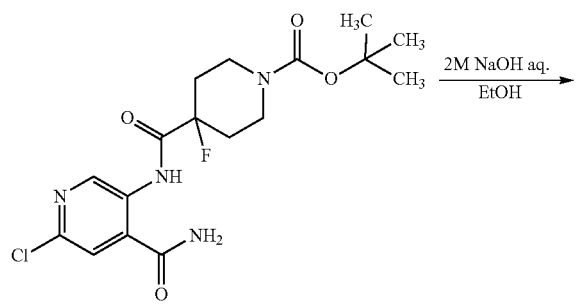

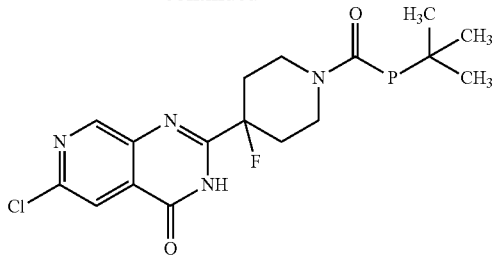

To a mixture of tert-butyl 4-[(4-carbamoyl-6-chloropyridin-3-yl)carbamoyl-4-fluoropiperidine-1-carboxylate (3.93 g) and ethanol (35 mL) was added dropwise a 2.0 M aqueous sodium hydroxide solution (14.7 mL) at room temperature. After the obtained mixture was stirred at room temperature for 2 hours and neutralized with 2.0 M hydrochloric acid, water was added thereto and then the precipitate was isolated by filtration and washed with ethanol/water to obtain the title compound (3.68 g).

$^1$H-NMR (300 MHz, DMSO-$d_6$) δ: 1.43 (9H, s), 1.98-2.23 (4H, m), 3.10 (2H, brs), 3.96 (2H, d, J=14.0 Hz), 8.00 (1H, d, J=0.8 Hz), 8.91 (1H, d, J=0.8 Hz), 12.86 (1H, s). MS: [M+H]$^+$405.2.

(D) 6-Chloro-2-(4-fluoropiperidin-4-yl)pyrido[3,4-d]pyrimidin-4(3H)-one

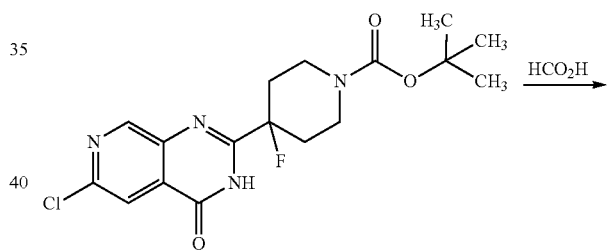

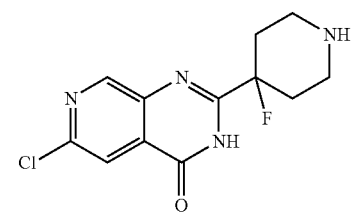

After a mixture of tert-butyl 4-(6-chloro-4-oxo-3,4-dihydropyrido[3,4-d]pyrimidin-2-yl)-4-fluoropiperidine-1-carboxylate (1.0 g) and formic acid (5 mL) was stirred at 70° C. for 30 minutes, the volatile components were distilled off under reduced pressure. The remaining solid was washed with a 5% ammonium hydroxide solution and water to obtain the title compound (735 mg).

$^1$H-NMR (300 MHz, DMSO-$d_6$) δ: 2.06-2.43 (4H, m), 2.96-3.21 (4H, m), 7.78 (1H, s), 8.68 (1H, s). MS: [M+H]$^+$ 283.2.

(E) 6-Chloro-2-(1-cyclopropyl-4-fluoropiperidin-4-yl)pyrido[3,4-d]pyrimidin-4(3H)-one

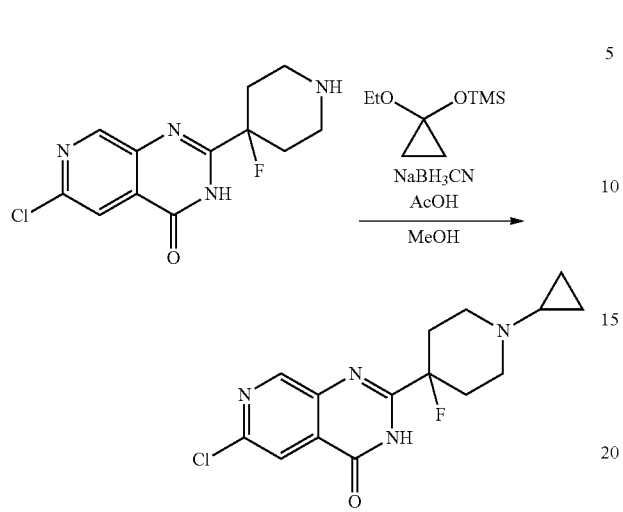

A mixture of 6-chloro-2-(4-fluoropiperidin-4-yl)pyrido[3,4-d]pyrimidin-4(3H)-one (306 mg), (1-ethoxycyclopropoxy)trimethylsilane (1.1 mL), sodium cyanotrihydridoborate (136 mg), acetic acid (0.62 mL) and methanol (6 mL) was stirred at 60° C. for 2 hours and a saturated aqueous sodium hydrogen carbonate solution was further added thereto at room temperature, followed by mixing. Then, the mixture was extracted with ethyl acetate. The obtained organic layer was washed with water and saturated brine and then dried over anhydrous magnesium sulfate, and the volatile components were distilled off under reduced pressure. The remaining solid was washed with diisopropyl ether to obtain the title compound (215 mg).

$^1$H-NMR (300 MHz, DMSO-$d_6$) δ: 0.29-0.38 (2H, m), 0.39-0.49 (2H, m), 1.71 (1H, tt, J=6.6, 3.5 Hz), 2.00-2.30 (4H, m), 2.41-2.57 (2H, m), 2.92 (2H, d, J=11.3 Hz), 7.98 (1H, d, J=0.8 Hz), 8.88 (1H, d, J=0.8 Hz), 12.76 (1H, brs). MS: [M+H]$^+$323.2.

(F) 2-(1-Cyclopropyl-4-fluoropiperidin-4-yl)-6-(8-fluoro-2-methylimidazo[1,2-α]pyridin-6-yl)pyrido[3,4-d]pyrimidin-4(3H)-one

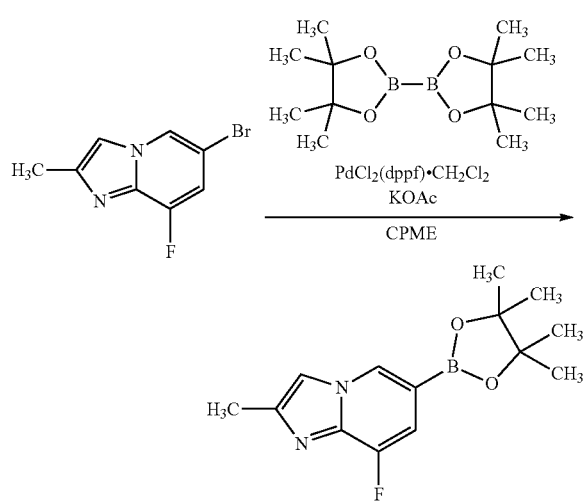

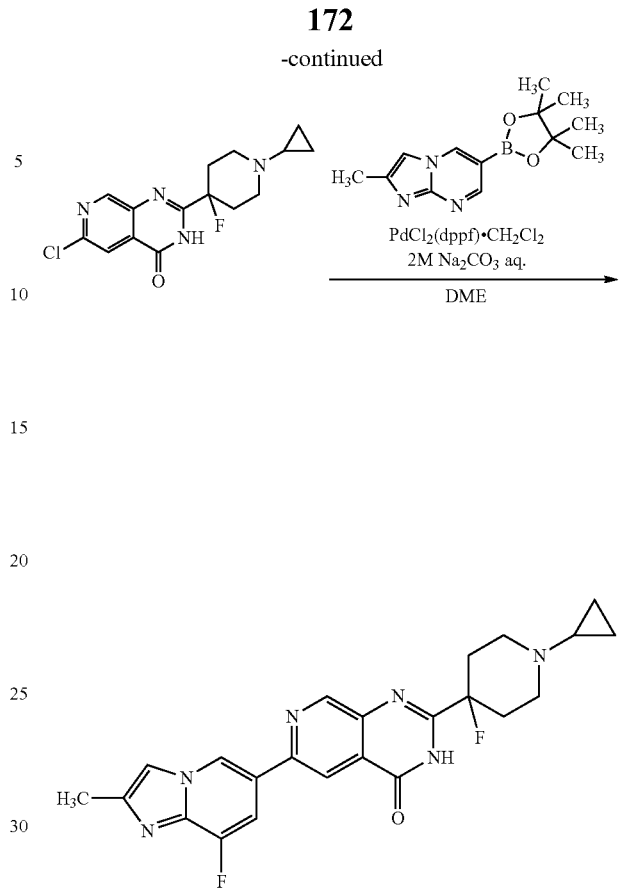

After a mixture of 6-brome-8-fluoro-2-methylimidazo[1,2-α]pyridine (156 mg), bis(pinacolato)diboron (208 mg), potassium acetate (134 mg), dichloro[1,1'-bis(diphenylphosphino)ferrocene]palladium(II) dichloromethane adduct (27.8 mg) and cyclopentyl methyl ether (3 mL) was stirred under microwave irradiated conditions at 130° C. for 30 minutes and the resulting mixture was filtered through Celite, the volatile components were distilled off from the filtrate under reduced pressure. A mixture of the obtained substance, 6-chloro-2-(1-cyclopropyl-4-fluoropiperidin-4-yl)pyrido[3,4-d]pyrimidin-4(3H)-one (200 mg), dichloro[1,1'-bis(diphenylphosphino)ferrocene]palladiumdichloromethane adduct (25.3 mg), a 2.0 M aqueous sodium carbonate solution (0.62 mL) and 1,2-dimethoxyethane (3 mL) was stirred under microwave irradiated conditions at 130° C. for 30 minutes and water was further added thereto at room temperature, followed by mixing. Then, the debris was removed by filtration through Celite. The obtained filtrate was extracted with ethyl acetate and the organic layer was dried over anhydrous magnesium sulfate. Then, the volatile components were distilled off under reduced pressure. The remaining solid was purified by silica gel column chromatography (NH, methanol/ethyl acetate) to obtain the title compound (150 mg).

$^1$H-NMR (300 MHz, DMSO-$d_6$) δ: 0.29-0.39 (2H, m), 0.40-0.52 (2H, m), 1.65-1.80 (1H, m), 2.01-2.32 (4H, m), 2.38 (3H, s), 2.44-2.58 (2H, m), 2.94 (2H, d, J=11.7 Hz), 7.84-7.96 (2H, m), 8.48 (1H, s), 9.07 (1H, s), 9.33 (1H, d, J=1.1 Hz), 12.68 (1H, brs). MS: [M+H]$^+$437.2.

Working Example 105

2-(1-Cyclopro-4-fluoropiperidin-4-yl)-8-fluoro-6-(2-methylimidazo[1,2-α]pyrimidin-6-yl)quinazolin-4(3H)-one (A) tert-Butyl 4-fluoro-4-[8-fluoro-6-(2-methylimidazo[1,2-α]pyrimidin-6-yl)-4-oxo-3,4-dihydroquinazolin-2-yl]piperidine-1-carboxylate

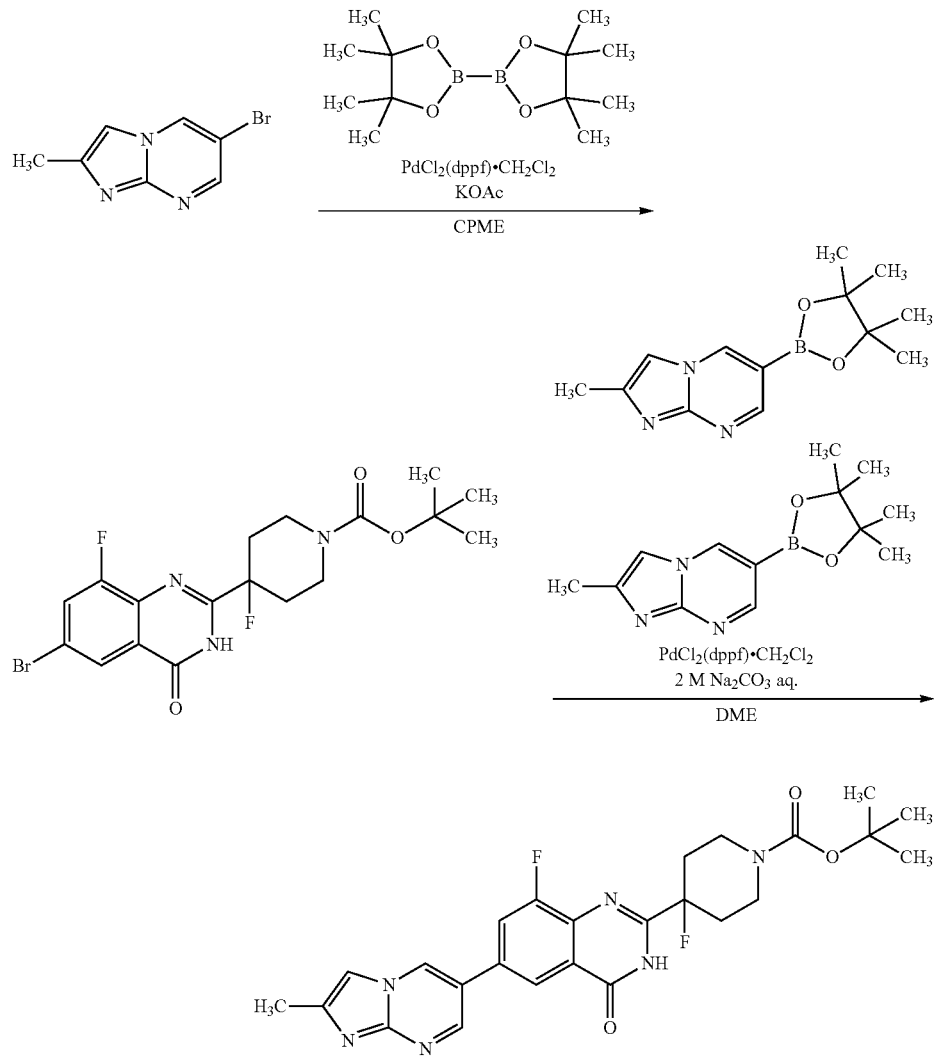

A mixture of 6-brome-2-methylimidazo[1,2-α]pyrimidine (300 mg), bis(pinacolato)diboron (431 mg), potassium acetate (278 mg), dichloro[1,1'-bis(diphenylphosphino)ferrocene]palladium(II) dichloromethane adduct (57.8 mg) and cyclopentyl methyl ether (3 mL) was stirred under microwave irradiated conditions at 130° C. for 2 hours. After the obtained mixture was filtered through Celite, the volatile components were distilled off from the filtrate under reduced pressure. A mixture of the obtained substance, tert-butyl 4-(6-bromo-8-fluoro-4-oxo-3,4-dihydroquinazolin-2-yl]-4-fluoropiperidine-1-carboxylate (500 mg), dichloro[1,1'-bis(diphenylphosphino)ferrocene]palladiumdichloromethane adduct (46.0 mg), a 2.0 M aqueous sodium carbonate solution (1.13 mL) and 1,2-dimethoxyethane (13 mL) was stirred under microwave irradiated conditions at 130° C. for 30 minutes and the precipitate was filtered off and then washed with water. The obtained solid was dissolved in a 7 N ammonia/methanol solution and activate carbon was added thereto. The obtained mixture was filtered through Celite and washed with methanol. The volatile components were distilled off from the obtained filtrate under reduced pressure. The remaining solid was washed with methanol/ethyl acetate to obtain the title compound (322 mg).

$^1$H-NMR (300 MHz, DMSO-$d_6$) δ: 1.44 (9H, s), 2.05-2.30 (4H, m), 2.41 (3H, s), 3.11 (2H, brs), 3.98 (2H, d, J=12.5 Hz), 7.69 (1H, d, J=0.8 Hz), 8.18-8.32 (2H, m), 8.93 (1H, d, J=2.6 Hz), 9.47 (1H, d, J=2.6 Hz), 12.69 (1H, brs). MS: [M+H]$^+$497.3.

(B) 8-Fluoro-2-(4-fluoropiperidin-4-yl)-6-(2-methyl-imidazo[1,2-α]pyrimidin-6-yl)quinazolin-4(3H)-one

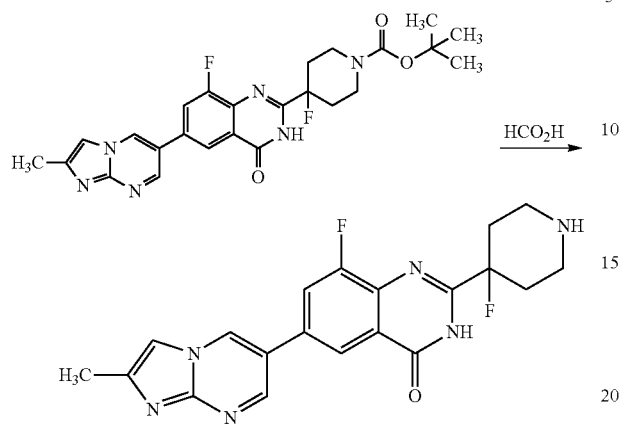

After a mixture of tert-butyl 4-fluoro-4-[8-fluoro-6-(2-methylimidazo[1,2-α]pyrimidin-6-yl)-4-oxo-3,4-dihydroquinazolin-2-yl]piperidine-1-carboxylate (322 mg) and formic acid (3 mL) was stirred at 60° C. for 10 minutes, the volatile components were distilled off under reduced pressure. To the remaining solid was added a 7 M ammonia/methanol solution and the volatile components were distilled off under reduced pressure. The remaining substance was purified by silica gel column chromatography (methanol) to obtain the title compound (196 mg).

$^1$H-NMR (300 MHz, DMSO-$d_6$) δ: 2.03-2.36 (4H, m), 2.40 (3H, s), 2.79-3.05 (4H, m), 7.68 (1H, s), 8.11 (1H, dd, J=11.7, 1.9 Hz), 8.25 (1H, d, J=1.9 Hz), 8.91 (1H, d, J=2.6 Hz), 9.44 (1H, d, J=2.6 Hz). MS: [M+H]$^+$397.3.

(C) 2-(1-Cyclopro-4-fluoropiperidin-4-yl)-8-fluoro-6-(2-methylimidazo[1,2-α]pyrimidin-6-yl)quinazolin-4(3H)-one

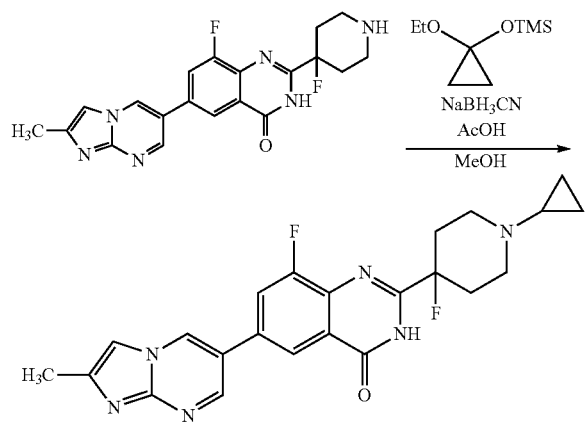

A mixture of 8-fluoro-2-(4-fluoropiperidin-4-yl)-6-(2-methylimidazo[1,2-α]pyrimidin-6-yl)quinazolin-4(3H)-one (70 mg), ((1-ethoxycyclopropyl)oxy)(trimethyl)silane (0.18 mL), sodium cyanotrihydridoborate (22 mg), acetic acid (0.053 mL) and methanol (3 mL) was stirred at 60° C. for 3 hours and the volatile components were distilled off under reduced pressure. The remaining substance was purified by silica gel column chromatography (NH, methanol/ethyl acetate) and the obtained solid was washed with ethyl acetate to obtain the title compound (8 mg).

MS: [M+H]$^+$437.3.

Working Example 106

2-(1-Cyclopropylpiperidin-4-yl)-6-(4-fluoro-2-methyl-1,3-benzoxazol-6-yl)pyrido[3,2-d]pyrimidin-4(3H)-one

(A) tert-Butyl 4-(6-bromo-4-oxo-3,4-dihydropyrido[3,2-d]pyrimidin-2-yl)piperidine-1-carboxylate

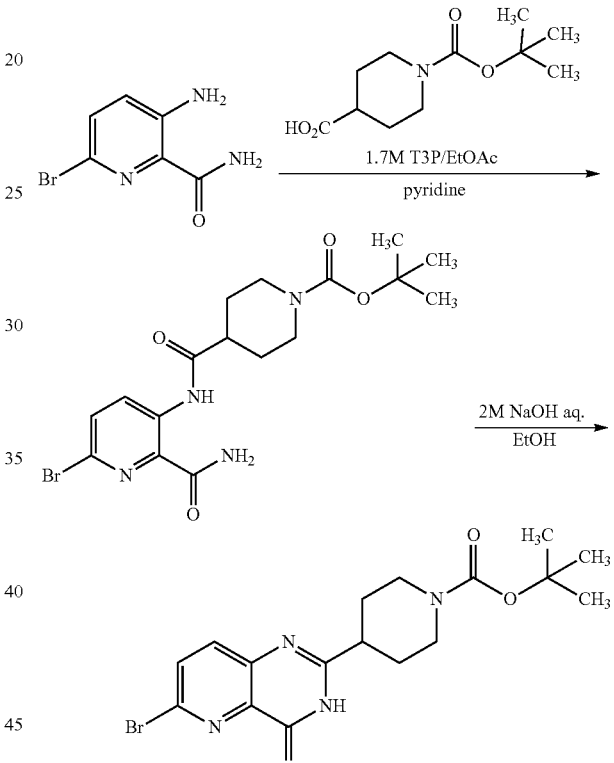

After a mixture of 1-(tert-butoxycarbonyl)piperidine-4-carboxylic acid (1.27 g), 3-amino-6-bromopicolinamide (1.00 g), a 1.7 M propylphosphonic acid anhydride/ethyl acetate solution (4.1 mL) and pyridine (20 mL) was stirred at room temperature for 16 hours, the volatile components were distilled off under reduced pressure. To the remaining solid were added ethyl acetate and water, and then the organic layer was separated, washed with a saturated aqueous sodium hydrogen carbonate solution and saturated brine and then dried over anhydrous magnesium sulfate. Then, the volatile components were distilled off under reduced pressure. To the remaining solid was added ethanol (20 mL), followed by mixing, and a 2.0 M aqueous sodium hydroxide solution (4.63 mL) was further added thereto at room temperature. Then, the mixture was stirred at room temperature for 2 hours and neutralized with 2.0 M hydrochloric acid. The precipitate was filtered off to obtain the title compound (1.20 g).

¹H-NMR (300 MHz, DMSO-d₆) δ: 1.38-1.45 (9H, m), 1.54-1.71 (2H, m), 1.88 (2H, d, J=9.1 Hz), 2.64-2.93 (3H, m), 4.04 (2H, d, J=12.5 Hz), 7.86-7.97 (2H, m), 12.64 (1H, brs).

(B) 6-Bromo-2-(piperidin-4-yl)pyrido[3,2-d]pyrimidin-4(3H)-one

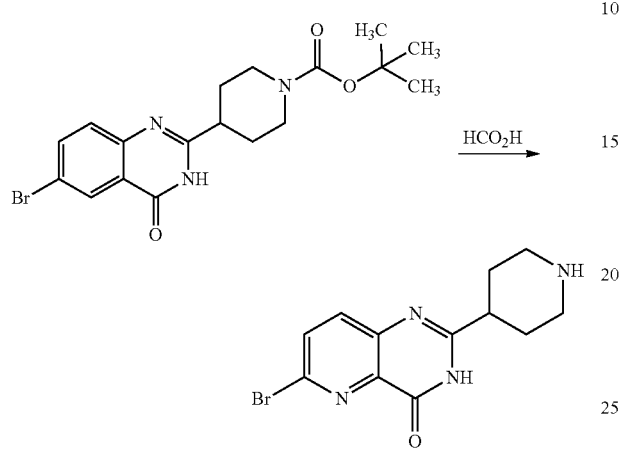

After a mixture of tert-butyl 4-(6-bromo-4-oxo-3,4-dihydropyrido[3,2-d]pyrimidin-2-yl)piperidine-1-carboxylate (1.23 g) and formic acid (12 mL) was stirred at 60° C. for 10 minutes, the volatile components were distilled off under reduced pressure. After a 5% ammonium hydroxide solution was added to the remaining solid and the mixture was stirred at room temperature for 30 minutes. Then, the resulting solid was washed with water to obtain the title compound (929 mg).
MS: [M+H]⁺309.2.

(C) 6-Bromo-2-(1-cyclopropylpiperidin-4-yl)pyrido[3,2-d]pyrimidin-4(3H)-one

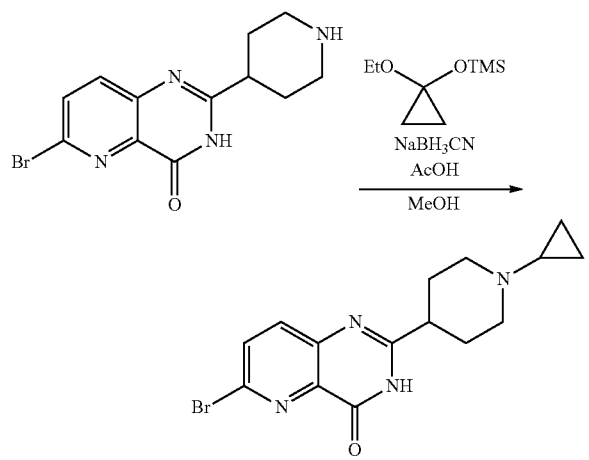

A mixture of 6-bromo-2-(piperidin-4-yl)pyrido[3,2-d]pyrimidin-4(3H)-one (929 mg), ((1-ethoxycyclopropyl)oxy)(trimethyl)silane (3.02 mL), sodium cyanotrihydridoborate (378 mg), acetic acid (1.80 mL) and methanol (20 mL) was stirred at 60° C. for 16 hours and cooled to room temperature. The resulting precipitate was filtered off and then washed with methanol and water to obtain the title compound (630 mg).
¹H-NMR (300 MHz, DMSO-d₆) δ: 0.24-0.34 (2H, m), 0.37-0.46 (2H, m), 1.55-1.78 (3H, m), 1.80-1.91 (2H, m), 2.12-2.27 (2H, m), 2.54-2.66 (1H, m), 3.02 (2H, d, J=11.3 Hz), 7.93 (2H, s), 12.50 (1H, brs). MS: [M+H]⁺349.2.

(D) 2-(1-Cyclopropylpiperidin-4-yl)-6-(4-fluoro-2-methyl-1,3-benzoxazol-6-yl)pyrido[3,2-d]pyrimidin-4(3H)-one

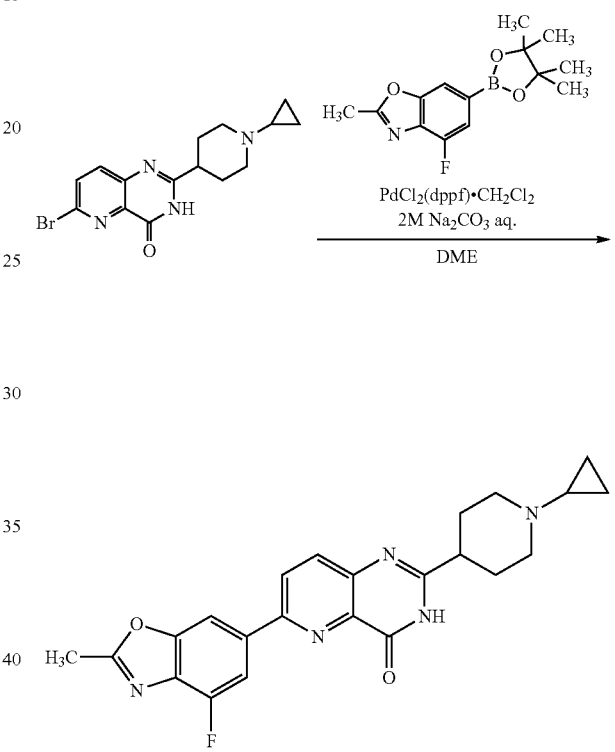

A mixture of 4-fluoro-2-methyl-6-(4,4,5,5-tetramethyl-1,3,2-dioxaborolane-2-yl)-1,3-benzoxazole (286 mg), 6-bromo-2-(1-cyclopropylpiperidin-4-yl)pyrido[3,2-d]pyrimidin-4(3H)-one (300 mg), dichloro[1,1'-bis(diphenylphosphino)ferrocene]palladiumdichloromethane adduct (35.1 mg), a 2.0 M aqueous sodium carbonate solution (1.29 mL) and 1,2-dimethoxyethane (15 mL) was stirred under microwave irradiated conditions at 130° C. for 40 minutes and the precipitate was filtered off and then washed with 1,2-dimethoxyethane and water. The obtained solid was dissolved in a 7 N ammonia/methanol solution and the mixture was filtered through silica gel (NH). Then, the volatile components were distilled off from the filtrate under reduced pressure. The remaining solid was washed with ethyl acetate and ethanol/water to obtain the title compound (70 mg).
¹H-NMR (300 MHz, DMSO-d₆) δ: 0.25-0.35 (2H, m), 0.37-0.47 (2H, m), 1.59-1.70 (1H, m), 1.70-1.83 (2H, m), 1.84-1.94 (2H, m), 2.13-2.32 (2H, m), 2.54-2.67 (1H, m), 2.69 (3H, s), 3.03 (2H, d, J=11.3 Hz), 8.06-8.14 (2H, m), 8.38 (1H, d, J=1.1 Hz), 8.48 (1H, d, J=8.7 Hz), 12.30 (1H, brs). MS: [M+H]⁺420.3.

Working Example 107

2-(1-Cyclopropyl-4-fluoropiperidin-4-yl)-6-(4-fluoro-2-methyl-1,3-benzoxazol-6-yl)pyrido[3,4-d]pyrimidin-4(3H)-one

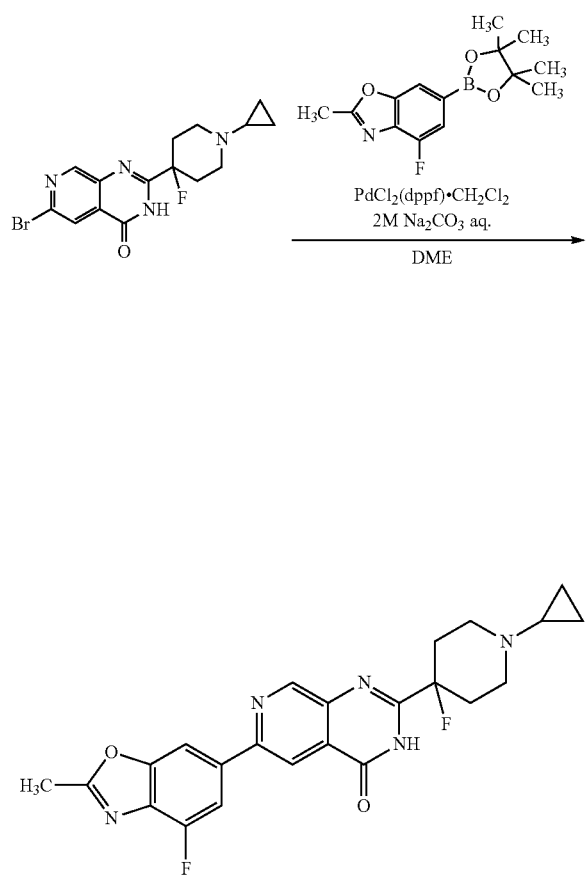

A mixture of 4-fluoro-2-methyl-6-(4,4,5,5-tetramethyl-1,3,2-dioxaborolane-2-yl)-1,3-benzoxazole (250 mg), 6-chloro-2-(4-fluoro-1-cyclopropylpiperidin-4-yl)pyrido[3,4-d]pyrimidin-4(3H)-one (243 mg), dichloro[1,1'-bis(diphenylphosphino)ferrocene]palladiumdichloromethane adduct (30.7 mg), a 2.0 M aqueous sodium carbonate solution (1.13 mL) and 1,2-dimethoxyethane (15 mL) was stirred under microwave irradiated conditions at 130° C. for 40 minutes and the precipitate was filtered off. To the obtained solid were added ethyl acetate and water, and then the organic layer was separated, washed with saturated brine and dried over anhydrous magnesium sulfate. Then, the volatile components were distilled off under reduced pressure. The remaining solid was washed with ethyl acetate, methanol and water to obtain the title compound (40 mg).

$^1$H-NMR (300 MHz, DMSO-d$_6$) δ: 0.30-0.51 (4H, m), 1.67-1.77 (1H, m), 2.01-2.17 (3H, m), 2.19-2.33 (1H, m), 2.53-2.57 (1H, m), 2.68 (3H, s), 2.93 (2H, d, J=11.7 Hz), 8.09 (1H, dd, J=11.9, 1.3 Hz), 8.39 (1H, d, J=1.1 Hz), 8.57 (1H, d, J=0.8 Hz), 9.10 (1H, d, J=0.8 Hz), 12.67 (1H, brs). MS: [M+H]$^+$438.3.

Working Example 108

2-(4-Fluoro-1-methylpiperidin-4-yl)-6-(8-fluoro-2-methylimidazo[1,2-α]pyridin-6-yl)pyrido[3,4-d]pyrimidin-4(3H)-one (A) tert-Butyl midin-2-yl]piperidine-1-carboxylate

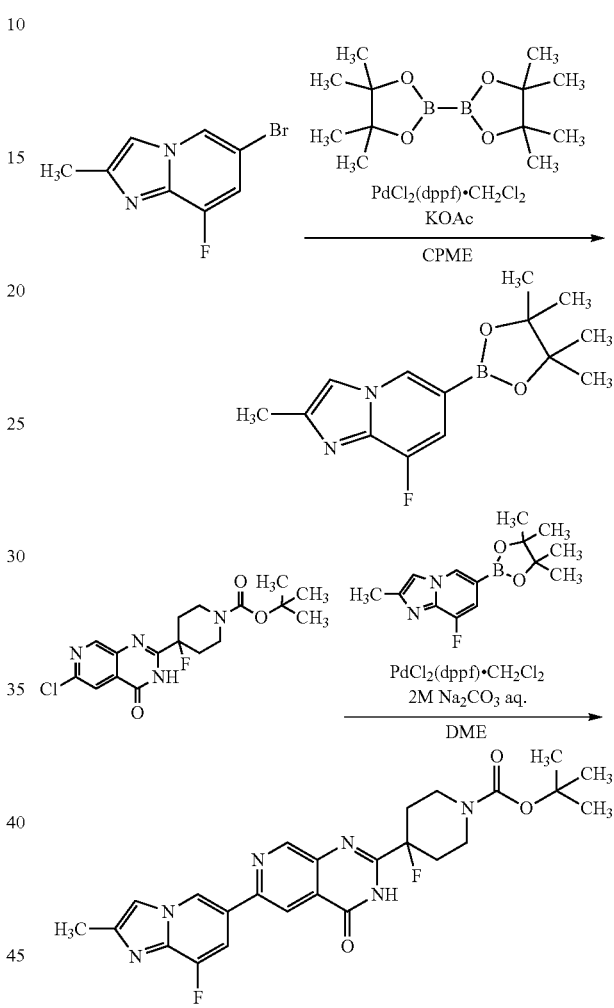

A mixture of 6-brome-8-fluoro-2-methylimidazo[1,2-α]pyridine (360 mg), bis(pinacolato)diboron (478 mg), potassium acetate (308 mg), dichloro[1,1'-bis(diphenylphosphino)palladium(II) dichloromethane adduct (64.1 mg) and cyclopentyl methyl ether (5 mL) was stirred under microwave irradiated conditions at 130° C. for 30 minutes. After the obtained mixture was filtered through Celite, the volatile components were distilled off from the filtrate under reduced pressure. A mixture of the obtained substance, tert-butyl 4-(6-chloro-4-oxo-3,4-dihydropyrido[3,4-d]pyrimidin-2-yl]-4-fluoropiperidine-1-carboxylate (600 mg), dichloro[1,1'-bis(diphenylphosphino)ferrocene]palladiumdichloromethane adduct (64.0 mg), a 2.0 M aqueous sodium carbonate solution (1.57 mL) and 1,2-dimethoxyethane (9 mL) was stirred under microwave irradiated conditions at 130° C. for 30 minutes. After water was added to the mixture and insoluble components were removed by filtration, the filtrate was extracted with ethyl acetate. The obtained organic layer was dried over anhydrous magnesium sulfate. The obtained mixture was filtered through silica gel (NH) and the volatile components were distilled off from the filtrate under reduced pressure. The remaining solid was washed with ethyl acetate to obtain the title compound (573 mg).

$^1$H-NMR (300 MHz, DMSO-$d_6$) δ: 1.43 (9H, s), 1.94-2.30 (4H, m), 2.37 (3H, s), 3.17 (2H, d, J=5.3 Hz), 3.82 (2H, d, J=12.8 Hz), 7.81 (1H, d, J=12.8 Hz), 7.89 (1H, d, J=2.6 Hz), 8.30 (1H, s), 8.87 (1H, s), 9.21 (1H, s). MS: [M+H]$^+$ 497.3.

(B) 6-(8-Fluoro-2-methylimidazo[1,2-α]pyridin-6-yl)-2-(4-fluoropiperidin-4-yl)pyrido[3,4-d]pyrimidin-4(3H)-one

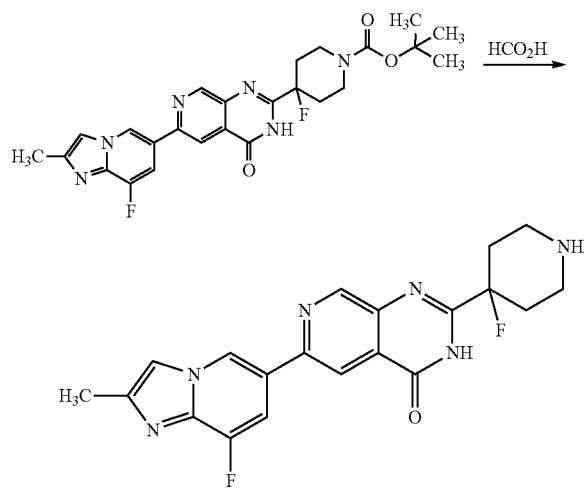

After a mixture of tert-butyl midin-2-yl]piperidine-1-carboxylate (573 mg) and formic acid (2 mL) was stirred at 70° C. for 30 minutes, the volatile components were distilled off under reduced pressure. To the remaining solid were added a 7 M ammonia/methanol solution (5 mL) and water (5 mL), and then the precipitate was filtered. The obtained solid was washed with ethanol/water to obtain the title compound (403 mg).

$^1$H-NMR (300 MHz, DMSO-$d_6$) δ: 2.03-2.40 (7H, m), 2.88-3.12 (4H, m), 7.83-7.92 (2H, m), 8.40 (1H, s), 8.99 (1H, s), 9.29 (1H, d, J=1.1 Hz). MS: [M+H]$^+$397.3.

(C) 2-(4-Fluoro-1-methylpiperidin-4-yl)-6-(8-fluoro-2-methylimidazo[1,2-α]pyridin-6-yl)pyrido[3,4-d]pyrimidin-4(3H)-one

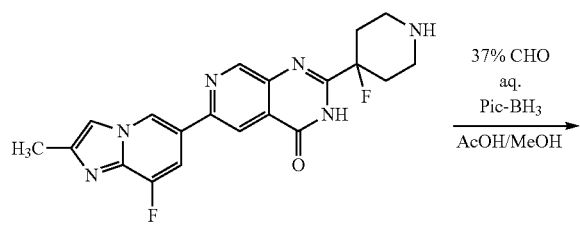

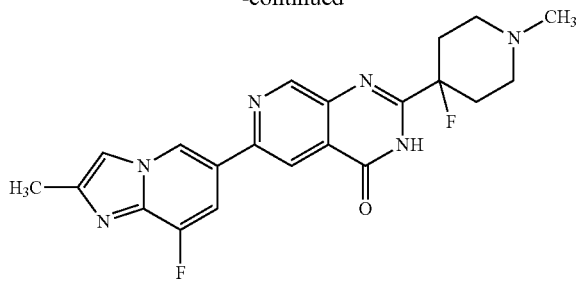

To a mixture of 6-(8-fluoro-2-methylimidazo[1,2-α]pyridin-6-yl)-2-(4-fluoropiperidin-4-yl)pyrido[3,4-d]pyrimidin-4(3H)-one (122 mg), methanol (2 mL), acetic acid (0.2 mL) and a 37% aqueous formaldehyde solution (0.125 mL) was added borane-2-methylpyridine complex (49.5 mg) and the mixture was stirred at room temperature for 15 hours. The volatile components were distilled off from the obtained mixture under reduced pressure and the remaining solid was purified by silica gel column chromatography (NH, methanol/ethyl acetate). The obtained solid was washed with ethyl acetate to obtain the title compound (55.0 mg).

$^1$H-NMR (300 MHz, DMSO-$d_6$) δ: 2.04-2.35 (9H, m), 2.38 (3H, d, J=0.8 Hz), 2.71-2.84 (2H, m), 7.86-7.98 (2H, m), 8.50 (1H, s), 9.10 (1H, s), 9.35 (1H, d, J=1.5 Hz), 12.58 (1H, s). MS: [M+H]$^+$411.3.

Working Example 109

2-(1-Ethyl-4-fluoropiperidin-4-yl)-6-(8-fluoro-2-methylimidazo[1,2-α]pyridin-6-yl)pyrido[3,4-d]pyrimidin-4(3H)-one

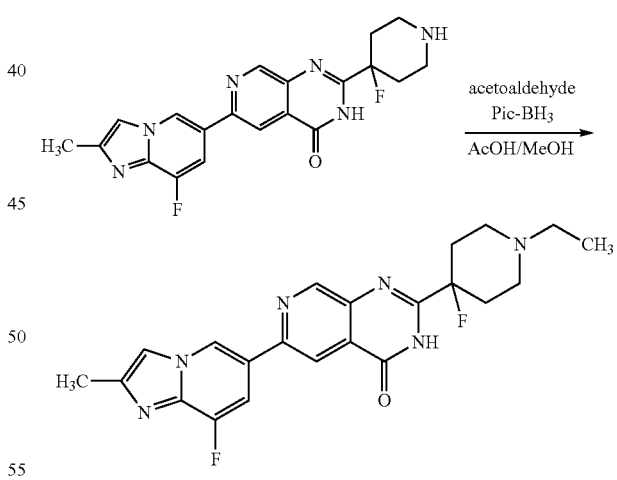

To a mixture of 6-(8-fluoro-2-methylimidazo[1,2-α]pyridin-6-yl)-2-(4-fluoropiperidin-4-yl)pyrido[3,4-d]pyrimidin-4(3H)-one (128 mg), methanol (2 mL), acetic acid (0.2 mL) and acetaldehyde (0.18 mL) was added borane-2-methylpyridine complex (51.7 mg) and the mixture was stirred at room temperature for 15 hours. The volatile components were distilled off from the obtained mixture under reduced pressure and the remaining solid was purified by silica gel column chromatography (NH, methanol/ethyl acetate). The obtained solid was washed with ethyl acetate to obtain the title compound (55.0 mg).

¹H-NMR (300 MHz, DMSO-d₆) δ: 1.05 (3H, t, J=7.2 Hz), 2.04-2.47 (11H, m), 2.87 (2H, d, J=9.4 Hz), 7.91 (2H, dd, J=7.2, 4.5 Hz), 8.49 (1H, s), 9.09 (1H, s), 9.35 (1H, d, J=1.1 Hz), 12.60 (1H, s). MS: [M+H]⁺425.3.

Working Example 110

2-[4-Fluoro-1-(2-methoxyethyl)piperidin-4-yl]-6-(8-fluoro-2-methylimidazo[1,2-α]pyridin-6-yl)quinazolin-4(3H)-one (A) 6-Bromo-2-(4-fluoropiperidin-4-yl)quinazolin-4(3H)-one

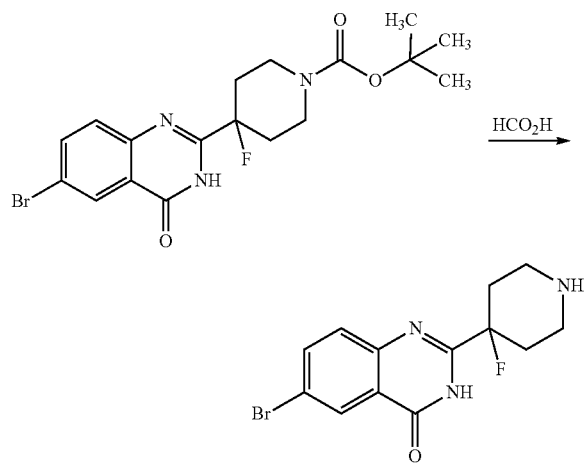

After a mixture of tert-butyl 4-(6-bromo-4-oxo-3,4-dihydroquinazolin-2-yl)-4-fluoropiperidine-1-carboxylate (0.99 g) and formic acid (10 mL) was stirred at 70° C. for 30 minutes, the volatile components were distilled off under reduced pressure. To the remaining solid were added a 7 M ammonia/methanol solution (5 mL) and water (5 mL), and then the volatile components were distilled off under reduced pressure. Then, the remaining solid was washed with water to obtain the title compound (750 mg).

¹H-NMR (300 MHz, DMSO-d₆) δ: 1.90-2.26 (4H, m), 2.82 (2H, td, J=12.0, 2.8 Hz), 2.89-3.02 (2H, m), 7.58 (1H, d, J=8.7 Hz), 7.92 (1H, dd, J=8.7, 2.3 Hz), 8.18 (1H, d, J=2.3 Hz). MS: [M+H]⁺326.1.

(B) 6-bromo-2-[4-fluoro-1-(2-methoxyethyl)piperidin-4-yl]quinazolin-4(3H)-one

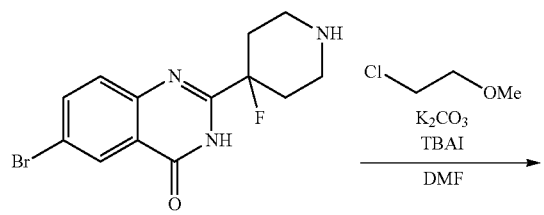

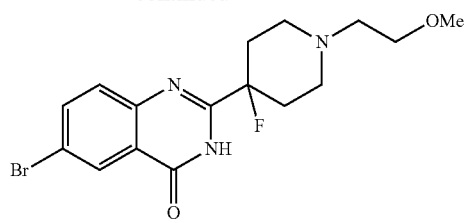

After a mixture of 6-bromo-2-(4-fluoropiperidin-4-yl)quinazolin-4(3H)-one (400 mg), 1-chloro-2-methoxyethane (0.123 mL), potassium carbonate (339 mg), tetrabutylammonium iodide (45.3 mg) and DMF (5 mL) was stirred at 90° C. overnight and water was added thereto at room temperature, followed by mixing. The mixture was extracted with ethyl acetate. The obtained organic layer was washed with water and saturated brine and then dried over anhydrous magnesium sulfate, and the volatile components were distilled off under reduced pressure. The remaining solid was purified by silica gel column chromatography (NH, hexane/ethyl acetate) to obtain the title compound (150 mg).

¹H-NMR (300 MHz, DMSO-d₆) δ: 1.99-2.38 (6H, m), 2.52-2.58 (2H, m), 2.78-2.92 (2H, m), 3.25 (3H, s), 3.46 (2H, t, J=5.9 Hz), 7.62 (1H, d, J=8.7 Hz), 7.97 (1H, dd, J=8.7, 2.3 Hz), 8.20 (1H, d, J=2.3 Hz), 12.47 (1H, brs). MS: [M+H]⁺384.2.

(C) 2-[4-fluoro-1-(2-methoxyethyl)piperidin-4-yl]-6-(8-fluoro-2-methylimidazo[1,2-α]pyridin-6-yl)quinazolin-4(3H)-one

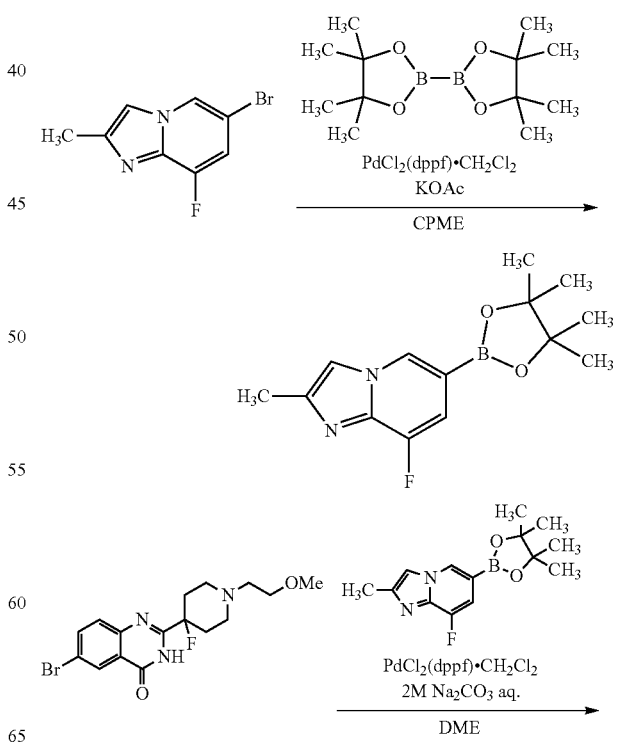

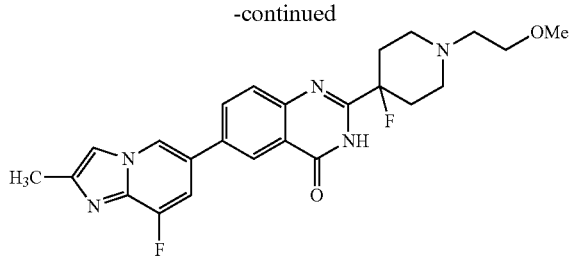

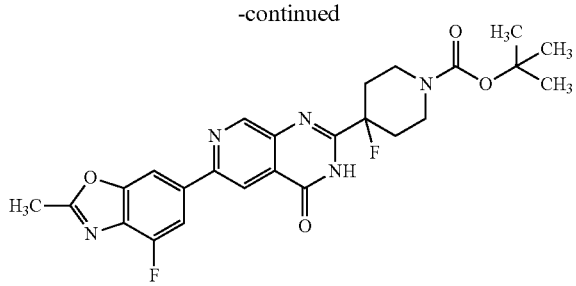

A mixture of 6-brome-8-fluoro-2-methylimidazo[1,2-α]pyridine (116 mg), bis(pinacolato)diboron (154 mg), potassium acetate (99.5 mg), dichloro[1,1'-bis(diphenylphosphino)ferrocene]palladium(II) dichloromethane adduct (20.7 mg) and cyclopentyl methyl ether (2 mL) was stirred under microwave irradiated conditions at 130° C. for 60 minutes. After the mixture was filtered through Celite, the volatile components were distilled off from the filtrate under reduced pressure. A mixture of the obtained substance, 6-bromo-2-[4-fluoro-1-(2-methoxyethyl)piperidin-4-yl]quinazolin-4(3H)-one (150 mg), dichloro[1,1'-bis(diphenylphosphino)ferrocene]palladiumdichloromethane adduct (15.9 mg), a 2.0 M aqueous sodium carbonate solution (0.586 mL) and 1,2-dimethoxyethane (15 mL) was stirred under microwave irradiated conditions at 130° C. for 50 minutes. After insoluble components were removed by filtration, ethyl acetate and water were added to the filtrate and the organic layer was separated. The obtained organic layer was washed with saturated brine and dried over anhydrous magnesium sulfate, and then the volatile components were distilled off under reduced pressure. The remaining solid was purified by silica gel column chromatography (methanol/ethyl acetate) and washed with ethyl acetate and water to obtain the title compound (97 mg).

$^1$H-NMR (300 MHz, DMSO-$d_6$) δ: 2.02-2.35 (6H, m), 2.38 (3H, s), 2.55 (2H, t, J=5.9 Hz), 2.81-2.93 (2H, m), 3.26 (3H, s), 3.47 (2H, t, J=5.9 Hz), 7.63 (1H, dd, J=12.5, 1.5 Hz), 7.76 (1H, d, J=8.7 Hz), 7.83-7.88 (1H, m), 8.18 (1H, dd, J=8.7, 2.3 Hz), 8.41 (1H, d, J=2.3 Hz), 8.95 (1H, d, J=1.5 Hz), 12.40 (1H, brs). MS: [M+H]$^+$454.3.

Example 111

6-(4-fluoro-2-methy-1,3-benzoxazol-6-yl)-2-(4-fluoropiperidin-4-yl)pyrido[3,4-d]pyrimidin-4(3H)-one (A) tert-Butyl 4-fluoro-4-[6-(4-fluoro-2-methy-1,3-benzoxazol-6-yl)-4-oxo-3,4-dihydropyrido[3,4-d]pyrimidin-2-yl]piperidine-1-carboxylate

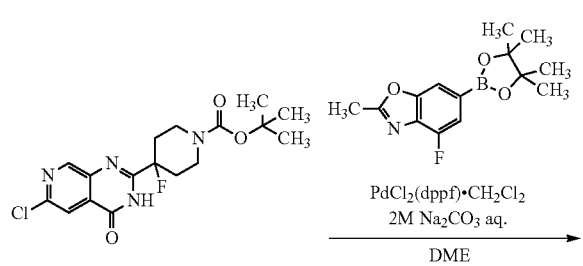

A mixture of 4-fluoro-2-methyl-6-(4,4,5,5-tetramethyl-1,3,2-dioxaborolane-2-yl)-1,3-benzoxazole (261 mg), tert-butyl 4-(6-chloro-4-oxo-3,4-dihydropyrido[3,4-d]pyrimidin-2-yl)-4-fluoropiperidine-1-carboxylate (300 mg), dichloro[1,1'-bis(diphenylphosphino)ferrocene]palladium (II) dichloromethane adduct (72.1 mg), a 2.0 M aqueous sodium carbonate solution (1.18 mL) and 1,2-dimethoxyethane (15 mL) was stirred under microwave irradiated conditions at 130° C. for 40 minutes. To the obtained mixture were added ethyl acetate and water, and then the organic layer was separated. The obtained organic layer was washed with water and saturated brine and then dried over anhydrous magnesium sulfate, and the volatile components were distilled off under reduced pressure. The remaining solid was washed with ethyl acetate and ethanol/water to obtain the title compound (70 mg).

$^1$H-NMR (300 MHz, DMSO-$d_6$) δ: 1.41-1.49 (9H, m), 2.14 (4H, d, J=17.4 Hz), 2.69 (3H, s), 3.12 (2H, brs), 3.98 (2H, d, J=14.0 Hz), 8.10 (1H, dd, J=11.7, 1.1 Hz), 8.41 (1H, d, J=1.1 Hz), 8.59 (1H, d, J=0.8 Hz), 9.13 (1H, s), 12.81 (1H, s).

(B) 6-(4-Fluoro-2-methy-1,3-benzoxazol-6-yl)-2-(4-fluoropiperidin-4-yl)pyrido[3,4-d]pyrimidin-4(3H)-one

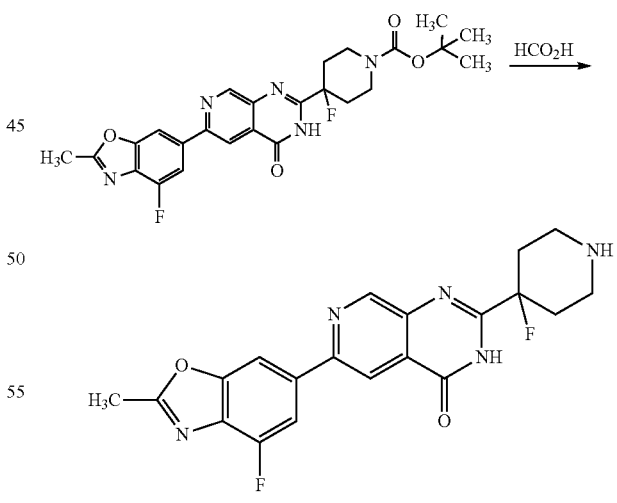

After a mixture of tert-butyl 4-fluoro-4-[6-(4-fluoro-2-methy-1,3-benzoxazol-6-yl)-4-oxo-3,4-dihydropyrido[3,4-d]pyrimidin-2-yl]piperidine-1-carboxylate (72 mg) and formic acid (1 mL) was stirred at 60° C. for 10 minutes, the volatile components were distilled off under reduced pressure. After a 5% ammonium hydroxide solution was added to the remaining solid, the volatile components were distilled off under reduced pressure and the resulting solid was washed with ethyl acetate and water to obtain the title compound (30.0 mg).

¹H-NMR (300 MHz, DMSO-d₆) δ: 2.08-2.41 (4H, m), 2.68 (3H, s), 2.98 (2H, d, J=11.7 Hz), 3.07 (2H, brs), 8.04 (1H, dd, J=11.9, 1.3 Hz), 8.33 (1H, d, J=1.1 Hz), 8.48 (1H, d, J=0.8 Hz), 8.96-9.09 (1H, m). MS: [M+H]⁺398.3.

Working Example 112

6-(8-Fluoro-2-methylimidazo[1,2-α]pyridin-6-yl)-2-[1-(2-methoxyethyl)piperidin-4-yl]pyrido[3, 4-d]pyrimidin-4(3H)-one (A) tert-Butyl 4-[(4-carbamoyl-6-chloropyridin-3-yl)carbamoyl]piperidine-1-carboxylate

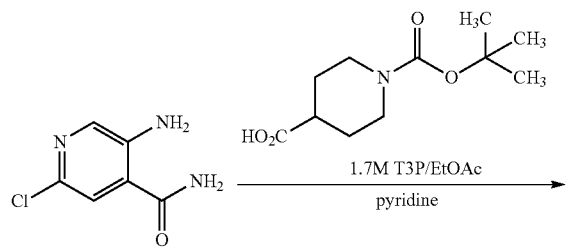

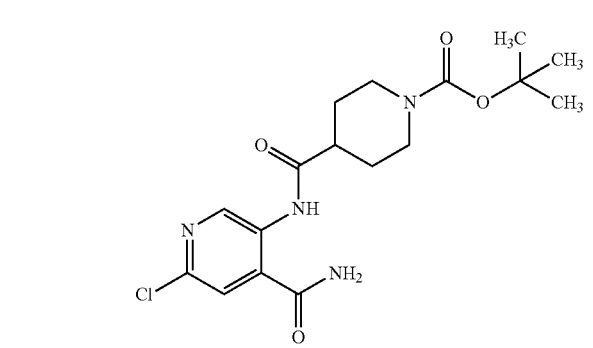

After a mixture of 1-(tert-butoxycarbonyl)piperidine-4-carboxylic acid (3.38 g), 5-amino-2-chloroisonicotinic acid (2.53 g), a 1.7 M propylphosphonic acid anhydride/ethyl acetate solution (13 mL) and pyridine (30 mL) was stirred at room temperature overnight, the volatile components were distilled off under reduced pressure. 0.1 M hydrochloric acid was further added thereto and the mixture was extracted with ethyl acetate. The obtained organic layer was washed with water and saturated brine and then dried over anhydrous magnesium sulfate, and the volatile components were distilled off under reduced pressure. The remaining solid was washed with diisopropyl ether to obtain the title compound (4.94 g).

MS: [M+Na]⁺405.3.

(B) tert-butyl 4-(6-chloro-4-oxo-3,4-dihydropyrido[3,4-d]pyrimidin-2-yl)piperidine-1-carboxylate

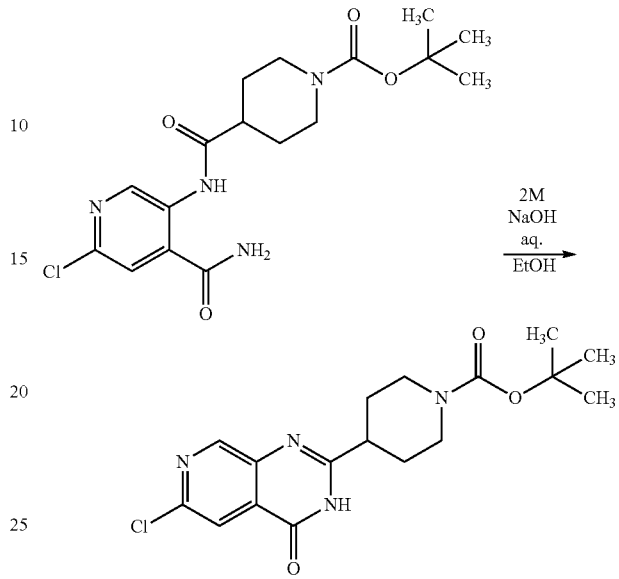

To tert-butyl 4-[(4-carbamoyl-6-chloropyridin-3-yl)carbamoyl]piperidine-1-carboxylate (4.94 g) was added ethanol (40 mL), followed by mixing, and a 2.0 M aqueous sodium hydroxide solution (19.4 mL) was further added thereto at room temperature. Then, the mixture was stirred at the same temperature for 2 hours and neutralized with 2.0 M hydrochloric acid. To the obtained mixture was added water and the precipitate was isolated by filtration and washed with ethanol/water (1/1) to obtain the title compound (4.47 g).

MS: [M+H]⁺365.2.

(C) 6-chloro-2-(piperidin-4-yl)pyrido[3,4-d]pyrimidin-4(3H)-one

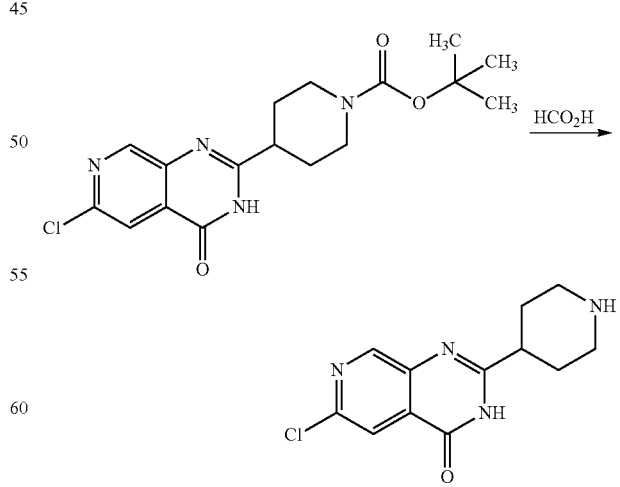

After a mixture of tert-butyl 4-(6-chloro-4-oxo-3,4-dihydropyrido[3,4-d]pyrimidin-2-yl)piperidine-1-carboxylate (3.41 g) and formic acid (15 mL) was stirred at 70° C. for 30 minutes, the volatile components were distilled off under reduced pressure. To the remaining solid was added a 5% ammonium hydroxide solution and the precipitate was filtered off and washed with water to obtain the title compound (2.91 g).

$^1$H-NMR (300 MHz, DMSO-$d_6$) δ: 1.64-1.94 (4H, m), 2.57-2.77 (3H, m), 3.11 (2H, d, J=12.1 Hz), 7.86 (1H, s), 8.75 (1H, d, J=0.8 Hz). MS: [M+H]$^+$265.2.

(D) 6-chloro-2-[1-(2-methoxyethyl)piperidin-4-yl]pyrido[3,4-d]pyrimidin-4(3H)-one

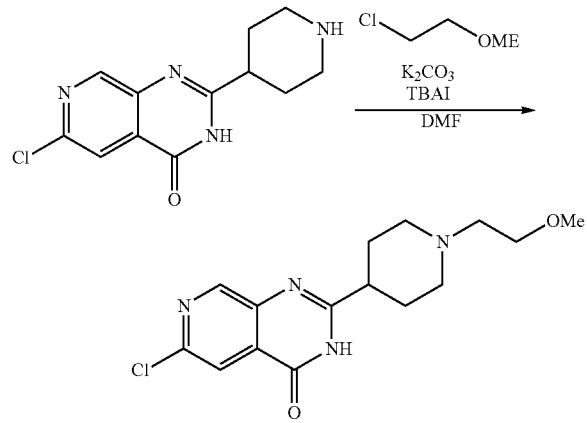

After a mixture of 6-chloro-2-(piperidin-4-yl)pyrido[3,4-d]pyrimidin-4(3H)-one (1.20 g), 1-chloro-2-methoxyethane (0.455 mL), potassium carbonate (1.25 g), tetrabutylammonium iodide (167 mg) and DMF (15 mL) was stirred at 90° C. overnight and saturated brine was further added thereto at room temperature, followed by mixing. The mixture was extracted with THF/1,2-dimethoxyethane. The obtained organic layer was washed with saturated brine and dried over anhydrous magnesium sulfate, and then the volatile components were distilled off under reduced pressure. The remaining solid was washed with diisopropyl ether/ethyl acetate to obtain the title compound (701 mg).

$^1$H-NMR (300 MHz, DMSO-$d_6$) δ: 1.70-1.93 (4H, m), 1.95-2.10 (2H, m), 2.42-2.64 (3H, m), 2.97 (2H, d, J=11.7 Hz), 3.24 (3H, s), 3.44 (2H, t, J=5.9 Hz), 7.93 (1H, d, J=0.8 Hz), 8.84 (1H, d, J=0.8 Hz), 12.56 (1H, brs). MS: [M+H]$^+$ 323.2.

(E) 6-(8-fluoro-2-methylimidazo[1,2-α]pyridin-6-yl)-2-[1-(2-methoxyethyl)piperidin-4-yl]pyrido[3,4-d]pyrimidin-4(3H)-one

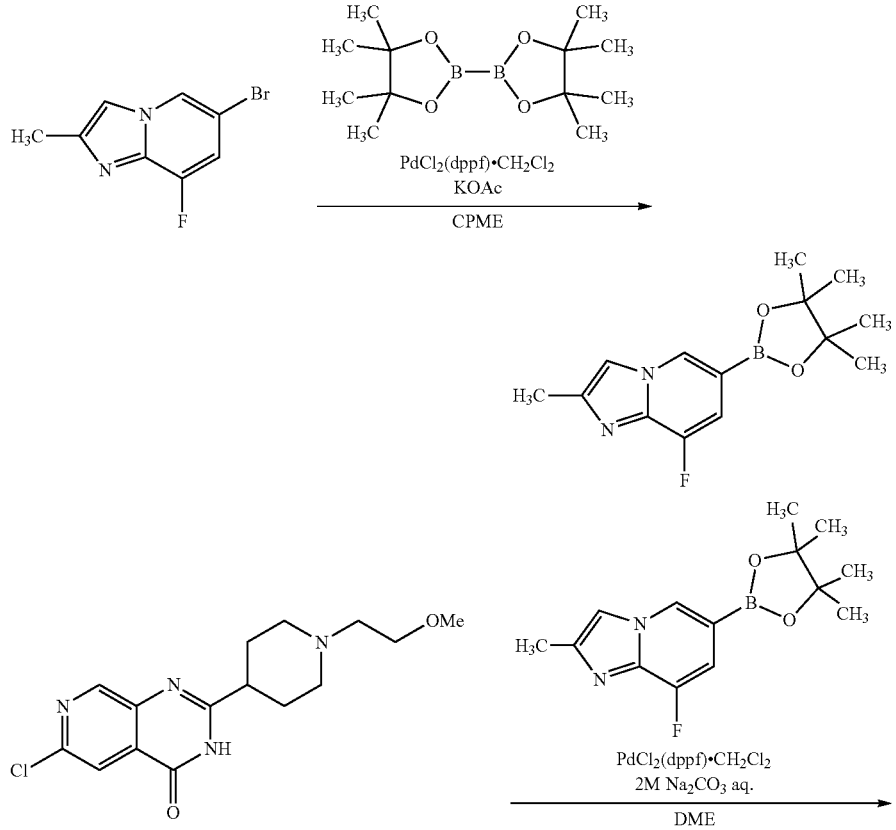

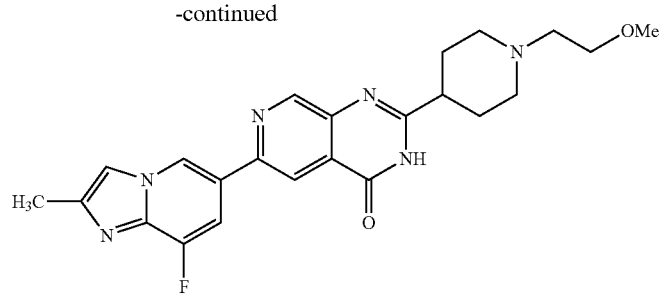

A mixture of 6-brome-8-fluoro-2-methylimidazo[1,2-α]pyridine (120 mg), bis(pinacolato)diboron (160 mg), potassium acetate (103 mg), dichloro[1,1'-bis(diphenylphosphino)ferrocene]palladium(II) dichloromethane adduct (21.4 mg) and cyclopentyl methyl ether (3 mL) was stirred under microwave irradiated conditions at 130° C. for 30 minutes. After the obtained mixture was filtered through Celite, the volatile components were distilled off from the filtrate under reduced pressure. A mixture of the obtained substance, 6-chloro-2-[1-(2-methoxyethyl)piperidin-4-yl]pyrido[3,4-d]pyrimidin-4(3H)-one (155 mg), dichloro[1,1'-bis(diphenylphosphino)ferrocene]palladium(II) dichloromethane adduct (19.6 mg), a 2.0 M aqueous sodium carbonate solution (0.48 mL) and 1,2-dimethoxyethane (3 mL) was stirred under microwave irradiated conditions at 130° C. for 30 minutes. After water was added to the obtained mixture and insoluble components were removed by filtration, the filtrate was extracted with ethyl acetate. After the obtained organic layer was dried over anhydrous magnesium sulfate, the volatile components were distilled off under reduced pressure. After the remaining solid was purified by silica gel column chromatography (NH, methanol/ethyl acetate), the obtained solid was washed with ethyl acetate to obtain the title compound (101 mg).

$^1$H-NMR (300 MHz, DMSO-d$_6$) δ: 1.73-1.95 (4H, m), 2.05 (2H, t, J=10.8 Hz), 2.38 (3H, s), 2.42-2.66 (3H, m), 3.00 (2H, d, J=11.3 Hz), 3.25 (3H, s), 3.45 (2H, t, J=5.9 Hz), 7.83-7.94 (2H, m), 8.44 (1H, d, J=0.8 Hz), 9.04 (1H, d, J=0.8 Hz), 9.30 (1H, d, J=1.5 Hz), 12.50 (1H, brs). MS: [M+H]$^+$ 437.3.

Working Example 113

6-(4-Fluoro-2-methyl-1,3-benzoxazol-6-yl)-2-[1-(2-methoxyethyl)piperidin-4-yl]pyrido[3,4-d]pyrimidin-4(3H)-one

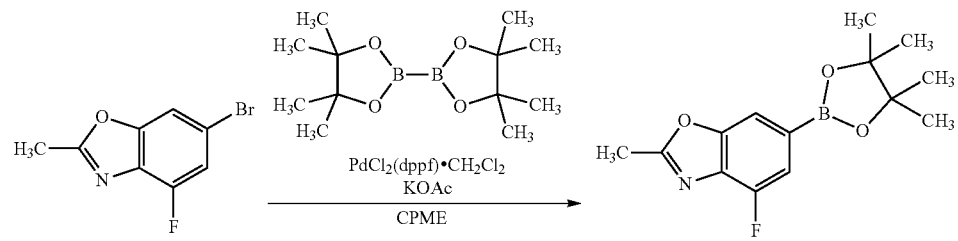

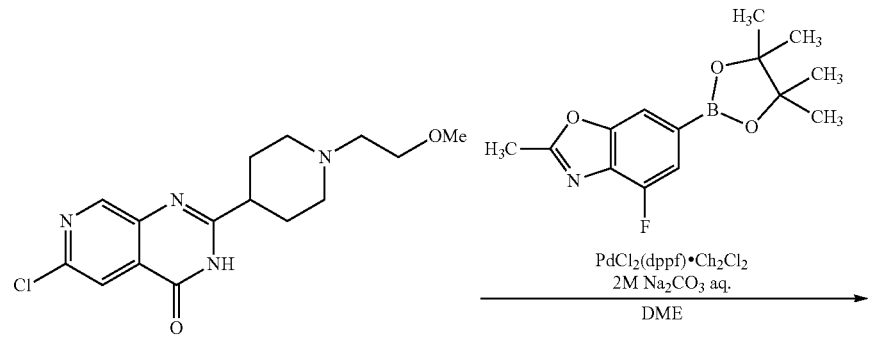

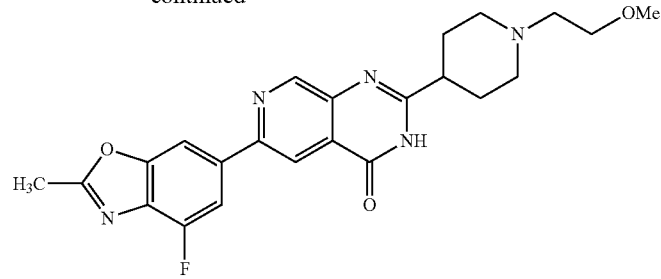

A mixture of 6-brome-4-fluoro-2-methyl-1,3-benzoxazole (202 mg), bis(pinacolato)diboron (268 mg), potassium acetate (173 mg), dichloro[1,1'-bis(diphenylphosphino)ferrocene]palladium(II) dichloromethane adduct (35.9 mg) and cyclopentyl methyl ether (3 mL) was stirred under microwave irradiated conditions at 130° C. for 30 minutes. After the obtained mixture was filtered through Celite, the volatile components were distilled off from the filtrate under reduced pressure. A mixture of the obtained substance, 6-chloro-2-[1-(2-methoxyethyl)piperidin-4-yl]pyrido[3,4-d]pyrimidin-4(3H)-one (200 mg), dichloro[1,1'-bis(diphenylphosphino)ferrocene]palladium(II) dichloromethane adduct (101 mg), a 2.0 M aqueous sodium carbonate solution (0.62 mL) and 1,2-dimethoxyethane (4 mL) was stirred under microwave irradiated conditions at 130° C. for 30 minutes. After water was added to the obtained mixture and insoluble components were removed by filtration, the filtrate was extracted with ethyl acetate/THF. After the obtained organic layer was dried over anhydrous magnesium sulfate, the mixture was purified by silica gel column chromatography (NH, methanol/ethyl acetate) and the obtained solid was washed with ethyl acetate to obtain the title compound (98.9 mg).

$^1$H-NMR (300 MHz, DMSO-$d_6$) δ: 1.73-1.95 (4H, m), 1.97-2.10 (2H, m), 2.57 (3H, d, J=11.7 Hz), 2.68 (3H, s), 2.99 (2H, d, J=11.3 Hz), 3.25 (3H, s), 3.45 (2H, t, J=5.9 Hz), 8.07 (1H, dd, J=11.9, 1.3 Hz), 8.37 (1H, d, J=1.5 Hz), 8.53 (1H, s), 9.06 (1H, s), 12.53 (1H, brs). MS: [M+H]$^+$438.3.

Working Example 114

2-(1-Cyclopropylpiperidin-4-yl)-6-(8-fluoro-2-methylimidazo[1,2-α]pyridin-6-yl)pyrido[3,4-d]pyrimidin-4(3H)-one (A) 6-Chloro-2-(1-cyclopropylpiperidin-4-yl)pyrido[3,4-d]pyrimidin-4(3H)-one

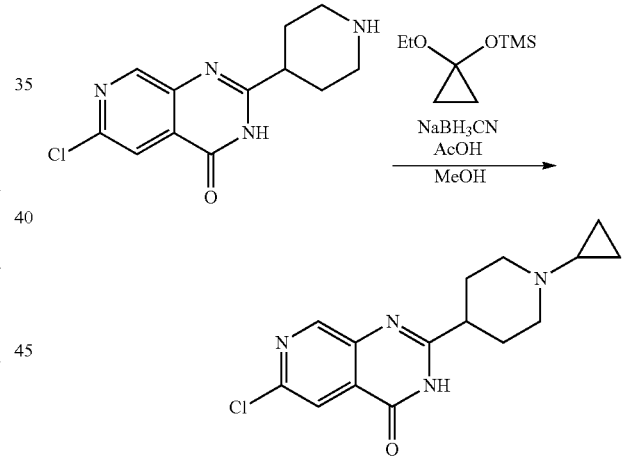

A mixture of 6-chloro-2-(piperidin-4-yl)pyrido[3,4-d]pyrimidin-4(3H)-one (1.0 g), ((1-ethoxycyclopropyl)oxy)(trimethyl)silane (3.8 mL), sodium cyanotrihydridoborate (475 mg), acetic acid (2.27 mL) and methanol (14 mL) was stirred at 60° C. for 15 hours, and a saturated aqueous sodium hydrogen carbonate solution was further added thereto at room temperature and they were mixed. Then, the organic layer was separated. The obtained organic layer was washed with water and saturated brine and then dried over anhydrous magnesium sulfate, and the volatile components were distilled off under reduced pressure. The remaining solid was washed with diisopropyl ether to obtain the title compound (910 mg).

MS: [M+H]$^+$305.2.

(B) 2-(1-cyclopropylpiperidin-4-yl)-6-(8-fluoro-2-methylimidazo[1,2-α]pyridin-6-yl)pyrido[3,4-d]pyrimidin-4(3H)-one

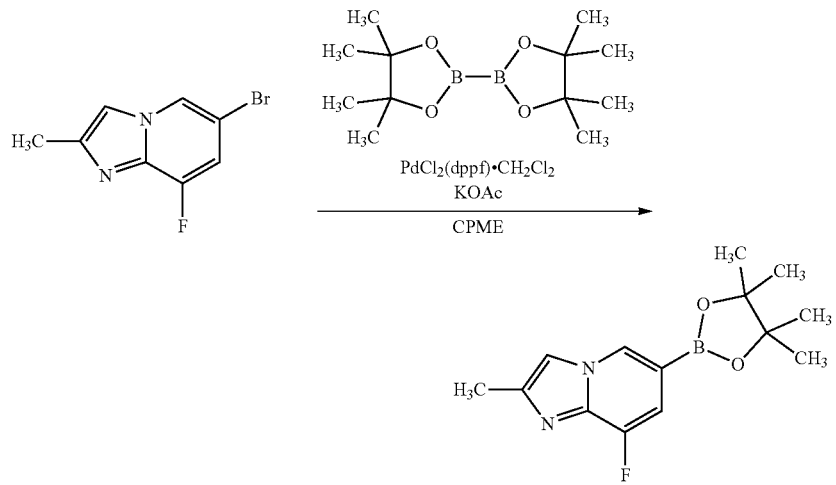

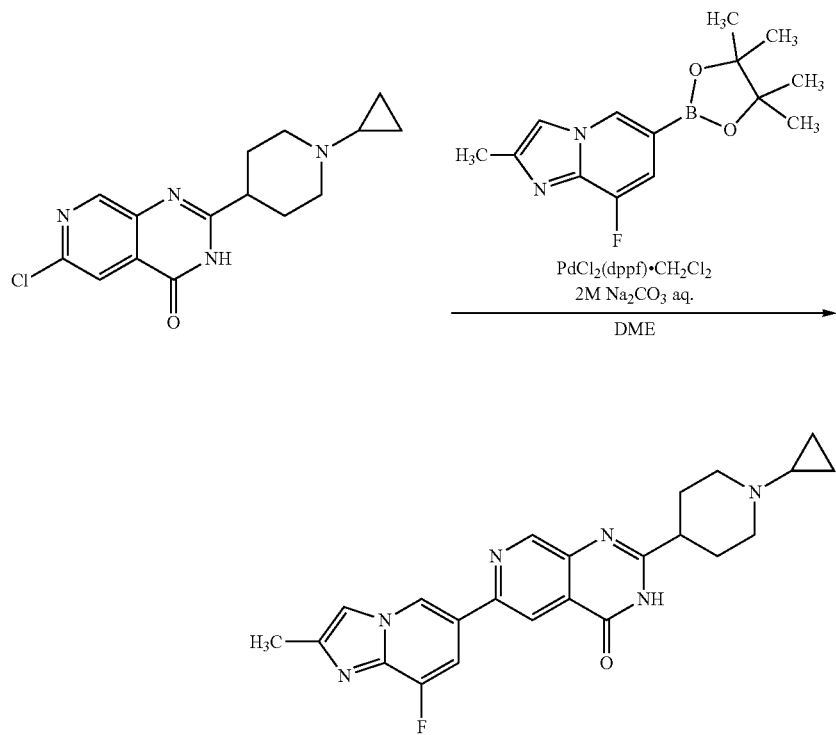

A mixture of 6-brome-8-fluoro-2-methylimidazo[1,2-α]pyridine (293 mg), bis(pinacolato)diboron (390 mg), potassium acetate (251 mg), dichloro[1,1'-bis(diphenylphosphino)ferrocene]palladium(II) dichloromethane adduct (52.3 mg) and cyclopentyl methyl ether (3 mL) was stirred under microwave irradiated conditions at 130° C. for 60 minutes. After the obtained mixture was filtered through Celite, the volatile components were distilled off from the filtrate under reduced pressure. A mixture of obtained substance, 6-chloro-2-(1-cyclopropylpiperidin-4-yl)pyrido[3,4-d]pyrimidin-4(3H)-one (300 mg), dichloro[1,1'-bis(diphenylphosphino)ferrocene]palladium(II) dichloromethane adduct (40.2 mg), a 2.0 M aqueous sodium carbonate solution (1.48 mL) and 1,2-dimethoxyethane (15 mL) was stirred under microwave irradiated conditions at 130° C. for 50 minutes and the precipitate was filtered off. The filtrate was purified by silica gel column chromatography (methanol/ethyl acetate) and washed with ethyl acetate to obtain the title compound (62 mg).

MS: [M+H]$^+$419.3.

Working Example 115

2-(1-Cyclopropylpiperidin-4-yl)-6-(4-fluoro-2-methyl-1,3-benzoxazol-6-yl)pyrido[3,4-d]pyrimidin-4(3H)-one

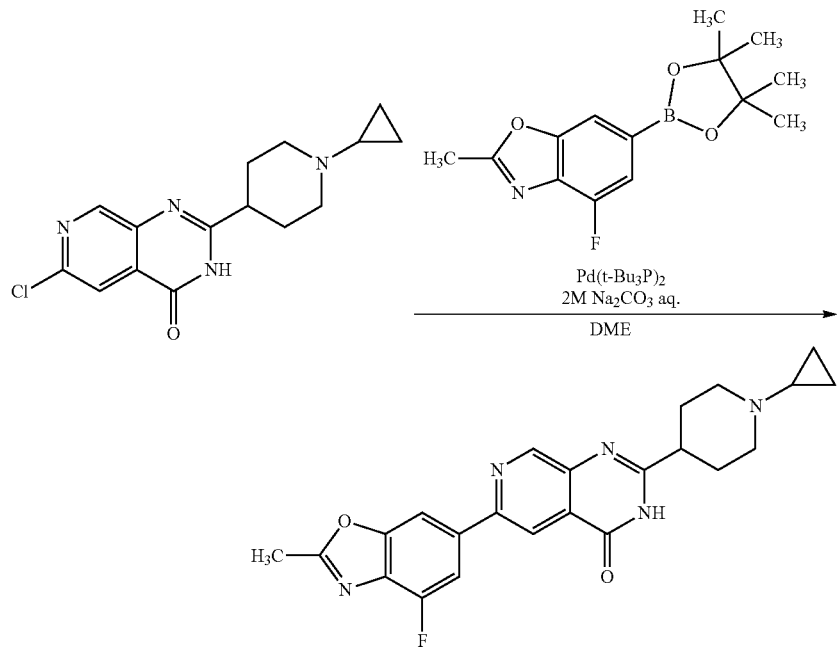

A mixture of 4-fluoro-2-methyl-6-(4,4,5,5-tetramethyl-1,3,2-dioxaborolane-2-yl)-1,3-benzoxazole (409 mg), 6-chloro-2-(1-cyclopropylpiperidin-4-yl)pyrido[3,4-d]pyrimidin-4(3H)-one (300 mg), bis(tri-tert-butylphosphine) palladium (0) (50.3 mg), 2.0M aqueous sodium carbonate solution (1.48 mL) and 1,2-dimethoxyethane (15 mL) was stirred under microwave irradiated conditions at 130° C. for 50 minutes and the precipitate was filtered off. The filtrate was purified by silica gel column chromatography (hexane/ethyl acetate) to obtain the title compound (27 mg).
$^1$H-NMR (300 MHz, DMSO-d$_6$) δ: 0.27-0.50 (4H, m), 1.59-1.70 (1H, m), 1.71-1.84 (2H, m), 1.85-1.95 (2H, m), 2.14-2.30 (2H, m), 2.57-2.65 (1H, m), 2.68 (3H, s), 3.04 (2H, d, J=11.3 Hz), 8.06 (1H, dd, J=11.9, 1.3 Hz), 8.36 (1H, d, J=1.5 Hz), 8.52 (1H, s), 8.97-9.14 (1H, m), 12.51 (1H, brs). MS: [M+H]$^+$420.3.

Working Example 116

6-(4-Cyclopropylpiperazin-1-yl)-2-(6-methylpyrazolo[1,5-α]pyrazin-2-yl)quinazolin-4(3H)-one (A) Ethyl 6-methylpyrazolo[1,5-α]pyrazine-2-carboxylate

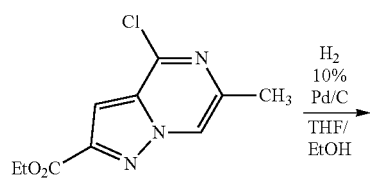

-continued

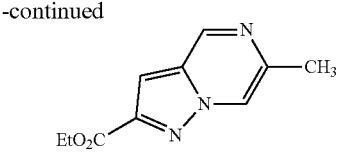

After a mixture of ethyl 4-chloro-6-methylpyrazolo[1,5-α]pyrazine-2-carboxylate (1 g), palladium-activated carbon (10% palladium) (261 mg), triethylamine (1.16 mL), ethanol (150 mL) and THF (50 mL) was stirred under normal pressure and hydrogen atmosphere at room temperature for 13 minutes, the catalyst was removed by filtration and the volatile components were distilled off from the filtrate under reduced pressure. The obtained substance was purified by silica gel column chromatography (hexane/ethyl acetate) to obtain the title compound (553 mg).
$^1$H-NMR (300 MHz, DMSO-d$_6$) δ: 1.34 (3H, t, J=7.2 Hz), 2.48 (3H, d, J=1.1 Hz), 4.37 (2H, q, J=7.2 Hz), 7.40 (1H, d, J=1.1 Hz), 8.72 (1H, d, J=1.1 Hz), 9.21 (1H, d, J=1.5 Hz). MS: [M+H]$^+$206.1.

(B) 6-methylpyrazolo[1,5-α]pyrazin-2-carboxylic acid

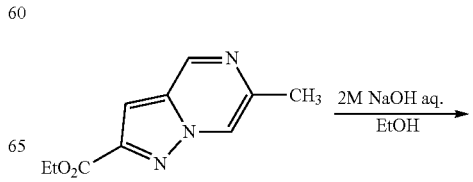

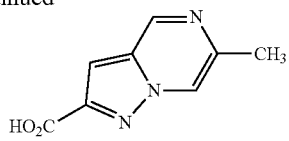

To a mixture of ethyl 6-methylpyrazolo[1,5-α]pyrazine-2-carboxylate (545 mg) and ethanol (6 mL) was added a 2.0 M aqueous sodium hydroxide solution (6.64 mL) and the mixture was stirred at room temperature for 10 minutes. Then, the volatile components were distilled off under reduced pressure and a 2.0 M hydrochloric acid was added thereto at room temperature to adjust pH to about 3. The resulting precipitate was filtered off and the obtained solid was washed with water, ethanol and ethyl acetate to obtain the title compound (439 mg).

$^1$H-NMR (300 MHz, DMSO-d$_6$) δ: 2.48 (3H, d, J=0.8 Hz), 7.34 (1H, d, J=0.8 Hz), 8.67-8.70 (1H, m), 9.19 (1H, d, J=1.5 Hz), 13.28 (1H, s). MS: [M+H]$^+$178.1.

(C) N-[2-carbamoyl-4-(4-cyclopropylpiperazin-1-yl)phenyl]-6-methylpyrazolo[1,5-α]pyrazin-2-carb oxamide

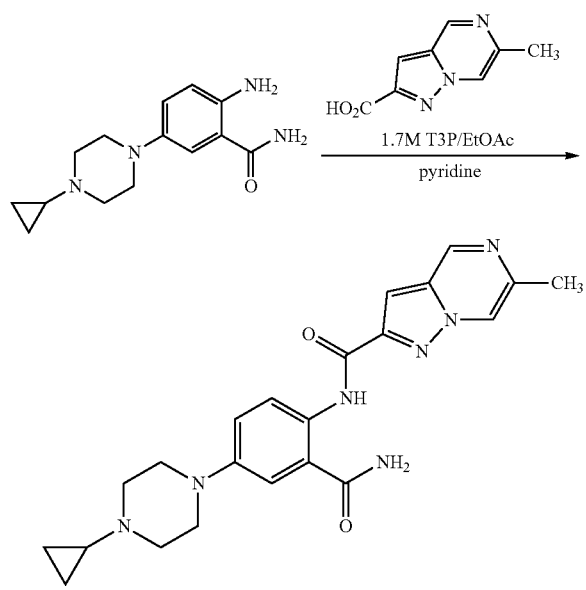

A mixture of 6-methylpyrazolo[1,5-α]pyrazine-2-carboxylic acid (300 mg), a 1.7 M propylphosphonic acid anhydride/ethyl acetate solution (1.49 mL) and pyridine (5 mL) was stirred at room temperature for 1 hour and 2-amino-5-(4-cyclopropylpiperizin-1-yl)benzamide (529 mg) was further added thereto. Then, the mixture was stirred at room temperature for 90 minutes. After the volatile components were distilled off under reduced pressure, water (2 mL) and a 15% aqueous potassium carbonate solution (1 mL) were added to the remaining solid and the mixture was stirred at room temperature for 10 minutes. Then, the solid obtained by filtering the precipitate was washed with water, methanol and ethyl acetate. The obtained solid was stirred in THF/methanol and the precipitate was filtered off. Then, the obtained solid was washed with methanol and ethyl acetate to obtain the title compound (636 mg).

$^1$H-NMR (300 MHz, DMSO-d$_6$) δ: 0.32-0.49 (4H, m), 1.62-1.72 (1H, m), 2.49 (3H, s), 2.62-2.77 (4H, m), 3.10-3.20 (4H, m), 7.15 (1H, dd, J=9.1, 2.6 Hz), 7.31 (1H, d, J=2.6 Hz), 7.36 (1H, d, J=0.8 Hz), 7.62 (1H, brs), 8.28 (1H, brs), 8.54 (1H, d, J=9.1 Hz), 8.70-8.74 (1H, m), 9.21 (1H, d, J=1.5 Hz), 12.50 (1H, s). MS: [M+H]$^+$420.2.

(D) 6-(4-cyclopropylpiperazin-1-yl)-2-(6-methylpyrazolo[1,5-c]pyrazin-2-yl)quinazolin-4(3H)-one

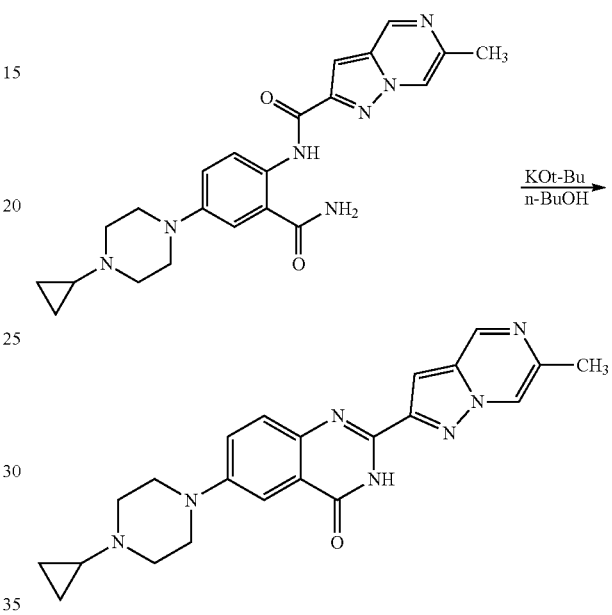

A mixture of N-[2-carbamoyl-4-(4-cyclopropylpiperazin-1-yl)phenyl]-6-methylpyrazolo[1,5-α]pyrazin-2-carb oxamide (610 mg), potassium tert-butoxide (catalytic amount) and 1-butanol (20 mL) was stirred at 120° C. for 10 hours and cooled to room temperature. The resulting precipitate was filtered off and the obtained solid was washed with water, ethanol and ethyl acetate to obtain the title compound (405 mg).

$^1$H-NMR (300 MHz, CDCl$_3$) δ: 0.45-0.53 (4H, m), 1.64-1.74 (1H, m), 2.59 (3H, d, J=0.8 Hz), 2.77-2.84 (4H, m), 3.29-3.39 (4H, m), 7.41-7.49 (2H, m), 7.67 (1H, d, J=2.6 Hz), 7.72 (1H, d, J=9.1 Hz), 8.17-8.21 (1H, m), 9.07 (1H, d, J=1.1 Hz), 10.02 (1H, brs). MS: [M+H]$^+$402.2.

Working Example 117

6-(4-cyclopropylpiperazin-1-yl)-2-(5,7-dimethylimidazo[1,2-α]pyrimidin-2-yl)quinazolin-4(3H)-one (A) Ethyl 5,7-dimethylimidazo[1,2-α]pyrimidine-2-carboxylate

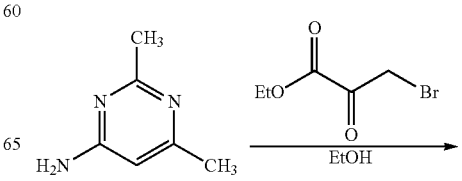

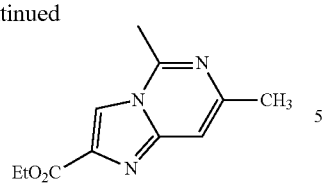

To a mixture of 2,6-dimethyl-4-aminopyrimidine (5.0 g) and ethanol (20 mL) was added ethyl 3-bromo-2-oxopropionate (9.9 g) at room temperature and the mixture was heated under reflux for 1 hour. The obtained mixture was concentrated by distilling off the volatile components under reduced pressure and the precipitate was filtered off. Then, the volatile components were distilled off from the filtrate under reduced pressure. To the obtained substance was added a saturated aqueous sodium hydrogen carbonate solution and the mixture was extracted with ethyl acetate. The organic layer was washed with water and saturated brine and then dried over anhydrous sodium sulfate, and the volatile components were distilled off under reduced pressure. The remaining substance was purified by silica gel column chromatography (ethyl acetate/hexane) and recrystallized from ethanol/diisopropyl ether to obtain the title compound (837 mg).

$^1$H-NMR (300 MHz, DMSO-$d_6$) δ: 1.33 (3H, t, J=7.2 Hz), 2.42 (3H, d, J=0.8 Hz), 2.80 (3H, s), 4.33 (2H, q, J=7.2 Hz), 7.30-7.33 (1H, m), 8.50 (1H, d, J=1.1 Hz). MS: [M+H]$^+$ 220.1.

(B) 5,7-dimethylimidazo[1,2-α]pyrimidine-2-carboxylic acid

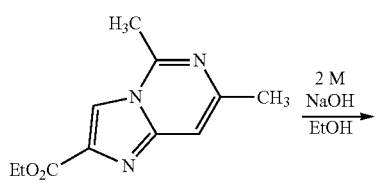

To a mixture of ethyl 5,7-dimethylimidazo[1,2-α]pyrimidine-2-carboxylate (930 mg) and ethanol (10 mL) was added a 2.0 M aqueous sodium hydroxide solution (848 mg) and then the mixture was stirred at room temperature for 1 hour and at 50° C. for 1 hour. The volatile components were distilled off under reduced pressure and 6.0 M hydrochloric acid was added thereto at room temperature to adjust pH to 3-4. The mixture was purified by HP-20 resin column (water and acetone) and recrystallized from water/acetone to obtain the title compound (742 mg).

$^1$H-NMR (300 MHz, DMSO-$d_6$) δ: 2.41 (3H, s), 2.77 (3H, s), 7.25 (1H, s), 8.23 (1H, s). MS: [M+H]$^+$192.1.

(C) N-[2-carbamoyl-4-(4-cyclopropylpiperazin-1-yl)phenyl]-(5,7-dimethylimidazo[1,2-α]pyrimidine-2-carboxamide

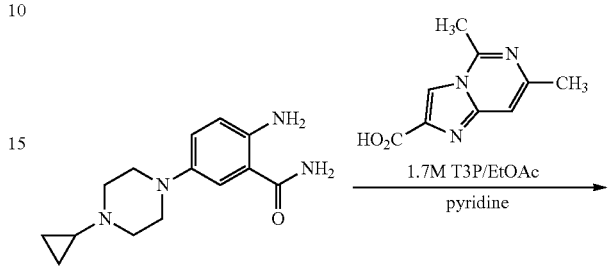

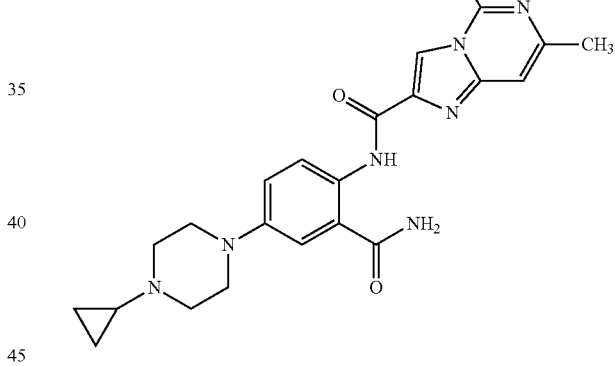

A mixture of 5,7-dimethylimidazo[1,2-α]pyrimidine-2-carboxylic acid (250 mg), a 1.7 M propylphosphonic acid anhydride/ethyl acetate solution (1.25 mL) and pyridine (5 mL) was stirred at room temperature for 30 minutes and 2-amino-5-(4-cyclopropylpiperidin-1-yl)benzamide (441 mg) was further added thereto. Then, the mixture was stirred at room temperature for 3 hours. After the volatile components were distilled off under reduced pressure, water (2 mL) and a 15% aqueous potassium carbonate solution (1 mL) were added to the remaining solid and the mixture was stirred at room temperature for 30 minutes. The precipitate was filtered off and the obtained solid was washed with water, methanol and diisopropyl ether to obtain the title compound (262 mg).

$^1$H-NMR (300 MHz, DMSO-$d_6$) δ: 0.32-0.49 (4H, m), 1.47-1.71 (1H, m), 2.44 (3H, s), 2.63-2.74 (4H, m), 2.82 (3H,$), 3.06-3.22 (4H, m), 7.14 (1H, dd, J=9.1, 2.6 Hz), 7.28 (1H, d, J=2.6 Hz), 7.37 (1H, s), 7.59 (1H, brs), 8.22 (1H, brs), 8.42 (1H, d, J=0.8 Hz), 8.55 (1H, d, J=9.4 Hz), 12.32 (1H, s). MS: [M+H]$^+$434.3.

(D) 6-(4-cyclopropylpiperazin-1-yl)-2-(5,7-dimethylimidazo[1,2-α]pyrimidin-2-yl)quinazolin-4(3H)-one

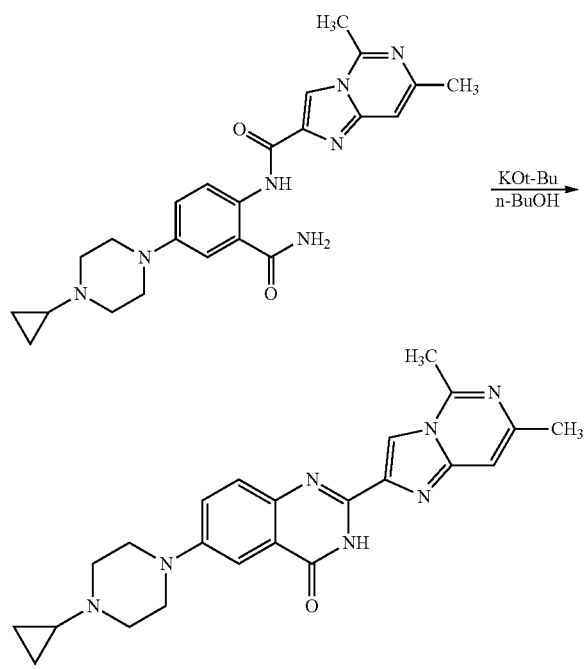

A mixture of N-[2-carbamoyl-4-(4-cyclopropylpiperazin-1-yl)phenyl]-(5,7-dimethylimidazo[1,2-α]pyrimidine-2-carboxamide (260 mg), potassium tert-butoxide (catalytic amount) and 1-butanol (10 mL) was stirred at 120° C. for 10 hours and cooled to room temperature. After the resulting precipitate was filtered off and washed with ethanol, the obtained solid was recrystallized from THF/methanol/water to obtain the title compound (148 mg).

$^1$H-NMR (300 MHz, CDCl$_3$) δ: 0.44-0.54 (4H, m), 1.65-1.73 (1H, m), 2.54 (3H, s), 2.76-2.85 (4H, m), 2.86 (3H, s), 3.29-3.37 (4H, m), 7.21 (1H, s), 7.43 (1H, dd, J=9.1, 3.0 Hz), 7.63-7.69 (2H, m), 8.23 (1H, d, J=0.8 Hz), 10.31 (1H, brs). MS: [M+H]$^+$416.3.

Working Example 118

6-(4-Cyclopropylpiperazin-1-yl)-2-(2-methylimidazo[1,2-b]pyridazin-6-yl)quinazolin-4(3H)-one (A) 6-Chloro-2-methylimidazo[1,2-b]pyridazine

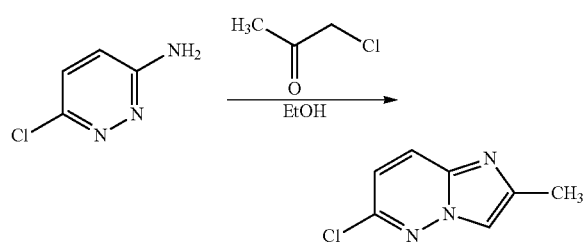

A mixture of 3-amino-6-chloropyridazine (5.5 g), 1-chloroacetone (3.93 g) and ethanol (20 mL) was heated under reflux for 3 hours. 1-Chloroacetone (1.85 mL) was added thereto and the mixture was heated under reflux for 1 hour. After 1-chloroacetone (1.85 g) was added thereto again and the mixture was heated under reflux for 2 hours, the volatile components were distilled off under reduced pressure. The resulting precipitate was filtered off and washed with ethanol and then water and a saturated aqueous sodium hydrogen carbonate solution were added to the obtained solid. Then, the mixture was extracted with ethyl acetate/THF. The obtained organic layer was washed with water and saturated brine and then dried over anhydrous sodium sulfate, and the volatile components were distilled off under reduced pressure. The obtained solid was recrystallized from methanol/diisopropyl ether to obtain the title compound (691 mg).

$^1$H-NMR (300 MHz, DMSO-d$_6$) δ: 2.40 (3H, s), 7.28 (1H, d, J=9.4 Hz), 8.08 (1H, d, J=9.4 Hz), 8.11 (1H, s). MS: [M+H]$^+$168.1.

(B) Ethyl 2-methylimidazo[1,2-b]pyridazine-2-carboxylate

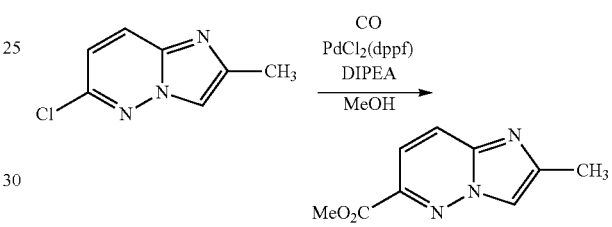

After a mixture of 6-chloro-2-methylimidazo[1,2-b]pyridazine (1.38 g), dichloro[1,1'-bis(diphenylphosphino)ferrocene]palladium(II) dichloromethane (602 mg), diisopropylethylamine (3.19 g) and methanol (10 mL) was stirred under carbon monoxide atmosphere (0.5 MPa) at 120° C. for 8 hours, the volatile components were distilled off under reduced pressure. The remaining substance was purified by silica gel column chromatography (ethyl acetate/methanol) to obtain the title compound (318 mg).

$^1$H-NMR (300 MHz, DMSO-d$_6$) δ: 2.44 (3H, d, J=0.8 Hz), 3.94 (3H, s), 7.67 (1H, d, J=9.4 Hz), 8.13 (1H, d, J=9.4 Hz), 8.25 (1H, s). MS: [M+H]$^+$192.1.

(C) 2-Methylimidazo[1,2-b]pyridazine-2-carboxylic acid

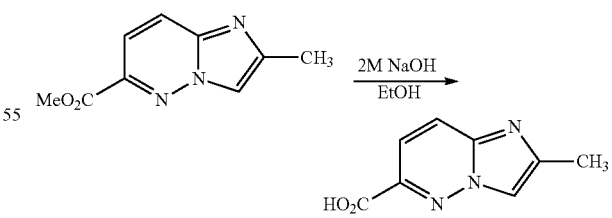

To a mixture of ethyl 2-methylimidazo[1,2-b]pyridazine-2-carboxylate (310 mg) and ethanol (4 mL) was added a 2.0 M aqueous sodium hydroxide solution (4.05 mL) and the mixture was stirred at room temperature for 10 minutes. The volatile components were distilled off under reduced pressure and 2.0 M hydrochloric acid was added thereto at room temperature to adjust pH to about 3. The resulting precipitate was filtered off and then washed with water, ethanol and ethyl acetate to obtain the title compound (144 mg).
$^1$H-NMR (300 MHz, DMSO-d$_6$) δ: 2.44 (3H, brs), 7.65 (1H, d, J=9.1 Hz), 8.10 (1H, d, J=8.3 Hz), 8.21 (1H, brs), 13.84 (1H, brs). MS: [M+H]$^+$178.1.

(D) N-[2-Carbamoyl-4-(4-cyclopropylpiperazin-1-yl)phenyl]-2-methylimidazo[1,2-b]pyridazine-2-carboxamide

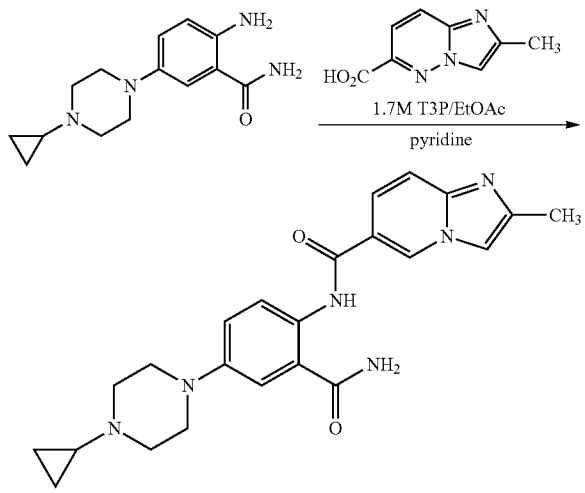

A mixture of 2-methylimidazo[1,2-b]pyridazine-2-carboxylic acid (140 mg), a 1.7 M propylphosphonic acid anhydride/ethyl acetate solution (0.65 mL) and pyridine (3 mL) was stirred at room temperature for 1 hour and 2-amino-5-(4-cyclopropylpiperidin-1-yl)benzamide (229 mg) was further added thereto. Then, the mixture was stirred at room temperature for 3 hours. After the volatile components were distilled off under reduced pressure, water (2 mL) and a 15% aqueous potassium carbonate solution (1 mL) were added to the remaining solid and the mixture was stirred at room temperature for 30 minutes. The solid obtained by filtering the precipitate was washed with water, methanol and diisopropyl ether to obtain the title compound (275 mg).
$^1$H-NMR (300 MHz, DMSO-d$_6$) δ: 0.18-0.75 (4H, m), 1.67 (1H, brs), 2.46 (3H, brs), 2.69 (4H, brs), 3.16 (4H, brs), 7.17 (1H, d, J=7.6 Hz), 7.34 (1H, brs), 7.53-7.87 (2H, m), 8.02-8.25 (2H, m), 8.32 (1H, brs), 8.54 (1H, d, J=9.1 Hz), 12.89 (1H, brs). MS: [M+H]$^+$420.2.

(E) 6-(4-Cyclopropylpiperazin-1-yl)-2-(2-methylimidazo[1,2-b]pyridazin-6-yl)quinazolin-4(3H)-one

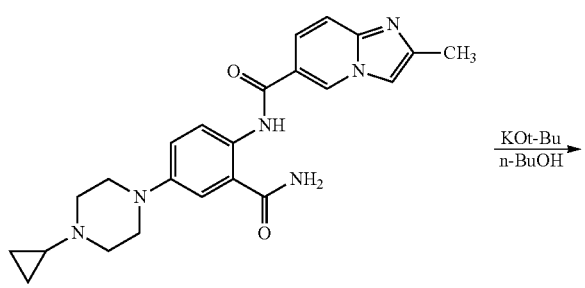

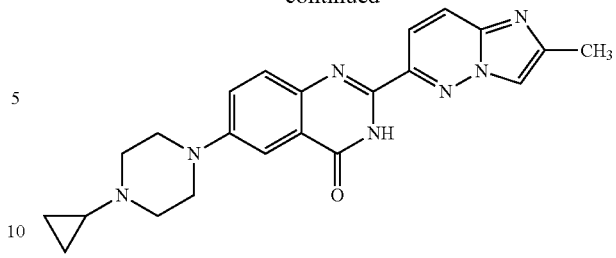

A mixture of N-[2-carbamoyl-4-(4-cyclopropylpiperazin-1-yl)phenyl]-2-methylimidazo[1,2-b]pyridazine-2-carboxamide (260 mg) and 1-butanol (10 mL) was stirred at 120° C. for 2 hours and potassium tert-butoxide (catalytic amount) was added thereto. Then, the mixture was stirred at 120° C. for 3 hours and cooled to room temperature. The resulting precipitate was filtered off and washed with ethanol to obtain the title compound (158 mg).
$^1$H-NMR (300 MHz, CDCl$_3$) δ: 0.45-0.54 (4H, m), 1.63-1.75 (1H, m), 2.56 (3H, s), 2.76-2.85 (4H, m), 3.32-3.41 (4H, m), 7.44 (1H, dd, J=9.1, 3.0 Hz), 7.68 (1H, d, J=3.0 Hz), 7.74 (1H, d, J=9.1 Hz), 7.79 (1H, s), 7.96 (1H, d, J=9.4 Hz), 8.18 (1H, d, J=9.4 Hz), 10.29 (1H, brs). MS: [M+H]$^+$ 402.2.

Working Example 119

2-(4,6-dimethylpyrazolo[1,5-α]pyrazin-2-yl)-6-(4-isopropylpiperazin-1-yl)quinazolin-4(3H)-one 2trifluoroacetate (A) 2-(4,6-dimethylpyrazolo[1,5-α]pyrazin-2-yl)-6-iodoquinazolin-4(3H)-one

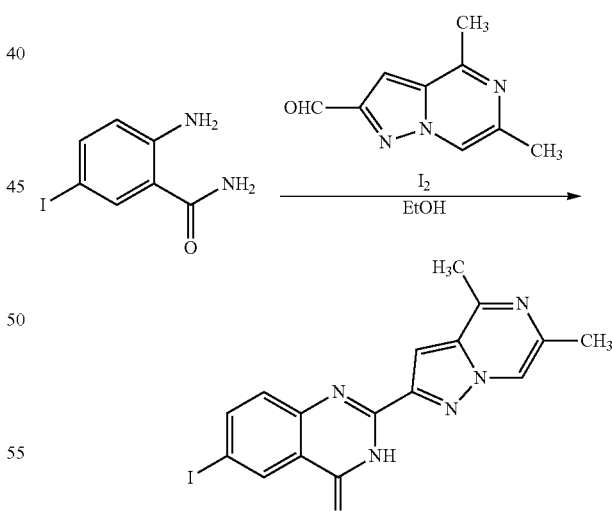

To a mixture of 2-amino-5-iodobenzamide (2.00 g), 4,6-dimethylpyrazolo[1,5-α]pyrazine-2-carbaldehyde (1.34 g) and ethanol (65 mL) was added iodine (2.91 g) at room temperature and the mixture was heated under refluxed for 3 days. After the mixture was cooled to room temperature, the resulting precipitate was filtered off and washed with ethanol. The obtained solid was washed with ethanol/water (2:1) and ethanol to obtain the title compound (2.86 g).

¹H-NMR (300 MHz, DMSO-d₆) δ: 8.55 (1H, s), 8.44 (1H, d, J=1.9 Hz), 8.16 (1H, dd, J=8.5, 2.1 Hz), 7.75 (1H, s), 7.57 (1H, d, J=8.7 Hz), 2.76 (3H, s), 2.48 (3H, s).

(B) 2-(4,6-dimethylpyrazolo[1,5-α]pyrazin-2-yl)-6-(4-isopropylpiperazin-1-yl)quinazolin-4(3H)-one bistrifluoroacetate

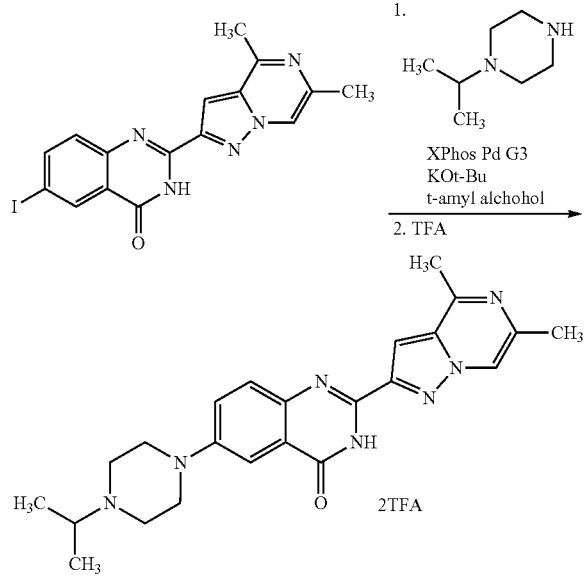

A mixture of 2-(4,6-dimethylpyrazolo[1,5-α]pyrazin-2-yl)-6-iodoquinazolin-4(3H)-one (125 mg), potassium tert-butoxide (135 mg), (2-dicyclohexylphosphino-2',4',6'-triisopropyl-1,1'-biphenyl)[2-(2'-amino-1, 1'-biphenyl)]palladium(II) methanesulfonate (25.5 mg), tert-amyl alcohol (1 mL) and 1-isopropylpiperazine (115 mg) was stirred under microwave irradiated conditions at 180° C. for 1 hour. After dimethyl sulfoxide (1 mL) and methanol (3 mL) were added thereto and the mixture was filtered through Celite, the volatile components were distilled off by heating the filtrate to 60° C. The obtained substance was purified by HPLC [YMC-Triart C18, acetonitrile containing 0.1% trifluoroacetic acid/water containing 0.1% trifluoroacetic acid] to obtain the title compound (32.6 mg).

MS: [M-2TFA+H]⁺418.2.

Working Example 120

6-[4-(cyclopropylmethyl)piperazin-1-yl]-2-(4,6-dimethylpyrazolo[1,5-α]pyrazin-2-yl)quinazolin-4(3H)-one trifluoroacetate

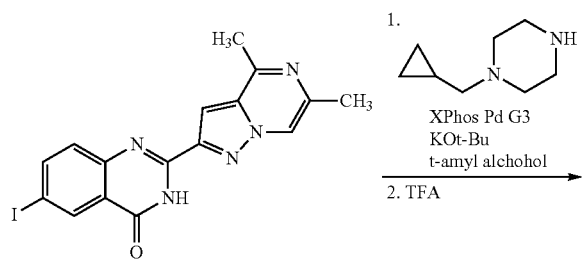

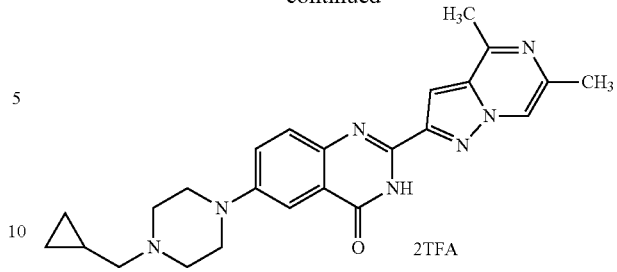

A mixture of 2-(4,6-dimethylpyrazolo[1,5-α]pyrazin-2-yl)-6-iodoquinazolin-4(3H)-one (83.4 mg), potassium tert-butoxide (89.8 mg), (2-dicyclohexylphosphino-2',4',6'-triisopropyl-1,1'-biphenyl)[2-(2'-amino-1,1'-biphenyl)]palladium(II) methanesulfonate (17 mg), tert-amyl alcohol (1 mL) and 1-cyclopropylmethyl)piperazine (84 mg) was stirred under microwave irradiated conditions at 180° C. for 1 hour. After dimethyl sulfoxide (1 mL) and methanol (3 mL) were added thereto and the mixture was filtered through Celite, the volatile components were distilled off by heating the filtrate to 60° C. The obtained substance was purified by HPLC [YMC-Triart C18, acetonitrile containing 0.1% trifluoroacetic acid/water containing 0.1% trifluoroacetic acid] to obtain the title compound (33.3 mg).

MS: [M-2TFA+H]⁺430.2.

Working Example 121

(S)-2-(4,6-Dimethylpyrazolo[1,5-α]pyrazin-2-yl)-6-(hexahydropyrrolo[1,2-α]pyrazin-2(1H)-yl)quinazolin-4(3H)-one trifluoroacetate

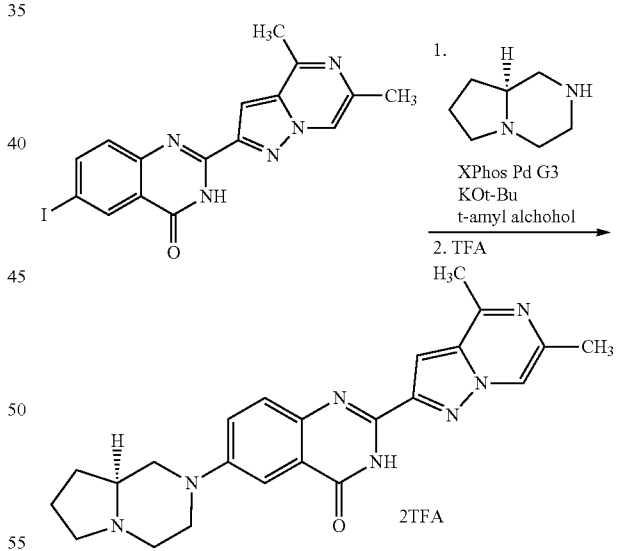

A mixture of 2-(4,6-dimethylpyrazolo[1,5-α]pyrazin-2-yl)-6-iodoquinazolin-4(3H)-one (83.4 mg), potassium tert-butoxide (89.8 mg), (2-dicyclohexylphosphino-2',4',6'-triisopropyl-1,1'-biphenyl)[2-(2'-amino-1, 1'-biphenyl)]palladium(II) methanesulfonate (17 mg), tert-amyl alcohol (1 mL) and (S)-octahydropyrrolo[1,2-α]pyrazine (76 mg) was stirred under microwave irradiated conditions at 180° C. for 1 hour. After dimethyl sulfoxide (1 mL) and methanol (3 mL) were added thereto and the mixture was filtered through Celite, the volatile components were distilled off by heating the filtrate to 60° C. The obtained substance was purified by HPLC [YMC-Triart C18, acetonitrile containing 0.1% trifluoroacetic acid/water containing 0.1% trifluoroacetic acid] to obtain the title compound (14.2 mg).

MS: [M-2TFA+H]$^+$416.2.

Working Example 122

6-(3,3-dimethylpiperazin-1-yl)-2-(4, 6-dimethylpyrazolo[1,5-a]pyrazin-2-yl)quinazolin-4(3H)-on e bistrifluoroacetate

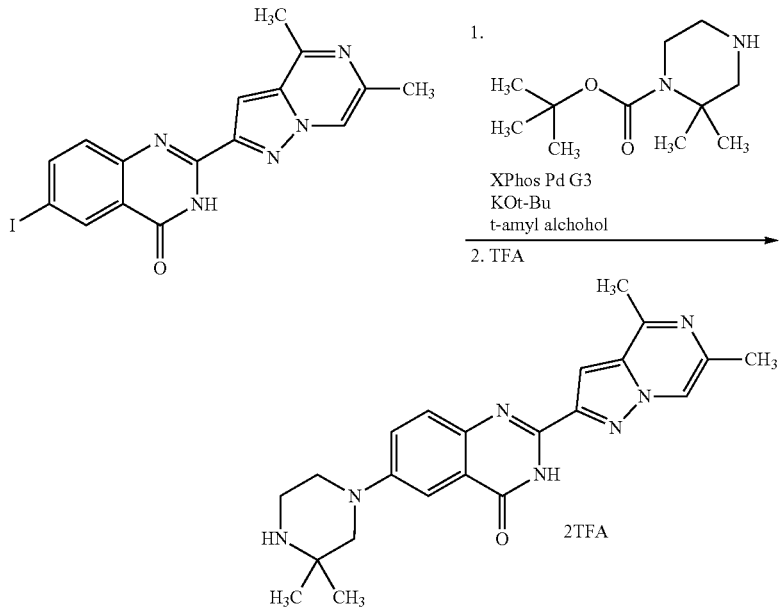

A mixture of 2-(4,6-dimethylpyrazolo[1,5-α]pyrazin-2-yl)-6-iodoquinazolin-4(3H)-one (125 mg), potassium tert-butoxide (134.7 mg), (2-dicyclohexylphosphino-2',4',6'-triisopropyl-1,1'-biphenyl)[2-(2'-amino-1, 1'-biphenyl)]palladiu m(II) methanesulfonate (25.5 mg), tert-amyl alcohol (1 mL) and tert-butyl 2,2-dimethylpiperazine-1-carboxylate (193 mg) was stirred under microwave irradiated conditions at 180° C. for 1 hour. After dimethyl sulfoxide (1 mL) and methanol (3 mL) were added thereto and the mixture was filtered through Celite, the volatile components were distilled off by heating the filtrate to 60° C. The obtained substance was purified by HPLC [YMC-Triart C18, acetonitrile containing 0.1% trifluoroacetic acid/water containing 0.1% trifluoroacetic acid]. After trifluoroacetic acid (0.3 mL) was added to the obtained solid and the mixture was stirred at room temperature for 1 hour, the volatile components were distilled off to obtain the title compound (33.5 mg).
MS: [M-2TFA+H]$^+$404.2.

Working Example 123

2-(4,6-Dimethylpyrazolo[1,5-α]pyrazin-2-yl)-6-(4,7-di azaspiro[2.5]octan-7-yl)quinazolin-4(3H)-one bistrifluoroacetate

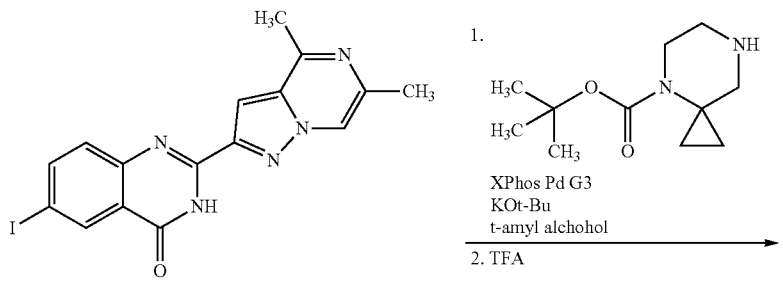

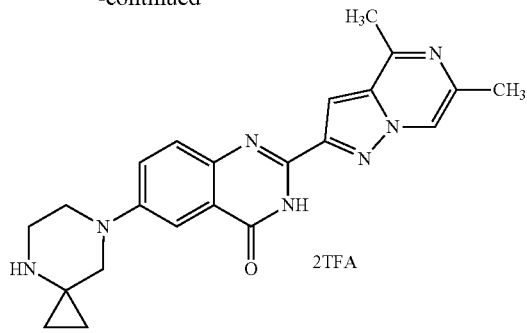

A mixture of 2-(4,6-dimethylpyrazolo[1,5-α]pyrazin-2-yl)-6-iodoquinazolin-4(3H)-one (125 mg), potassium tert-butoxide (134.7 mg), (2-dicyclohexylphosphino-2',4',6'-triisopropyl-1,1'-biphenyl)[2-(2'-amino-1, 1'-biphenyl)]palladiu m(II) methanesulfonate (25.5 mg), tert-amyl alcohol (1 mL) and tert-butyl 4,7-diazaspiro[2.5]octane-4-carboxylate (191 mg) was stirred under microwave irradiated conditions at 180° C. for 1 hour. After dimethyl sulfoxide (1 mL) and methanol (3 mL) were added thereto and the mixture was filtered through Celite, the volatile components were distilled off by heating the filtrate to 60° C. The obtained substance was purified by HPLC [YMC-Triart C18, acetonitrile containing 0.1% trifluoroacetic acid/water containing 0.1% trifluoroacetic acid]. After trifluoroacetic acid (0.3 mL) was added to the obtained solid and the mixture was stirred at room temperature for 1 hour, the volatile components were distilled off to obtain the title compound (33.5 mg).

MS: [M-2TFA+H]$^+$402.2.

Working Example 124

2-(4,6-dimethylpyrazolo[1,5-α]pyrazin-2-yl)-6-(octahydro-2H-pyrido[1,2-α]pyrazin-2-yl)quinazo lin-4(3H)-one (eutomer

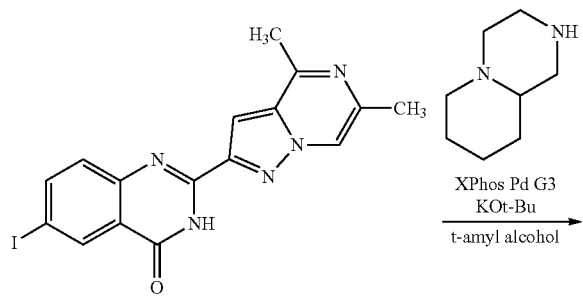

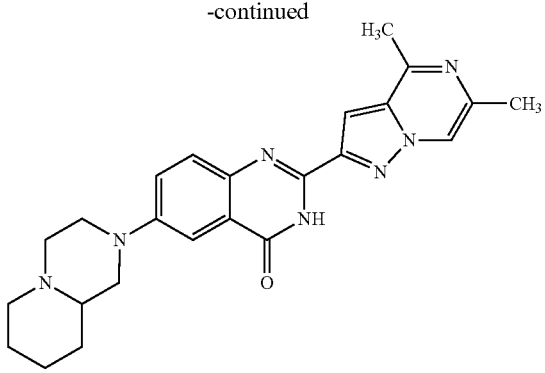

A mixture of 2-(4,6-dimethylpyrazolo[1,5-α]pyrazin-2-yl)-6-iodoquinazolin-4(3H)-one (83.4 mg), potassium tert-butoxide (89.8 mg), (2-dicyclohexylphosphino-2',4',6'-triisopropyl-1,1'-biphenyl)[2-(2'-amino-1, 1'-biphenyl) biphenyl)]palladiu m(II) methanesulfonate (17 mg), tert-amyl alcohol (1 mL) and octahydro-2H-pyrido[1,2-α]pyrazine (84 mg) (racemate) was stirred under microwave irradiated conditions at 180° C. for 1 hour. After dimethyl sulfoxide (1 mL) and methanol (3 mL) were added thereto and the mixture was filtered through Celite, the volatile components were distilled off by heating the filtrate to 60° C. The obtained substance was purified by HPLC [YMC-Triart C18, acetonitrile containing 0.1% trifluoroacetic acid/water containing 0.1% trifluoroacetic acid]. The obtained solid was optically resolved (CHIRALCEL OJ-H, hexane/ethanol/diethylamine) to obtain the title compound (9.6 mg).

(Eutomer) MS: [M+H]$^+$430.3. Retention time: TR1=14.4 min.

Working Example 125

2-(4,6-dimethylpyrazolo[1,5 pyrazin-2-yl)-6-(octahydro-2H-pyrido[1,2-α]pyrazin-2-yl)quinazo lin-4(3H)-one (eutomer) and 2-(4,6-dimethylpyrazolo[1,5 pyrazin-2-yl)-6-(octahydro-2H-pyrido[1,2-α]pyrazin-2-yl)quinazo lin-4(3H)-one (distomer

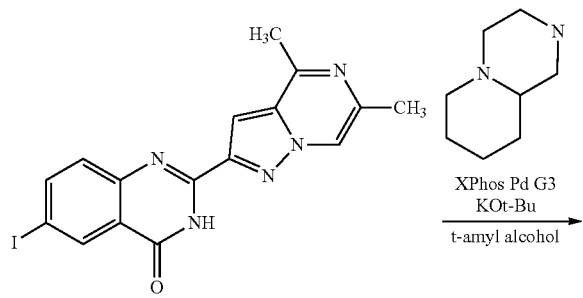

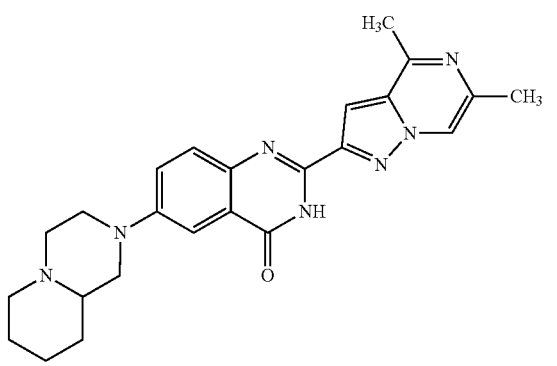

A mixture of 2-(4,6-dimethylpyrazolo[1,5-α]pyrazin-2-yl)-6-iodoquinazolin-4(3H)-one (83.4 mg), potassium tert-butoxide (89.8 mg), (2-dicyclohexylphosphino-2',4',6'-triisopropyl-1,1'-biphenyl)[2-(2'-amino-1, 1'-biphenyl)]palladiu m(II) methanesulfonate (17 mg), tert-amyl alcohol (1 mL) and octahydro-2H-pyrido[1,2-α]pyrazine (84 mg) (racemate) was stirred under microwave irradiated conditions at 180° C. for 1 hour. After DMSO (1 mL) and methanol (3 mL) were added thereto and the mixture was filtered through Celite, the volatile components were distilled off by heating the filtrate to 60° C. The obtained substance was purified by HPLC [YMC-Triart C18, acetonitrile containing 0.1% trifluoroacetic acid/water containing 0.1% trifluoroacetic acid]. The obtained solid was optically resolved (CHIRALCEL OJ-H, hexane/ethanol/diethylamine) to obtain the title compound (8.8 mg).

(Distomer) MS: [M+H]⁺430.2. Retention time: TR2=19.7 min.

Working Example 126

(R)-2-(4,6-dimethylpyrazolo[1,5-α]pyrazin-2-yl)-6-(hexahydropyrrolo[1,2-α]pyrazin-2(1H)-yl)qu inazolin-4(3H)-one (A) (R)-5-(hexahydropyrrolo[1,2-α]pyrazin-2(1H)-yl)-2-nitrobenzamide

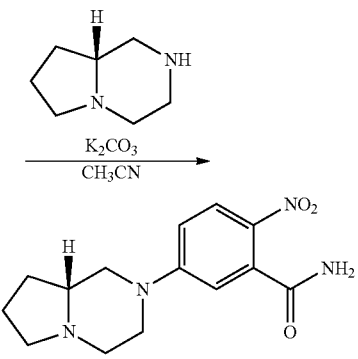

A mixture of ethyl 5-fluoro-2-nitrobenzamide (5.84 g), (R)-octahydropyrrolo[1,2-α]pyrazine (5.20 g), potassium carbonate (6.57 g) and acetonitrile (130 mL) was stirred at 50° C. overnight. After water (130 mL) was added thereto and the volatile components were distilled off under reduced pressure, the precipitate was filtered off and washed with water to obtain the title compound (8.79 g).

(B) (R)-2-Amino-5-(hexahydropyrrolo[1,2-α]pyrazin-2(1H)-yl)benzamide

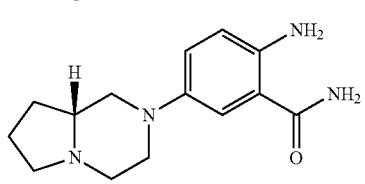

After a mixture of (R)-5-(hexahydropyrrolo[1,2-α]pyrazin-2(1H)-yl)-2-nitrobenzamide (8.79 g), palladium-activated carbon (5% palladium) (879 mg), methanol (90 mL) and THF (90 mL) was stirred under normal pressure and hydrogen atmosphere at room temperature overnight, the catalyst was removed by filtration and the filtrate was washed with methanol. The volatile components were distilled off from the filtrate under reduced pressure and the obtained solid was recrystallized from ethyl acetate/hexane) to obtain the title compound (6.21 g).

¹H-NMR (300 MHz, DMSO-d₆) δ: 7.74 (1H, s), 7.05 (1H, J=2.6 Hz, d), 6.99 (1H, s), 6.88-6.93 (1H, m), 6.58-6.61 (1H, m), 6.04 (2H, s), 3.51 (1H, J=9.8 Hz, d), 3.29-3.38 (1H, m), 2.96-3.02 (2H, m), 2.57-2.65 (1H, m), 2.18-2.32 (2H, m), 2.01-2.10 (2H, m), 1.66-1.79 (3H, m), 1.28-1.41 (1H, m). MS: [M+H]⁺261.2.

(C) (R)-2-(4,6-Dimethylpyrazolo[1,5-α]pyrazin-2-yl)-6-(hexahydropyrrolo[1,2-α]pyrazin-2(1H)-yl)quinazolin-4(3H)-one

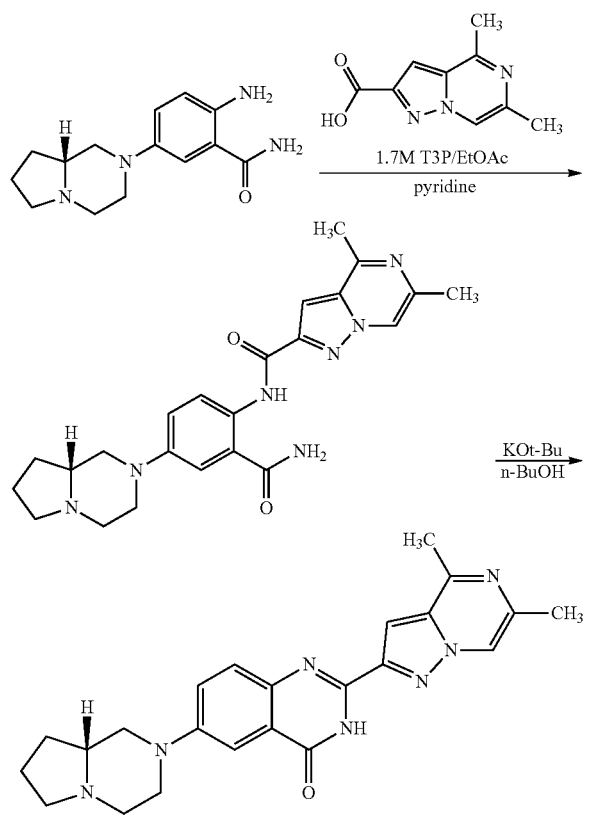

A mixture of 4,6-dimethylpyrazolo[1,5 pyrazin-2-carboxylic acid (4.55 g), (R)-2-amino-5-(hexahydropyrrolo[1,2-α] pyrazin-2(1H)-yl)benzamide (6.19 g), a 1.7 M propylphosphonic acid anhydride/ethyl acetate solution (21 mL) and pyridine (60 mL) was stirred at room temperature overnight. After the volatile components were distilled off under reduced pressure, water (120 mL) and a 15% aqueous potassium carbonate solution (120 mL) were added to the remaining solid and then the mixture was stirred at room temperature for 1 hour. The solid obtained by filtration was washed with water and diisopropyl ether. To the obtained solid were added 1-butanol (150 mL) and potassium tert-butoxide (267 mg) and then the mixture was stirred at 120° C. overnight and cooled to 60° C. Ethyl acetate (150 mL) was further added thereto and the mixture was stirred at 60° C. for 1 hour, cooled to room temperature and stirred at room temperature overnight. The precipitate was filtered off and then washed with 1-butanol/ethyl acetate (1/1) and ethyl acetate. The obtained solid was recrystallized from 1-butanol/heptane to obtain the title compound (6.84 g).
¹H-NMR (300 MHz, DMSO-d₆) δ: 12.09 (1H, s), 8.52 (1H, s), 7.62-7.67 (3H, m), 7.49 (1H, s), 3.98 (1H, d, J=9.4 Hz), 3.83 (1H, d, J=11.7 Hz), 3.03-3.14 (2H, m), 2.84-2.92 (1H, m), 2.75 (3H, s), 2.51-2.58 (1H, m), 2.48 (3H, d, J=0.8 Hz), 2.25-2.32 (1H, m), 2.11 (2H, q, J=8.8 Hz), 1.89 (1H, dd, J=15.9, 9.8 Hz), 1.69-1.77 (2H, m), 1.45 (1H, td, J=11.0, 7.0 Hz). MS: [M+H]⁺416.3.

Working Example 127

(S)-6-(2,4-dimethylpiperazin-1-yl)-2-(4,6-dimethylpyrazolo[1,5-a]pyrazin-2-yl)-quinazolin-4(3H)-one (A) Ethyl 5-fluoro-2-nitrobenzoate

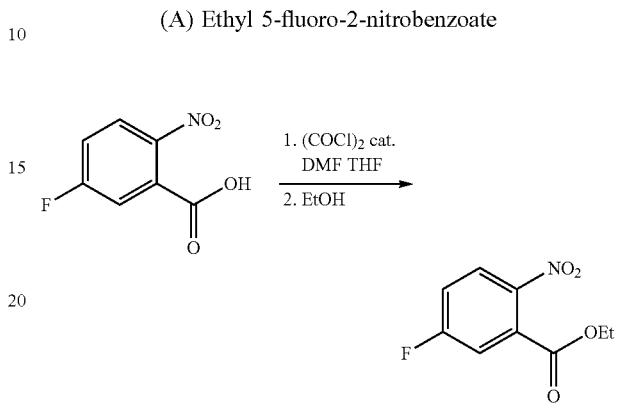

To a mixture of 5-fluoro-2-nitrobenzoic acid (20.0 g), DMF (0.084 mL) and THF (100 mL) was added dropwise oxalyl chloride (10.4 mL) at room temperature and then the mixture was stirred at the same temperature for 1 hour. After the volatile components were distilled off from the obtained mixture under reduced pressure, ethanol (50 mL) was added thereto at room temperature, followed by mixing. The mixture was stirred at the same temperature overnight. An aqueous saturated sodium hydrogen carbonate solution was further added thereto at the same temperature and then the mixture was extracted with ethyl acetate. The organic layer was washed with saturated brine and dried over anhydrous magnesium sulfate, and then the volatile components were distilled off under reduced pressure. The remaining substance was purified by silica gel column chromatography (ethyl acetate/hexane) to obtain the title compound (24.5 g).
¹H-NMR (300 MHz, DMSO-d₆) δ: 8.22 (1H, J=8.9, 4.7 Hz, dd), 7.77 (1H, J=8.3, 2.6 Hz, dd), 7.65-7.72 (1H, m), 4.34 (2H, J=7.0 Hz, q), 1.29 (3H, J=7.0 Hz, t).

(B) tert-Butyl (S)-4-(3-ethoxycarbonyl-4-nitrophenyl)-3-methyl piperadine-1-carboxylate

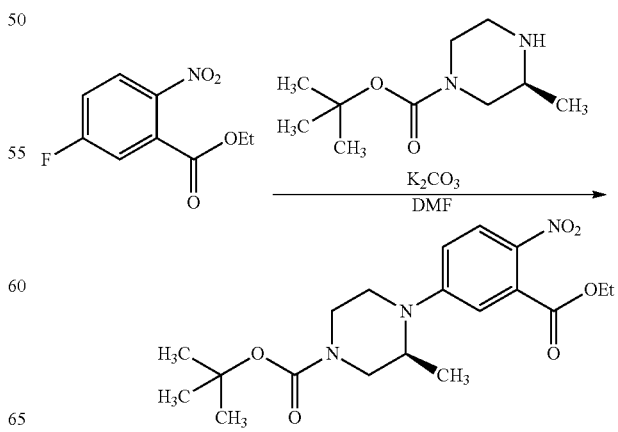

A mixture of ethyl 5-fluoro-2-nitrobenzoate (4.00 g), tert-butyl (S)-3-methylpiperadine-1-carboxylate (4.13 g), potassium carbonate (3.89 g) and DMF (20 mL) was stirred at 100° C. for 1 day. After water was added to the obtained mixture at room temperature and the mixture was extracted with ethyl acetate, the organic layer was washed with water and saturated brine and then dried over anhydrous magnesium sulfate. The volatile components were distilled off under reduced pressure and the remaining substance was purified by silica gel column chromatography (NH, ethyl acetate/hexane) to obtain the title compound (5.76 g).

MS: [M+H]$^+$394.3.

(C) Ethyl (S)-5-(2,4-dimethylpiperadin-1-yl)-2-nitrobenzoate

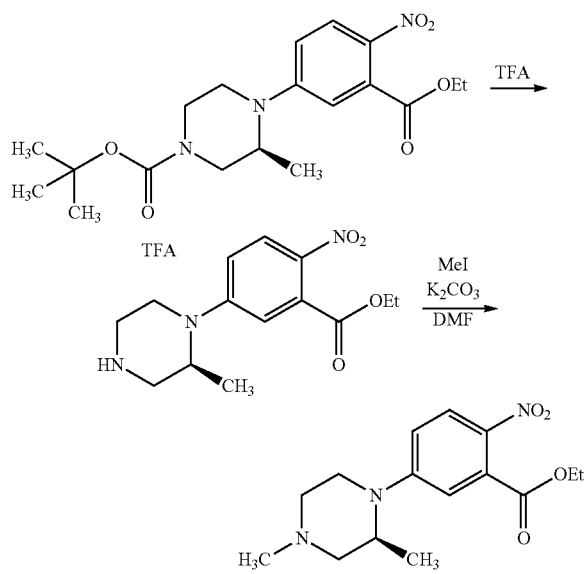

After a mixture of tert-butyl (S)-4-(3-ethoxycarbonyl-4-nitrophenyl)-3-methyl piperadine-1-carboxylate (3.42 g) and trifluoroacetic acid (20 mL) was stirred at room temperature for 30 minutes, the volatile components were distilled off under reduced pressure. To the remaining substance was added toluene and the volatile components were distilled off under reduced pressure. To the remaining substance was added toluene again and the volatile components were distilled off under reduced pressure. To a mixture of the obtained substance and DMF (35 mL) was added potassium carbonate (6.00 g) at room temperature and the mixture was stirred at the same temperature for 30 minutes. Then, iodomethane (0.706 mL) was further added thereto and the mixture was stirred at room temperature for 30 minutes. After water was added to the mixture at room temperature and the mixture was extracted with ethyl acetate, the organic layer was washed with water and saturated brine. The mixture was dried over anhydrous magnesium sulfate and the volatile components were distilled off under reduced pressure. The remaining substance was purified by silica gel column chromatography (NH, ethyl acetate/hexane) to obtain the title compound (1.97 g).

$^1$H-NMR (300 MHz, DMSO-d$_6$) δ: 8.01 (1H, J=9.4 Hz, d), 6.99-7.06 (2H, m), 4.30 (3H, J=7.2 Hz, q), 3.74-3.79 (1H, m), 3.08-3.17 (1H, m), 2.84-2.89 (1H, m), 2.70-2.73 (1H, m), 2.11-2.20 (4H, m), 1.91-1.99 (1H, m), 1.27 (3H, J=7.2 Hz, t), 1.16 (3H, J=6.4 Hz, d). MS: [M+H]$^+$308.2.

(D) (S)-5-(2,4-dimethylpiperadin-1-yl)-2-nitrobenzamide

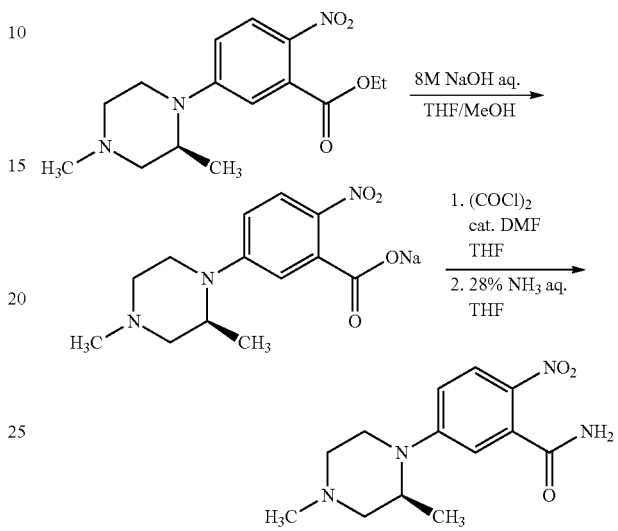

To a mixture of ethyl (S)-5-(2,4-dimethylpiperadin-1-yl)-2-nitrobenzoate (1.76 g), methanol (8 mL) and THF (8 mL) was added an 8 M aqueous sodium hydroxide solution (0.93 mL) at room temperature and then the mixture was stirred at 60° C. for 12 hours. After the volatile components were distilled off from the obtained mixture under reduced pressure, toluene/THF was added to the remaining solid and the volatile components were further distilled off under reduced pressure. To the remaining solid was added toluene/THF again and the volatile components were distilled off under reduced pressure. To a mixture of the obtained solid, DMF (0.045 mL) and THF (30 mL) was added dropwise oxalyl chloride (1.50 mL) at room temperature and the mixture was stirred at room temperature for 1 hour. After the volatile components were distilled off from the obtained mixture under reduced pressure, THF (30 mL) was added thereto and they were mixed, and the mixture was added dropwise to a 28% ammonium hydroxide solution (30 mL) at room temperature. Then, the mixture was stirred at the same temperature for 1 hour. Water was further added thereto at the same temperature and the mixture was extracted with ethyl acetate. The organic layer was separated, washed with saturated brine and dried over anhydrous magnesium sulfate, and then the volatile components were distilled off under reduced pressure. The remaining substance was purified by silica gel column chromatography (NH, ethyl acetate/hexane) to obtain the title compound (1.08 g).

$^1$H-NMR (300 MHz, DMSO-d$_6$) δ: 7.95 (1H, J=9.4 Hz, d), 7.85 (1H, s), 7.49 (1H, s), 6.96 (1H, J=9.4, 3.0 Hz, dd), 6.79 (1H, J=3.0 Hz, d), 4.24-4.31 (1H, m), 3.69-3.74 (1H, m), 3.05-3.15 (1H, m), 2.84-2.88 (1H, m), 2.70-2.74 (1H, m), 2.10-2.20 (4H, m), 1.90-1.99 (1H, m), 1.15 (3H, J=6.8 Hz, d). MS: [M+H]$^+$279.2.

(E) (S)-2-Amino-5-(2,4-dimethylpiperadin-1-yl)benzamide

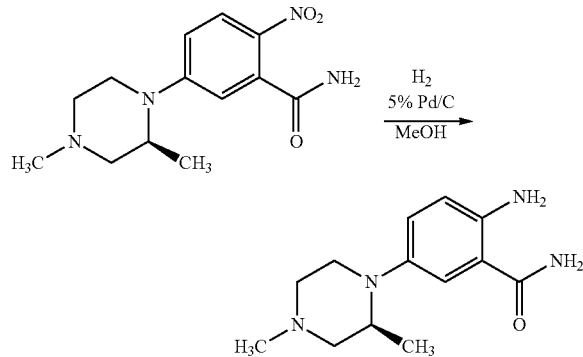

After a mixture of (S)-5-(2,4-dimethylpiperadin-1-yl)-2-nitrobenzamide (1.24 g), palladium-activated carbon (5% palladium) (124 mg) and methanol (10 mL) was stirred under normal pressure and hydrogen atmosphere at room temperature overnight, the catalyst was removed by filtration and the filtrate was washed with methanol. The volatile components were distilled off from the filtrate under reduced pressure and the obtained substance was purified by silica gel column chromatography (NH, ethyl acetate/hexane) to obtain the title compound (1.06 G).

$^1$H-NMR (300 MHz, DMSO-$d_6$) δ: 7.73 (1H, s), 7.15 (1H, J=2.6 Hz, d), 6.97 (1H, s), 6.91 (1H, J=8.7, 2.6 Hz, dd), 6.61 (1H, J=8.7 Hz, d), 6.18 (2H, s), 3.32-3.38 (1H, m), 2.82-2.96 (2H, m), 2.34-2.44 (2H, m), 2.14-2.20 (4H, m), 0.81 (3H, J=6.0 Hz, d). MS: [M+H]$^+$249.2.

(F) (S)-6-(2,4-Dimethylpiperazin-1-yl)-2-(4,6-dimethylpyrazolo[1, 5-a]pyrazin-2-yl)quinazolin-4(3H)-one

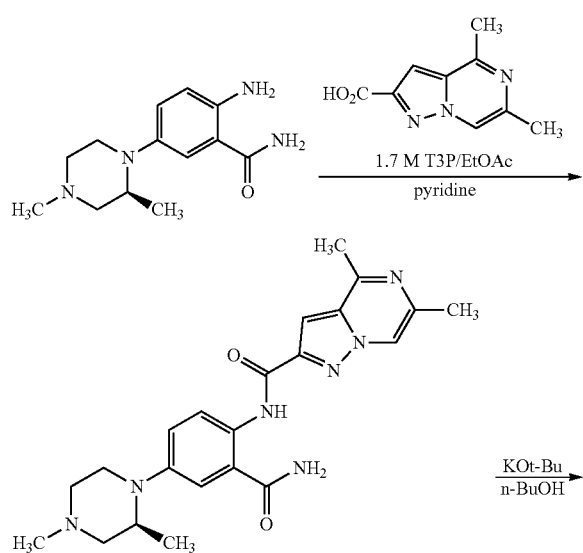

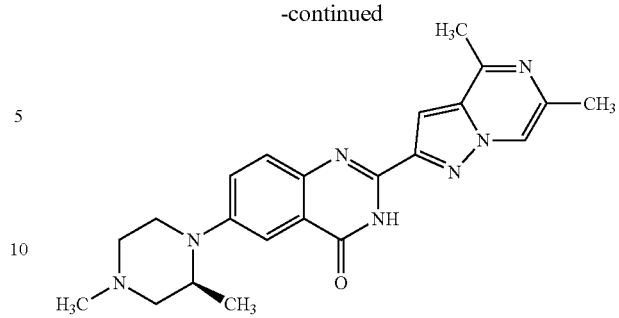

A mixture of 4,6-dimethylpyrazolo[1,5-α]pyrazin-2-carboxylic acid (0.816 g), (S)-2-amino-5-(2,4-dimethylpiperadin-1-yl)benzamide (1.06 g), a 1.7 M propylphosphonic acid anhydride/ethyl acetate solution (3.8 mL) and pyridine (10 mL) was stirred at room temperature for 90 minutes. After the volatile components were distilled off under reduced pressure, water (20 mL) and a 15% aqueous potassium carbonate solution (20 mL) were added to the remaining solid and the mixture was stirred at room temperature for 2 hours. The solid obtained by filtration was washed with water and diisopropyl ether. After 1-butanol (30 mL) and potassium tert-butoxide (50.0 mg) were added to the obtained solid and the mixture was stirred at 120° C. overnight, the volatile components were distilled off under reduced pressure. The remaining solid was purified by silica gel column chromatography (NH, methanol/ethyl acetate) and the obtained solid was recrystallized from ethanol/hexane to obtain the title compound (1.22 g).

$^1$H-NMR (300 MHz, DMSO-$d_6$) δ: 12.03 (1H, s), 8.49 (1H, s), 7.62-7.65 (2H, m), 7.53 (1H, J=9.3, 2.8 Hz, dd), 7.40 (1H, J=3.0 Hz, d), 4.18-4.20 (1H, m), 3.43-3.47 (1H, m), 3.03-3.11 (1H, m), 2.85-2.89 (1H, m), 2.69-2.73 (4H, m), 2.45 (3H, s), 2.22-2.28 (4H, m), 2.02-2.10 (1H, m), 1.08 (3H, J=6.8 Hz, d). MS: [M+H]$^+$404.2.

Working Example 128

(R)-6-(2,4-Dimethylpiperazin-1-yl)-2-(4, 6-dimethylpyrazolo[1,5-a]pyrazin-2-yl)-quinazolin-4(3H)-one

(A) tert-Butyl (R)-4-(3-ethoxycarbonyl-4-nitrophenyl)-3-methylpiperadine-1-carboxylate

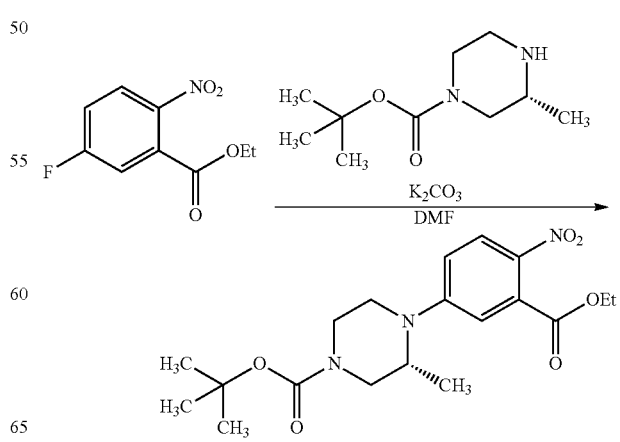

A mixture of ethyl 5-fluoro-2-nitrobenzoate (5.00 g), tert-butyl (R)-3-methylpiperadine-1-carboxylate (5.17 g), potassium carbonate (4.86 g) and DMF (20 mL) was stirred at 100° C. for 12 hours. After water was added to the obtained mixture at room temperature and the mixture was extracted with ethyl acetate, the organic layer was washed with water and saturated brine. The mixture was dried over anhydrous magnesium sulfate and the volatile components were distilled off under reduced pressure. The remaining substance was purified by silica gel column chromatography (NH, ethyl acetate/hexane) to obtain the title compound (6.07 g).

$^1$H-NMR (300 MHz, DMSO-$d_6$) δ: 8.03 (1H, J=9.1 Hz, d), 6.99-7.06 (2H, m), 4.27-4.34 (3H, m), 3.75-3.91 (3H, m), 3.10-3.24 (2H, m), 1.42 (9H, s), 1.27 (3H, J=7.0 Hz, t), 1.07 (3H, J=6.4 Hz, d). MS: [M+H]$^+$394.2.

(B) Ethyl (R)-5-(2,4-dimethylpiperadin-1-yl)-2-nitrobenzoate

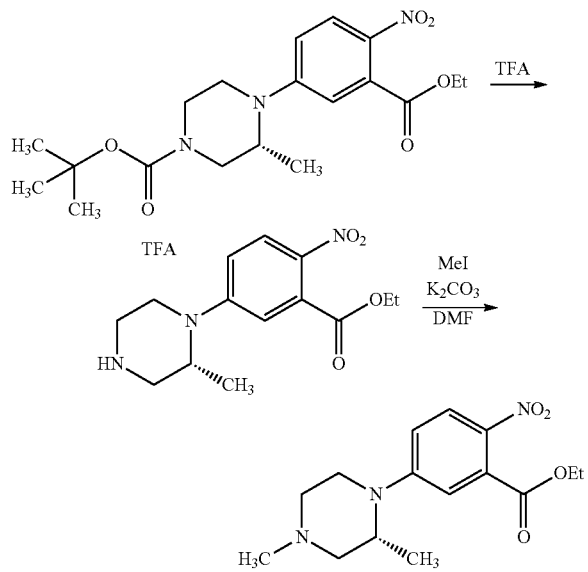

After a mixture of tert-butyl (R)-4-(3-ethoxycarbonyl-4-nitrophenyl)-3-methylpiperadine-1-carboxylate (2.95 g) and trifluoroacetic acid (30 mL) was stirred at room temperature for 1 hour, the volatile components were distilled off under reduced pressure. To the remaining substance was added toluene and the volatile components were distilled off under reduced pressure. To the remaining substance was added toluene again and the volatile components were distilled off under reduced pressure. To a mixture of the obtained substance and DMF (30 mL) was added potassium carbonate (5.18 g) at room temperature and the mixture was stirred at the same temperature for 30 minutes. Then, iodomethane (0.563 mL) was further added thereto and the mixture was stirred at room temperature overnight. After water was added to the obtained mixture at room temperature and the mixture was extracted with ethyl acetate, the organic layer was washed with water and saturated brine. The mixture was dried over anhydrous magnesium sulfate and the volatile components were distilled off under reduced pressure. The remaining substance was purified by silica gel column chromatography (NH, ethyl acetate/hexane) to obtain the title compound (2.14 g).

$^1$H-NMR (300 MHz, DMSO-$d_6$) δ: 8.01 (1H, J=9.4 Hz, d), 6.99-7.06 (2H, m), 4.26-4.33 (3H, m), 3.74-3.78 (1H, m), 3.08-3.17 (1H, m), 2.84-2.89 (1H, m), 2.70-2.73 (1H, m), 2.11-2.23 (4H, m), 1.91-1.99 (1H, m), 1.27 (3H, J=7.2 Hz, t), 1.16 (3H, J=6.4 Hz, d). MS: [M+H]$^+$308.2.

(C) (R)-5-(2,4-Dimethylpiperadin-1-yl)-2-nitrobenzamide

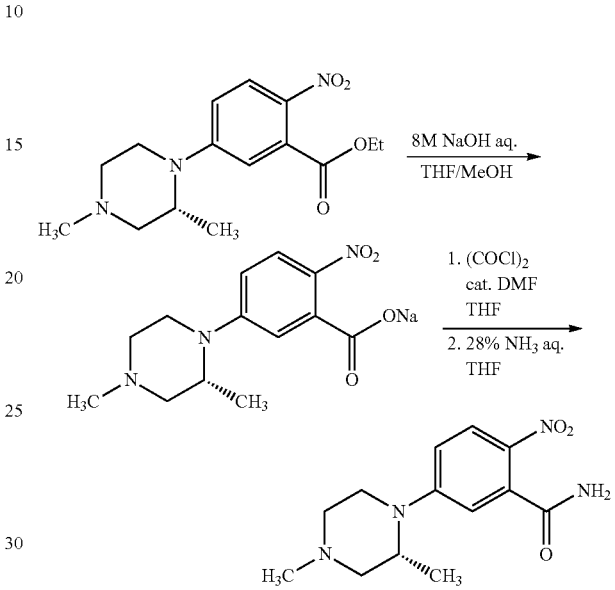

To a mixture of ethyl (R)-5-(2,4-dimethylpiperadin-1-yl)-2-nitrobenzoate (2.14 g), methanol (10 mL) and THF (10 mL) was added an 8 M aqueous sodium hydroxide solution (1.1 mL) at room temperature and the mixture was stirred at 60° C. overnight. After the volatile components were distilled off from the obtained mixture under reduced pressure, toluene/THF was added to the remaining solid and the volatile components were further distilled off under reduced pressure. To the remaining solid was added toluene/TH again and the volatile components were distilled off under reduced pressure. To a mixture of the obtained solid, DMF (0.054 mL) and THF (20 mL) was added dropwise oxalyl chloride (1.83 mL) at room temperature and the mixture was stirred at room temperature for 1 hour. After the volatile components were distilled off from the obtained mixture under reduced pressure, THF (30 mL) was added thereto and they were mixed. The mixture was added dropwise to a 28% ammonium hydroxide solution (20 mL) at room temperature. Then, the mixture was stirred at the same temperature for 1 hour. Water was further added thereto at the same temperature and the mixture was extracted with ethyl acetate. The organic layer was separated, washed with saturated brine and dried over anhydrous magnesium sulfate, and then the volatile components were distilled off under reduced pressure. The remaining substance was purified by silica gel column chromatography (NH, ethyl acetate/hexane) to obtain the title compound (1.12 g).

$^1$H-NMR (300 MHz, DMSO-$d_6$) δ: 7.95 (1H, J=9.4 Hz, d), 7.85 (1H, s), 7.49 (1H, s), 6.96 (1H, J=9.4, 2.6 Hz, dd), 6.79 (1H, J=2.6 Hz, d), 4.26-4.31 (1H, m), 3.69-3.73 (1H, m), 3.05-3.15 (1H, m), 2.84-2.88 (1H, m), 2.70-2.74 (1H, m), 2.10-2.20 (4H, m), 1.90-1.99 (1H, m), 1.15 (3H, J=6.4 Hz, d). MS: [M+H]$^+$279.2.

(D) (R)-2-Amino-5-(2,4-dimethylpiperadin-1-yl)benzamide

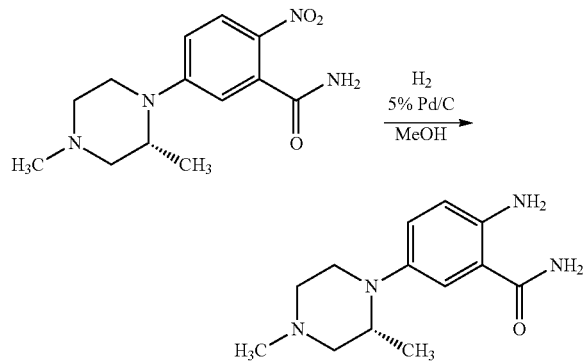

After a mixture of (R)-5-(2,4-dimethylpiperadin-1-yl)-2-nitrobenzamide (1.48 g), palladium-activated carbon (5% palladium) (148 mg), methanol (15 mL) was stirred under normal pressure and hydrogen atmosphere at room temperature overnight, the catalyst was removed by filtration and the filtrate was washed with methanol. The volatile components were distilled off from the filtrate under reduced pressure and the obtained substance was purified by silica gel column chromatography (NH, ethyl acetate/hexane) to obtain the title compound (1.22 g).

$^1$H-NMR (300 MHz, DMSO-$d_6$) δ: 7.72 (1H, s), 7.15 (1H, J=2.6 Hz, d), 6.97 (1H, s), 6.91 (1H, J=9.1, 2.6 Hz, dd), 6.61 (1H, J=9.1 Hz, d), 6.18 (2H, s), 3.29-3.39 (2H, m), 2.82-2.96 (2H, m), 2.33-2.46 (2H, m), 2.14-2.20 (4H, m), 0.81 (3H, J=6.4 Hz, d). MS: [M+H]$^+$249.2.

(E) (R)-6-(2,4-dimethylpiperazin-1-yl)-2-(4,6-dimethylpyrazolo[1,5-a]pyrazin-2-yl)-quinazolin-4(3H)-one

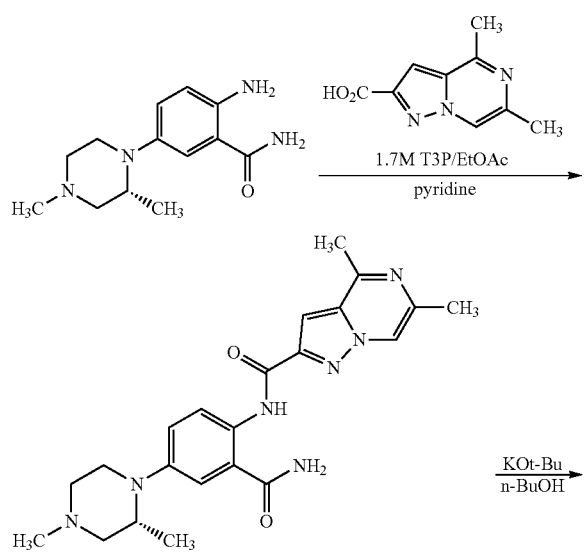

A mixture of 4,6-dimethylpyrazolo[1,5-α]pyrazin-2-carboxylic acid (0.940 g), (R)-2-amino-5-(2,4-dimethylpiperadin-1-yl)benzamide (1.22 g), a 1.7 M propylphosphonic acid anhydride/ethyl acetate solution (4.34 mL) and pyridine (15 mL) was stirred at room temperature overnight. After the volatile components were distilled off under reduced pressure, water (15 mL) and a 15% aqueous potassium carbonate solution (15 mL) were added to the remaining solid and then the mixture was stirred at room temperature for 2 hours. The solid obtained by filtration was washed with water and diisopropyl ether. After 1-butanol (20 mL) and potassium tert-butoxide (45.5 mg) were added to the obtained solid and the mixture was stirred at 120° C. overnight, the volatile components were distilled off under reduced pressure. The remaining solid was purified by silica gel column chromatography (NH, methanol/ethyl acetate) and recrystallized from ethyl acetate/hexane to obtain the title compound (0.968 g).

$^1$H-NMR (300 MHz, DMSO-$d_6$) δ: 12.02 (1H, s), 8.49 (1H, J=0.8 Hz, d), 7.61-7.64 (2H, m), 7.53 (1H, J=9.1, 2.6 Hz, dd), 7.40 (1H, J=2.6 Hz, d), 4.18-4.20 (1H, m), 3.43-3.47 (1H, m), 3.03-3.12 (1H, m), 2.85-2.89 (1H, m), 2.69-2.73 (4H, m), 2.45 (3H, J=0.8 Hz, d), 2.22-2.28 (4H, m), 2.02-2.10 (1H, m), 1.08 (3H, J=6.4 Hz, d). MS: [M+H]$^+$ 404.2.

Working Example 129

(S)-2-(4,6-Dimethylpyrazolo[1,5-a]pyrazin-2-yl)-6-(2-ethyl-4-methylpiperazin-1-yl)quinazolin-4 (3H)-one

(A) tert-Butyl (S)-4-(3-ethoxycarbonyl-4-nitrophenyl)-3-ethylpiperadine-1-carboxylate

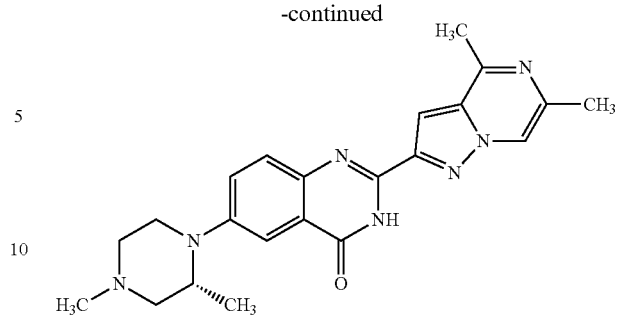

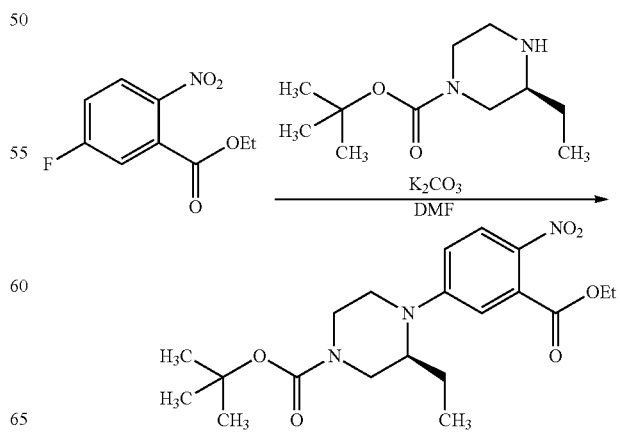

A mixture of ethyl 5-fluoro-2-nitrobenzoate (2.00 g), tert-butyl (S)-3-ethylpiperadine-1-carboxylate (2.21 g), potassium carbonate (1.95 g) and DMF (10 mL) was stirred at 100° C. for 1 day. After water was added to the obtained mixture at room temperature and the mixture was extracted with ethyl acetate, the organic layer was washed with water and saturated brine. After the mixture was dried over anhydrous magnesium sulfate, the volatile components were distilled off under reduced pressure. The remaining substance was purified by silica gel column chromatography (NH, ethyl acetate/hexane) to obtain the title compound (2.02 g).

$^1$H-NMR (300 MHz, DMSO-$d_6$) δ: 8.02 (1H, J=9.4 Hz, d), 6.99-7.06 (2H, m), 4.27-4.36 (2H, m), 3.99-4.07 (3H, m), 3.91—0.96 (1H, m), 3.78-3.83 (1H, m), 3.13-3.16 (3H, m), 1.46-1.63 (1H, m), 1.44 (9H, s), 1.27 (3H, J=7.2 Hz, t), 0.88 (3H, J=7.2 Hz, t). MS: [M+H]$^+$408.3.

(B) Ethyl (S)-5-(2-ethyl-4-methylpiperadin-1-yl)-2-nitrobenzoate

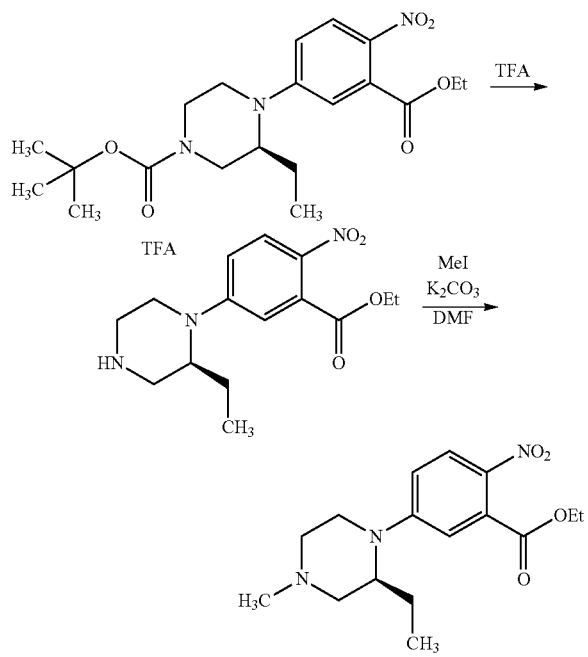

After a mixture of tert-butyl (S)-4-(3-ethoxycarbonyl-4-nitrophenyl)-3-ethylpiperadine-1-carboxylate (2.02 and trifluoroacetic acid (15 mL) was stirred at room temperature for 30 minutes, the volatile components were distilled off under reduced pressure. To the remaining substance was added toluene and the volatile components were distilled off under reduced pressure. To the remaining substance was added toluene again and the volatile components were distilled off under reduced pressure. To a mixture of the obtained substance and DMF (10 mL) was added potassium carbonate (2.74 g) at room temperature and the mixture was stirred at the same temperature for 30 minutes. Then, iodomethane (0.372 mL) was added thereto and the mixture was stirred at room temperature for 30 minutes. After water was added to the obtained mixture at room temperature and the mixture was extracted with ethyl acetate, the organic layer was washed with water and saturated brine. After the mixture was dried over anhydrous magnesium sulfate, the volatile components were distilled off under reduced pressure. The remaining substance was purified by silica gel column chromatography (NH, ethyl acetate/hexane) to obtain the title compound (1.36 g).

$^1$H-NMR (300 MHz, DMSO-$d_6$) δ: 7.99 (1H, J=9.1 Hz, d), 6.98-7.05 (2H, m), 4.26-4.34 (2H, m), 4.04 (1H, J=7.2 Hz, t), 3.78-3.83 (1H, m), 3.09-3.19 (1H, m), 2.82-2.85 (2H, m), 2.19 (3H, s), 1.88-2.04 (2H, m), 1.73-1.86 (1H, m), 1.48-1.62 (1H, m), 1.25-1.30 (3H, m), 0.83 (3H, J=7.4 Hz, t). MS: [M+H]$^+$322.2.

(C) (5)-5-(2-Ethyl-4-methylpiperadin-1-yl)-2-nitrobenzamide

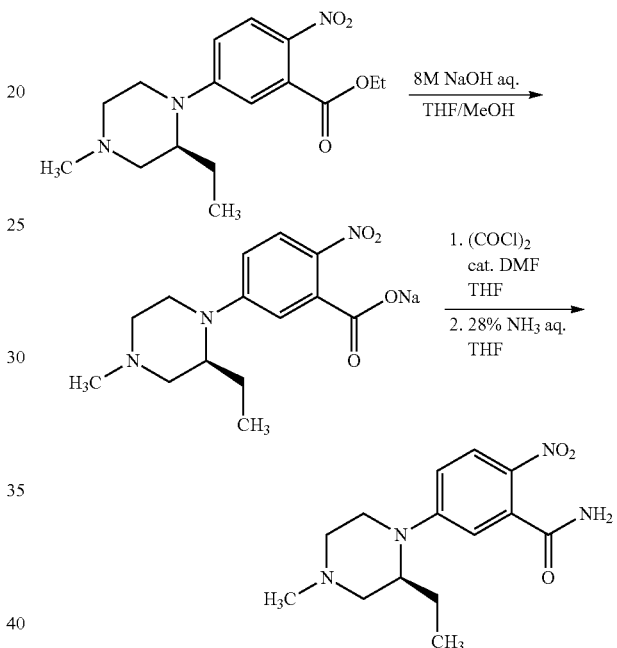

To a mixture of ethyl (S)-5-(2-ethyl-4-methylpiperadin-1-yl)-2-nitrobenzoate (1.35 g), methanol (6 mL) and THF (6 mL) was added an 8 M aqueous sodium hydroxide solution (0.68 mL) at room temperature and the mixture was stirred at 60° C. for 12 hours. After the volatile components were distilled off from the obtained mixture under reduced pressure, toluene/THF was added to the remaining solid and the volatile components were further distilled off under reduced pressure. To the remaining solid was added toluene/THF again and the volatile components were distilled off under reduced pressure. To a mixture of the obtained solid, DMF (0.033 mL) and THF (25 mL) was added dropwise oxalyl chloride (1.10 mL) at room temperature and the mixture was stirred at room temperature for 1 hour. After the volatile components were distilled off from the obtained mixture under reduced pressure, THF (30 mL) was added thereto and the mixture was added dropwise to a 28% ammonium hydroxide solution (25 mL) at room temperature. Then, the mixture was stirred at the same temperature for 1 hour. Water was further added thereto at the same temperature and the mixture was extracted with ethyl acetate. The organic layer was separated, washed with saturated brine and dried over anhydrous magnesium sulfate, and then the volatile components were distilled off under reduced pressure. The remaining substance was purified by silica gel column chromatography (NH, ethyl acetate/hexane) to obtain the title compound (1.11 g).

$^1$H-NMR (300 MHz, DMSO-$d_6$) δ: 7.93 (1H, J=9.4 Hz, d), 7.83 (1H, s), 7.48 (1H, s), 6.95 (1H, J=9.6, 2.8 Hz, dd), 6.77 (1H, J=3.0 Hz, d), 3.99-4.04 (1H, m), 3.73-3.78 (1H, m), 3.08-3.17 (1H, m), 2.82-2.86 (2H, m), 2.19 (3H, s), 1.74-2.03 (3H, m), 1.46-1.60 (1H, m), 0.84 (3H, J=7.4 Hz, t). MS: [M+H]$^+$293.2.

(D) (S)-2-Amino-5-(2-ethyl-4-methylpiperadin-1-yl)benzamide

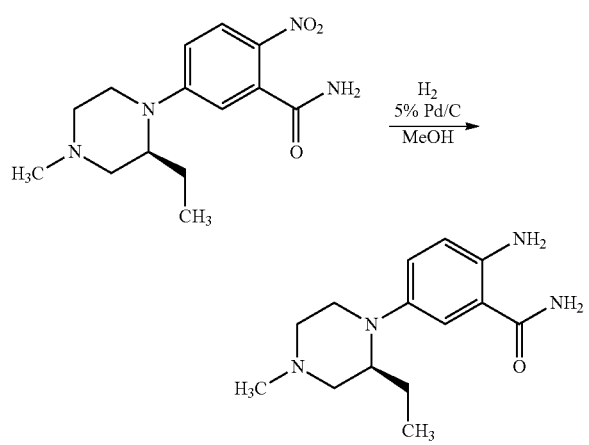

After a mixture of (S)-5-(2-ethyl-4-methylpiperadin-1-yl)-2-nitrobenzamide (1.10 g), palladium-activated carbon (5% palladium) (110 mg), methanol (10 mL) was stirred under normal pressure and hydrogen atmosphere at room temperature overnight, the catalyst was removed by filtration and the filtrate was washed with methanol. The volatile components were distilled off from the filtrate under reduced pressure and the obtained substance was purified by silica gel column chromatography (NH, ethyl acetate/hexane) to obtain the title compound (0.965 g). $^1$H-NMR (300 MHz, DMSO-$d_6$) δ: 7.72 (1H, s), 7.11 (1H, J=2.6 Hz, d), 6.97 (1H, s), 6.89 (1H, J=8.7, 2.6 Hz, dd), 6.60 (1H, J=8.7 Hz, d), 6.13 (2H, s), 3.14-3.21 (1H, m), 2.84-2.98 (2H, m), 2.43-2.47 (1H, m), 2.24-2.40 (2H, m), 2.19 (3H, s), 1.35-1.50 (1H, m), 1.13-1.27 (1H, m), 0.73 (3H, J=7.6 Hz, t). MS: [M+H]$^+$ 263.3.

(E) (S)-2-(4,6-dimethylpyrazolo[1,5-a]pyrazin-2-yl)-6-(2-ethyl-4-methylpiperazin-1-yl)quinazolin-4(3H)-one

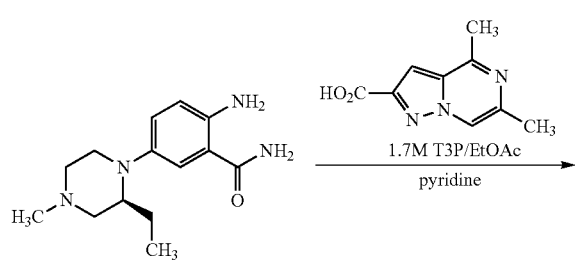

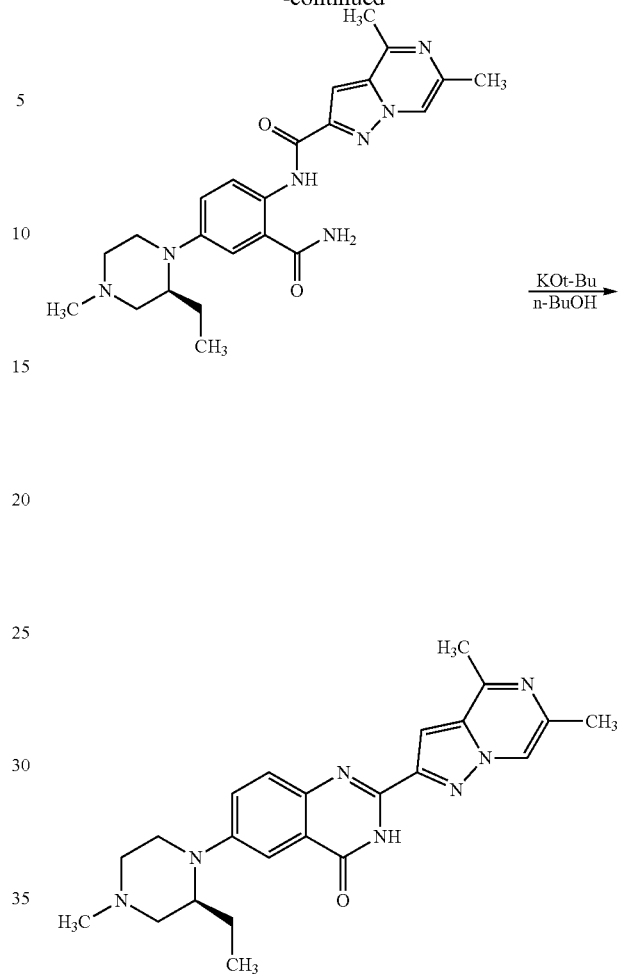

A mixture of 4,6-dimethylpyrazolo[1,5-α]pyrazin-2-carboxylic acid (0.703 g), (S)-2-amino-5-(2-ethyl-4-methylpiperadin-1-yl)benzamide (0.965 g), a 1.7 M propylphosphonic acid anhydride/ethyl acetate solution (3.2 mL) and pyridine (10 mL) was stirred at room temperature for 90 minutes. After the volatile components were distilled off under reduced pressure, water (20 mL) and a 15% aqueous potassium carbonate solution (20 mL) were added to the remaining solid and then the mixture was stirred at room temperature for 2 hours. The solid obtained by filtration was washed with water and diisopropyl ether. After 1-butanol (25 mL) and potassium tert-butoxide (41.3 mg) were added to the obtained solid and the mixture was stirred at 120° C. overnight, the volatile components were distilled off under reduced pressure. The obtained substance was purified by silica gel column chromatography (NH, methanol/ethyl acetate) and recrystallized from ethanol/hexane to obtain the title compound (0.753 g).

$^1$H-NMR (300 MHz, DMSO-$d_6$) δ: 12.02 (1H, s), 8.50 (1H, s), 7.60-7.63 (2H, m), 7.52 (1H, J=9.3, 2.8 Hz, dd), 7.37 (1H, J=3.0 Hz, d), 3.86-3.88 (1H, m), 3.48-3.52 (1H, m), 3.06-3.14 (1H, m), 2.84-2.88 (2H, m), 2.73 (3H, s), 2.45 (3H, s), 2.22 (3H, s), 2.01-2.15 (2H, m), 1.77-1.87 (1H, m), 1.33-1.42 (1H, m), 0.85 (3H, J=7.6 Hz, t). MS: [M+H]$^+$ 418.2.

Working Example 130

(S)-2-(4, 6-Dimethylpyrazolo[1,5-a]pyrazin-2-yl)-6-(4-ethyl-2-methylpiperazin-1-yl)quinazolin-4 (3H)-one (A) Ethyl (S)-5-(4-ethyl-2-methylpiperadin-1-yl)-2-nitrobenzoate

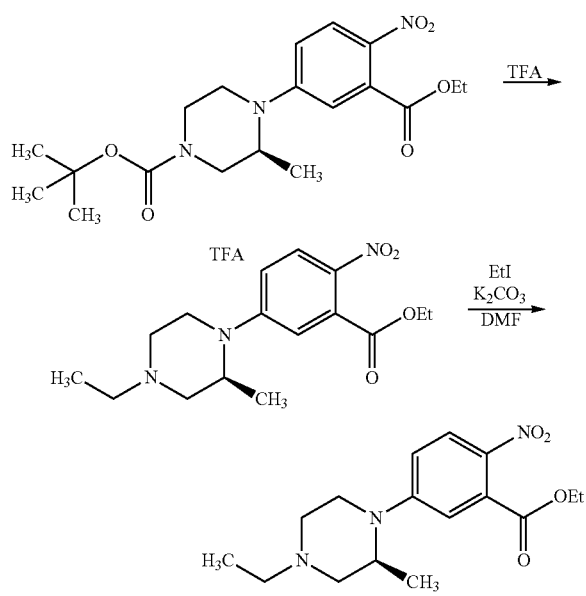

After a mixture of tert-butyl (S)-4-(3-ethoxycarbonyl-4-nitrophenyl)-3-methylpiperadine-1-carboxylate (2.34 g) and trifluoroacetic acid (25 mL) was stirred at room temperature for 30 minutes, the volatile components were distilled off under reduced pressure. To the remaining substance was added toluene and the volatile components were distilled off under reduced pressure. To the remaining substance was added toluene again and the volatile components were distilled off under reduced pressure. To a mixture of the obtained substance and DMF (25 mL) was added potassium carbonate (5.31 g) at room temperature and the mixture was stirred at the same temperature for 30 minutes. Then, iodomethane (0.577 mL) was further added thereto and the mixture was stirred at room temperature for 3 hours. After water was added to the obtained mixture at room temperature and the mixture was extracted with ethyl acetate, the organic layer was washed with water and saturated brine. After the mixture was dried over anhydrous magnesium sulfate, the volatile components were distilled off under reduced pressure. The remaining substance was purified by silica gel column chromatography (NH, ethyl acetate/hexane) to obtain the title compound (1.46 g).

$^1$H-NMR (300 MHz, DMSO-$d_6$) δ: 8.01 (1H, J=9.1 Hz, d), 6.98-7.06 (2H, m), 4.26-4.33 (3H, m), 3.76-3.80 (1H, m), 3.06-3.15 (1H, m), 2.93-2.97 (1H, m), 2.79-2.83 (1H, m), 2.25-2.42 (2H, m), 2.09-2.14 (1H, m), 1.92-2.01 (1H, m), 1.28 (3H, J=7.2 Hz, t), 1.15 (3H, J=6.4 Hz, d), 1.03 (3H, J=7.2 Hz, t). MS: [M+H]$^+$322.2.

(B) (S)-5-(4-Ethyl-2-methylpiperadin-1-yl)-2-nitrobenzamide

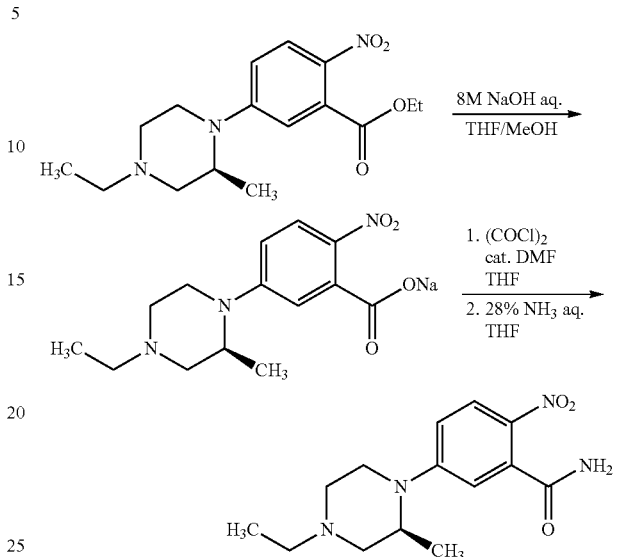

To a mixture of ethyl (S)-5-(4-ethyl-2-methylpiperadin-1-yl)-2-nitrobenzoate (1.45 g), methanol (10 mL) and THF (10 mL) was added an 8 M aqueous sodium hydroxide solution (0.73 mL) at room temperature and the mixture was stirred at 60° C. overnight. After the volatile components were distilled off from the obtained mixture under reduced pressure, toluene/THF was added to the obtained solid and the volatile components were further distilled off under reduced pressure. To the obtained solid was added toluene/THF again and the volatile components were distilled off under reduced pressure. To a mixture of the obtained solid, DMF (0.035 mL) and THF (20 mL) was added dropwise oxalyl chloride (1.18 mL) at room temperature and the mixture was stirred at room temperature for 1 hour. After the volatile components were distilled off from the obtained mixture under reduced pressure, THF (30 mL) was added thereto and they were mixed. After the mixture was added dropwise to a 28% ammonium hydroxide solution (20 mL) at room temperature, the resulting mixture was stirred at the same temperature for 1 hour. Water was further added thereto at the same temperature and the mixture was extracted with ethyl acetate. The organic layer was separated and washed with saturated brine. After the mixture was dried over anhydrous magnesium sulfate, the volatile components were distilled off under reduced pressure. The remaining substance was purified by silica gel column chromatography (NH, ethyl acetate/hexane) to obtain the title compound (0.988 g).

$^1$H-NMR (300 MHz, DMSO-$d_6$) δ: 7.95 (1H, J=9.4 Hz, d), 7.85 (1H, s), 7.49 (1H, s), 6.95 (1H, J=9.4, 2.6 Hz, dd), 6.78 (1H, J=2.6 Hz, d), 4.28-4.29 (1H, m), 3.71-3.75 (1H, m), 3.04-3.13 (1H, m), 2.94-2.98 (1H, m), 2.79-2.83 (1H, m), 2.28-2.39 (2H, m), 2.09-2.14 (1H, m), 1.91-1.99 (1H, m), 1.14 (3H, J=4.2 Hz, d), 1.03 (3H, J=7.2 Hz, t). MS: [M+H]$^+$293.2.

(C) (S)-2-Amino-5-(4-ethyl-2-methylpiperadin-1-yl)benzamide

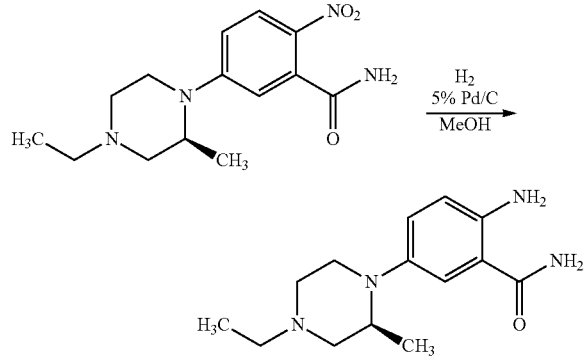

After a mixture of (S)-5-(4-ethyl-2-methylpiperadin-1-yl)-2-nitrobenzamide (0.988 g), palladium-activated carbon (5% palladium) (98.8 mg) and methanol (10 mL) was stirred under normal pressure and hydrogen atmosphere at room temperature overnight, the catalyst was removed by filtration and the filtrate was washed with methanol. The volatile components were distilled off from the filtrate under reduced pressure and the obtained substance was purified by silica gel column chromatography (NH, ethyl acetate/hexane) to obtain the title compound (0.755 g).

$^1$H-NMR (300 MHz, DMSO-$d_6$) δ: 7.72 (1H, s), 7.17 (1H, J=2.6 Hz, d), 6.97 (1H, s), 6.92 (1H, J=8.7, 2.6 Hz, dd), 6.60 (1H, J=8.7 Hz, d), 6.20 (2H, s), 3.31-3.35 (1H, m), 2.82-2.96 (2H, m), 2.55-2.59 (1H, m), 2.41-2.46 (2H, m), 2.24-2.38 (2H, m), 2.14-2.19 (1H, m), 1.01 (3H, J=7.2 Hz, t), 0.81 (3H, J=6.4 Hz, d). MS: [M+H]$^+$263.3.

(D) (S)-2-(4,6-dimethylpyrazolo[1,5-a]pyrazin-2-yl)-6-(4-ethyl-2-methylpiperazin-1-yl)quinazolin-4(3H)-one

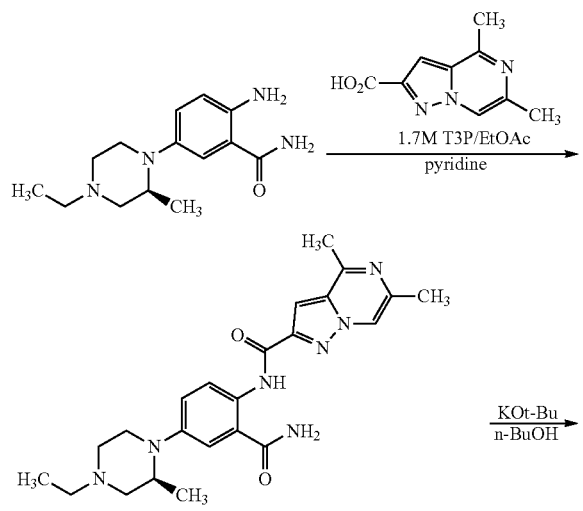

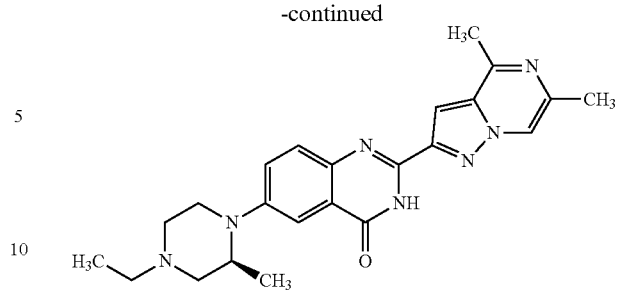

A mixture of 4,6-dimethylpyrazolo[1,5-α]pyrazin-2-carboxylic acid (0.547 g), (S)-2-amino-5-(4-ethyl-2-methylpiperadin-1-yl)benzamide (0.750 g), a 1.7 M propylphosphonic acid anhydride/ethyl acetate solution (2.52 mL) and pyridine (10 mL) was stirred at room temperature overnight. After the volatile components were distilled off under reduced pressure, water (10 mL) and a 15% aqueous potassium carbonate solution (10 mL) were added to the remaining solid and the mixture was stirred at room temperature for 2 hours. The solid obtained by filtration was washed with water and diisopropyl ether. To the obtained solid were added 1-butanol (15 mL) and potassium tert-butoxide (28.9 mg) and then the mixture was stirred at 120° C. overnight. Then, the volatile components were distilled off under reduced pressure. The remaining solid was recrystallized from ethanol/hexane to obtain the title compound (0.700 g).

$^1$H-NMR (300 MHz, DMSO-$d_6$) δ: 12.01 (1H, s), 8.48 (1H, s), 7.61-7.64 (2H, m), 7.53 (1H, J=9.3, 2.6 Hz, dd), 7.39 (1H, J=2.6 Hz, d), 4.19-4.21 (1H, m), 3.45-3.49 (1H, m), 3.02-3.10 (1H, m), 2.94-2.98 (1H, m), 2.78-2.82 (1H, m), 2.73 (3H, s), 2.45 (3H, s), 2.30-2.41 (2H, m), 2.22-2.27 (1H, m), 2.03-2.10 (1H, m), 1.03-1.09 (6H, m). MS: [M+H]$^+$ 418.2.

Working Example 131

(R)-2-(4,6-dimethylpyrazolo[1,5-α]pyrazin-2-yl)-6-(4-ethyl-2-methylpiperazin-1-yl)quinazolin-4(3H)-one

(A) Ethyl (R)-5-(4-ethyl-2-methylpiperadin-1-yl)-2-nitrobenzoate

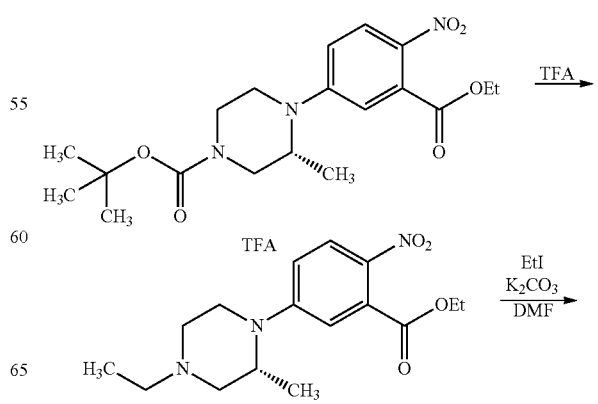

-continued

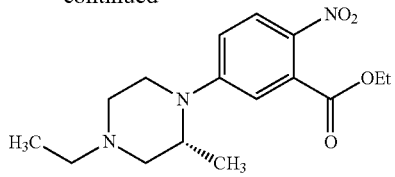

After a mixture of tert-butyl (R)-4-(3-(ethoxycarbonyl)-4-nitrophenyl)-3-methylpiperadine-1-carboxylate (3.02 g) and trifluoroacetic acid (30 mL) was stirred at room temperature for 30 minutes, the volatile components were distilled off under reduced pressure. To the remaining substance was added toluene and the volatile components were distilled off under reduced pressure. To the remaining substance was added toluene again and the volatile components were distilled off under reduced pressure. To a mixture of the obtained substance and DMF (30 mL) was added potassium carbonate (5.31 g) at room temperature and the mixture was stirred at the same temperature for 30 minutes. Then, iodomethane (0.807 mL) was added thereto and the mixture was stirred at room temperature for 3 hours. To the obtained mixture was added water at room temperature and the mixture was extracted with ethyl acetate. Then, the organic layer was washed with water and saturated brine. After the mixture was dried over anhydrous magnesium sulfate, the volatile components were distilled off under reduced pressure. The remaining substance was purified by silica gel column chromatography (NH, ethyl acetate/hexane) to obtain the title compound (2.16 g).

$^1$H-NMR (300 MHz, DMSO-d$_6$) δ: 8.02 (1H, J=9.4 Hz, d), 6.98-7.06 (2H, m), 4.26-4.33 (3H, m), 3.76-3.80 (1H, m), 3.06-3.15 (1H, m), 2.93-2.97 (1H, m), 2.79-2.83 (1H, m), 2.25-2.39 (2H, m), 2.09-2.14 (1H, m), 1.92-2.01 (1H, m), 1.28 (3H, J=7.2 Hz, t), 1.15 (3H, J=6.8 Hz, d), 1.03 (3H, J=7.2 Hz, t). MS: [M+H]$^+$322.2.

(B) (R)-5-(4-ethyl-2-methylpiperadin-1-yl)-2-nitrobenzamide

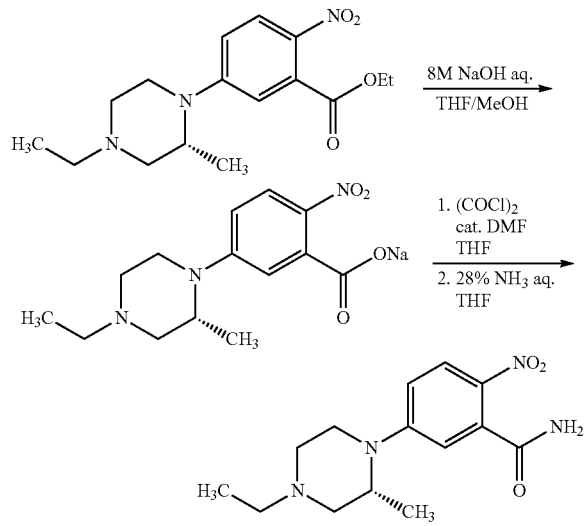

To a mixture of ethyl (R)-5-(4-ethyl-2-methylpiperadin-1-yl)-2-nitrobenzoate (2.16 g), methanol (10 mL) and THF (10 mL) was added an 8 M aqueous sodium hydroxide solution (1.1 mL) at room temperature and then the mixture was stirred at 60° C. overnight. After the volatile components were distilled off from the obtained mixture under reduced pressure, toluene/THF was added to the remaining solid and the volatile components were further distilled off under reduced pressure. To the remaining solid was added toluene/THF again and the volatile components were distilled off under reduced pressure. To a mixture of the obtained solid, DMF (0.052 mL) and THF (20 mL) was added dropwise oxalyl chloride (1.76 mL) at room temperature and the mixture was stirred at room temperature for 1 hour. After the volatile components were distilled off from the obtained mixture under reduced pressure, THF (30 mL) was added thereto and they were mixed. The mixture was added dropwise to a 28% ammonium hydroxide solution (20 mL) at room temperature. Then, the mixture was stirred at the same temperature for 1 hour. Water was further added thereto at the same temperature and the mixture was extracted with ethyl acetate. The organic layer was separated, washed with saturated aqueous sodium chloride and dried over anhydrous magnesium sulfate, and then the volatile components were distilled off under reduced pressure. The remaining substance was purified by silica gel column chromatography (NH, ethyl acetate/hexane) to obtain the title compound (1.54 g).

$^1$H-NMR (300 MHz, DMSO-d$_6$) δ: 7.95 (1H, J=9.1 Hz, d), 7.85 (1H, s), 7.49 (1H, s), 6.96 (1H, J=9.1, 2.6 Hz, dd), 6.78 (1H, J=2.6 Hz, d), 4.22-4.28 (1H, m), 3.71-3.75 (1H, m), 3.04-3.13 (1H, m), 2.94-2.99 (1H, m), 2.79-2.83 (1H, m), 2.28-2.42 (2H, m), 2.09-2.14 (1H, m), 1.91-1.99 (1H, m), 1.14 (3H, J=4.5 Hz, d), 1.03 (3H, J=7.2 Hz, t). MS: [M+H]$^+$293.2.

(C) (R)-2-amino-5-(4-ethyl-2-methylpiperadin-1-yl)benzamide

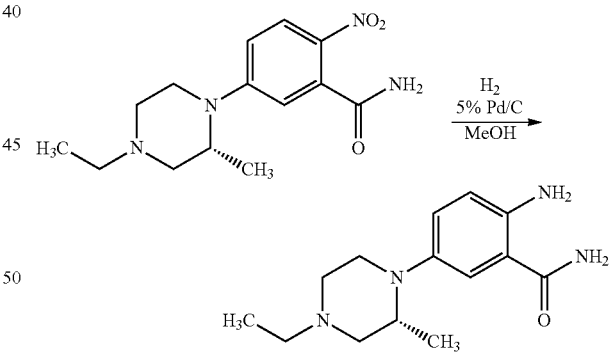

After a mixture of (R)-5-(4-ethyl-2-methylpiperadin-1-yl)-2-nitrobenzamide (1.54 g), palladium-activated carbon (5% palladium) (154 mg) and methanol (15 mL) was stirred under normal pressure and hydrogen atmosphere at room temperature overnight, the catalyst was removed by filtration and the filtrate was washed with methanol. The volatile components were distilled off from the filtrate under reduced pressure and the obtained substance was purified by silica gel column chromatography (NH, ethyl acetate/hexane) to obtain the title compound (1.21 g). $^1$H-NMR (300 MHz, DMSO-d$_6$) δ: 7.72 (1H, s), 7.17 (1H, J=2.3 Hz, d), 6.96 (1H, s), 6.92 (1H, J=8.7, 2.3 Hz, dd), 6.61 (1H, J=8.7 Hz, d), 6.20 (2H, s), 3.32-3.33 (1H, m), 2.82-2.96 (2H, m), 2.55-2.59

(1H, m), 2.41-2.46 (2H, m), 2.24-2.38 (2H, m), 2.14-2.19 (1H, m), 1.02 (3H, J=7.0 Hz, t), 0.82 (3H, J=6.2 Hz, d). MS: [M+H]$^+$263.3.

(D) (R)-2-(4,6-Dimethylpyrazolo[1,5-α]pyrazin-2-yl)-6-(4-ethyl-2-methylpiperazin-1-yl)quinazolin-4 (3H)-one

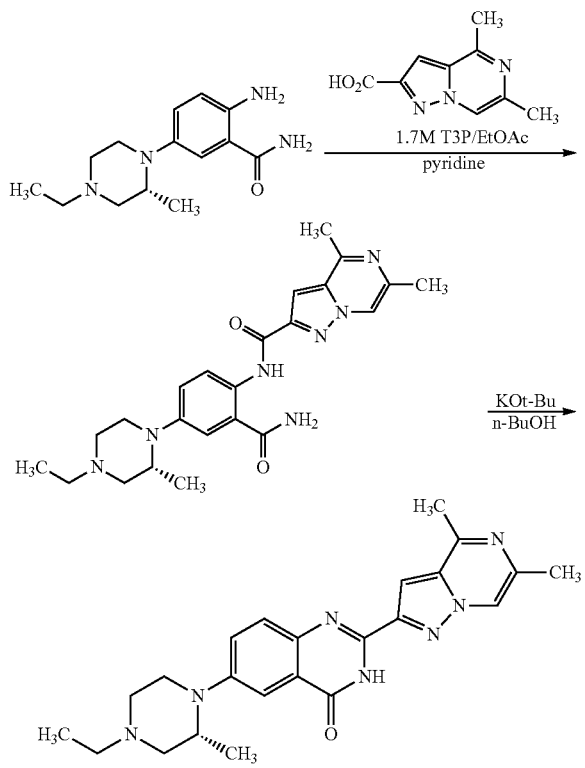

A mixture of 4,6-dimethylpyrazolo[1,5-α]pyrazin-2-carboxylic acid (0.881 g), (R)-2-amino-5-(4-ethyl-2-methylpiperadin-1-yl)benzamide (1.21 g), a 1.7 M propylphosphonic acid anhydride/ethyl acetate solution (4.1 mL) and pyridine (15 mL) was stirred at room temperature overnight. After the volatile components were distilled off under reduced pressure, water (15 mL) and a 15% aqueous potassium carbonate solution (15 mL) were added to the remaining solid and the mixture was stirred at room temperature for 2 hours. The solid obtained by filtration was washed with water and diisopropyl ether. To the obtained solid were added 1-butanol (20 mL) and potassium tert-butoxide (43.5 mg) and then the mixture was stirred at 120° C. overnight. Then, the volatile components were distilled off under reduced pressure. The remaining solid was recrystallized from ethanol/hexane to obtain the title compound (0.987 g).

$^1$H-NMR (300 MHz, DMSO-d$_6$) δ: 12.02 (1H, s), 8.49 (1H, s), 7.62-7.64 (2H, m), 7.53 (1H, J=9.1, 3.0 Hz, dd), 7.40 (1H, J=3.0 Hz, d), 4.19-4.21 (1H, m), 3.45-3.49 (1H, m), 3.02-3.11 (1H, m), 2.95-2.98 (1H, m), 2.78-2.82 (1H, m), 2.73 (3H, s), 2.45 (3H, s), 2.30-2.39 (2H, m), 2.22-2.27 (1H, m), 2.03-2.10 (1H, m), 1.03-1.09 (6H, m). MS: [M+H]$^+$ 418.2.

Working Example 132

(R)-2-(4,6-Dimethylpyrazolo[1,5 pyrazin-2-yl)-6-(2-ethyl-4-methylpiperazin-1-yl)quinazolin-4 (3H)-one (A) tert-Butyl (R)-4-(3-ethoxycarbonyl-4-nitrophenyl)-3-ethylpiperadine-1-carboxylate

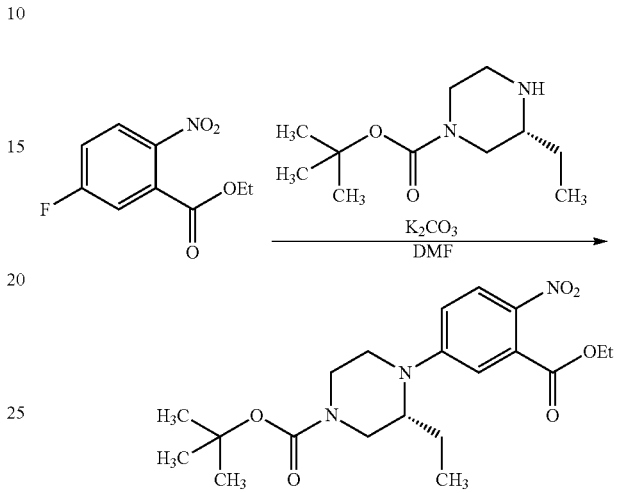

A mixture of ethyl 5-fluoro-2-nitrobenzoate (3.00 g), tert-butyl (R)-3-ethylpiperadine-1-carboxylate (3.32 g), potassium carbonate (2.92 g) and DMF (15 mL) was stirred at 100° C. for 1 day. After water was added to the obtained mixture at room temperature and the mixture was extracted with ethyl acetate, the organic layer was washed with water and saturated brine. After the mixture was dried over anhydrous magnesium sulfate, the volatile components were distilled off under reduced pressure. The remaining substance was purified by silica gel column chromatography (NH, ethyl acetate/hexane) to obtain the title compound (4.13 g).

MS: [M+H]$^+$408.3.

(B) Ethyl (R)-5-(2-ethyl-4-methylpiperadin-1-yl)-2-nitrobenzoate

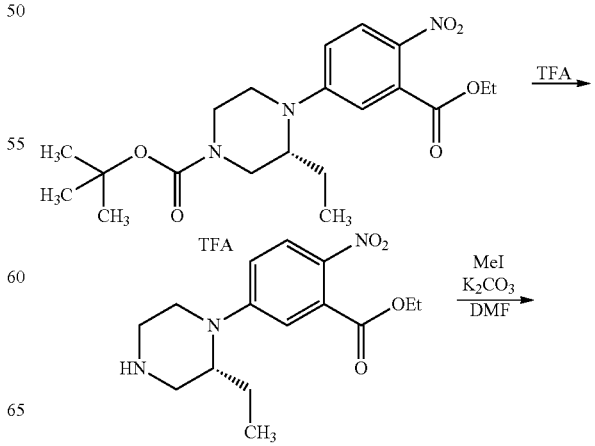

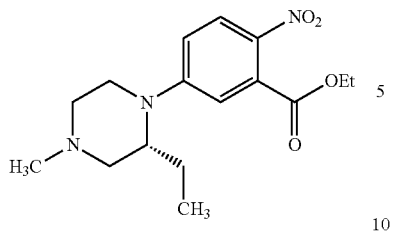

After a mixture of tert-butyl (R)-4-(3-ethoxycarbonyl-4-nitrophenyl)-3-ethylpiperadine-1-carboxylate (4.13 g) and trifluoroacetic acid (40 mL) was stirred at room temperature for 1 hour, the volatile components were distilled off under reduced pressure. To the remaining substance was added toluene and the volatile components were distilled off under reduced pressure. To the remaining substance was added toluene again and the volatile components were distilled off under reduced pressure. To a mixture of the obtained substance and DMF (45 mL) was added potassium carbonate (6.98 g) at room temperature and the mixture was stirred at the same temperature for 30 minutes. Then, iodomethane (0.758 mL) was further added thereto and the mixture was stirred at room temperature overnight. To the obtained mixture was added iodomethane (0.189 mL) and the mixture was stirred at room temperature for 2 hours. Then, iodomethane (0.189 mL) was further added thereto and the mixture was stirred at room temperature for 1 hour. After water was added to the obtained mixture at room temperature and the mixture was extracted with ethyl acetate, the organic layer was washed with water and saturated brine. After the mixture was dried over anhydrous magnesium sulfate, the volatile components were distilled off under reduced pressure. The remaining substance was purified by silica gel column chromatography (NH, ethyl acetate/hexane) to obtain the title compound (2.41 g).

MS: [M+H]$^+$322.2.

(C) (R)-5-(2-Ethyl-4-methylpiperadin-1-yl)-2-nitrobenzamide

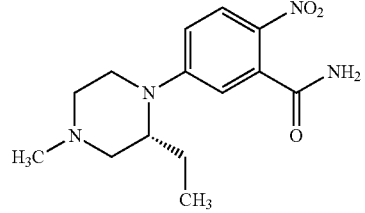

To a mixture of ethyl (R)-5-(2-ethyl-4-methylpiperadin-1-yl)-2-nitrobenzoate (2.41 g), methanol (10 mL) and THF (10 mL) was added an 8 M aqueous sodium hydroxide solution (1.2 mL) at room temperature and the mixture was stirred at 60° C. overnight. After the volatile components were distilled off from the obtained mixture under reduced pressure, toluene/THF was added to the remaining solid and the volatile components were further distilled off under reduced pressure. To the remaining solid was added toluene/THF again and the volatile components were distilled off under reduced pressure. To a mixture of the obtained solid, DMF (0.058 mL) and THF (25 mL) was added dropwise oxalyl chloride (1.97 mL) at room temperature and the mixture was stirred at room temperature for 1 hour. After the volatile components were distilled off from the obtained mixture under reduced pressure, THF (30 mL) was added thereto and they were mixed. The mixture was added dropwise to a 28% ammonium hydroxide solution (25 mL) at room temperature. Then, the mixture was stirred at the same temperature for 1 hour. Water was further added thereto at the same temperature and the mixture was extracted with ethyl acetate. The organic layer was separated, washed with saturated brine and dried over anhydrous magnesium sulfate, and then the volatile components were distilled off under reduced pressure. The remaining substance was purified by silica gel column chromatography (NH, ethyl acetate/hexane) to obtain the title compound (1.42 g).

$^1$H-NMR (300 MHz, DMSO-d$_6$) δ: 7.93 (1H, J=9.4 Hz, d), 7.83 (1H, s), 7.48 (1H, s), 6.95 (1H, J=9.4, 2.6 Hz, dd), 6.77 (1H, J=2.6 Hz, d), 3.99-4.06 (1H, m), 3.73-3.78 (1H, m), 3.08-3.17 (1H, m), 2.82-2.86 (2H, m), 2.19 (3H, s), 1.89-2.03 (2H, m), 1.74-1.86 (1H, m), 1.46-1.60 (1H, m), 0.84 (3H, J=7.6 Hz, t). MS: [M+H]$^+$293.2.

(D) (R)-2-Amino-5-(2-ethyl-4-methylpiperadin-1-yl)benzamide

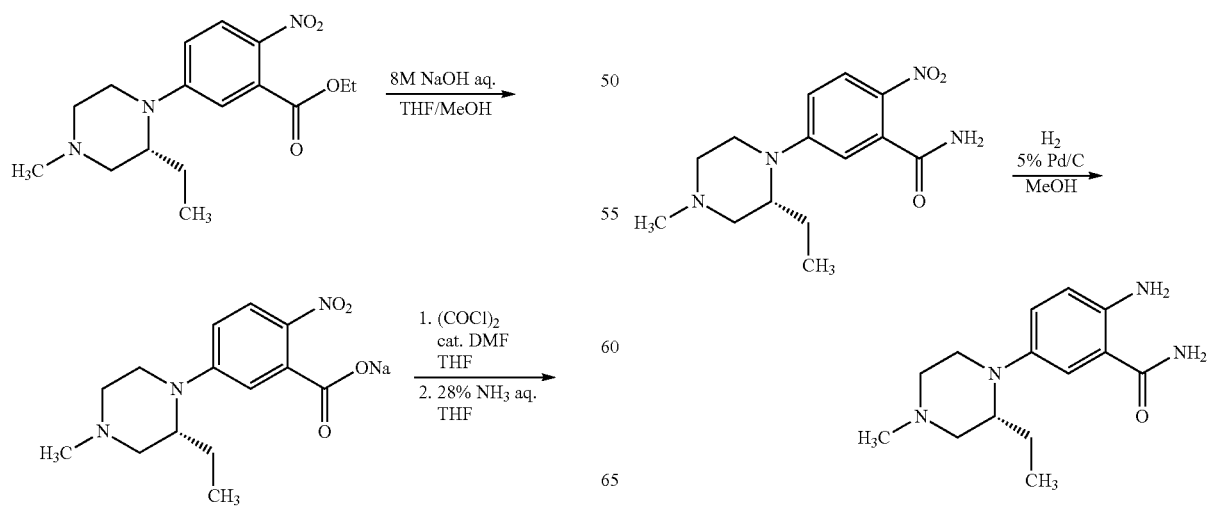

After a mixture of (R)-5-(2-ethyl-4-methylpiperadin-1-yl)-2-nitrobenzamide (1.42 g), palladium-activated carbon (5% palladium) (142 mg) and methanol (15 mL) was stirred under normal pressure and hydrogen atmosphere at room temperature overnight, the catalyst was removed by filtration and washed with methanol. The volatile components were distilled off from the filtrate under reduced pressure and the obtained substance was purified by silica gel column chromatography (NH, ethyl acetate/hexane) to obtain the title compound (0.984 g).

$^1$H-NMR (300 MHz, DMSO-$d_6$) δ: 7.72 (1H, s), 7.10 (1H, J=2.6 Hz, d), 6.97 (1H, s), 6.89 (1H, J=8.7, 2.6 Hz, dd), 6.60 (1H, J=8.7 Hz, d), 6.13 (2H, s), 3.17-3.20 (1H, m), 2.84-2.98 (2H, m), 2.24-2.51 (4H, m), 2.19 (3H, s), 1.35-1.48 (1H, m), 1.15-1.27 (1H, m), 0.73 (3H, J=7.6 Hz, t). MS: [M+H]$^+$ 263.3.

(E) (R)-2-(4,6-Dimethylpyrazolo[1,5-a]pyrazin-2-yl)-6-(2-ethyl-4-methylpiperazin-1-yl)quinazolin-4(3H)-one

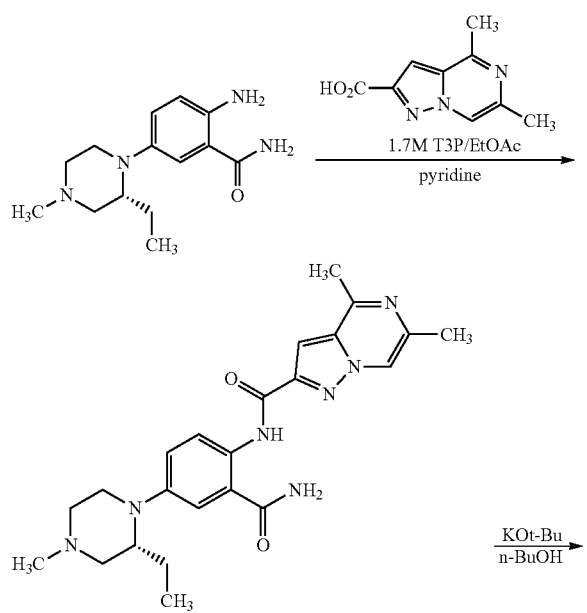

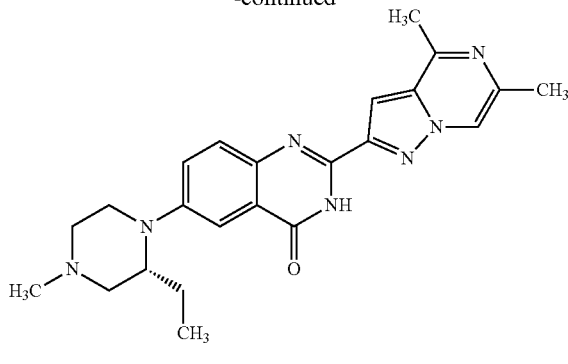

A mixture of 4,6-dimethylpyrazolo[1,5-α]pyrazin-2-carboxylic acid (0.714 g), (R)-2-amino-5-(2-ethyl-4-methylpiperadin-1-yl)benzamide (0.980 g), a 1.7 M propylphosphonic acid anhydride/ethyl acetate solution (3.30 mL) and pyridine (10 mL) was stirred at room temperature overnight. After the volatile components were distilled off under reduced pressure, water (10 mL) and a 15% aqueous potassium carbonate solution (10 mL) were added to the remaining solid and the mixture was stirred at room temperature for 2 hours. The solid obtained by filtration was washed with water and diisopropyl ether. To the obtained solid were added 1-butanol (15 mL) and potassium tert-butoxide (34.8 mg) and then the mixture was stirred at 120° C. overnight. Then, the volatile components were distilled off under reduced pressure. The remaining solid was recrystallized from ethanol/hexane to obtain the title compound (0.674 g).

$^1$H-NMR (300 MHz, DMSO-$d_6$) δ:12.01 (1H, s), 8.49 (1H, s), 7.60-7.63 (2H, m), 7.51 (1H, J=9.3, 2.8 Hz, dd), 7.37 (1H, J=2.6 Hz, d), 3.86-3.90 (1H, m), 3.48-3.52 (1H, m), 3.07-3.14 (1H, m), 2.84-2.88 (2H, m), 2.73 (3H, s), 2.45 (3H, s), 2.22 (3H, s), 2.00-2.14 (2H, m), 1.74-1.89 (1H, m), 1.31-1.42 (1H, m), 0.85 (3H, J=7.4 Hz, t). MS: [M+H]$^+$ 418.2.

A List of the Compounds

The compounds used as the Examples are given in the table below. "MS" in the table denotes a measured value. The compounds of the Examples given in the following Table 1 were produced using a method described in one of the Examples above or similar methods.

TABLE 1

| Ex. # | IUPAC name | Structural formula | Salt | MS |
|---|---|---|---|---|
| 1 | 2-(4,6-dimethylpyrazolo[1,5-a]pyrazin-2-yl)-7-fluoro-6-(1-methylpiperidin-4-yl)quinazolin-4(3H)-one | 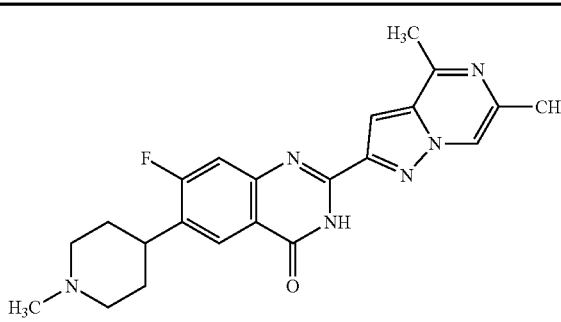 | | 407.2 |

TABLE 1-continued

| Ex. # | IUPAC name | Structural formula | Salt | MS |
|---|---|---|---|---|
| 2 | 2-(4,6-dimethylpyrazolo[1,5-a]pyrazin-2-yl)-6-(1-methylpiperidin-4-yl)quinazolin-4(3H)-one | | | 389.2 |
| 3 | 2-(4,6-dimethylpyrazolo[1,5-a]pyrazin-2-yl)-8-fluoro-6-(1-methylpiperidin-4-yl)quinazolin-4(3H)-one | | | 407.2 |
| 4 | 2-(4,6-dimethylpyrazolo[1,5-a]pyrazin-2-yl)-5-fluoro-6-(1-methylpiperidin-4-yl)quinazolin-4(3H)-one | | | 407.2 |
| 5 | 2-(4-ethyl-6-methylpyrazolo[1,5-a]pyrazin-2-yl)-6-(4-methylpiperazin-1-yl)quinazolin-4(3H)-one | | | 404.3 |
| 6 | 2-(4,6-dimethylpyrazolo[1,5-a]pyrazin-2-yl)-6-(4-methylpiperazin-1-yl)quinazolin-4(3H)-one dihydrochloride | | 2HCl | 390.3 |

TABLE 1-continued

| Ex. # | IUPAC name | Structural formula | Salt | MS |
|---|---|---|---|---|
| 7 | 2-(4,6-dimethylpyrazolo[1,5-a]pyrazin-2-yl)-7-fluoro-6-(4-methylpiperazin-1-yl)quinazolin-4(3H)-one | | | 408.1 |
| 8 | 2-(4,6-dimethylpyrazolo[1,5-a]pyrazin-2-yl)-6-(4-methylpiperazin-1-yl)quinazolin-4(3H)-one | | | 390.3 |
| 9 | 6-(2-methylimidazo[1,2-a]pyridin-6-yl)-2-(1-methylpiperidin-4-yl)quinazolin-4(3H)-one | | | 374.2 |
| 10 | 6-(8-fluoro-2-methylimidazo[1,2-a]pyridin-6-yl)-2-(1-methylpiperidin-4-yl)quinazolin-4(3H)-one | | | 392.1 |
| 11 | 2-(4,6-dimethylfuro[3,2-c]pyridin-2-yl)-6-(4-methylpiperazin-1-yl)quinazolin-4(3H)-one | | | 390.0 |

TABLE 1-continued

| Ex. # | IUPAC name | Structural formula | Salt | MS |
|---|---|---|---|---|
| 12 | 2-(4,6-dimethylpyrazolo[1,5-a]pyrazin-2-yl)-6-(4-ethylpiperazin-1-yl)quinazolin-4(3H)-one | | | 404.4 |
| 13 | 6-(2-methyl-1,3-benzoxazol-6-yl)-2-(1-methylpiperidin-4-yl)quinazolin-4(3H)-one | | | 375.3 |
| 14 | 6-(2-methyl-1,3-benzothiazol-6-yl)-2-(1-methylpiperidin-4-yl)quinazolin-4(3H)-one | | | 391.3 |
| 15 | 2-(1-methylpiperidin-4-yl)-6-(3-methylpyrrolo[1,2-a]pyrazin-7-yl)quinazolin-4(3H)-one | | | 374.3 |
| 16 | 2-(4,6-dimethylpyrazolo[1,5-a]pyrazin-2-yl)-6-(piperazin-1-yl)quinazolin-4(3H)-one dihydrochloride | | 2HCl | 376.3 |

TABLE 1-continued

| Ex. # | IUPAC name | Structural formula | Salt | MS |
|---|---|---|---|---|
| 17 | 6-(8-chloro-2-methylimidazo[1,2-a]pyridin-6-yl)-2-(1-methylpiperidin-4-yl)quinazolin-4(3H)-one | | | 408.3 |
| 18 | 6-(4-fluoro-2-methyl-1,3-benzoxazol-6-yl)-2-(1-methylpiperidin-4-yl)quinazolin-4(3H)-one | | | 393.3 |
| 19 | 8-methyl-6-(2-methylimidazo[1,2-a]pyridin-6-yl)-2-(1-methylpiperidin-4-yl)quinazolin-4(3H)-one | | | 388.3 |
| 20 | 6-(1,3-dimethylpyrrolo[1,2-a]pyrazin-7-yl)-2-(1-methylpiperidin-4-yl)quinazolin-4(3H)-one | | | 388.3 |
| 21 | 2-(4,6-dimethylpyrazolo[1,5-a]pyrazin-2-yl)-8-methyl-6-(4-methylpiperazin-1-yl)quinazolin-4(3H)-one | | | 404.4 |

TABLE 1-continued

| Ex. # | IUPAC name | Structural formula | Salt | MS |
|---|---|---|---|---|
| 22 | 6-(8-methoxy-2-methylimidazo[1,2-a]pyridin-6-yl)-2-(1-methylpiperidin-4-yl)quinazolin-4(3H)-one | | | 404.3 |
| 23 | 6-(2,8-dimethylimidazo[1,2-a]pyridin-6-yl)-2-(1-methylpiperidin-4-yl)quinazolin-4(3H)-one | | | 388.1 |
| 24 | 8-fluoro-6-(4-fluoro-2-methyl-1,3-benzoxazol-6-yl)-2-(1-methylpiperidin-4-yl)quinazolin-4(3H)-one | | | 411.3 |
| 25 | 2-(1-ethylpiperidin-4-yl)-6-(4-fluoro-2-methyl-1,3-benzoxazol-6-yl)quinazolin-4(3H)-one | | | 407.3 |
| 26 | 7-(2-methylimidazo[1,2-a]pyridin-6-yl)-3-(1-methylpiperidin-4-yl)quinazolin-4(3H)-one | | | 374.2 |

TABLE 1-continued

| Ex. # | IUPAC name | Structural formula | Salt | MS |
|---|---|---|---|---|
| 27 | 2-(1-cyclopropylpiperidin-4-yl)-6-(4-fluoro-2-methyl-1,3-benzoxazol-6-yl)quinazolin-4(3H)-one | | | 419.3 |
| 28 | 2-(1-cyclopropylpiperidin-4-yl)-8-fluoro-6-(4-fluoro-2-methyl-1,3-benzoxazol-6-yl)quinazolin-4(3H)-one | | | 437.3 |
| 29 | 7-(4-fluoro-2-methyl-1,3-benzoxazol-6-yl)-3-(1-methylpiperidin-4-yl)quinazolin-4(3H)-one | | | 393.3 |
| 30 | 8-fluoro-6-(2-methyl-1,3-benzoxazol-6-yl)-2-(1-methylpiperidin-4-yl)quinazolin-4(3H)-one | | | 393.3 |
| 31 | 2-(1-cyclopropylpiperidin-4-yl)-8-fluoro-6-(2-methyl-1,3-benzoxazol-6-yl)quinazolin-4(3H)-one | | | 419.3 |

TABLE 1-continued

| Ex. # | IUPAC name | Structural formula | Salt | MS |
|---|---|---|---|---|
| 32 | 2-(1-cyclopropylpiperidin-4-yl)-6-(3-methylpyrrolo[1,2-a]pyrazin-7-yl)quinazolin-4(3H)-one | | AcOH | 400.4 |
| 33 | 2-(1-cyclopropylpiperidin-4-yl)-8-fluoro-6-(3-methylpyrrolo[1,2-a]pyrazin-7-yl)quinazolin-4(3H)-one acetate | | AcOH | 418.3 |
| 34 | 3-(1-cyclopropylpiperidin-4-yl)-7-(4-fluoro-2-methyl-1,3-benzoxazol-6-yl)quinazolin-4(3H)-one | | | 419.3 |
| 35 | 2-(1-cyclopropylpiperidin-4-yl)-8-fluoro-6-(3-fluoro-4-methoxyphenyl)quinazolin-4(3H)-one | | | 412.3 |
| 36 | 6-(4-cyclopropylpiperazin-1-yl)-2-(4,6-dimethylpyrazolo[1,5-a]pyrazin-2-yl)quinazolin-4(3H)-one | | | 416.4 |

TABLE 1-continued

| Ex. # | IUPAC name | Structural formula | Salt | MS |
|---|---|---|---|---|
| 37 | 2-(4-fluoro-1-methylpiperidin-4-yl)-6-(2-methylimidazo[1,2-a]pyridin-6-yl)quinazolin-4(3H)-one | | | 392.2 |
| 38 | 6-(4-Fluoro-2-methyl-1,3-benzoxazol-6-yl)-2-(1-isopropylpiperidin-4-yl)quinazolin-4(3H)-one | | | 421.3 |
| 39 | 3-(1-cyclopropylpiperidin-4-yl)-7-(8-fluoro-2-methylimidazo[1,2-a]pyridin-6-yl)quinazolin-4(3H)-one | | | 418.3 |
| 40 | 2-(1-cyclopropylpiperidin-4-yl)-6-(8-fluoro-2-methylimidazo[1,2-a]pyridin-6-yl)-8-methylquinazolin-4(3H)-one | | | 432.3 |
| 41 | 7-methyl-2-(2-methyl-1,3-benzoxazol-6-yl)-6-(1-methylpiperidin-4-yl)quinazolin-4(3H)-one | | | 389.2 |

TABLE 1-continued

| Ex. # | IUPAC name | Structural formula | Salt | MS |
|---|---|---|---|---|
| 42 | 2-(8-methyl-1-oxa-2,8-diazaspiro[4.5]dec-2-en-3-yl)-6-(4-methylpiperazin-1-yl)quinazolin-4(3H)-one | | | 397.2 |
| 43 | 2-(8-methyl-1-oxa-2,8-diazaspiro[4.5]dec-2-en-3-yl)-6-(1-methylpiperidin-4-yl)quinazolin-4(3H)-one | | | 396.2 |
| 44 | 2-(1,6-dimethyl-2-oxo-1,2-dihydropyridin-3-yl)-6-(1-methylpiperidin-4-yl)quinazolin-4(3H)-one | | | 365.2 |
| 45 | 2-(6-methoxypyridin-2-yl)-6-(1-methylpiperidin-4-yl)quinazolin-4(3H)-one | | | 351.2 |
| 46 | 2-(6,7-dihyrdo-4H-pyrazolo[5,1-c][1,4]oxazin-2-yl)-6-(1-methylpiperidin-4-yl)quinazolin-4(3H)-one | | | 366.1 |

TABLE 1-continued

| Ex. # | IUPAC name | Structural formula | Salt | MS |
|---|---|---|---|---|
| 47 | 2-(2-fluoro-3-methoxyphenyl)-6-(1-methylpiperidin-4-yl)quinazolin-4(3H)-one | 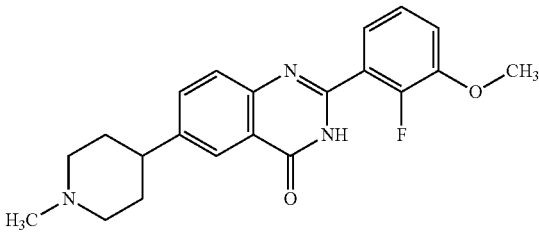 | | 368.1 |
| 48 | 2-(4-Methoxypyridin-2-yl)-6-(1-methylpiperidin-4-yl)quinazolin-4(3H)-one | 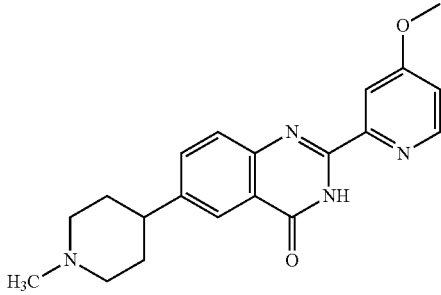 | | 351.2 |
| 49 | 2-(2-fluoro-5-methoxyphenyl)-6-(1-methylpiperidin-4-yl)quinazolin-4(3H)-one | 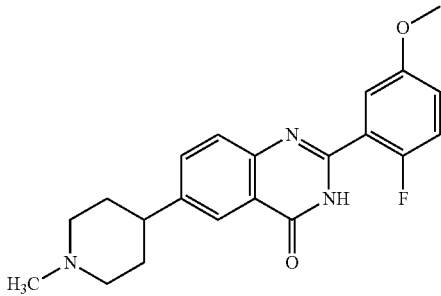 | | 368.1 |
| 50 | 2-(6,8-dimethylimidazo[1,2-a]pyrazin-2-yl)-6-(4-methylpiperazin-1-yl)quinazolin-4(3H)-one | 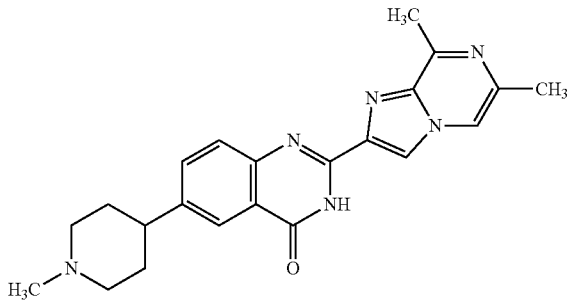 | | 390.1 |
| 51 | 2-(4,6-dimethylpyrazolo[1,5-a]pyrazin-2-yl)-7-methoxy-6-(1-methylpiperidin-4-yl)quinazolin-4(3H)-one | 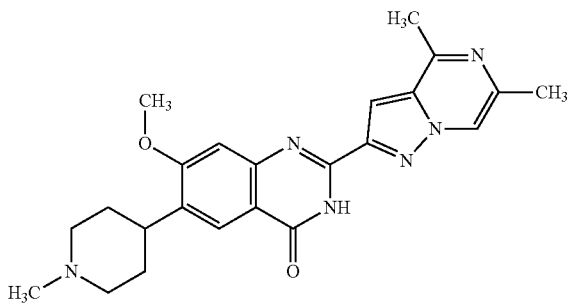 | | 419.3 |

TABLE 1-continued

| Ex. # | IUPAC name | Structural formula | Salt | MS |
|---|---|---|---|---|
| 52 | 2-(4,6-dimethylpyrazolo[1,5-a]pyrazin-2-yl)-8-methoxy-6-(1-methylpiperidin-4-yl)quinazolin-4(3H)-one | | | 419.3 |
| 53 | 2-(8-fluoro-2-methylimidazo[1,2-a]pyridin-6-yl)-6-(4-methylpiperazin-1-yl)quinazolin-4(3H)-one | | | 393.3 |
| 54 | 6-(4-methylpiperazin-1-yl)-2-(4,6,7-trimethylpyrazolo[1,5-a]pyrazin-2-yl)quinazolin-4(3H)-one | | | 404.2 |
| 55 | 2-(2,8-dimethylimidazo[1,2-a]pyridin-6-yl)-6-(4-methylpiperazin-1-yl)quinazolin-4(3H)-one | | | 389.3 |
| 56 | 7-fluoro-2-(8-fluoro-2-methylimidazo[1,2-a]pyridin-6-yl)-6-(4-methylpiperazin-1-yl)quinazolin-4(3H)-one | | | 411.2 |

TABLE 1-continued

| Ex. # | IUPAC name | Structural formula | Salt | MS |
|---|---|---|---|---|
| 57 | 2-(2,8-dimethylimidazo[1,2-a]pyridin-6-yl)-7-fluoro-6-(4-methylpiperazin-1-yl)quinazolin-4(3H)-one | | | 407.2 |
| 58 | 2-(2-methylimidazo[1,2-a]pyridin-6-yl)-6-(4-methylpiperazin-1-yl)quinazolin-4(3H)-one | | | 375.2 |
| 59 | 2-(6-fluoro-1,3-dimethyl-1H-indazol-5-yl)-6-(4-methylpiperazin-1-yl)quinazolin-4(3H)-one | | | 407.3 |
| 60 | 5-methyl-6-(2-methylimidazo[1,2-a]pyridin-6-yl)-2-(1-methylpiperidin-4-yl)quinazolin-4(3H)-one | | | 388.3 |
| 61 | 6-(2,5-dimethylimidazo[1,2-a]pyridin-6-yl)-2-(1-methylpiperidin-4-yl)quinazolin-4(3H)-one | | | 388.2 |
| 62 | 7-methyl-6-(2-methylimidazo[1,2-a]pyridin-6-yl)-2-(1-methylpiperidin-4-yl)quinazolin-4(3H)-one | | | 388.1 |

TABLE 1-continued

| Ex. # | IUPAC name | Structural formula | Salt | MS |
|---|---|---|---|---|
| 63 | 6-(2,7-dimethylimidazo[1,2-a]pyridin-6-yl)-2-(1-methylpiperidin-4-yl)quinazolin-4(3H)-one | | | 388.4 |
| 64 | 2-(1,3-dimethylpyrrolo[1,2-a]pyrazin-7-yl)-6-(4-methylpiperazin-1-yl)quinazolin-4(3H)-one | | | 389.2 |
| 65 | 6-(imidazo[1,2-a]pyridin-6-yl)-2-(1-methylpiperidin-4-yl)quinazolin-4(3H)-one | | | 360.3 |
| 66 | 2-(1-methylpiperidin-4-yl)-6-[2-(trifluoromethyl)imidazo[1,2-a]pyridin-6-yl]quinazolin-4(3H)-one | | | 428.3 |
| 67 | 6-(2,3-dimethylimidazo[1,2-a]pyridin-6-yl)-2-(1-methylpiperidin-4-yl)quinazolin-4(3H)-one | | | 388.3 |
| 68 | 6-(2-ethylimidazo[1,2-a]pyridin-6-yl)-2-(1-methylpiperidin-4-yl)quinazolin-4(3H)-one | | | 388.3 |

TABLE 1-continued

| Ex. # | IUPAC name | Structural formula | Salt | MS |
|---|---|---|---|---|
| 69 | 3-methyl-6-(2-methylimidazo[1,2-a]pyridin-6-yl)-2-(1-methylpiperidin-4-yl)quinazolin-4(3H)-one | | | 388.3 |
| 70 | 1-methyl-6-(2-methylimidazo[1,2-a]pyridin-6-yl)-2-(1-methylpiperidin-4-yl)quinazolin-4(1H)-one | | | 388.3 |
| 71 | 6-(2,4-dimethyl-1,3-benzoxazol-6-yl)-2-(1-methylpiperidin-4-yl)quinazolin-4(3H)-one | | | 389.3 |
| 72 | 6-(2-methyl-1,3-benzoxazol-5-yl)-2-(1-methylpiperidin-4-yl)quinazolin-4(3H)-one | | | 375.3 |
| 73 | 6-(2-methylimidazo[1,2-a]pyridin-6-yl)-2-[1-(2,2,2-trifluoroethyl)piperidin-4-yl]quinazolin-4(3H)-one | | | 442.3 |
| 74 | 2-(1-cyclopropylpiperidin-4-yl)-6-(2-methylimidazo[1,2-a]pyridin-6-yl)quinazolin-4(3H)-one | | | 400.3 |

TABLE 1-continued

| Ex. # | IUPAC name | Structural formula | Salt | MS |
|---|---|---|---|---|
| 75 | 2-(1-methylpiperidin-4-yl)-6-[2-methyl-8-(trifluoromethyl)imidazo[1,2-a]pyridin-6-yl]quinazolin-4(3H)-one | | | 442.3 |
| 76 | 2-(5-methoxy-4-methylpyridin-2-yl)-6-(4-methylpiperazin-1-yl)quinazolin-4(3H)-one | | | 366.3 |
| 77 | 2-(1-methylpiperidin-4-yl)-6-[4-(1-methyl-1H-pyrazol-4-yl)phenyl]quinazolin-4(3H)-one | | | 400.3 |
| 78 | 2-(4,6-dimethylpyrazolo[1,5-a]pyrazin-2-yl)-6-(4-methyl-2-oxopiperazin-1-yl)quinazolin-4(3H)-one | | | 404.3 |
| 79 | 2-(4,6-dimethylpyrazolo[1,5-a]pyrazin-2-yl)-6-(morpholin-4-yl)quinazolin-4(3H)-one | | | 377.2 |

TABLE 1-continued

| Ex. # | IUPAC name | Structural formula | Salt | MS |
|---|---|---|---|---|
| 80 | 6-(2-methylimidazo[1,2-a]pyridin-7-yl)-3-(1-methylpiperidin-4-yl)quinazolin-4(3H)-one | | | 374.3 |
| 81 | 6-(2-methylimidazo[1,2-a]pyridin-6-yl)-2-(tetrahydro-2H4-pyran-4-yl)quinazolin-4(3H)-one | | | 361.3 |
| 82 | 2-(4,6-dimethylpyrazolo[1,5-a]pyrazin-2-yl)-6-[4-(2-methoxyethyl)piperazin-1-yl]quinazolin-4(3H)-one | | | 434.3 |
| 83 | 2-(1-cyclopropylpiperidin-4-yl)-6-(2-methyl-1,3-benzoxazol-6-yl)quinazolin-4(3H)-one | | | 401.3 |
| 84 | 2-(1,4-dimethylpiperidin-4-yl)-6-(2-methylimidazo[1,2-a]pyridin-6-yl)quinazolin-4(3H)-one | | | 388.3 |
| 85 | 2-(4-fluoro-1-cyclopropylpiperidin-4-yl)-6-(8-fluoro-2-methylimidazo[1,2-a]pyridin-6-yl)quinazolin-4(3H)-one | | | 436.3 |

TABLE 1-continued

| Ex. # | IUPAC name | Structural formula | Salt | MS |
|---|---|---|---|---|
| 86 | 2-(4-fluoro-1-methylpiperidin-4-yl)-6-(8-fluoro-2-methylimidazo[1,2-a]pyridin-6-yl)quinazolin-4(3H)-one | | | 410.3 |
| 87 | 8-fluoro-6-(3-fluoro-4-methoxyphenyl)-2-(1-methylpiperidin-4-yl)quinazolin-4(3H7)-one | | | 386.2 |
| 88 | 2-(4,6-dimethylpyrazolo[1,5-a]pyrazin-2-yl)-6-(4-methylpiperazin-1-yl)quinazolin-4(3H)-one | | コハク酸 ($C_4H_6O_4$) | 390.2 |
| 89 | 6-(8-fluoro-2-methylimidazo[1,2-a]pyridin-6-yl)-2-(4-fluoro-1-methylpiperidin-4-yl)-8-methylquinazolin-4(3H4)-one | | | 424.3 |
| 90 | 2-(1-ethyl-4-fluoropiperidin-4-yl)-6-(8-fluoro-2-methylimidazo[1,2-a]pyridin-6-yl)-8-methylquinazolin-4(3H4)-one | | | 438.3 |

TABLE 1-continued

| Ex. # | IUPAC name | Structural formula | Salt | MS |
|---|---|---|---|---|
| 91 | 2-(4-fluoro-1-isopropylpiperidin-4-yl)-6-(8-fluoro-2-methylimidazo[1,2-a]pyridin-6-yl)quinazolin-4(3H)-one | | | 438.3 |
| 92 | 2-(1-Ethyl-4-fluoropiperidin-4-yl)-6-(8-fluoro-2-methylimidazo[1,2-a]pyridin-6-yl)quinazolin-4(3H)-one | | | 424.3 |
| 93 | 2-[1-(2,2-difluoroethyl)-4-fluoropiperidin-4-yl]-6-(8-fluoro-2-methylimidazo[1,2-a]pyridin-6-yl)quinazolin-4(3H)-one | | | 460.3 |
| 94 | 8-fluoro-2-(4-fluoro-1-methylpiperidin-4-yl)-6-(2-methylimidazo[1,2-a]pyridin-6-yl)quinazolin-4(3H)-one | | | 410.3 |
| 95 | 2-(1-ethyl-4-fluoropiperidin-4-yl)-8-fluoro-6-(2-methylimidazo[1,2-a]pyridin-6-yl)quinazolin-4(3H)-one | | | 424.3 |

TABLE 1-continued

| Ex. # | IUPAC name | Structural formula | Salt | MS |
|---|---|---|---|---|
| 96 | 8-fluoro-2-(4-fluoro-1-isopropylpiperidin-4-yl)-6-(2-methylimidazo[1,2-a]pyridin-6-yl)quinazolin-4(3H)-one | | | 438.3 |
| 97 | 8-fluoro-6-(8-fluoro-2-methylimidazo[1,2-a]pyridin-6-yl)-2-(4-fluoro-1-methylpiperidin-4-yl)quinazolin-4(3H)-one | | | 428.3 |
| 98 | 2-(1-ethyl-4-fluoropiperidin-4-yl)-8-fluoro-6-(8-fluoro-2-methylimidazo[1,2-a]pyridin-6-yl)quinazolin-4(3H)-one | | | 442.3 |
| 99 | 8-fluoro-2-(4-fluoro-1-isopropylpiperidin-4-yl)-6-(8-fluoro-2-methylimidazo[1,2-a]pyridin-6-yl)quinazolin-4(3H)-one | | | 456.3 |
| 100 | 2-(1-ethyl-4-fluoropiperidin-4-yl)-6-(8-fluoro-2-methylimidazo[1,2-a]pyridin-6-yl)-8-methylpyrido[3,2-d]pyrimidin-4(3H)-one | | | 439.3 |

TABLE 1-continued

| Ex. # | IUPAC name | Structural formula | Salt | MS |
|---|---|---|---|---|
| 101 | 2-(4-fluoro-1-isopropylpiperidin-4-yl)-6-(8-fluoro-2-methylimidazo[1,2-a]pyridin-6-yl)-8-methylpyrido[3,2-d]pyrimidin-4(3H)-one | | | 453.4 |
| 102 | 2-(1-cyclopropyl-4-fluoropiperidin-4-yl)-6-(8-fluoro-2-methylimidazo[1,2-a]pyridin-6-yl)pyrido[3,2-d]pyrimidin-4(3H)-one | | | 437.3 |
| 103 | 2-(1-cyclopropyl-4-fluoropiperidin-4-yl)-6-(2-methylimidazo[1,2-a]pyrimidin-6-yl)-8-methylquinazolin-4(3H4)-one | | | 433.3 |
| 104 | 2-(1-cyclopropyl-4-fluoropiperidin-4-yl)-6-(8-fluoro-2-methylimidazo[1,2-a]pyridin-6-yl)pyrido[3,4-d]pyrimidin-4(3H)-one | | | 437.2 |
| 105 | 2-(1-cyclopro-4-fluoropiperidin-4-yl)-8-fluoro-6-(2-methylimidazo[1,2-a]pyrimidin-6-yl)quinazolin-4(3H)-one | | | 437.3 |

TABLE 1-continued

| Ex. # | IUPAC name | Structural formula | Salt | MS |
|---|---|---|---|---|
| 106 | 2-(1-cyclopropylpiperidin-4-yl)-6-(4-fluoro-2-methyl-1,3-benzoxazol-6-yl)pyrido[3,2-d]pyrimidin-4(3H)-one | | | 420.3 |
| 107 | 2-(1-cyclopropyl-4-fluoropiperidin-4-yl)-6-(4-fluoro-2-methyl-1,3-benzoxazol-6-yl)pyrido[3,4-d]pyrimidin-4(3H)-one | | | 438.3 |
| 108 | 2-(4-fluoro-1-methylpiperidin-4-yl)-6-(8-fluoro-2-methylimidazo[1,2-a]pyridin-6-yl)pyrido[3,4-d]pyrimidin-4(3H)-one | | | 411.3 |
| 109 | 2-(1-ethyl-4-fluoropiperidin-4-yl)-6-(8-fluoro-2-methylimidazo[1,2-a]pyridin-6-yl)pyrido[3,4-d]pyrimidin-4(3H)-one | | | 425.3 |
| 110 | 2-[4-fluoro-1-(2-methoxyethyl)piperidin-4-yl]-6-(8-fluoro-2-methylimidazo[1,2-a]pyridin-6-yl)quinazolin-4(3H)-one | | | 454.3 |

TABLE 1-continued

| Ex. # | IUPAC name | Structural formula | Salt | MS |
|---|---|---|---|---|
| 111 | 6-(4-fluoro-2-methy-1,3-benzoxazol-6-yl)-2-(4-fluoropiperidin-4-yl)pyrido[3,4-d]pyrimidin-4(3H)-one | | | 398.3 |
| 112 | 6-(8-fluoro-2-methylimidazo[1,2-a]pyridin-6-yl)-2-[1-(2-methoxyethyl)piperidin-4-yl]pyrido[3,4-d]pyrimidin-4(3H)-one | | | 437.3 |
| 113 | 6-(4-fluoro-2-methyl-1,3-benzoxazol-6-yl)-2-[1-(2-methoxyethyl)piperidin-4-yl]pyrido[3,4-d]pyrimidin-4(3H)-one | | | 438.3 |
| 114 | 2-(1-cyclopropylpiperidin-4-yl)-6-(8-fluoro-2-methylimidazo[1,2-a]pyridin-6-yl)pyrido[3,4-d]pyrimidin-4(3H)-one | | | 419.3 |
| 115 | 2-(1-cyclopropylpiperidin-4-yl)-6-(4-fluoro-2-methyl-1,3-benzoxazol-6-yl)pyrido[3,4-d]pyrimidin-4(3H)-one | | | 420.3 |

TABLE 1-continued

| Ex. # | IUPAC name | Structural formula | Salt | MS |
|---|---|---|---|---|
| 116 | 6-(4-cyclopropylpiperazin-1-yl)-2-(6-methylpyrazolo[1,5-a]pyrazin-2-yl)quinazolin-4(3H)-one | | | 402.2 |
| 117 | 6-(4-cyclopropylpiperazin-1-yl)-2-(5,7-dimethylimidazo[1,2-c]pyrimidin-2-yl)quinazolin-4(3H)-one | | | 416.3 |
| 118 | 6-(4-cyclopropylpiperazin-1-yl)-2-(2-methylimidazo[1,2-b]pyridazin-6-yl)quinazolin-4(3H)-one | | | 402.2 |
| 119 | 2-(4,6-dimethylpyrazolo[1,5-a]pyrazin-2-yl)-6-(4-isopropylpiperazin-1-yl)quinazolin-4(3H)-one bistrifluoroacetate | | 2TFA | 418.2 |
| 120 | 6-[4-(cyclopropylmethyl)piperazin-1-yl]-2-(4,6-dimethylpyrazolo[1,5-a]pyrazin-2-yl)quinazolin-4(3H)-one bistrifluoroacetate | | 2TFA | 430.2 |

TABLE 1-continued

| Ex. # | IUPAC name | Salt | MS |
|---|---|---|---|
| 121 | (S)-2-(4,6-dimethylpyrazolo[1,5-a]pyrazin-2-yl)-6-(hexahydropyrrolo[1,2-a]pyrazin-2(1H)-yl)quinazolin-4(3H)-one bistrifluoroacetate | 2TFA | 416.2 |
| 122 | 6-(3,3-Dimethylpiperazin-1-yl)-2-(4,6-dimethylpyrazolo[1,5-a]pyrazin-2-yl)quinazolin-4(3H)-one bistrifluoroacetate | 2TFA | 404.2 |
| 123 | 2-(4,6-dimethylpyrazolo[1,5-a]pyrazin-2-yl)-6-(4,7-diazaspiro[2.5]octan-7-yl)quinazolin-4(3H)-one bistrifluoroacetate | 2TFA | 402.2 |
| 124 | 2-(4,6-dimethylpyrazolo[1,5-a]pyrazin-2-yl)-6-(octahydro-2H-pyrido[1,2-a]pyrazin-2-yl)quinazolin-4(3H)-one | | 430.3 |

(eutomer)

TABLE 1-continued

| Ex. # | IUPAC name | Structural formula | Salt | MS |
|---|---|---|---|---|
| 125 | 2-(4,6-dimethylpyrazolo[1,5-a]pyrazin-2-yl)-6-(octahydro-2H-pyrido[1,2-a]pyrazin-2-yl)quinazolin-4(3H)-one (distomer) | (distomer) | | 430.2 |
| 126 | (R)-2-(4,6-dimethylpyrazolo[1,5-a]pyrazin-2-yl)-6-(hexahydropyrrolo[1,2-a]pyrazin-2(1H)-yl)quinazolin-4(3H)-one | | | 416.3 |
| 127 | (S8)-6-(2,4-simethylpiperazin-1-yl)-2-(4,6-dimethylpyrazolo[1,5-a]pyrazin-2-yl)quinazolin-4(3H)-one | | | 404.2 |
| 128 | (R)-6-(2,4-simethylpiperazin-1-yl)-2-(4,6-dimethylpyrazolo[1,5-a]pyrazin-2-yl)quinazolin-4(3H)-one | | | 404.2 |
| 129 | (S)-2-(4,6-dimethylpyrazolo[1,5-a]pyrazin-2-yl)-6-(2-ethyl-4-methylpiperazin-1-yl)quinazolin-4(3H)-one | | | 418.2 |

TABLE 1-continued

| Ex. # | IUPAC name | Structural formula | Salt | MS |
|---|---|---|---|---|
| 130 | (S)-2-(4,6-dimethylpyrazolo[1,5-a]pyrazin-2-yl)-6-(4-ethyl-2-methylpiperazin-1-yl)quinazolin-4(3H)-one | | | 418.2 |
| 131 | (R)-2-(4,6-dimethylpyrazolo[1,5-a]pyrazin-2-yl)-6-(4-ethyl-2-methylpiperazin-1-yl)quinazolin-4(3H)-one | | | 418.2 |
| 132 | (R)-2-(4,6-dimethylpyrazolo[1,5-a]pyrazin-2-yl)-6-(2-ethyl-4-methylpiperazin-1-yl)quinazolin-4(3H4)-one | | | 418.2 |

Figures 1, 5:
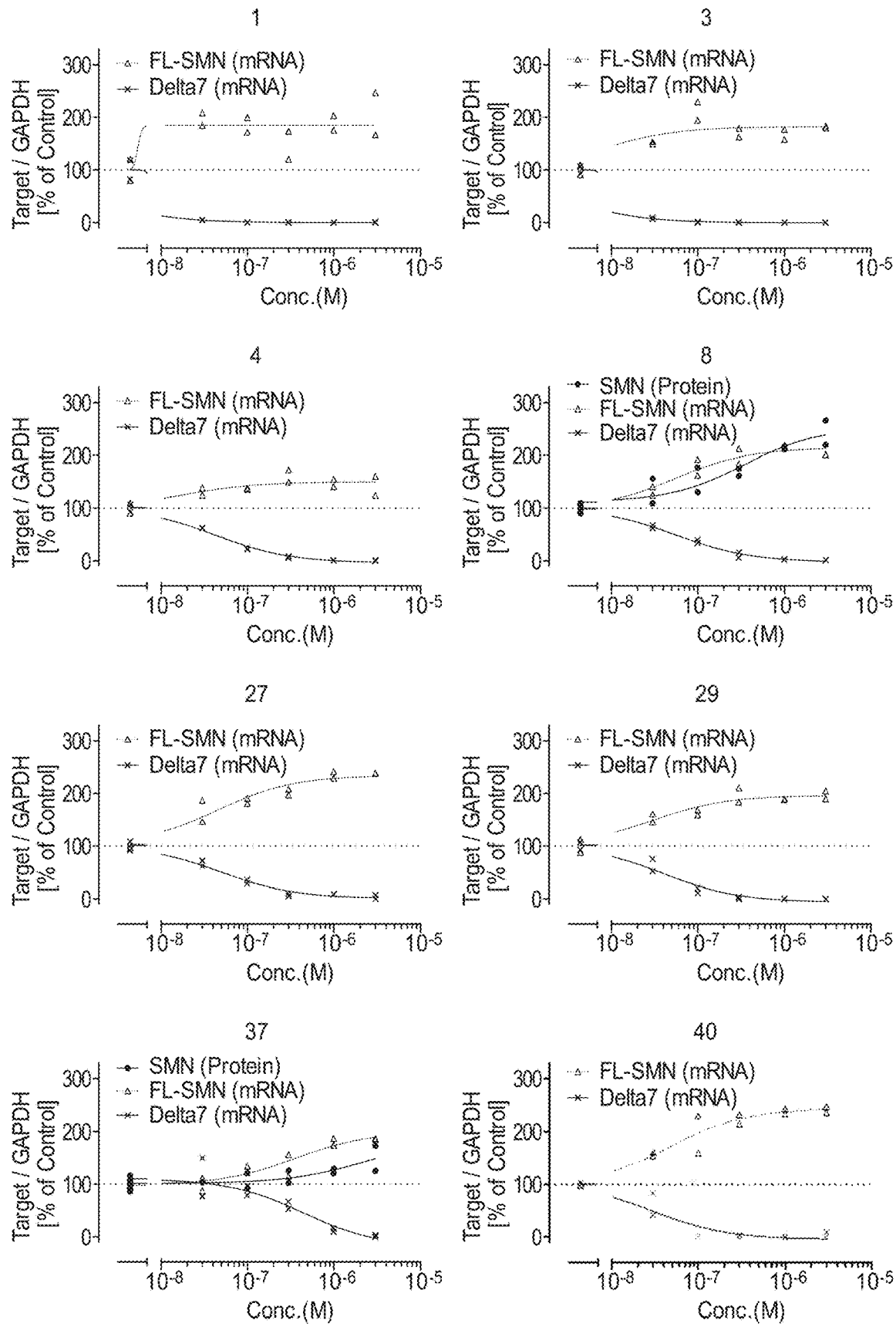
Figures 2, 5:
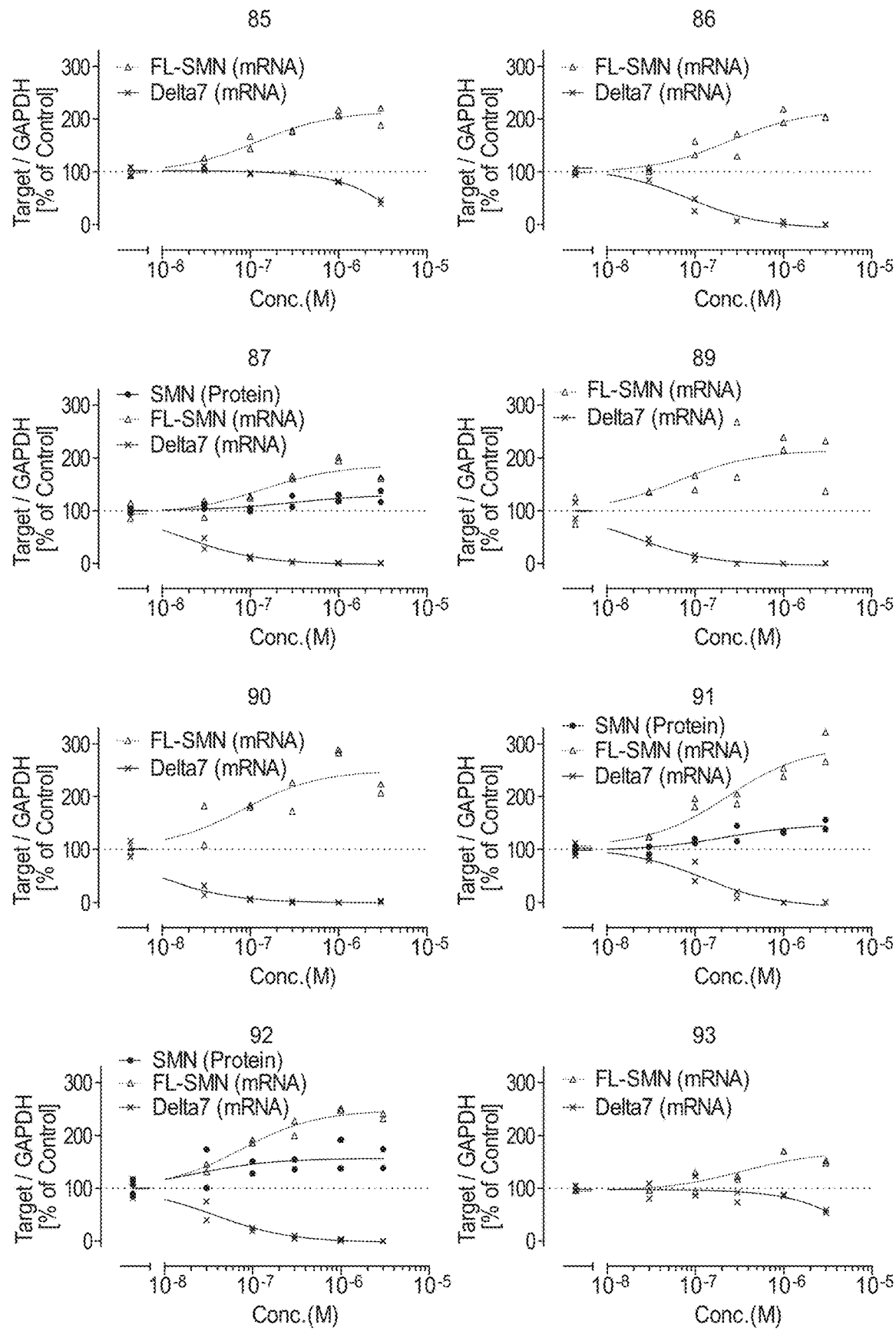
Figures 3, 5:
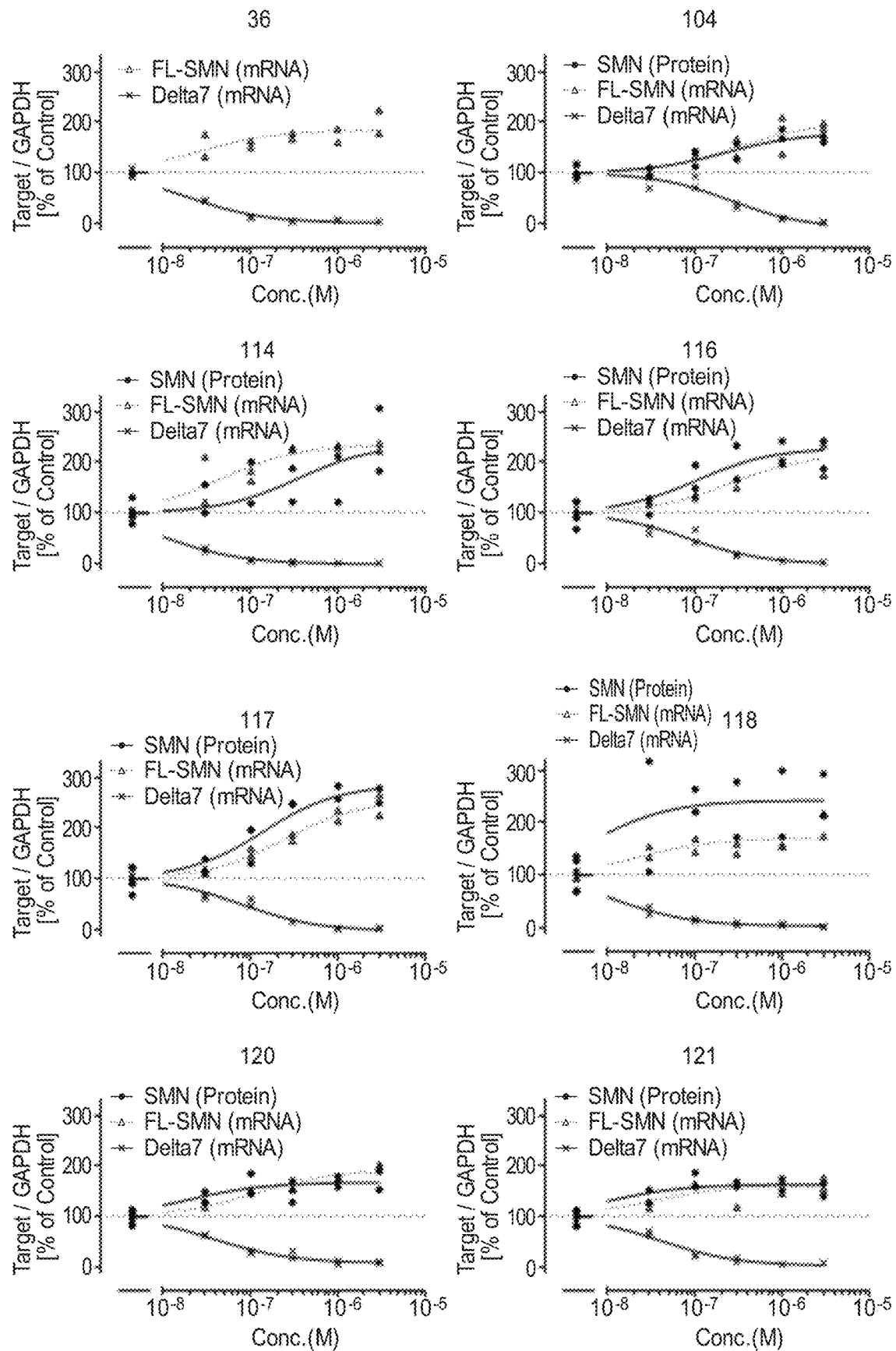
Figures 4, 5:
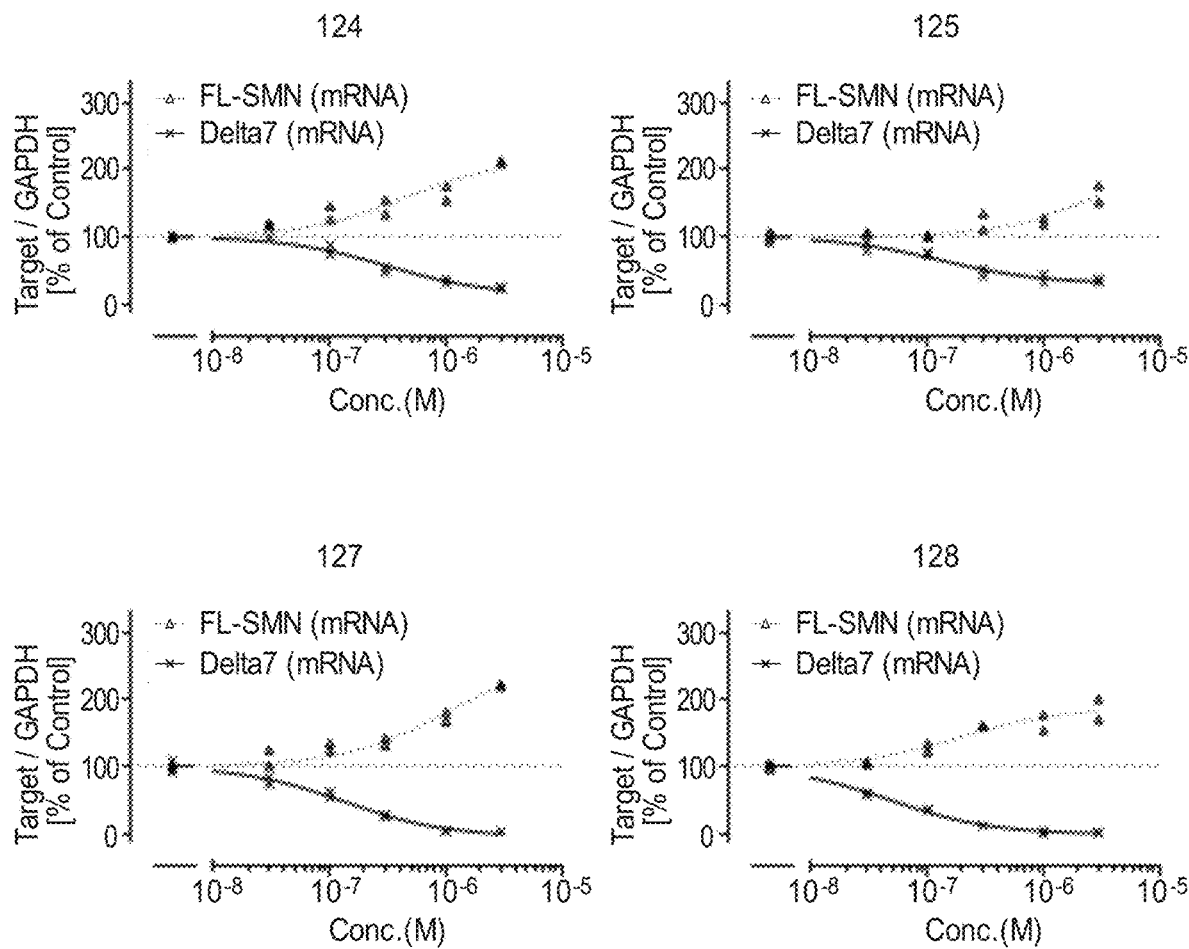

[Experimental Example 2] Live-Cell Assay to Measure the Changes in mRNA Levels after Exposure to the Compounds In this example, each test compound was administered to cultured cells, and changes in the expression levels of mRNA transcripts of SMN, i.e., FL-SMN containing exons 7 and 8 and Delta7 with exon 7 skipped, were examined using PCR. In principle, as shown in FIGS. 3B and 3D, FL-SMN and Delta7 were distinguished from each other using a primer (003-Fw-FL-SMN) matching a sequence in exon 7 to examine the expression of FL-SMN and a primer (006-Fw-delta7) with a nucleotide sequence spanning the junction between exons 6 and 8 to examine the expression of Delta7.

(Experimental Methods)

Fibroblasts derived from patients SMA (GM03813) (Coriell Cell Repositories) were cultured with passages using DMEM (High Glucose) (Life Technologies) supplemented with 10% FBS (Life Technologies). Cells were seeded in tissue-culture-treated 96-well plates (Corning) at 1.5 or $0.5 \times 10^4$ cells/well in 100 µL of medium. The cells were incubated in 5% $CO_2$ for 6 hours, and the medium was replaced with 100 µL of medium (with DMSO, 0.1% final concentration) containing each of the compounds given in the Examples. After additional incubation for 24 hours under the same conditions, the cells were washed once with D-PBS(—) (Wako) and 25 µL/well of the lysis solution (with gDNA Remove) contained in the SuperPrep (registered trademark) Cell Lysis & RT Kit for qPCR (Toyobo life science) was added according to the manufacturer's instructions so that the cells were lysed and the genomic DNA was degraded. Furthermore, 5 µL of the STOP solution (with RNase Inhibitor) contained in the kit was added to provide RNA-containing solutions. Six microliters of the RNA-containing solutions were each mixed with 14 µL of a reverse transcription solution containing transcriptase together with dNTP, random primers and an oligodT primer. Reverse transcription was performed at 37° C. (15 min), 50° C. (5 min), and 98° C. (5 min), to give total cDNAs. The total cDNAs were diluted 30-fold with Ultra-pure water (Invitrogen) to measure the expression levels of FL-SMN, delta7, and GAPDH. For quantitative PCR (qPCR), a PCR solution was prepared according to the instructions of the manufacturer of the THUNDERBIRD (registered trademark) Probe qPCR Mix (Toyobo life science). Five microliters of the diluted total cDNA solutions and oligo DNA standard solutions, each containing either 001-Standard FL-SMN (SEQ ID NO. 1) or 002-Standard delta7 (SEQ ID NO. 2), were each mixed with 10 μL of each of the PCR solutions containing a qPCR probe, primers, and PCR enzyme. FIG. 1 shows the nucleotide sequences of 001-Standard FL-SMN and 002-Standard delta7. The oligoDNA standard solutions were prepared as those containing either of $5\times10^8$, $5\times10^7$, $5\times10^6$, $5\times10^5$, $5\times10^4$, $5\times10^3$, $5\times10^2$, $5\times10$, 5, or 0 copies. For the oligo DNA standards, primers, and probes, oligonucleotides synthesized by Integrated DNA Technologies, Inc. (IDT) were used. FIG. 2 shows the nucleotide sequences of the primers and the probes used for detecting FL-SMN containing exons 7 and 8 of SMN and those for detecting Delta7 with exon 7 skipped. FIGS. 3B and 3D show their detection mechanisms. The final concentrations of the primers and probes added were 0.4 μM and 0.15 μM, respectively. The qPCR was performed using the following conditions on a ViiA7 instrument (Applied Biosystems): first stage: 95° C. (1 min)→second stage: 95° C. (15 sec)→third stage: 60° C. (1 min)→40 repeated cycles of the second and third stages. The GAPDH mRNA was used as the internal control, and the commercially available 20×gene expression PCR assay (Life Technologies, 4326317E, Hs99999905_m1) and Standard GAPDH (SEQ ID NO. 7) (see FIG. 1) was used to determine the number of copies of this gene. The measurement values obtained for the samples to be measured were standardized against the respective value obtained for GAPDH.

(Generation of Calibration Curves)

As described above, the combination (B) of the primers and the probe detects the cDNA derived from the FL-SMN mRNA containing exon 7, whereas the combination (D) of the primers and the probe detects the cDNA derived from the delta7 mRNA without exon 7.

First, PCR was performed using the oligo DNA standard solution and each primer—probe pair, and calibration curves were generated based on Ct values obtained. FIGS. 3C and 3E show the results obtained for the experiments using 001-Standard FL-SMN and 002-Standard delta7 as a template, respectively.

As shown in FIG. 3C, for the 001-Standard FL-SMN template, the PCR efficiency was at least 95% and 5 to $5\times10^8$ copies of template could be detected linearly for the combination (B), whereas no Ct value was detected for the combination (D) (denoted as "ND" in the figure). In addition, as shown in FIG. 3E, for the 002-Standard delta7 template, the PCR efficiency was at least 95% and 5 to $5\times10^8$ copies of template could be detected linearly for the combination (D), whereas the Ct value was 23.5 for $5\times10^8$ copies of template for the combination (B). This corresponds to $1.9\times10^4$ copies based on the standard curve obtained for the combination (D); thus, the selectivity for the combination (D) was 26316 times that for the combination (B).

Thus, the combinations (B) and (D) of the primers and the probe specifically detect 001-Standard FL-SMN and 002-Standard delta7, respectively, and could detect at least 5 to $5\times10^8$ copies of template linearly.

Next, similar experiments were performed for GAPDH using the above-mentioned templates and the 20×gene expression PCR assay. As shown in FIG. 4, the PCR efficiency was at least 95%, and 5 to $5\times10^8$ copies of template could be detected linearly.

(Results of the Experiments Performed Using the Compounds)

Using the above-mentioned assays, the activities of the compounds of the Examples were evaluated. Specifically, the percentages of the FL-SMN and delta7 values obtained using DMSO without the compounds and standardized against GAPDH were set as 100% and those of the FL-SMN and delta7 values obtained at the time of administration of the compounds and standardized against GAPDH were calculated. Table 2 shows the results of the calculations for the FL-SMN mRNA at a concentration of 11.1M of the compounds obtained in the Working Examples 1 to 132. In Table 2, the calculation results for the FL-SMN mRNA equal to or higher than 100% but lower than 120% are denoted by a single asterisk (*), those equal to or higher than 120% but lower than 150% are denoted by a double asterisk (), those equal to or higher than 150% but lower than 180% are denoted by a triple asterisk (*), and those equal to or higher than 180% are denoted by four asterisks (****).

It should be noted that, for delta7, representative compounds were chosen for measurements, and the results obtained at different concentrations within a certain range (30 nM to 3 μM) are presented below, together with the results obtained for FL-SMN measured using the same conditions, as well as the results pertaining to protein expression described later.

TABLE 2

| Example # | Percentage of increase |
|---|---|
| 1 | **** |
| 2 | **** |
| 3 | **** |
| 4 | **** |
| 5 | *** |
| 6 | **** |
| 7 | *** |
| 8 | **** |
| 9 | **** |
| 10 | **** |
| 11 | *** |
| 12 | **** |
| 13 | **** |
| 14 | *** |
| 15 | **** |
| 16 | **** |
| 17 | *** |
| 18 | **** |
| 19 | **** |
| 20 | **** |
| 21 | **** |
| 22 | **** |
| 23 | *** |
| 24 | **** |
| 25 | **** |
| 26 | **** |
| 27 | **** |
| 28 | **** |
| 29 | **** |
| 30 | **** |
| 31 | **** |
| 32 | **** |
| 33 | *** |
| 34 | **** |
| 35 | **** |
| 36 | **** |
| 37 | *** |
| 38 | **** |
| 39 | *** |
| 40 | **** |
| 41 | * |
| 42 | * |
| 43 | * |
| 44 | ** |
| 45 | ** |
| 46 | * |
| 47 | * |
| 48 | * |

TABLE 2-continued

| Example # | Percentage of increase |
|---|---|
| 49 | * |
| 50 | ** |
| 51 | * |
| 52 | ** |
| 53 | ** |
| 54 | * |
| 55 | ** |
| 56 | ** |
| 57 | ** |
| 58 | ** |
| 59 | * |
| 60 | ** |
| 61 | * |
| 62 | * |
| 63 | * |
| 64 | * |
| 65 | ** |
| 66 | * |
| 67 | ** |
| 68 | * |
| 69 | ** |
| 70 | * |
| 71 | * |
| 72 | * |
| 73 | * |
| 74 | ** |
| 75 | ** |
| 76 | * |
| 77 | * |
| 78 | * |
| 79 | * |
| 80 | * |
| 81 | * |
| 82 | ** |
| 83 | ** |
| 84 | * |
| 85 | **** |
| 86 | *** |
| 87 | **** |
| 88 | **** |
| 89 | **** |
| 90 | **** |
| 91 | **** |
| 92 | **** |
| 93 | *** |
| 94 | *** |
| 95 | *** |
| 96 | *** |
| 97 | **** |
| 98 | **** |
| 99 | **** |
| 100 | **** |
| 101 | *** |
| 102 | ** |
| 103 | ** |
| 104 | *** |
| 105 | ** |
| 106 | ** |
| 107 | ** |
| 108 | ** |
| 109 | *** |
| 110 | ** |
| 111 | **** |
| 112 | **** |
| 113 | **** |
| 114 | **** |
| 115 | **** |
| 116 | **** |
| 117 | **** |
| 118 | *** |
| 119 | **** |
| 120 | **** |
| 121 | **** |
| 122 | **** |
| 123 | **** |
| 124 | *** |
| 125 | ** |
| 126 | **** |
| 127 | *** |
| 128 | **** |
| 129 | *** |
| 130 | *** |
| 131 | *** |
| 132 | *** |

As shown in Table 2, the expression level of FL-SMN was increased by all compounds of the Examples. Therefore, the compounds according to the present invention are useful as therapeutic agents for spinal muscular atrophy.

[Experimental Example 3] Live-Cell Assay to Measure the Changes in Protein Expression after Exposure to the Compounds In this example, representative test compounds were administered to cultured cells at different concentrations, and changes in the expression levels of the SMN protein were examined using Western blotting.

(Experimental Method)

Fibroblasts derived from patients SMA (GM03813) (Coriell Cell Repositories) were cultured with passages using DMEM, High Glucose, (Life Technologies) supplemented with 10% FBS (Life Technologies). Cells were seeded in each well of a tissue-culture-treated 96-well plate (Corning) at $1.5 \times 10^4$ or $0.5 \times 10^4$ cells in 100 µL. Six hours later, the medium was replaced with media (with DMSO, 0.1% final concentration) each containing one of the compounds given in the Examples at a concentration of 30 nM to 3 µM. Twenty-four hours or 3 days later, the cells were washed once with D-PBS(—) (Wako) and collected from 3-4 wells in 50 µL of a lysis solution [RIPA buffer (Wako) containing a protease inhibitor cocktail (Roche, PhosSTOP (Roche)]. The proteins in the supernatants obtained by centrifugation at 150,000 rpm for 15 minutes at 4° C. were quantitated using a BCA kit (Wako). For Western blotting, the samples were prepared to be 15 µL with 0.1-0.2 µg of protein, 1×LDS sample buffer (Invitrogen, NP0007), and 12.5 mM DTT and heated at 95° C. for 5 minutes. The samples were added to a Perfect NT Gel 7.5-15% Gel (DRC, NTH-7E7HP10) at 10-15 µL/well (1.0-2.0 µg/well) and subjected to electrophoresis at 150 V for 60-70 minutes. Subsequently, blotting was performed using a blotting unit, Criterion blotter, in which the proteins were transferred from the gel to an Immobilon Transfer membrane (Millipore, Cat. IPVH00010) at 25 V for 180-240 minutes using a transfer solution [1720 mL of MilliQ water, 200 mL of methanol, and 80 mL of 25× buffer (LC3675, Invitrogen)]. The membrane was then blocked for 1 hour using the Protein free T20 blocking reagent (Pierce, Prod #37571). Subsequently, the membrane was incubated with the primary antibody diluted with Can Get Signal solution 1 at room temperature for 1 hour. The primary antibody used was either an anti-SMN antibody (BD, BD610646, 1000-fold dilution) or a GAPDH antibody (Wako, cat 016-25523, 2000-fold dilution). The membranes were then incubated with the secondary antibody diluted with Can Get Signal solution 2 at room temperature for 1 hour. The secondary antibody used was an HPR-conjugated anti-mouse IgG antibody (GE healthcare, HRP Anti-Mouse IgG, HRP-Linked F(ab')2 Fragment Sheep, NA9310-1ML, 5000-fold dilution). The chemiluminescence produced using Immunostar Zeta (Wako) was detected using a LAS-4000 instrument (GE Heathcare).

(Results of the Experiments Performed Using the Compounds)

Using the above-mentioned systems, the activities of the compounds of the representative Examples were evaluated. Specifically, the percentages of the expression levels of the SMN protein obtained using DMSO without the compounds and standardized against GAPDH were set as 100% and the expression levels of the SMN protein obtained at the time of administration of the compounds and standardized against GAPDH were calculated. Subsequently, the results were plotted on graphs together with the results obtained for delta7 and FL-SMN obtained using a method similar to the Experimental example 2.

As shown in FIG. 5, the test compounds increased the amount of the FL-SMN mRNA in a concentration-dependent manner, decreased the amount of the delta7 mRNA, and increased the amount of the SMN protein. The increase in the expression level of the FL-SMN mRNA was almost in inverse proportion to the reduction in the expression level of the delta7 mRNA. The results demonstrated that the compounds of interest regulate splicing, thereby increasing the FL-SMN mRNA, which is a normal splicing product. Thus, the compounds according to the present invention are useful as splicing regulators for SMN genes, particularly, mutated SMN genes. Moreover, the increase in the FL-SMN concentration was almost proportional to the increase of the expression level of the SMN protein, demonstrating that the FL-SMN mRNA produced after the regulation by the compounds was translated into the normal protein.

INDUSTRIAL APPLICABILITY

The present invention has made it possible to provide prophylactic or therapeutic agents for spinal muscular atrophy.

The invention claimed is:

1. A compound represented by formula (I):

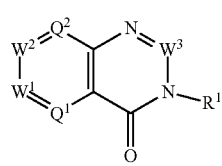

or a pharmaceutically acceptable salt or stereoisomer thereof,
wherein:
$R^1$ is H;
$Q^1$ is $CR^a$ or N;
$R^a$ is H, halogen, CN, $C_{1-8}$ alkyl, or $OC_{1-8}$ alkyl;
$Q^2$ is $CR^a$ or N;
$R^b$ is H, halogen, CN, $C_{1-8}$ alkyl, or $OC_{1-8}$ alkyl;
$W^1$ is $CR^3$;
$R^3$ is azetidinyl, pyrrolidinyl, piperidinyl, piperazinyl, morpholinyl, azepanyl, 1,4-diazepanyl, 1,4-oxazepanyl, octahydropyrrolo[3,4-b]pyrrolyl, octahydropyrrolo[3,4-c]pyrrolyl, octahydropyrrolo[3,2-b]pyrrolyl, octahydro-1H-pyrrolo[3,2-b]pyridinyl, octahydro-5H-pyrrolo[3,2-c]pyridinyl, octahydro-1H-pyrrolo[2,3-c]pyridinyl, octahydro-6H-pyrrolo[3,4-b]pyridinyl, octahydro-1H-pyrrolo[3,4-c]pyridinyl, octahydro-1H-cyclopentapyrazinyl, octahydro-1H-pyrrolo[1,2-a]pyrazinyl, decahydro-1,6-naphthyridinyl, decahydro-1,7-naphthyridinyl, decahydro-2,6-naphthyridinyl, decahydro-2,7-naphthyridinyl, decahydroquinoxalinyl, octahydro-2H-pyrido[1,2-a]pyrazinyl, 3-azabicyclo[3.1.0]hexanyl, 1-azabicyclo[2.2.1]heptanyl, 2-azabicyclo[2.2.1]heptanyl, 7-azabicyclo[2.2.1]heptanyl, 1-azabicyclo[2.2.2]octanyl, 2-azabicyclo[2.2.2]octanyl, 1-azabicyclo[3.2.1]octanyl, 2-azabicyclo[3.2.1]octanyl, 3-azabicyclo[3.2.1]octanyl, 6-azabicyclo[3.2.1]octanyl, 8-azabicyclo[3.2.1]octanyl, 1-azabicyclo[3.2.2]nonanyl, 2-azabicyclo[3.2.2]nonanyl, 3-azabicyclo[3.2.2]nonanyl, 6-azabicyclo[3.2.2]nonanyl, 1-azabicyclo[3.3.1]nonanyl, 2-azabicyclo[3.3.1]nonanyl, 3-azabicyclo[3.3.1]nonanyl, 9-azabicyclo[3.3.1]nonanyl, 2,5-diazabicyclo[2.2.1]heptanyl, 1,4-diazabicyclo[2.2.2]octanyl, 2,5-diazabicyclo[2.2.2]octanyl, 1,4-diazabicyclo[3.2.1]octanyl, 2,6-diazabicyclo[3.2.1]octanyl, 3,6-diazabicyclo[3.2.1]octanyl, 3,8-diazabicyclo[3.2.1]octanyl, 1,4-diazabicyclo[3.2.2]nonanyl, 1,5-diazabicyclo[3.2.2]nonanyl, 2,6-diazabicyclo[3.2.2]nonanyl, 3,6-diazabicyclo[3.2.2]nonanyl, 6,8-diazabicyclo[3.2.2]nonanyl, 1-azaspiro[3.3]heptanyl, 2-azaspiro[3.3]heptanyl, 1-azaspiro[3.4]octanyl, 2-azaspiro[3.4]octanyl, 5-azaspiro[3.4]octanyl, 6-azaspiro[3.4]octanyl, 1-azaspiro[4.4]nonanyl, 2-azaspiro[4.4]nonanyl, 1-azaspiro[4.5]decanyl, 2-azaspiro[4.5]decanyl, 6-azaspiro[4.5]decanyl, 7-azaspiro[4.5]decanyl, 8-azaspiro[4.5]decanyl, 1,6-diazaspiro[3.3]heptanyl, 2,6-diazaspiro[3.3]heptanyl, 1,7-diazaspiro[4.4]nonanyl, 2,7-diazaspiro[4.4]nonanyl, 1,6-diazaspiro[3.5]nonanyl, 1,7-diazaspiro[3.5]nonanyl, 2,5-diazaspiro[3.5]nonanyl, 2,6-diazaspiro[3.5]nonanyl, 2,7-diazaspiro[3.5]nonanyl, 5,8-diazaspiro[3.5]nonanyl, 1,7-diazaspiro[4.5]decanyl, 1,8-diazaspiro[4.5]decanyl, 2,6-diazaspiro[4.5]decanyl, 2,7-diazaspiro[4.5]decanyl, 2,8-diazaspiro[4.5]decanyl, or 6,9-diazaspiro[4.5]decanyl;

wherein each optionally contains one, two, or three double bonds;
wherein each is optionally substituted with one, two, or three =O substituents; and
wherein each is optionally substituted with one, two, or three independently selected $R^5$ substituents;
each $R^5$ is independently halogen, CN, $NO_2$, $C_{1-6}$ alkyl, $NH_2$, $NHC_{1-6}$ alkyl, $NHC_{3-10}$ cycloalkyl, OH, $OC_{1-6}$ alkyl, $OC_{3-10}$ cycloalkyl, or $C_{3-10}$ cycloalkyl, wherein each $C_{1-6}$ alkyl, $NHC_{1-6}$ alkyl, $NHC_{3-10}$ cycloalkyl, $OC_{1-6}$ alkyl, $OC_{3-10}$ cycloalkyl, and $C_{3-10}$ cycloalkyl is optionally and independently substituted with one, two, three, four, or five substituents independently selected from the group consisting of halogen, CN, $NO_2$, $NHC_{1-6}$ alkyl, $N(C_{1-6}$ alkyl$)_2$, and $OC_{1-6}$ alkyl;
$W^2$ is CRC or N;
W is H, halogen, CN, $C_{1-8}$ alkyl, or $OC_{1-8}$ alkyl;
$W^3$ is $CR^2$;
$R^2$ is pyrazolo[1,5-α]pyrazinyl, wherein the pyrazolo[1,5-c]pyrazinyl is optionally substituted with one, two, or three independently selected $R^4$ substituents; and
each $R^4$ is independently halogen, CN, $NO_2$, $C_{1-6}$ alkyl, $NH_2$, $NHC_{1-6}$ alkyl, $NHC_{3-10}$ cycloalkyl, OH, $OC_{1-6}$ alkyl, $OC_{3-10}$ cycloalkyl, or $C_{3-10}$ cycloalkyl, wherein each $C_{1-6}$ alkyl, $NHC_{1-6}$ alkyl, $NHC_{3-10}$ cycloalkyl, $OC_{1-6}$ alkyl, $OC_{3-10}$ cycloalkyl, and $C_{3-10}$ cycloalkyl is optionally and independently substituted with one, two, three, four, or five substituents independently selected from the group consisting of halogen, CN, $NO_2$, $NHC_{1-6}$ alkyl, $N(C_{1-6}$ alkyl$)_2$, and $OC_{1-6}$ alkyl.

2. The compound according to claim 1, or a pharmaceutically acceptable salt or stereoisomer thereof, wherein:
   $Q^1$ is $CR^a$; and
   $Q^2$ is $CR^b$.

3. The compound according to claim 1, or a pharmaceutically acceptable salt or stereoisomer thereof, wherein $R^3$ is piperidinyl, piperazinyl, morpholinyl, octahydro-1H-pyrrolo[1,2-α]pyrazinyl, or octahydro-2H-pyrido[1,2-α]pyrazinyl.

4. The compound according to claim 3, or a pharmaceutically acceptable salt or stereoisomer thereof, wherein:
   each $R^4$ is independently halogen, $C_{1-6}$ alkyl, OH, $OC_{1-6}$ alkyl, $OC_{3-10}$ cycloalkyl, or $C_{3-10}$ cycloalkyl, wherein each $C_{1-6}$ alkyl and $C_{3-10}$ cycloalkyl is optionally and independently substituted with one independently selected $OC_{1-6}$ alkyl substituent; and
   each $R^5$ is independently halogen, $C_{1-6}$ alkyl, OH, $OC_{1-6}$ alkyl, $OC_{3-10}$ cycloalkyl, or $C_{3-10}$ cycloalkyl, wherein each $C_{1-6}$ alkyl and $C_{3-10}$ cycloalkyl is optionally and independently substituted with one independently selected $OC_{1-6}$ alkyl substituent.

5. The compound according to claim 1, wherein the compound is:

or a pharmaceutically acceptable salt thereof.

6. The compound according to claim 1, wherein the compound is:

or a pharmaceutically acceptable salt thereof.

7. The compound according to claim 1, wherein the compound is:

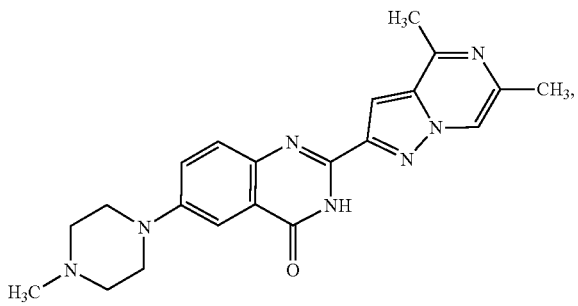 [SMILES: Cc1cn2nc(-c3nc4ccc(N5CCN(C)CC5)cc4c(=O)[nH]3)cc2c(C)n1]

or a pharmaceutically acceptable salt thereof.

8. The compound according to claim 1, wherein the compound is:

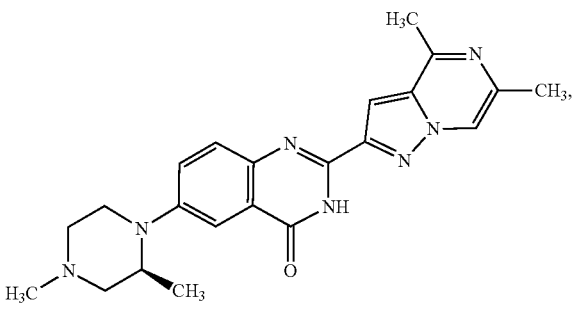 [SMILES: Cc1cn2nc(-c3nc4ccc(N5CCN(C)C[C@@H]5C)cc4c(=O)[nH]3)cc2c(C)n1]

or a pharmaceutically acceptable salt thereof.

9. The compound according to claim 1, wherein the compound is:

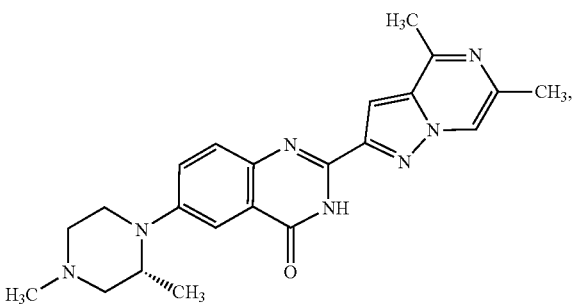 [SMILES: Cc1cn2nc(-c3nc4ccc(N5CCN(C)C[C@H]5C)cc4c(=O)[nH]3)cc2c(C)n1]

or a pharmaceutically acceptable salt thereof.

10. The compound according to claim 1, wherein the compound is:

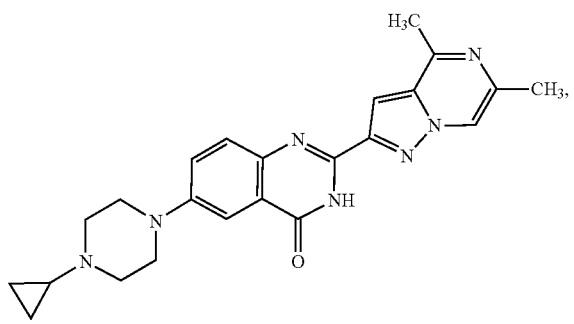 [SMILES: Cc1cn2nc(-c3nc4ccc(N5CCN(C6CC6)CC5)cc4c(=O)[nH]3)cc2c(C)n1]

or a pharmaceutically acceptable salt thereof.

11. A medicament comprising one or more pharmaceutically acceptable vehicles and the compound according to claim 1, or a pharmaceutically acceptable salt or stereoisomer thereof.

12. A method for regulating splicing in a mammal, wherein the method comprises administering to the mammal in need thereof a therapeutically effective amount of the compound according to claim 1, or a pharmaceutically acceptable salt or stereoisomer thereof.

13. A method for enhancing expression in a mammal, wherein the method comprises administering to the mammal in need thereof a therapeutically effective amount of the compound according to claim 1, or a pharmaceutically acceptable salt or stereoisomer thereof;
wherein the expression is of survival motor neuron (SMN) mRNA having a normal function and/or survival motor neuron (SMN) protein having a normal function.

14. A method for examining the enhancement of expression of survival motor neuron (SMN) mRNA having a normal function and/or survival motor neuron (SMN) protein having a normal function in a cell, wherein the method comprises the following steps:
(a) contacting a cell comprising a survival motor neuron (SMN) gene, with a nucleotide at position 6 in exon 7 mutated from C to T, with the compound according to claim 1, or a pharmaceutically acceptable salt or stereoisomer thereof; and
(b) examining whether an expression level of survival motor neuron (SMN) mRNA comprising exon 7 in the cell is enhanced by the compound according to claim 1, or a pharmaceutically acceptable salt or stereoisomer thereof; or
(c) examining whether an expression level of survival motor neuron (SMN) protein comprising an amino acid sequence encoded by exon 7 is enhanced by the compound according to claim 1, or a pharmaceutically acceptable salt or stereoisomer thereof.

15. The method according to claim 14, wherein the enhancement of expression of survival motor neuron (SMN) mRNA having a normal function or survival motor neuron (SMN) protein having a normal function is examined using polymerase chain reaction (PCR) or Western blotting.

16. A method for treating spinal muscular atrophy in a mammal, wherein the method comprises administering to the mammal in need thereof a therapeutically effective amount of the compound according to claim 1, or a pharmaceutically acceptable salt or stereoisomer thereof.

17. A compound, wherein the compound is:

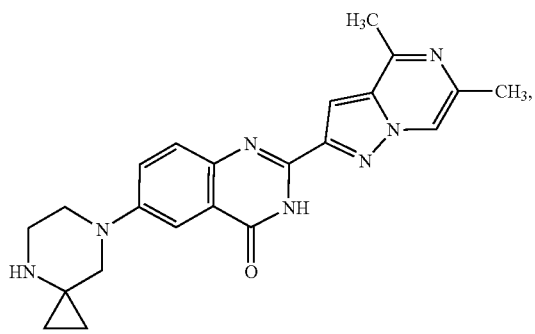 [SMILES: Cc1cn2nc(-c3nc4ccc(N5CCNC6(CC6)C5)cc4c(=O)[nH]3)cc2c(C)n1]

or a pharmaceutically acceptable salt thereof.

18. A compound, wherein the compound is:

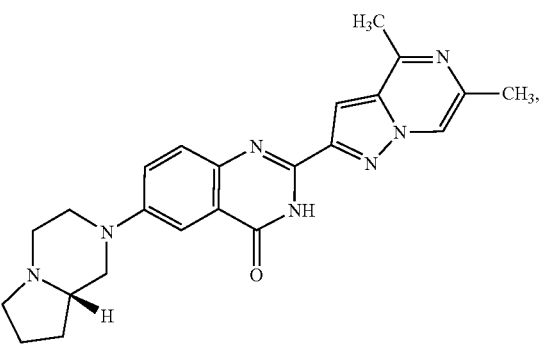 [SMILES: Cc1cn2nc(-c3nc4ccc(N5CCN6CCC[C@H]6C5)cc4c(=O)[nH]3)cc2c(C)n1]

or a pharmaceutically acceptable salt thereof.

19. A compound, wherein the compound is:

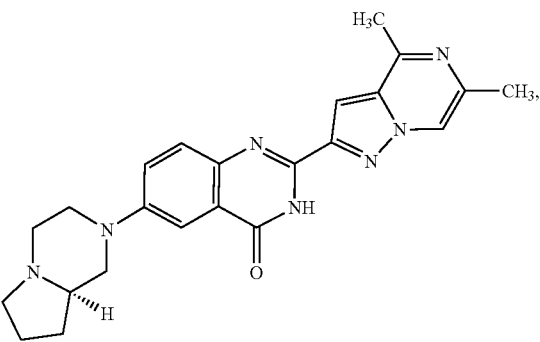 [SMILES: Cc1cn2nc(-c3nc4ccc(N5CCN6CCC[C@@H]6C5)cc4c(=O)[nH]3)cc2c(C)n1]

or a pharmaceutically acceptable salt thereof.

* * * * *